United States Patent
Engels et al.

(10) Patent No.: US 12,344,651 B2
(45) Date of Patent: Jul. 1, 2025

(54) CD19 AND CD22 CHIMERIC ANTIGEN RECEPTORS AND USES THEREOF

(71) Applicant: Novartis AG, Basel (CH)

(72) Inventors: Boris Engels, Arlington, MA (US); Carla Patricia Guimaraes, Boston, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 18/617,912

(22) Filed: Mar. 27, 2024

(65) Prior Publication Data

US 2024/0390492 A1    Nov. 28, 2024

Related U.S. Application Data

(62) Division of application No. 17/104,961, filed on Nov. 25, 2020, now Pat. No. 11,975,026.

(60) Provisional application No. 62/940,600, filed on Nov. 26, 2019.

(51) Int. Cl.
| | |
|---|---|
| *A61K 39/00* | (2006.01) |
| *A61K 40/11* | (2025.01) |
| *A61K 40/31* | (2025.01) |
| *A61K 40/42* | (2025.01) |
| *C07K 14/705* | (2006.01) |
| *C12N 5/0783* | (2010.01) |

(52) U.S. Cl.
CPC ........ *C07K 14/70503* (2013.01); *A61K 40/11* (2025.01); *A61K 40/31* (2025.01); *A61K 40/4211* (2025.01); *A61K 40/4212* (2025.01); *C12N 5/0636* (2013.01); *A61K 2239/29* (2023.05); *A61K 2239/31* (2023.05); *A61K 2239/38* (2023.05); *A61K 2239/48* (2023.05)

(58) Field of Classification Search
None
See application file for complete search history.

(56) References Cited

U.S. PATENT DOCUMENTS

| | | |
|---|---|---|
| 5,359,046 A | 10/1994 | Capon et al. |
| 5,686,281 A | 11/1997 | Roberts |
| 5,712,149 A | 1/1998 | Roberts |
| 5,874,240 A | 2/1999 | Ni et al. |
| 5,906,936 A | 5/1999 | Eshhar et al. |
| 6,103,521 A | 8/2000 | Capon et al. |
| 6,319,494 B1 | 11/2001 | Capon et al. |
| 6,355,779 B1 | 3/2002 | Goodwin et al. |
| 6,410,319 B1 | 6/2002 | Raubitschek et al. |
| 6,569,997 B1 | 5/2003 | Kwon |
| 7,049,136 B2 | 5/2006 | Seed et al. |
| 7,052,906 B1 | 5/2006 | Lawson et al. |
| 7,070,995 B2 | 7/2006 | Jensen |
| 7,265,209 B2 | 9/2007 | Jensen |
| 7,319,143 B2 | 1/2008 | Gross et al. |
| 7,320,787 B2 | 1/2008 | Seed et al. |
| 7,446,190 B2 | 11/2008 | Sadelain et al. |
| 7,446,191 B2 | 11/2008 | Jensen |
| 7,514,537 B2 | 4/2009 | Jensen |
| 7,638,326 B2 | 12/2009 | June et al. |
| 7,741,465 B1 | 6/2010 | Eshhar et al. |
| 7,745,140 B2 | 6/2010 | June et al. |
| 7,754,482 B2 | 7/2010 | Riley et al. |
| 7,994,298 B2 | 8/2011 | Zhang et al. |
| 8,211,422 B2 | 7/2012 | Eshhar et al. |
| 8,252,914 B2 | 8/2012 | Zhang et al. |
| 8,389,282 B2 | 3/2013 | Sadelain et al. |
| 8,399,645 B2 | 3/2013 | Campana et al. |
| 8,465,743 B2 | 6/2013 | Rosenberg et al. |
| 8,637,307 B2 | 1/2014 | June et al. |
| 8,722,400 B2 | 5/2014 | Riley et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,394,368 B2 | 7/2016 | Brogdon et al. |
| 9,573,988 B2 | 2/2017 | Brogdon et al. |
| 9,745,368 B2 | 8/2017 | Milone et al. |
| 9,777,061 B2 | 10/2017 | Ebersbach et al. |

(Continued)

FOREIGN PATENT DOCUMENTS

| | | |
|---|---|---|
| EP | 0574512 B1 | 12/1993 |
| EP | 0871495 B1 | 10/1998 |

(Continued)

OTHER PUBLICATIONS

Hekele et al., "Growth Retardation of Tumors by Adoptive Transfer of Cytotoxic T Lymphocytes Reprogrammed by CD44V6-Specific SCFV:zeta-Chimera" Int J. Cancer (1996) vol. 68 pp. 232-238.

(Continued)

*Primary Examiner* — Allison M Fox
*Assistant Examiner* — Alyssa G Weston
(74) *Attorney, Agent, or Firm* — K&L Gates LLP

(57) ABSTRACT

The present disclosure provides compositions and methods for treating diseases associated with expression of CD19 and/or CD22, e.g., by administering a recombinant T cell or natural killer (NK) cell comprising a CD22 CAR and a CD19 CAR as described herein. The disclosure also relates to CAR molecules specific to CD22 and/or CD19, methods of making a cell comprising the same and vectors encoding the same.

12 Claims, 14 Drawing Sheets
Specification includes a Sequence Listing.

(56) References Cited

U.S. PATENT DOCUMENTS

| | | |
|---|---|---|
| 9,815,901 B2 | 11/2017 | Brogdon et al. |
| 10,689,431 B2 * | 6/2020 | Orentas .............. A61K 40/4212 |
| 11,747,346 B2 | 9/2023 | Garfall et al. |
| 11,980,640 B2 * | 5/2024 | Qin ........................ A61K 40/11 |
| 2003/0060444 A1 | 3/2003 | Finney et al. |
| 2003/0077249 A1 | 4/2003 | Bebbington et al. |
| 2003/0147869 A1 | 8/2003 | Riley et al. |
| 2003/0148982 A1 | 8/2003 | Brenner et al. |
| 2003/0224520 A1 | 12/2003 | June et al. |
| 2004/0038886 A1 | 2/2004 | Finney et al. |
| 2004/0043401 A1 | 3/2004 | Sadelain et al. |
| 2004/0101519 A1 | 5/2004 | June et al. |
| 2004/0110290 A1 | 6/2004 | June et al. |
| 2005/0113564 A1 | 5/2005 | Campana et al. |
| 2005/0129671 A1 | 6/2005 | Cooper et al. |
| 2006/0034810 A1 | 2/2006 | Riley et al. |
| 2007/0036773 A1 | 2/2007 | Cooper et al. |
| 2008/0131415 A1 | 6/2008 | Riddell et al. |
| 2009/0257994 A1 | 10/2009 | Jensen |
| 2010/0261269 A1 | 10/2010 | June et al. |
| 2011/0052554 A1 | 3/2011 | Zakrzewski et al. |
| 2011/0262467 A1 | 10/2011 | Riley et al. |
| 2012/0148552 A1 | 6/2012 | Jensen |
| 2012/0321667 A1 | 12/2012 | Sentman |
| 2013/0071409 A1 | 3/2013 | Riley et al. |
| 2013/0071414 A1 | 3/2013 | Dotti et al. |
| 2013/0149337 A1 | 6/2013 | Cooper et al. |
| 2013/0155909 A1 | 6/2013 | Jackson et al. |
| 2013/0287748 A1 | 10/2013 | June et al. |
| 2013/0288368 A1 | 10/2013 | June et al. |
| 2013/0309258 A1 | 11/2013 | June et al. |
| 2014/0011988 A1 | 1/2014 | Deziel et al. |
| 2014/0050708 A1 | 2/2014 | Powell et al. |
| 2014/0099309 A1 | 4/2014 | Powell, Jr. et al. |
| 2014/0099340 A1 | 4/2014 | June et al. |
| 2014/0106449 A1 | 4/2014 | June et al. |
| 2014/0138704 A1 | 5/2014 | Tanaka et al. |
| 2014/0186947 A1 | 7/2014 | June et al. |
| 2014/0212446 A1 | 7/2014 | Riley et al. |
| 2014/0219975 A1 | 8/2014 | June et al. |
| 2014/0227237 A1 | 8/2014 | June et al. |
| 2014/0271635 A1 | 9/2014 | Brogdon et al. |
| 2014/0322169 A1 | 10/2014 | Harper et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0370017 A1 | 12/2014 | June et al. |
| 2014/0370045 A1 | 12/2014 | June et al. |
| 2015/0017141 A1 | 1/2015 | June et al. |
| 2015/0024482 A1 | 1/2015 | Frigault et al. |
| 2015/0050729 A1 | 2/2015 | June et al. |
| 2015/0075470 A1 | 3/2015 | Kubota et al. |
| 2015/0093822 A1 | 4/2015 | June et al. |
| 2015/0099299 A1 | 4/2015 | June et al. |
| 2015/0118202 A1 | 4/2015 | June et al. |
| 2015/0140019 A1 | 5/2015 | June et al. |
| 2015/0190428 A1 | 7/2015 | June et al. |
| 2015/0202286 A1 | 7/2015 | June et al. |
| 2015/0283178 A1 | 10/2015 | June et al. |
| 2015/0290244 A1 | 10/2015 | June et al. |
| 2015/0342994 A1 | 12/2015 | Riley et al. |
| 2016/0046724 A1 | 2/2016 | Brogdon et al. |
| 2016/0051651 A1 | 2/2016 | Brogdon et al. |
| 2016/0068601 A1 | 3/2016 | Brogdon et al. |
| 2016/0096892 A1 | 4/2016 | Brogdon et al. |
| 2016/0185861 A1 | 6/2016 | Bedoya et al. |
| 2016/0311907 A1 | 10/2016 | Brogdon et al. |
| 2016/0311917 A1 | 10/2016 | Beatty et al. |
| 2016/0340406 A1 | 11/2016 | Zhao et al. |
| 2016/0362472 A1 | 12/2016 | Bitter et al. |
| 2017/0008963 A1 | 1/2017 | Brogdon et al. |
| 2017/0081411 A1 | 3/2017 | Engels et al. |
| 2017/0137783 A1 | 5/2017 | Bedoya et al. |
| 2017/0183415 A1 | 6/2017 | Brogdon et al. |
| 2017/0209492 A1 | 7/2017 | June et al. |
| 2017/0211055 A1 | 7/2017 | Brogdon et al. |
| 2017/0226495 A1 | 8/2017 | Guimaraes |
| 2017/0239294 A1 | 8/2017 | Thomas-Tikhonenko et al. |
| 2017/0260268 A1 | 9/2017 | Beatty et al. |
| 2017/0274014 A1 | 9/2017 | Brogdon et al. |
| 2017/0306416 A1 | 10/2017 | Bedoya et al. |
| 2017/0335281 A1 | 11/2017 | Loew et al. |
| 2018/0022795 A1 | 1/2018 | Milone et al. |
| 2018/0044423 A1 | 2/2018 | Ebersbach et al. |
| 2018/0044424 A1 | 2/2018 | June et al. |
| 2018/0118834 A1 | 5/2018 | Brogdon et al. |
| 2018/0125892 A1 | 5/2018 | Brannetti et al. |
| 2018/0133296 A1 | 5/2018 | Barrett et al. |
| 2018/0140602 A1 | 5/2018 | Angst et al. |
| 2018/0230193 A1 | 8/2018 | Loew et al. |
| 2018/0252727 A1 | 9/2018 | Garfall et al. |
| 2018/0258149 A1 | 9/2018 | Motz et al. |
| 2018/0298068 A1 | 10/2018 | Albelda |
| 2018/0312595 A1 | 11/2018 | Brogdon et al. |
| 2019/0000880 A1 | 1/2019 | Motz et al. |
| 2019/0000944 A1 | 1/2019 | Brogdon et al. |
| 2019/0135940 A1 | 5/2019 | Brogdon et al. |
| 2019/0151365 A1 | 5/2019 | Anak et al. |
| 2019/0153061 A1 | 5/2019 | Brogdon et al. |
| 2019/0161542 A1 | 5/2019 | Gill et al. |
| 2019/0263914 A1 | 8/2019 | Brogdon et al. |
| 2019/0269727 A1 | 9/2019 | Fachin et al. |
| 2019/0292238 A1 | 9/2019 | Bitter et al. |
| 2019/0292257 A1 | 9/2019 | Bedoya et al. |
| 2019/0298715 A1 | 10/2019 | Motz et al. |
| 2019/0330356 A1 | 10/2019 | Brogdon et al. |
| 2019/0336504 A1 | 11/2019 | Gill et al. |
| 2019/0375815 A1 | 12/2019 | Engels et al. |
| 2019/0382500 A1 | 12/2019 | Abujoub et al. |
| 2019/0388471 A1 | 12/2019 | June et al. |
| 2019/0389928 A1 | 12/2019 | Posey et al. |
| 2020/0048359 A1 | 2/2020 | Albelda et al. |
| 2020/0055948 A1 | 2/2020 | Daley et al. |
| 2020/0061113 A1 | 2/2020 | Kassim et al. |
| 2020/0085869 A1 | 3/2020 | Schuster et al. |
| 2020/0087376 A1 | 3/2020 | Fraietta et al. |
| 2020/0113941 A1 | 4/2020 | Brannetti et al. |
| 2020/0179511 A1 | 6/2020 | Daley et al. |
| 2020/0215171 A1 | 7/2020 | Brogdon et al. |
| 2020/0281973 A1 | 9/2020 | Dranoff |
| 2020/0283729 A1 | 9/2020 | Loew et al. |
| 2020/0291354 A1 | 9/2020 | Johnson et al. |
| 2020/0339704 A1 | 10/2020 | Bradner et al. |
| 2020/0360431 A1 | 11/2020 | Garfall et al. |
| 2020/0370012 A1 | 11/2020 | Fraietta et al. |
| 2020/0371091 A1 | 11/2020 | Pruteanu-Malinici et al. |
| 2020/0399383 A1 | 12/2020 | Scholler et al. |
| 2021/0002377 A1 | 1/2021 | Brogdon et al. |
| 2021/0047405 A1 | 2/2021 | Nobles et al. |
| 2021/0079073 A1 | 3/2021 | Milone et al. |
| 2021/0087279 A1 | 3/2021 | Engels et al. |
| 2021/0139595 A1 | 5/2021 | Ebersbach et al. |
| 2021/0171909 A1 | 6/2021 | Golovina |
| 2021/0172020 A1 | 6/2021 | Bedoya et al. |
| 2021/0177896 A1 | 6/2021 | Porter et al. |
| 2021/0177900 A1 | 6/2021 | Engels et al. |
| 2021/0213063 A1 | 7/2021 | Isaacs et al. |
| 2021/0220404 A1 | 7/2021 | Abujoub et al. |
| 2021/0246423 A1 | 8/2021 | Bedoya et al. |
| 2021/0284752 A1 | 9/2021 | Brogdon et al. |
| 2021/0317183 A1 | 10/2021 | Zhao et al. |
| 2021/0347851 A1 | 11/2021 | Isaacs et al. |
| 2021/0396739 A1 | 12/2021 | Pruteanu-Malinici et al. |
| 2022/0047633 A1 | 2/2022 | Grupp |
| 2022/0064316 A1 | 3/2022 | Brogdon et al. |
| 2022/0089750 A1 | 3/2022 | June et al. |
| 2022/0152150 A1 | 5/2022 | Koshy et al. |
| 2022/0168389 A1 | 6/2022 | Ghassemi et al. |
| 2022/0195010 A1 | 6/2022 | Bitter et al. |
| 2022/0251152 A1 | 8/2022 | Carbonneau et al. |
| 2022/0364055 A1 | 11/2022 | Treanor et al. |
| 2022/0387486 A1 | 12/2022 | Brannetti et al. |
| 2023/0026049 A1 | 1/2023 | Brogdon et al. |
| 2023/0071283 A1 | 3/2023 | Golosov et al. |

(56) References Cited

U.S. PATENT DOCUMENTS

| | | |
|---|---|---|
| 2023/0074800 A1 | 3/2023 | Berger et al. |
| 2023/0111593 A1 | 4/2023 | Schuster et al. |
| 2023/0139800 A1 | 5/2023 | Motz et al. |
| 2023/0174933 A1 | 6/2023 | Brogdon et al. |
| 2023/0183368 A1 | 6/2023 | Abujoub et al. |
| 2023/0220090 A1 | 7/2023 | Brogdon et al. |
| 2023/0250179 A1 | 8/2023 | Abujoub et al. |
| 2023/0256017 A1 | 8/2023 | Brogdon et al. |
| 2023/0295296 A1 | 9/2023 | Bedoya et al. |
| 2023/0302155 A1 | 9/2023 | Koshy et al. |
| 2023/0312677 A1 | 10/2023 | Posey et al. |
| 2023/0332104 A1 | 10/2023 | Estevez Silva et al. |
| 2023/0357717 A1 | 11/2023 | Johnson et al. |
| 2023/0374105 A1 | 11/2023 | Bitter et al. |
| 2023/0416390 A1 | 12/2023 | Abujoub et al. |
| 2024/0024360 A1 | 1/2024 | Fachin et al. |
| 2024/0033358 A1 | 2/2024 | Chadbourne et al. |
| 2024/0083968 A1 | 3/2024 | Loew et al. |
| 2024/0139244 A1 | 5/2024 | Dranoff |
| 2024/0238396 A1 | 7/2024 | Brogdon et al. |
| 2024/0252538 A1 | 8/2024 | Brannetti et al. |
| 2024/0288444 A1 | 8/2024 | Garfall et al. |
| 2024/0343783 A1 | 10/2024 | Milone et al. |
| 2024/0384007 A1 | 11/2024 | Bradner et al. |
| 2024/0390492 A1 | 11/2024 | Engels et al. |
| 2024/0398913 A1 | 12/2024 | Barrett et al. |

FOREIGN PATENT DOCUMENTS

| | | |
|---|---|---|
| EP | 1226244 B1 | 7/2002 |
| EP | 3237442 B1 | 7/2019 |
| WO | 1992015322 A1 | 9/1992 |
| WO | 199530014 A1 | 11/1995 |
| WO | 9623814 A1 | 8/1996 |
| WO | 9624671 A1 | 8/1996 |
| WO | 1997015669 A1 | 5/1997 |
| WO | 9723613 A2 | 7/1997 |
| WO | 9818809 A1 | 5/1998 |
| WO | 9900494 A2 | 1/1999 |
| WO | 9957268 A1 | 11/1999 |
| WO | 0014257 A1 | 3/2000 |
| WO | 2002033101 A1 | 4/2002 |
| WO | 02077029 A2 | 10/2002 |
| WO | 02088334 A1 | 11/2002 |
| WO | 2003057171 A2 | 7/2003 |
| WO | 2005019429 A2 | 3/2005 |
| WO | 2005044996 A2 | 5/2005 |
| WO | 2005118788 A2 | 12/2005 |
| WO | 2006060878 A1 | 6/2006 |
| WO | 2008045437 A2 | 4/2008 |
| WO | 2010085660 A2 | 7/2010 |
| WO | 2011059836 A2 | 5/2011 |
| WO | 2011097477 A1 | 8/2011 |
| WO | 2012058460 A2 | 5/2012 |
| WO | 2012079000 A1 | 6/2012 |
| WO | 2012082841 A2 | 6/2012 |
| WO | 2012099973 A2 | 7/2012 |
| WO | 2012127464 A2 | 9/2012 |
| WO | 2012129514 A1 | 9/2012 |
| WO | 2012135854 A2 | 10/2012 |
| WO | 2012138858 A1 | 10/2012 |
| WO | 2013019615 A2 | 2/2013 |
| WO | 2013033626 A2 | 3/2013 |
| WO | 2013040371 A2 | 3/2013 |
| WO | 2013040557 A2 | 3/2013 |
| WO | 2013059593 A1 | 4/2013 |
| WO | 2013123061 A1 | 8/2013 |
| WO | 2013126712 A1 | 8/2013 |
| WO | 2013126729 A1 | 8/2013 |
| WO | 2013126733 A1 | 8/2013 |
| WO | 2013185552 A1 | 12/2013 |
| WO | 2014011984 A1 | 1/2014 |
| WO | 2014011987 A1 | 1/2014 |
| WO | 2014011988 A2 | 1/2014 |
| WO | 2014011993 A2 | 1/2014 |
| WO | 2014011996 A1 | 1/2014 |
| WO | 2014012001 A2 | 1/2014 |
| WO | 2014031687 A1 | 2/2014 |
| WO | 2014039513 A2 | 3/2014 |
| WO | 2014055442 A2 | 4/2014 |
| WO | 2014055657 A1 | 4/2014 |
| WO | 2014055668 A1 | 4/2014 |
| WO | 2014124143 A1 | 8/2014 |
| WO | 2014130635 A1 | 8/2014 |
| WO | 2014130657 A1 | 8/2014 |
| WO | 2014138704 A1 | 9/2014 |
| WO | 2014145252 A2 | 9/2014 |
| WO | 2015075468 A1 | 5/2015 |
| WO | 2015075470 A1 | 5/2015 |
| WO | 2015090229 A1 | 6/2015 |
| WO | 2015090230 A1 | 6/2015 |
| WO | 2015092024 A2 | 6/2015 |
| WO | 2015112626 A1 | 7/2015 |
| WO | 2015142661 A1 | 9/2015 |
| WO | 2015142675 A2 | 9/2015 |
| WO | 2015157252 A1 | 10/2015 |
| WO | 2016014501 A1 | 1/2016 |
| WO | 2016014530 A1 | 1/2016 |
| WO | 2016014535 A1 | 1/2016 |
| WO | 2016014553 A1 | 1/2016 |
| WO | 2016014565 A2 | 1/2016 |
| WO | 2016014576 A1 | 1/2016 |
| WO | 2016019300 A1 | 2/2016 |
| WO | 2016025880 A1 | 2/2016 |
| WO | 2016028896 A1 | 2/2016 |
| WO | 2016044605 A1 | 3/2016 |
| WO | 2016102965 A1 | 6/2016 |
| WO | 2016164731 A2 | 10/2016 |
| WO | 2016174405 A1 | 11/2016 |
| WO | 2016210293 A1 | 12/2016 |
| WO | 2018067992 A1 | 4/2018 |
| WO | 2018213337 A1 | 11/2018 |

OTHER PUBLICATIONS

Ho et al., "Adoptive immunotherapy: Engineering T cell responses as biological weapons for tumor mass destruction" Cancer Cell (2003) vol. 3 pp. 431-437.

Hollyman et al. "Manufacturing validation of biologically functional T cells targeted to CD19 antigen for autologous adoptive cell therapy" J Immunother (2009) vol. 32 No 2 pp. 169-180.

Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).

Hudecek et al. "The Nonsignaling Extracellular Spacer Domain of Chimeric Antigen Receptors is Decisive for In Vivo Antitumor Activity" Cancer Immunology Research (2015) vol. 3, pp. 125-135.

Imai et al., "Chimeric receptors with 4-1BB signaling capacity provoke potent cytotoxicity against acute lymphoblastic leukemia," Leukemia 18: 676-684 (2004).

Imai et al., "Genetic modification of primary natural killer cells overcomes inhibitory signals and induces specific killing of leukemic cells" Blood (2005) vol. 106 No. 1 pp. 376-383.

International Search Report and Written Opinion received in PCT/US2020/062304, mailed Mar. 19, 2021, 11 pages.

International Search Report from PCT/US2011/064191 dated Jan. 5, 2012.

Irving et al., "The cytoplasmic domain of the T cell receptor zeta chain is sufficient to couple to receptor-associated signal transduction pathways," Cell 64: 891-901 (1991).

James et al. "Antigen Sensitivity of CD22-Specific Chimeric TCR Is Modulated by Target Epitope Distance from the Cell Membrane" The Journal of Immunology (2008) vol. 180, pp. 7028-7038.

Jan et al., "Reversible ON- and OFF-switch chimeric antigen receptors controlled by lenalidomide," Sci. Transl. Med. (2021), vol. 13, Article eabb6295, 13 pages.

Jena et al. "Driving CAR-Based T-Cell Therapy to Success" Curr Hematol Malig Rep (2014) vol. 9, No. 1, pp. 50-56.

(56) References Cited

OTHER PUBLICATIONS

Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No 9 pp. 1245-1256.
Jia et al., "Haploidentical CD19/CD22 bispecific CAR-T cells induced MRD-negative remission in a patient with relapsed and refractory adult B-ALL after haploidentical hematopoietic stem cell transplantation," Journal of Hematology & Oncology (2019), vol. 12, Article 57, 9 pages.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kloss et al. "Combinatorial antigen recognition with balanced signaling promotes selective tumor eradication by engineered T cells" Nature Biotechnology (2013) vol. 31, No. 1, pp. 71-75.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180, 52nd Annual Meeting of the American- Society-of-Hematology (ASH); Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 389-702.
Kochenderfer et al., "Eradication of B-lineage cells and regression of lymphoma in a patient treated with autologous T cells genetically-engineered to recognize CD19," Blood 116: 4099-4102 (2010).
Kowolik et al., "CD28 Costimulation Provided through a CD19-Specific Chimeric Antigen Receptor Enhances In vivo Persistence and Antitumor Efficacy of Adoptively Transferred T Cells," Cancer Res (2006) vol. 66, No. 22.
Krause et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Krebs et al., "T cells redirected to IL13Ralpha2 with IL13 mutein-CARs have antiglioma activity but also recognize IL13Ralpha1," Cytotherapy (2014), vol. 16, No. 8, pp. 1121-1131.
Kumaresan et al., "Bioengineering T cells to target carbohydrate to treat opportunistic fungal infection," PNAS (2014), vol. 111, No. 29, pp. 10660-10665.
Kumaresan et al., "Dual-Specificity CAR+ T Cells to Target B-Cell Malignancies and Opportunistic Fungal Infection," Biol Blood Marrow Transplant (2014), vol. 20, No. 2, Supplement 1, Abstract 180, pp. S132.
Kussie et al., "A single engineered amino acid substitution changes antibody fine specificity," J Immunol (1994) vol. 152, No. 1, pp. 146-152.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.

Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Lanitis et al. "Chimeric Antigen Receptor T Cells with Dissociated Signaling Domains Exhibit Focused Antitumor Activity with Reduced Potential for Toxicity in Vivo" Cancer Immunology Research (2013) vol. 1, No. 1, pp. 43-53.
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
Liu et al., "Affinity-Tuned ErbB2 or EGFR Chimeric Antigen Receptor T Cells Exhibit an Increased Therapeutic Index against Tumors in Mice," Cancer Res (2015), vol. 75, No. 17, pp. 3596-3607.
Liu et al., "Systematic comparison of 2A peptides for cloning multi-genes in a polycistronic vector," Nature Scientific Reports (2017), vol. 7, pp. 1-9.
Lohmueller, "Synthetic Biology Approaches to Engineering Human Cells," Doctoral dissertation, Harvard University (2013).
Macallan et al., "Measurement and modeling of human T cell kinetics" European Journal of Immunology (2003) vol. 33 pp. 2316-2326.
Mackall et al. "Immune-based therapies for childhood cancer" Nature Reviews Clinical Oncology (2014) vol. 11, pp. 693-703.
Maher "Immunotherapy of Malignant Disease Using Chimeric Antigen Receptor Engrafted T Cells" ISRN Oncology (2012) vol. 2012, Article ID 278093, pp. 1-23.
Maher et al., "Human T lymphocyte cytotoxicity and proliferation directed by a single chimeric TCRzeta/CD28 receptor," Nat. Biotechnol. 20: 70-75 (2002).
Majzner et al., "Tuning the Antigen Density Requirement for CAR T-cell Activity," Cancer Discovery (2020), vol. 10, pp. 702-723.
Maude et al. "Chimeric antigen receptor T-cell therapy for ALL" Hematology (2014) pp. 559-564.
McGuinness et al., "Anti-tumor activity of human T cells expressing the CC49-zeta chimeric immune receptor," Hum. Gene Ther. 10: 165-173 (1999).
Ahmed et al., "HER2-Specific T Cells Target Primary Glioblastoma Stem Cells and Induce Regression of Autologous Experimental Tumors," Clin Cancer Res (2010), vol. 16, No. 2, pp. 474-485.
Anurathapan et al., "Kinetics of Tumor Destruction by Chimeric Antigen Receptor-modified T Cells," Molecular Therapy (2014), vol. 22, No. 3, pp. 623-633.
Badri et al., "Optimization of radiation dosing schedules for proneural glioblastoma," J Math Biol (2016) vol. 72, pp. 1301-1336.
Baeksgaard and Sorensen, "Acute tumor lysis syndrome in solid tumors—a case report and review of the literature" Cancer Chemotherapy Pharmacology (2003) vol. 51 pp. 187-192.
Baylot et al., "TCTP Has a Crucial Role in the Different Stages of Prostate Cancer Malignant Progression," Chapter 13 in Results and Problems in Cell Differentiation, vol. 64, Eds. Kubiak et al., TCTP/tpt1—Remodeling Signaling from Stem Cell Disease, Telerman et al., Eds., (2017) Springer International Publishing AG, Cham Switzerland, pp. 255-261.
Bondanza et al. "Suicide gene therapy of graft-versus-host disease induced by central memory human T lymphocytes" Blood (2006) vol. 107 No. 5 pp. 1828-1836.

(56) References Cited

OTHER PUBLICATIONS

Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Bridgeman et al., "Building Better Chimeric Antigen Receptors for Adoptive T Cell Therapy," Current Gene Therapy (2010), vol. 10, pp. 77-90.
Brocker and Karjalainen, "Signals through T Cell Receptor-Chain alone Are Insufficient to Prime Resting T Lymphocytes" J. Exp. Med. (1995) vol. 181 pp. 1653-1659.
Brunner et al., "Cytotoxic T cells; Double-barreled shot guns," Nature Medicine (1999) vol. 5, No. 1, pp. 20.
Call and Wucherpfennig, "The T Cell Receptor: Critical Role of the Membrane Environment in Receptor Assembly and Function" Annu. Rev. Immunol. (2005) vol. 23 pp. 101-125.
Carbonneau et al., "An IMiD-inducible degron provides reversible regulation for chimeric antigen receptor expression and activity," Cell Chemical Biology (2021), vol. 28, pp. 1-11.
Carpenito et al. "Control of large, established tumor xenografts with genetically retargeted human T cells containing CD28 and CD137 domains", Proc Natl Acad Sci USA (2009) vol. 106 pp. 3360-3365.
Cheadle et al., "Ligation of the CD2 co-stimulatory receptor enhances IL-2 production from first-generation chimeric antigen receptor T cells," Gene Therapy (2012), vol. 19, pp. 1114-1120.
Chen et al., "Generation and Analysis of Random Point Mutations in an Antibody CRD2 Sequence: Many Mutated Antibodies Lose Their Ability to Bind Antigen," J Exp Med (1992) vol. 176, pp. 855-866.
Chicaybam et al. "Moving Receptor Redirected Adoptive Cell Therapy Toward Fine Tuning of Antitumor Responses" International Reviews of Immunology (2014) vol. 33, No. 5, pp. 402-416.
Cradick et al., "On-Target Cleavage and Off-Target Activity of TALEN 'Nickases'," Molecular Therapy (2013), vol. 21, Supplement 1.
Davila et al. "B Cell Aplasia In a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dotti et al. "Design and Development of Therapies using Chimeric Antigen Receptor-Expressing T cells" Immunol. Rev. (2014) vol. 257, No. 1, pp. 1-35.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al., "A Third-Generation Lentivirus Vector with a Conditional Packaging System" Journal of Virology (1998) vol. 72 No. 11 pp. 8463-8471.

Eshhar et al. "Specific activation and targeting of cytotoxic lymphocytes through chimeric single chains consisting of antibody binding domains and the gamma or zeta subunits of the immunoglobulin and T-cell receptors" PNAS (1993) vol. 90, pp. 720-724.
Fedorov et al. "PD-1- and CTLA-4-Based Inhibitory Chimeric Antigen Receptors (iCARs) Divert Off-Target Immunotherapy Responses" Science Translational Medicine (2013) vol. 5, No. 215, 215ra172, pp. 1-12.
Finney et al. "Activation of Resting Human Primary T Cells with Chimeric Receptors: Costimulation from CD28, Inducible Costimulator, CD134, and CD137 in Series with Signals from the TCRzeta Chain" The Journal of Immunology (2004) vol. 172, pp. 104-113.
Finney et al., "Chimeric receptors providing both primary and costimulatory signaling in T cells from a single gene product," J. Immunol. 161: 2791-2797 (1998).
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Fry et al., "CD22-targeted Car T cells induce remission in B-ALL that is naive or resistant to CD19-targeted CAR immunotherapy," Nature Medicine (2017), pp. 1-9, doi:10.1038/nm.4441.
Geiger and Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Ghetie et al. "The Antitumor Activity of an Anti-CD22 Immunotoxin in SCID Mice With Disseminated Daudi Lymphoma Is Enhanced by Either an Anti-CD19 Antibody or an Anti-CD19 Immunotoxin" Blood (1992) vol. 80, No. 9, pp. 2315-2320.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Grada et al., "TanCAR: A Novel Bispecific Chimeric Antigen Receptor for Cancer Immunotherapy," Molecular Therapy-Nucleic Acids (2013), vol. 2, Article e105, 11 pages.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Haso et al. "Anti-CD22-chimeric antigen receptors targeting B cell precursor acute lymphoblastic leukemia" Blood (2013) vol. 121, No. 7, pp. 1165-1174.
Haynes et al., "Redirecting Mouse CTI Against Colon Carcinoma: Superior Signaling Efficacy of Single-Chain Variable Domain Chimeras Containing TCR-zeta vs FcepsilonRI-gamma," J Immunol (2001), vol. 166, pp. 182-187.

(56) References Cited

OTHER PUBLICATIONS

Hegde et al., "Combinational Targeting Offsets Antigen Escape and Enhances Effector Functions of Adoptively Transferred T Cells in Glioblastoma," Molecular Therapy (2013), vol. 21, No. 11, pp. 2087-2101.
Milone et al., "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Muller et al., "Spliceosomal Peptide P140 for Immunotherapy of Systemic Lupus Erythematosus," Arthritis & Rheumatism (2008) vol. 58, No. 12, pp. 3873-3883.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(16-17): 1157-1165 (1997).
Orentas et al., "Targeting B Cell Precursor Acute Lymphoblastic Leukemia (ALL) with Chimeric Antigen Receptors (CARs) Specific for CD19 or CD22" Molecular Therapy (2013), vol. 21, Supplement 1, pp. S125, Abstract 325.
Orentas et al. "Immunotherapy targets in pediatric cancer" Frontiers in Oncology (2012) vol. 2, Article 3, pp. 1-16.
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al., "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No 11 pp. 1264-1270.
Qin et al., "Novel CD19/CD22 Bicistronic Chimeric Antigen Receptors Outperform Single or Bivalent Cars in Eradicating CD19+ CD22+, CD19-, and CD22- Pre-B Leukemia," Blood (2017), vol. 130, Supplement 1, pp. 810.
Qin et al., "Preclinical Development of Bivalent Chimeric Antigen Receptors Targeting Both CD19 and CD22," Molecular Therapy: Oncolytics (2018), vol. 11, pp. 127-137.

Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Rossi et al. "Anti-CD22/CD20 Bispecific Antibody with Enhanced Trogocytosis for Treatment of Lupus" PLOSOne (2014) vol. 9, No. 5, e98315, pp. 1-8.
Rudikoff et al., "Single amino acid substitution altering antigen-binding specificity," Proc Natl Acad Sci USA (1982) vol. 79, pp. 1979-1983.
Ruella et al., "Dual CD19 and CD123 targeting prevents antigen-loss relapses after CD19-directed immunotherapies," J Clin Invest. (2016), vol. 126, No. 10, pp. 3814-3826.
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Schneider et al., "A tandem CD19/CD20 Car lentiviral vector drives on-target and off-target antigen modulation in leukemia cell lines," Journal for ImmunoTherapy of Cancer (2017), vol. 5, Article 42, 17 pages.
Schneider et al., "Minimizing leukemia escape: implementing a dual anti-CD20- and CD19-scFv-based chimeric antigen receptor (CAR)," Journal for ImmunoTherapy of Cancer (2015), vol. 3, Supplement 2, pp. P122.
Sebestyen et al., "Human TCR That Incorporate CD3 Induce Highly Preferred Pairing between TCR and Chains following Gene Transfer" Journal of Immunology (2008) vol. 180 pp. 7736-7746.
Sela-Culang et al., "The structural basis of antibody-antigen recognition," Frontiers in Immunology (2013) vol. 4, Article 302, 13 pages.
Shi et al. "Chimeric antigen receptor for adoptive immunotherapy of cancer: latest research and future prospects" Molecular Cancer (2014) vol. 13, No. 219, pp. 1-8.
Shirasu et al. "Functional Design of Chimeric T-Cell Antigen Receptors for Adoptive Immunotherapy of Cancer: Architecture and Outcomes" Anticancer Research (2012) vol. 32, pp. 2377-2384.
Singh et al., "Development of a quantitative relationship between CAR-affinity, antigen abundance, tumor cell depletion and CAR-T cell expansion using a multiscale systems PK-PD model," mAbs (2019) vol. 12, No. 1, Article e1688616, 21 pages.
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Thomas et al., "A Dual Targeting Car-T Cell Approach For The Treatment of B Cell Malgnancies," Hematological Oncology (2017), vol. 35, No. S2, Abstract 269, pp. 261.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vajdos et al., "Comprehensive Functional Maps of the Antigen-binding Site of an Anti-ErbB2 Antibody Obtained with Shotgun Scanning Mutagenesis," J Mol Biol (2002) vol. 320, pp. 415-428.
Vallera et al. "A Bispecific Recombinant Immunotoxin, DT2219, Targeting Human CD19 and CD22 Receptors in a Mouse Xenograft Model of B-Cell Leukemia/Lymphoma" Clinical Cancer Research (2005) vol. 11, No. 10, pp. 3879-3888.

(56) References Cited

OTHER PUBLICATIONS

Vinay and Kwon, "Role of 4-1BB in immune responses" Immunology (1998) vol. 10 pp. 481-489.
Wilkie et al. "Dual Targeting of ErbB2 and MUC1 in Breast Cancer Using Chimeric Antigen Receptors Engineered to Provide Complementary Signaling" Journal of Clinical Immunology (2012) vol. 32, pp. 1059-1070.
Willemsen et al., "Genetic Engineering of T Cell Specificity for Immunotherapy of Cancer" Human Immunology (2003) vol. 64 pp. 56-68.
Xiao et al., "Identification and characterization of fully human anti-(D22 monoclonal antibodies," mAbs (2009), vol. 1, No. 3, pp. 297-303.
Zah et al. "T cells expressing CD19/CD20 bi-specific chimeric antigen receptors prevent antigen escape by malignant B cells" Cancer Immunology Research (2016) vol. 4, No. 6, pp. 498-508.
Zhao et al., "A Herceptin-Based Chimeric Antigen Receptor with Modified Signaling Domains Leads to Enhanced Survival of Transduced T Lymphocytes and Antitumor Activity," J Immunol (2009) vol. 183, No. 9, pp. 5563-5574.
Zhu et al., "Closed-system manufacturing of CD19 and dual-targeted CD20/19 chimeric antigen receptor T cells using the CliniMACS Prodigy device at an academic medical center," Cytotherapy (2018), vol. 20, No. 3, p. 394-406 (Online early publication: Dec. 2017).
Zufferey et al., "Multiply attenuated lentiviral vector achieves efficient gene delivery in vivo" Nature Biotechnology (1997) vol. 15 pp. 871-876.

\* cited by examiner

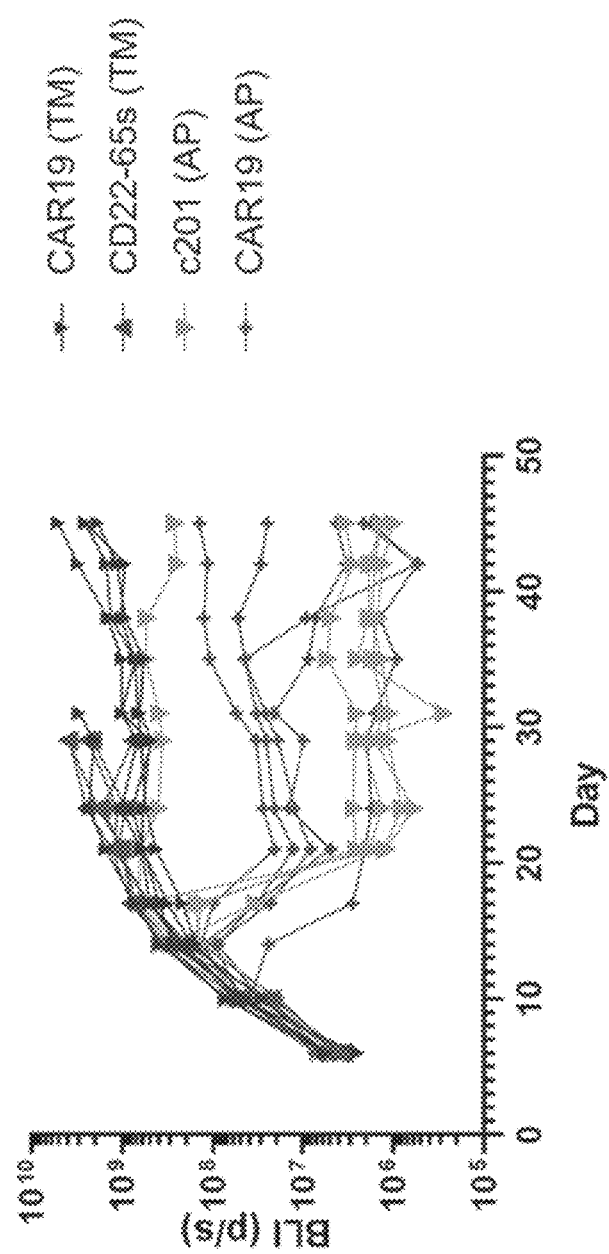

SEQUENCE LISTING

```
Sequence total quantity: 90
SEQ ID NO: 1           moltype = DNA  length = 2238
FEATURE                Location/Qualifiers
misc_feature           1..2238
                       note = Synthetic polynucleotide
source                 1..2238
                       mol_type = other DNA
                       organism = synthetic construct
SEQUENCE: 1
atggccctcc ctgtcaccgc cctgctgctt ccgctggctc ttctgctcca cgccgctcgg    60
cccgaaattg tgatgaccca gtcacccgcc actcttagcc tttcacccgg tgagcgcgca   120
accctgtctt gcagagcctc caagacatc  tcaaaatacc ttaattggta tcaacagaag   180
cccggacagg ctcctcgcct tctgatctac cacacccagcc ggctccattc tggaatccct  240
gccaggttca gcggtagcgg atctgggacc gactacaccc tcactatcag ctcactgcag   300
ccagaggact tcgctgtcta tttctgtcag caagggaaca ccctgcccta caccttga    360
cagggcacca agctcgagat taaagtgga  ggtggcagcg gaggaggtgg gtccggcggt   420
ggaggaagcc aggtccaact ccaagaaagc ggaccgggtc ttgtgaagcc atcagaaact   480
ctttcactga cttgtactgt gagcggagtg tctctcccg  attacggggt gtcttggatc   540
agacagccac cggggaaggg tctggaatgg attggagtga tttggggctc tgagactact   600
tactaccaat catccctcaa gtcacgcgtc accatctcaa aggacaactc taagaatcag   660
gtgtcactga aactgtcatc tgtgaccgca gccgacaccg ccgtgtacta ttgcgctaag   720
cattactatt atgcgggag  ctacgcaatg gattactggg gacagggtac tctggtcacc   780
gtgtccagct tggcagaagc cgccgcgaaa gaagtgcagc ttcaacaatc aggaccagga   840
ctcgtcaaac catcacagac cctctccctc acatgtgcca tctccggga  ctccatgttg   900
agcaattccg acacttggaa ttggattaga caaagccgt  cccgggtct  ggaatggttg   960
ggacgcacct accaccggtc tacttggtac gacgactacg cgtcatccgt gcggggaaga  1020
gtgtccatca acgtggacac ctccaagaac cagtacagcc tgcagcttaa tgccgtgact  1080
cctgaggata cgggcgtcta ctactgcgcc cgcgtccgc  tgcaagacgg gaacagctgg  1140
agcgatgcat tcgatgtctg gggccaggga actatgtca  ccgtgtcctc tggggggcggt 1200
ggatcgggtg gcggggttc  gggggcggc  ggctctcagt ccgctcttac ccaaccggcc  1260
tcagcctcgg ggagccccgg ccagagcgtg accatttcct gcaccggcac ttcatccgac  1320
gtgggcggct acaactacgt gtcctggtac caacagcacc cgggaaaggc ccccaagctc  1380
atgatctacg acgtgtccaa caggccctcg ggagtgtcca accggttctc gggttcgaaa  1440
tcgggaaaca cagccagcct gaccatcagc ggactgcagg ctgaagatga agccgactac  1500
tactgctcct cctacaccctc gtcatccacg ctctacgtgt tcggcactgg aactcagctg  1560
actgtgctga ccactacccc agcaccgagg ccacccaccc cggctcctac catcgcctcc  1620
cagcctctgt ccctgcgtcc ggaggcatgt agacccgcag ctggtgggc  cgtgcatacc  1680
cggggtcttg acttcgcctg cgatatctac atttgggccc ctctggctgg tacttgcggg  1740
gtcctgctgc tttcactcgt gatcactctt tactgtaagc gcggtcggaa gaagctgctg  1800
tacatcttta agcaacccttt catgaggcct gtgcagacta ctcaagagga ggacggctgt  1860
tcatgccggt tcccagagga ggaggaaggc ggctgcgaac tgcgcgtgaa attcagccgc  1920
agcgcagatg ctccagccta ccagcagggg cagaaccagc tctacaacga actcaatctt  1980
ggtcggagag aggagtacga cgtgctggac aagcggagag acgggaccc  agaaatgggc  2040
gggaagccgc gcagaaagaa tccccaagag ggcctgtaca acgagctcca aaaggataag  2100
atggcagaag cctatagcga gattggtatg aaagggaac  gcagaagagg caaaggccac  2160
gacggactgt accagggact cagcaccgcc accaaggaca cctatgacgc tcttcacatg  2220
caggccctgc cgcctcgg                                                2238

SEQ ID NO: 2           moltype = AA  length = 746
FEATURE                Location/Qualifiers
REGION                 1..746
                       note = Synthetic polypeptide
source                 1..746
                       mol_type = protein
                       organism = synthetic construct
SEQUENCE: 2
MALPVTALLL PLALLLHAAR PEIVMTQSPA TLSLSPGERA TLSCRASQDI SKYLNWYQQK    60
PGQAPRLLIY HTSRLHSGIP ARFSGSGSGT DYTLTISSLQ PEDFAVYFCQ QGNTLPYTFG   120
QGTKLEIKGG GGSGGGGSGG GGSQVQLQES GPGLVKPSET LSLTCTVSGV SLPDYGVSWI   180
RQPPGKGLEW IGVIWSETT  YYQSSLKSRV TISKDNSKNQ VSLKLSSVTA ADTAVYYCAK   240
HYYYGGSYAM DYWGQGTLVT VSSLAEAAAK EVQLQQSGPG LVKPSQTLSL TCAISGDSML   300
SNSDTWNWIR QSPSRGLEWL GRTYHRSTWY DDYASSVRGR VSINVDTSKN QYSLQLNAVT   360
PEDTGVYYCA RVRLQDGNSW SDAFDVWGQG TMVTVSSGGG GSGGGGSGGG GSQSALTQPA   420
```

```
SASGSPGQSV TISCTGTSSD VGGYNYVSWY QQHPGKAPKL MIYDVSNRPS GVSNRFSGSK  480
SGNTASLTIS GLQAEDEADY YCSSYTSSST LYVFGTGTQL TVLTTTPAPR PPTPAPTIAS  540
QPLSLRPEAC RPAAGGAVHT RGLDFACDIY IWAPLAGTCG VLLLSLVITL YCKRGRKKLL  600
YIFKQPFMRP VQTTQEEDGC SCRFPEEEEG GCELRVKFSR SADAPAYQQG QNQLYNELNL  660
GRREEYDVLD KRRGRDPEMG GKPRRKNPQE GLYNELQKDK MAEAYSEIGM KGERRRGKGH  720
DGLYQGLSTA TKDTYDALHM QALPPR                                     746

SEQ ID NO: 3            moltype = DNA   length = 2232
FEATURE                 Location/Qualifiers
misc_feature            1..2232
                        note = Synthetic polynucleotide
source                  1..2232
                        mol_type = other DNA
                        organism = synthetic construct
SEQUENCE: 3
atggccctcc ctgtcaccgc cctgctgctt ccgctggctc ttctgctcca cgccgctcgg  60
cccgaagtgc agcttcaaca atcaggacca ggactcgtca aaccatcaca gaccctctcc  120
ctcacatgtg ccatctccgg ggactccatg ttgagcaatt ccgacacttg gaattggatt  180
agacaaagcc cgtcccgggg tctggaatgg ttgggacgaa cctaccaccg gtctacttgg  240
tacgacgact acgcgtcatc cgtgcgggga agagtgtcca tcaacgtgga cacctccaag  300
aaccagtaca gcctgcagct taatgccgtg actcctgagg atacgggcgt ctactactgc  360
gcccgcgtcc gcctgcaaga cgggaacagc tggagcagtg cattcgatgt ctggggccaa  420
ggaactatgg tcaccgtgtc gtctgggggc ggtggatcgg gtggcggggg ttcgggggc  480
ggcggctctc agtccgctct tacccaaccg gcctcagcct cggggagccc cggccagagc  540
gtgaccattt cctgcaccgg cacttcatcc gacgtgggcg gctacaacta cgtgtcctgg  600
taccaacagc acccgggaaa ggcccccaag ctcatgatct acgacgtgtc caacaggccc  660
tcggagtgt ccaaccggtt tcgggttcg aaatcgggaa acacagccag cctgaccatc  720
agcggactgc aggctgaaga tgaagccgac tactactgct cctcctacac ctcgtcatcc  780
acgctctacg tgttcggcac tggaactcag ctgactgtgc tggagggggg agggagtgaa  840
attgtgatga cccagtcacc cgccactctt agcctttcac ccggtgagcg cgcaacctg  900
tcttgcagag cctcccaaga catctcaaaa tacttaatt ggtatcaaca gaagcccgga  960
caggctcctc gccttctgat ctaccacacc agccggctcc attctggaat ccctgccagg  1020
ttcagcggta gcggatctgg gaccgactac accctcacta tcagctcact gcagccgaag  1080
gacttcgctg tctatttctg tcagcaaggg aacaccctgc cctacacctt tggacagggc  1140
accaagctcg agattaaagg tggaggtggc agcggaggag gtgggtccgg cggtggagga  1200
agccaggtcc aactccaaga aagcggaccg ggtcttgtga agcccatcaga aactctttca  1260
ctgacttgta ctgtgagcgg agtgtctctc cccgattacg gggtgtcttg gatcagacag  1320
ccaccgggga agggtctgga atggattgga gtgatttggg gctctgagac tacttactac  1380
caatcatccc tcaagtcacg cgtcaccatc tcaaaggaca actctaagaa tcaggtgtca  1440
ctgaaactgt catctgtgac cgcagccgac accgccgtgt actattgcgc taagcattac  1500
tattatggcg ggagctacgc aatggattac tggggacagg gtactctggt caccgtgtcc  1560
agcaccacta cccccagcacc gaggccaccc accccggctc ctaccatcgc ctcccagcct  1620
ctgtccctgc gtccggaggc atgtagacc gcagctggtc gggccgtgca taccgggtgt  1680
cttgacttcg cctgcgatat ctacatttgg gcccctctgg ctggtacttg cggggtcctg  1740
ctgctttcac tcgtgatcac tctttactgt aagcgcggtc ggaagaagct gctgtacatc  1800
tttaagcaac ccttcatgag gcctgtgcag actactcaag aggaggacgg ctgttcatgc  1860
cggttcccag aggaggaga agccggctgc gaactgcgag tgaaattcag ccgcagcgca  1920
gatgctccag cctaccagca ggggcagaac cagctctaca cgaactcaa tcttggtcgg  1980
agagaggagt acgacgtgct ggacaagcgg agaggacggg acccagaaat ggcggaag  2040
ccgcgcagaa gaatcccca agagggcctg tacaacagc tccaaagga taagatggca  2100
gaagcctata gcgagattgg tatgaaaggg aacgcagaa gaggcaaagg ccacgacgga  2160
ctgtaccagg gactcagcac cgccaccaag gacacctatg acgctcttca catgcaggcc  2220
ctgccgcctc gg                                                      2232

SEQ ID NO: 4            moltype = AA    length = 744
FEATURE                 Location/Qualifiers
REGION                  1..744
                        note = Synthetic polypeptide
source                  1..744
                        mol_type = protein
                        organism = synthetic construct
SEQUENCE: 4
MALPVTALLL PLALLLHAAR PEVQLQQSGP GLVKPSQTLS LTCAISGDSM LSNSDTWNWI  60
RQSPSRGLEW LGRTYHRSTW YDDYASSVRG RVSINVDTSK NQYSLQLNAV TPEDTGVYYC  120
ARVRLQDGNS WSDAFDVWGQ GTMVTVSSGG GGSGGGGSGG GGSQSALTQP ASASGSPGQS  180
VTISCTGTSS DVGGYNYVSW YQQHPGKAPK LMIYDVSNRP SGVSNRFSGS KSGNTASLTI  240
SGLQAEDEAD YYCSSYTSSS TLYVFGTGTQ LTVLGGGGSE IVMTQSPATL SLSPGERATL  300
SCRASQDISK YLNWYQQKPG QAPRLLIYHT SRLHSGIPAR FSGSGSGTDY TLTISSLQPE  360
DFAVYFCQQG NTLPYTFGQG TKLEIKGGGG SGGGGSGGGG SQVQLQESGP GLVKPSETLS  420
LTCTVSGVSL PDYGVSWIRQ PPGKGLEWIG VIWGSETTYY QSSLKSRVTI SKDNSKNQVS  480
LKLSSVTAAD TAVYYCAKHY YYGGSYAMDY WGQGTLVTVS STTPAPRPP TPAPTIASQP  540
LSLRPEACRP AAGGAVHTRG LDFACDIYIW APLAGTCGVL LLSLVITLYC KRGRKKLLYI  600
FKQPFMRPVQ TTQEEDGCSC RFPEEEEGGC ELRVKFSRSA DAPAYQQGQN QLYNELNLGR  660
REEYDVLDKR RGRDPEMGGK PRRKNPQEGL YNELQKDKMA EAYSEIGMKG ERRRGKGHDG  720
LYQGLSTATK DTYDALHMQA LPPR                                        744

SEQ ID NO: 5            moltype = DNA   length = 2202
FEATURE                 Location/Qualifiers
misc_feature            1..2202
```

|  | note = Synthetic polynucleotide |
| --- | --- |
| source | 1..2202 |
|  | mol_type = other DNA |
|  | organism = synthetic construct |

SEQUENCE: 5

```
atggccctcc ctgtcaccgc cctgctgctt ccgctggctc ttctgctcca cgccgctcgg   60
ccccagtccg ctcttaccca accggcctca gcctcgggga gccccggcca gagcgtgacc  120
atttcctgca ccggcactcc atccgacgtg gcggctaca actacgtgtc ctggtaccaa  180
cagcacccgg gaaaggcccc caagctcatg atctacgacg tgtccaacag gccctcggga  240
gtgtccaacc ggttctcggg ttcgaaatcg ggaaacacag ccagcctgac catcagcgga  300
ctgcaggctg aagatgaagc cgactactac tgctcctcct acacctcgtc atccacgctc  360
tacgtgttcg gcactggaac tcagctgact gtgctgggcg gaggaggctc cgaagtgcag  420
cttcaacaat caggaccagg actcgtcaaa ccatcacaga ccctctccct cacatgtgcc  480
atctccgggg actccatgtt gagcaattcc gacacttgga attggattag acaaagcccg  540
tcccggggtc tggaatggtt gggacgcacc taccaccggt ctacttggta cgacgactac  600
gcgtcatccg tgcggggaag agtgtccatc aacgtggaca cctccaagaa ccagtacagc  660
ctgcagctta atgccgtgac tcctgaggat acgggcgtct actactgcgc ccgcgtccgc  720
ctgcaagacg gaacagctg gagcgatgca ttcgatgtct ggggccaggg aactatggtc  780
accgtgtcgt ctgagggggg agggagtgaa attgtgatga cccagtcacc cgccactctt  840
agcctttcac ccggtgagcg cgcaaccctg tcttgcagag cctccaagga catctcaaaa  900
taccttaatt ggtatcaaca gaagcccgga caggctcctc gccttctgat ctaccacacc  960
agccgctcc attctggaat ccctgccagg ttcagcggta gcggatctgg gaccgactac 1020
accctcacta tcagctcact gcagccagag gacttcgctg tctatttctg tcagcaaggg 1080
aacaccctgc cctacacctt ggacagggc accaagctcg agattaaagg tggaggtggc 1140
agcggaggag gtgggtccgg cggtggagga agccaggtcc aactccaaga aagcggaccg 1200
ggtcttgtga agccatcaga aactctttca ctgacttgta ctgtgagcg agtgtctctc 1260
cccgattacg gggtgtcttg gatcagacag ccaccgggga agggtctgga atggattgga 1320
gtgatttggg gctctgagac tacttactac caatcatccc tcaagtcacg cgtcaccatc 1380
tcaaggaca actctaagaa tcaggtgtca ctgaaactgt catctgtgac cgcagccgac 1440
accgccgtgt actattgcgc taagcattac tattatgccg ggagctacgc aatggattac 1500
tggggacagg gtactctggt caccgtgtcc agcaccacta cccagcacc gaggccaccc 1560
accccggctc ctaccatcgc ctcccagcct cgtccctgc gtccggaggc atgtagaccc 1620
gcagctggtg gggccgtgca tacccggggt cttgacttcg cctgcgatat ctacatttgg 1680
gccctctgg ctggtacttg cggggtcctg ctgcttcac tcgtgatcac tctttactgt 1740
aagcgcggtc ggaagaagct gctgtacatc tttaagcaac ccttcatgag gcctgtgcag 1800
actactcaag aggaggacgg ctgttcatgc cggttccag aggaggagga aggcggctgc 1860
gaactgcgcg tgaaattcag ccgcagcgca gatgctccag cctaccagca ggggcagaac 1920
cagctctaca cgaactcaa tcttggtcgg agagaggagt acgacgtgct ggacaagcgg 1980
agaggacgg acccagaaat gggcgggaag ccgcgcagaa agaatccca gagggcctg 2040
tacaacgagc tccaaaagga taagatggca gaagcctata gcgagattgg tatgaaaggg 2100
gaacgcagaa gaggcaaagg ccacgacgga ctgtaccagg gactcagcac cgccaccaag 2160
gacacctatg acgctcttca catgcaggcc ctgccgcctc gg                    2202
```

| SEQ ID NO: 6 | moltype = AA length = 734 |
| --- | --- |
| FEATURE | Location/Qualifiers |
| REGION | 1..734 |
|  | note = Synthetic polypeptide |
| source | 1..734 |
|  | mol_type = protein |
|  | organism = synthetic construct |

SEQUENCE: 6

```
MALPVTALLL PLALLLHAAR PQSALTQPAS ASGSPGQSVT ISCTGTSSDV GGYNYVSWYQ   60
QHPGKAPKLM IYDVSNRPSG VSNRFSGSKS GNTASLTISG LQAEDEADYY CSSYTSSSTL  120
YVFGTGTQLT VLGGGGSEVQ LQQSGPGLVK PSQTLSLTCA ISGDSMLSNS DTWNWIRQSP  180
SRGLEWLGRT YHRSTWYDDY ASSVRGRVSI NVDTSKNQYS LQLNAVTPED TGVYYCARVR  240
LQDGNSWSDA FDVWGQGTMV TVSSGGGGSE IVMTQSPATL SLSPGERATL SCRASQDISK  300
YLNWYQQKPG QAPRLLIYHT SRLHSGIPAR FSGSGSGTDY TLTISSLQPE DFAVYFCQQG  360
NTLPYTFGQG TKLEIKGGGG SGGGGSGGGG SQVQLQESGP GLVKPSETLS LTCTVSGVSL  420
PDYGVSWIRQ PPGKGLEWIG VIWGSETTYY QSSLKSRVTI SKDNSKNQVS LKLSSVTAAD  480
TAVYYCAKHY YYGGSYAMDY WGQGTLVTVS STTTPAPRPP TPAPTIASQP LSLRPEACRP  540
AAGGAVHTRG LDFACDIYIW APLAGTCGVL LLSLVITLYC KRGRKKLLYI FKQPFMRPVQ  600
TTQEEDGCSC RFPEEEEGGC ELRVKFSRSA DAPAYQQGQN QLYNELNLGR REEYDVLDKR  660
RGRDPEMGGK PRRKNPQEGL YNELQKDKMA EAYSEIGMKG ERRRGKGHDG LYQGLSTATK  720
DTYDALHMQA LPPR                                                   734
```

| SEQ ID NO: 7 | moltype = DNA length = 2232 |
| --- | --- |
| FEATURE | Location/Qualifiers |
| misc_feature | 1..2232 |
|  | note = Synthetic polynucleotide |
| source | 1..2232 |
|  | mol_type = other DNA |
|  | organism = synthetic construct |

SEQUENCE: 7

```
atggccctgc ccgtgactgc gctcctgctt ccgttggccc tgctcctgca tgccgccaga   60
cctcagtccg ctctgactca gccggcctca gcttcggggt ccctggtca aagcgtcact  120
atttcctgta ccggaacctc atcagacgtg gcggctaca attacgtgtc ctggtaccaa  180
cagcacccg gaaaggctcc taagcttatg atctacgacg tgtccaaccg gccgtcagga  240
gtgtccaaca gattctccgg ctccaagagc ggaaacactg ccagcttgac cattagcggc  300
ttgcaggccg aggacgaagc cgactactac tgctctagct acacatcctc gtctaccctc  360
```

```
tacgtgtttg gaacggggac ccagctgact gtgctcgggg gtggaggatc agaggtgcaa    420
ctccagcagt ccggtcctgg cctcgtgaaa ccgtcccaaa ccctgtccct gacttgcgcc    480
atctcgggcg actccatgct gtccaattcc gacacctgga actggattag caatcgcct    540
agccggggac tcgaatggct gggccggacc taccaccggt ccacgtggta tgacgactac    600
gcaagctccg tccggggaag ggtgtccatt aacgtcgata cctccaagaa ccagtacagc    660
cttcagctga acgctgtgac ccccgaggat accggcgtct actactgtgc aagagtgcga    720
ttgcaggatg gaaactcgtg gtcggacgca ttcgatgtct ggggacaggg aactatggtg    780
accgtgtcct cgggcggagg cgggagcgga ggaggaggct ggcggagg aggaagcgag    840
attgtcatga ctcagtcccc ggccacactc tccctgtcac ccggagaaag agcaaccctg    900
agctgcaggg cgtcccagga catctcgaag tacctgaact ggtaccagca gaagcctgga    960
caagcaccc gctcctgat ctaccacacc tcgcggctgc attcgggaat ccccgccaga    1020
ttctcaggga gcggatcagg aaccgactac accctgacta tctcgagcct gcaaccagag    1080
gatttcgccg tgtacttctg ccagcaagga aacaccctgc cctacacctt tggacaggga    1140
accaagctcg agattaaggg gggtggtgga tcgggaggga gtggatcagg aggaggcggc    1200
tcacaagtcc agctgcaaga atccggtccg gacttgtga agccgtccga aaccctgtca    1260
ctgacttgca ctgtgtccgg ggtgtcattg cccgactacg gcgtgagctg gattcggcag    1320
cccctggaa agggattgga atggatcggc gtgatctggg gttcggaaac tacctactat    1380
cagtcctcac tgaagtcccg cgtgaccatc agcaaggata attccaaaaa ccaagtgtct    1440
ctgaagctct ccagcgtcac tgccgccgat actgccgtgt actactgcgc caagcactac    1500
tattacggcg gttcgtacgc catggactac tggggccaag ggacactcgt gaccgtgtca    1560
tccaccacta ccccagcacc gaggccaccc accccggctc ctaccatcgc ctcccagcct    1620
ctgtccctgc gtccggaggc atgtagaccc gcagctggtg gggccgtgca taccggggcg    1680
cttgacttcg cctgcgatat ctacatttgg gcccctctgg ctggtacttg cggggtcctg    1740
ctgctttcac tcgtgatcac tctttactgt aagcgcggtc ggaagaagct gctgtacatc    1800
tttaagcaac ccttcatgag gcctgtgcag actactcaag aggaggacgg ctgttcatgc    1860
cggttcccag aggaggagga aggcggctgc gaactgcgag tgaaattcag ccgcagcgca    1920
gatgctccag cctaccagca ggggcagaac cagctctaca acgaactcaa tcttggtcgg    1980
agagaggagt acgacgtgct ggacaagcgg agaggacggg acccagaaat gggcgggaag    2040
ccgcgcagaa gaatcccca agagggcctg tacaacgagc tccaaaagga taagatggca    2100
gaagcctata cgcagattgg tatgaaaggg aacgcagaa gaggcaaagg ccacgacgga    2160
ctgtaccagg gactcagcac cgccaccaag gacacctatg acgctcttca catgcaggcc    2220
ctgccgcctc gg                                                       2232
```

```
SEQ ID NO: 8            moltype = AA   length = 744
FEATURE                 Location/Qualifiers
REGION                  1..744
                        note = Synthetic polypeptide
source                  1..744
                        mol_type = protein
                        organism = synthetic construct
SEQUENCE: 8
MALPVTALLL PLALLLHAAR PQSALTQPAS ASGSPGQSVT ISCTGTSSDV GGYNYVSWYQ     60
QHPGKAPKLM IYDVSNRPSG VSNRFSGSKS GNTASLTISG LQAEDEADYY CSSYTSSSTL    120
YVFGTGTQLT VLGGGGSEVQ LQQSGPGLVK PSQTLSLTCA ISGDSMLSNS DTWNWIRQSP    180
SRGLEWLGRT YHRSTWYDDY ASSVRGRVSI NVDTSKNQYS LQLNAVTPED TGVYYCARVR    240
LQDGNSWSDA FDVWGQGTMV TVSSGGGGSG GGGSGGGGSE IVMTQSPATL SLSPGERATL    300
SCRASQDISK YLNWYQQKPG QAPRLLIYHT SRLHSGIPAR FSGSGSGTDY TLTISSLQPE    360
DFAVYFCQQG NTLPYTFGQG TKLEIKGGGG SGGGGSGGGG SQVQLQESGP GLVKPSETLS    420
LTCTVSGVSL PDYGVSWIRQ PPGKGLEWIG VIWGSETTYY QSSLKSRVTI SKDNSKNQVS    480
LKLSSVTAAD TAVYYCAKHY YYGGSYAMDY WGQGTLVTVS STTTPAPRPP TPAPTIASQP    540
LSLRPEACRP AAGGAVHTRG LDFACDIYIW APLAGTCGVL LLSLVITLYC KRGRKKLLYI    600
FKQPFMRPVQ TTQEEDGCSC RFPEEEEGGC ELRVKFSRSA DAPAYQQGQN QLYNELNLGR    660
REEYDVLDKR RGRDPEMGGK PRRKNPQEGL YNELQKDKMA EAYSEIGMKG ERRRGKGHDG    720
LYQGLSTATK DTYDALHMQA LPPR                                          744

SEQ ID NO: 9            moltype = DNA   length = 2232
FEATURE                 Location/Qualifiers
misc_feature            1..2232
                        note = Synthetic polynucleotide
source                  1..2232
                        mol_type = other DNA
                        organism = synthetic construct
SEQUENCE: 9
atggccctgc ccgtgactgc gctcctgctt ccgttggccc tgctcctgca tgccgccaga     60
cctcagtccg ctctgactca gccggcctca gcttcggggt cccctggtca agcgtcact    120
atttcctgta ccggaacctc atcagacgtg ggcggctaca attacgtgtc ctggtaccaa    180
cagcaccccg gaaaggctcc taagcttatg atctacgacg tgtccaaccg gccgtcagga    240
gtgtccaaca gattctccgg ctccaagagc ggaaacactg ccagcttgac cattagcggc    300
ttgcaggccg aggacgaagc cgactactac tgctctagct acacatcctc gtctaccctc    360
tacgtgtttg gaacggggac ccagctgact gtgctcgggg gtggaggatc agaggtgcaa    420
ctccagcagt ccggtcctgg cctcgtgaaa ccgtcccaaa ccctgtccct gacttgcgcc    480
atctcgggcg actccatgct gtccaattcc gacacctgga actggattag caatcgcct    540
agccggggac tcgaatggct gggccggacc taccaccggt ccacgtggta tgacgactac    600
gcaagctccg tccggggaag ggtgtccatt aacgtcgata cctccaagaa ccagtacagc    660
cttcagctga acgctgtgac ccccgaggat accggcgtct actactgtgc aagagtgcga    720
ttgcaggatg gaaactcgtg gtcggacgca ttcgatgtct ggggacaggg aactatggtc    780
actgtgtcct ccggcggtgg aggctcgggg ggggcggct caggaggagg cggctcacaa    840
gtccagctgc aagaatccgg tccgggactt gtgaagccgt ccgaaaccct gtcactgact    900
tgcactgtgt ccggggtgtc attgcccgac tacggcgtga gctggattcg gcagcccct    960
```

```
ggaaagggat tggaatggat cggcgtgatc tggggttcgg aaactaccta ctatcagtcc   1020
tcactgaagt cccgcgtgac catcagcaag gataattcca aaaaccaagt gtctctgaag   1080
ctctccagcg tcactgccgc cgatactgcc gtgtactact gcgccaagca ctactattac   1140
ggcggttcgt acgccatgga ctactgggga caaggcactc ttgtgactgt gtcaagcggc   1200
ggtggaggga gcggtggggg cggttcagga ggaggcggat cagagatcgt gatgacccaa   1260
tccccagcca ccctgtccct cagccctgga gaaagagcca ccctgagctg ccgggcctcc   1320
caggatatca gcaagtactt gaactggtac aacaaaagc cggggcaggc gccccggctc    1380
ctgatctacc acacctcgcg cctccactca ggtatccccg ccagattctc agggagcggc   1440
tccggtactg actacaccct gactatttcc tcactgcagc cagaggactt tgccgtgtac   1500
ttctgccagc agggaaacac tctgccgtac accttcggcc agggaacgaa gcttgaaatt   1560
aagaccacta cccagcacc gaggccaccc acccggctc ctaccatcgc ctcccagcct     1620
ctgtccctgc gtccggaggc atgtagaccc gcagctggtg gggccgtgca tacccggggt   1680
cttgacttcg cctgcgatat ctacatttgg gcccctctgg ctggtacttg cggggtcctg   1740
ctgctttcac tcgtgatcac tctttactgt aagcgcggtc ggaagaagct gctgtacatc   1800
tttaagcaac ccttcatgag gcctgtgcag actactcaag aggaggacgg ctgttcatgc   1860
cggttcccag aggaggagga aggcggctgc gaactgcgcg tgaaattcag ccgcagcgca   1920
gatgctccag cctaccagca ggggcagaac cagctctaca cgaactcaa tcttggtcga    1980
agagaggagt acgacgtgct ggacaagcgg agaggacgg acccagaaat gggcgggaag    2040
ccgcgcagaa agaatcccca agagggcctg tacaacgagc tccaaaagga taagatggca   2100
gaagcctata gcgagattgg tatgaaaggg aacgcagaa gaggcaaagg ccacgacgga    2160
ctgtaccagg gactcagcac cgccaccaag gacacctatg acgctcttca catgcaggcc   2220
ctgccgcctc gg                                                        2232

SEQ ID NO: 10         moltype = AA   length = 744
FEATURE               Location/Qualifiers
REGION                1..744
                      note = Synthetic polypeptide
source                1..744
                      mol_type = protein
                      organism = synthetic construct
SEQUENCE: 10
MALPVTALLL PLALLLHAAR PQSALTQPAS ASGSPGQSVT ISCTGTSSDV GGYNYVSWYQ   60
QHPGKAPKLM IYDVSNRPSG VSNRFSGSKS GNTASLTISG LQAEDEADYY CSSYTSSSTL   120
YVFGTGTQLT VLGGGGSEVQ LQQSGPGLVK PSQTLSLTCA ISGDSMLSNS DTWNWIRQSP   180
SRGLEWLGRT YHRSTWYDDY ASSVRGRVSI NVDTSKNQYS LQLNAVTPED TGVYYCARVR   240
LQDGNSWSDA FDVWGQGTMV TVSSGGGGSG GGGSGGGGSQ VQLQESGPGL VKPSETLSLT   300
CTVSGVSLPD YGVSWIRQPP GKGLEWIGVI WGSETTYYQS SLKSRVTISK DNSKNQVSLK   360
LSSVTAADTA VYYCAKHYYY GGSYAMDYWG QGTLVTVSSG GGSGGGGSG GGGSEIVMTQ   420
SPATLSLSPG ERATLSCRAS QDISKYLNWY QQKPGQAPRL LIYHTSRLHS GIPARFSGSG   480
SGTDYTLTIS SLQPEDFAVY FCQQGNTLPY TFGQGTKLEI KTTTPAPRPP TPAPTIASQP   540
LSLRPEACRP AAGGAVHTRG LDFACDIYIW APLAGTCGVL LLSLVITLYC KRGRKKLLYI   600
FKQPFMRPVQ TTQEEDGCSC RFPEEEEGGC ELRVKFSRSA DAPAYQQGQN QLYNELNLGR   660
REEYDVLDKR RGRDPEMGGK PRRKNPQEGL YNELQKDKMA EAYSEIGMKG ERRRGKGHDG   720
LYQGLSTATK DTYDALHMQA LPPR                                         744

SEQ ID NO: 11         moltype = DNA   length = 2985
FEATURE               Location/Qualifiers
misc_feature          1..2985
                      note = Synthetic polynucleotide
source                1..2985
                      mol_type = other DNA
                      organism = synthetic construct
SEQUENCE: 11
atggccctcc ctgtcaccgc cctgctgctt ccgctggctc ttctgctcca cgccgctcgg   60
cccgaagtgc agctgcagca gtcagggcct ggcctggtca gccgtcgca gcccctctcc    120
ctgacatgcg ccattagcgg ggactccatg ctgagcaact cggacacctg gaactggatt   180
cggcagtccc cttcccgggg actcgagtgg ctcggacgca cctaccatcg gagcacttgg   240
tacgacgact acgcctcctc cgtgagaggt cgcgtgtcga tcaacgtgga tacctcgaag   300
aaccagtata gcttgcaact gaaccgccgtg accctgagg atacccggatg gtactattgt   360
gcgagagtca ggctgcaaga cggaaactcc tggtccgaca catttgatgt ctggggacaa   420
ggtactatgg tcacggtgtc atctggaggc ggaggatcgc aaagcgccct gactcagccg    480
gcttcggcta gcggttcacc ggggcagtcc gtgactatct cctgcaccgg gacttcctcc   540
gacgtgggag gctacaatta cgtgtcctgg taccagcaac ccccggcaa agcccccaag    600
ctgatgatct acgacgtcag caacagacc gcggagtcc ccaaccggtt cagcggctcc     660
aagtccggca cacccgcctc cctgaccatc agcgggcttc aggccgaaga tgaggcggat   720
tactactgct cctcgtacac ctcaagctca actctgtacg tgttcggcac cggtactcag   780
ctcaccgtgc tgaccactac cccagcaccg aggccaccca cccggctcc taccatcgcc   840
tcccagcctc tgtccctgcg tccggaggca tgtagacccg cagctggtgg ggccgtgcat   900
acccggggtc ttgacttcgc ctgcgatatc tacatttggg cccctctggc tggtacttgc   960
ggggtcctgc tgctttcact cgtgatcact ctttactgta agcgcggtcg gaagaagctg   1020
ctgtacatct ttaagcaacc cttcatgagg cctgtgcaga ctactcaaga ggaggacggc   1080
tgttcatgcc ggttcccaga ggaggaggaa ggcggctgcg aactgcgcgt gaaattcagc   1140
cgcagcgcag atgctccagc ctaccagcag gggcagaacc agctctacaa cgaactcaat   1200
cttggtcgga gagaggagta cgacgtgctg gacaagcgga gaggacggga cccagaaatg   1260
ggcgggaagc cgcgcagaaa gaatccccaa gagggcctgt acaacgagct ccaaaaggat   1320
aagatggcag aagcctatag cgagattggt atgaaagggg aacgcagaag gaggcaaaggc  1380
cacgacggac tgtaccaggg actcagcacc gccaccaagg acacctatga cgctcttcac   1440
atgcaggccc tgccgcctcg ggaagcggag ctactaact tcagcctgct gaagcaggct    1500
ggagacgtga aggagaaccc tggacctatg gccttaccag tgaccgcctt gctcctgccg   1560
```

```
ctggccttgc tgctccacgc cgccaggccg gaaattgtga tgacccagtc acccgccact   1620
cttagccttt cacccggtga gcgcgcaacc ctgtcttgca gagcctccca agacatctca   1680
aaataccttta attggtatca acagaagccc ggacaggctc ctcgccttct gatctaccac   1740
accagccggc tccattctgg aatccctgcc aggttcagcg gtagcggatc tgggaccgac   1800
tacaccctca ctatcagctc actgcagcca gaggacttcg ctgtctattt ctgtcagcaa   1860
gggaacaccc tgccctacac ctttggacag ggcaccaagc tcgagattaa aggtggaggt   1920
ggcagcggag gaggtgggtc cggcggtgga ggaagccagg tccaactcca agaaagcgga   1980
ccgggtcttg tgaagccatc agaaactctt tcactgactt gtactgtgag cggagtgtct   2040
ctccccgatt acggggtgtc ttggatcaga cagccaccgg ggaagggtct ggaatggatt   2100
ggagtgattt ggggctctga gactacttac taccaatcat ccctcaagtc acgcgtcacc   2160
atctcaaagg acaactctaa gaatcaggtg tcactgaaac tgtcatccgt gaccgcagcc   2220
gacaccgccg tgtactattg cgctaagcat tactattatg cgggagcta cgcaatggat   2280
tactggggac agggtactct ggtcaccgtg tccagcacca cgaccccagc cgcgcgacca   2340
ccaacaccgg cgcccaccat cgcgtcgcag ccctgtccca tgcgcccaga ggcgtgccgg   2400
ccagcggcgg ggggcgcagt gcacacgagg gggctggact tcgcctgtga tatctacatc   2460
tgggcgccct tggccgggac ttgtggggtc cttctcctgt cactggttat caccccttac   2520
tgcaaacggg gcagaaagaa actcctgtat atattcaaac aacctttat gagaccagta   2580
caaactactc aagaggaaga tggctgtagc tgccgtttca cagaagaaa agaaggagga   2640
tgtgaactga gagtgaagtt cagcaggagc gcagacgccc ccgcgtacca gcagggccaa   2700
aaccagctct ataacgagct caatctagga cgaagagagg agtacgatgt tttggacaag   2760
agacgtggcc gggaccctga gatgggggga aagccgagaa ggaagaaccc tcaggaaggc   2820
ctgtacaatg aactgcagaa agataagatg cggagccct ccagtgagat tgggatgaaa   2880
ggcgagcgcc ggaggggcaa ggggcacgat ggcctttacc agggtctcag tacagccacc   2940
aaggacacct acgacgccct tcacatgcag gccctgcccc ctcgc               2985

SEQ ID NO: 12            moltype = AA   length = 995
FEATURE                  Location/Qualifiers
REGION                   1..995
                         note = Synthetic polypeptide
source                   1..995
                         mol_type = protein
                         organism = synthetic construct
SEQUENCE: 12
MALPVTALLL PLALLLHAAR PEVQLQQSGP GLVKPSQTLS LTCAISGDSM LSNSDTWNWI    60
RQSPSRGLEW LGRTYHRSTW YDDYASSVRG RVSINVDTSK NQYSLQLNAV TPEDTGVYYC   120
ARVRLQDGNS WSDAFDVWGQ GTMVTVSSGG GGSQSALTQP ASASGSPGQS VTISCTGTSS   180
DVGGYNYVSW YQQHPGKAPK LMIYDVSNRP SGVSNRFSGS KSGNTASLTI SGLQAEDEAD   240
YYCSSYTSSS TLYVFGTGTQ LTVLTTTPAP RPPTPAPTIA SQPLSLRPEA CRPAAGGAVH   300
TRGLDFACDI YIWAPLAGTC GVLLLSLVIT LYCKRGRKKL LYIFKQPFMR PVQTTQEEDG   360
CSCRFPEEEE GGCELRVKFS RSADAPAYQQ GQNQLYNELN LGRREEYDVL DKRRGRDPEM   420
GGKPRRKNPQ EGLYNELQKD KMAEAYSEIG MKGERRRGKG HDGLYQGLST ATKDTYDALH   480
MQALPPRGSG ATNFSLLKQA GDVEENPGPM ALPVTALLLP LALLLHAARP EIVMTQSPAT   540
LSLSPGERAT LSCRASQDIS KYLNWYQQKP GQAPRLLIYH TSRLHSGIPA RFSGSGSGTD   600
YTLTISSLQP EDFAVYFCQQ GNTLPYTFGQ GTKLEIKGGG GSGGGGSGGG GSQVQLQESG   660
PGLVKPSETL SLTCTVSGVS LPDYGVSWIR QPPGKGLEWI GVIWGSETTY YQSSLKSRVT   720
ISKDNSKNQV SLKLSSVTAA DTAVYYCAKH YYYGGSYAMD YWGQGTLVTV SSTTTPAPRP   780
PTPAPTIASQ PLSLRPEACR PAAGGAVHTR GLDFACDIYI WAPLAGTCGV LLLSLVITLY   840
CKRGRKKLLY IFKQPFMRPV QTTQEEDGCS CRFPEEEEGG CELRVKFSRS ADAPAYQQGQ   900
NQLYNELNLG RREEYDVLDK RRGRDPEMGG KPRRKNPQEG LYNELQKDKM AEAYSEIGMK   960
GERRRGKGHD GLYQGLSTAT KDTYDALHMQ ALPPR                              995

SEQ ID NO: 13            moltype = AA   length = 508
FEATURE                  Location/Qualifiers
REGION                   1..508
                         note = Synthetic polypeptide
source                   1..508
                         mol_type = protein
                         organism = synthetic construct
SEQUENCE: 13
MALPVTALLL PLALLLHAAR PEVQLQQSGP GLVKPSQTLS LTCAISGDSM LSNSDTWNWI    60
RQSPSRGLEW LGRTYHRSTW YDDYASSVRG RVSINVDTSK NQYSLQLNAV TPEDTGVYYC   120
ARVRLQDGNS WSDAFDVWGQ GTMVTVSSGG GGSQSALTQP ASASGSPGQS VTISCTGTSS   180
DVGGYNYVSW YQQHPGKAPK LMIYDVSNRP SGVSNRFSGS KSGNTASLTI SGLQAEDEAD   240
YYCSSYTSSS TLYVFGTGTQ LTVLTTTPAP RPPTPAPTIA SQPLSLRPEA CRPAAGGAVH   300
TRGLDFACDI YIWAPLAGTC GVLLLSLVIT LYCKRGRKKL LYIFKQPFMR PVQTTQEEDG   360
CSCRFPEEEE GGCELRVKFS RSADAPAYQQ GQNQLYNELN LGRREEYDVL DKRRGRDPEM   420
GGKPRRKNPQ EGLYNELQKD KMAEAYSEIG MKGERRRGKG HDGLYQGLST ATKDTYDALH   480
MQALPPRGSG ATNFSLLKQA GDVEENPG                                      508

SEQ ID NO: 14            moltype = AA   length = 487
FEATURE                  Location/Qualifiers
REGION                   1..487
                         note = Synthetic polypeptide
source                   1..487
                         mol_type = protein
                         organism = synthetic construct
SEQUENCE: 14
PMALPVTALL LPLALLLHAA RPEIVMTQSP ATLSLSPGER ATLSCRASQD ISKYLNWYQQ    60
KPGQAPRLLI YHTSRLHSGI PARFSGSGSG TDYTLTISSL QPEDFAVYFC QQGNTLPYTF   120
```

```
GQGTKLEIKG  GGGSGGGGSG  GGGSQVQLQE  SGPGLVKPSE  TLSLTCTVSG  VSLPDYGVSW   180
IRQPPGKGLE  WIGVIWGSET  TYYQSSLKSR  VTISKDNSKN  QVSLKLSSVT  AADTAVYYCA   240
KHYYYGGSYA  MDYWGQGTLV  TVSSTTTPAP  RPPTPAPTIA  SQPLSLRPEA  CRPAAGGAVH   300
TRGLDFACDI  YIWAPLAGTC  GVLLLSLVIT  LYCKRGRKKL  LYIFKQPFMR  PVQTTQEEDG   360
CSCRFPEEEE  GGCELRVKFS  RSADAPAYQQ  GQNQLYNELN  LGRREEYDVL  DKRRGRDPEM   420
GGKPRRKNPQ  EGLYNELQKD  KMAEAYSEIG  MKGERRRGKG  HDGLYQGLST  ATKDTYDALH   480
MQALPPR                                                                 487

SEQ ID NO: 15            moltype = DNA  length = 2985
FEATURE                  Location/Qualifiers
misc_feature             1..2985
                         note = Synthetic polynucleotide
source                   1..2985
                         mol_type = other DNA
                         organism = synthetic construct
SEQUENCE: 15
atggccttac cagtgaccgc cttgctcctg ccgctggcct tgctgctcca cgccgccagg    60
ccggaaattg tgatgaccca gtcacccgcc actcttagcc ctggaagacg tgagcgcgca   120
accctgtctt gcagagcctc ccaagacatc tcaaaatacc ttaattggta tcaacagaag   180
cccggacagg ctcctcgcct tctgatctac cacaccagcc ggctccattc tggaatccct   240
gccaggttca gcgtagcgg atctgggacc gactacaccc tcactatcag ctcactgcag   300
ccagaggact tcgctgtcta tttctgtcag caagggaaca ccctgcccta cacctttgga   360
cagggcacca agctcgagat taaaggtgga ggtggcagcg gaggaggtgg gtccggcggt   420
ggaggaagcc aggtccaact ccaagaaagc ggaccgggtc ttgtgaagcc atcagaaact   480
cttttcactga cttgtactgt gagcggagtg tctctcccg attacggggt gtcttggatc   540
agacagccac cggggaaggg tctgaatgg attggagtga tttgggggctc tgagactact   600
tactaccaat catccctcaa gtcacgcgtc accatctcaa aggacaactc taagaatcag   660
gtgtcactga aactgtcatc tgtgaccgca gccgacaccg ccgtgtacta ttgcgctaag   720
cattactatt atggcgggag ctacgcaatg gattactggg gacagggtac tctggtcacc   780
gtgtccagca ccacgacgcc agcgccgcga ccaccaacac cggcgcccac catcgcctcg   840
cagcccctgt ccctgcgccc agaggcgtgc cggccagcgg cggggggcgc agtgcacacg   900
aggggctgg acttcgcctg tgatatctac atctgggcgc ccttggccgg acttgtgggg   960
gtccttctcc tgtcactggt tatcacccctt tactgcaaac ggggcagaaa gaaactcctg  1020
tatatattca aacaaccatt tatgagacca gtacaaacta ctcaagagga agatggctgt  1080
agctgccgat ttccagaaga agaagaagga ggatgtgaac tgagagtgaa gttcagcagg  1140
agcgcagacg cccccgcgta ccagcagggc cagaaccagc tctataacga gctcaatcta  1200
ggacgaagag aggagtacga tgttttggac aagagacgtg gccgggaccc tgagatgggg  1260
ggaaagccga aaggaagaa ccctcaggaa ggcctgtaca tgaactgca gaaagataag  1320
atggcggagg cctacagtga gattgggatg aaaggcgagc gccggagggg caagggggcac  1380
gatggccttt accagggtct cagtacagcc accaaggaca cctacgacgc ccttcacatg  1440
caggccctgc ccctcgcgg aagcggagct actaacttca gcctgctgaa gcaggctgga  1500
gacgtggagg agaaccctgg acctatggcc tccctgtca ccgccctgct gcttccgctg  1560
gctcttctgc tccacgccgc tcggcccgaa gtgcagctgc agcagtcagg gcctggcctg  1620
gtcaagccgt cgcagaccct ctccctgaca tgcgccatta gcggggactc catgctgagc  1680
aactcggaca cctggaactg gattcggcag tccccttccc ggggactcga gtggctcgga  1740
cgcacctacc atcggagcac ttggtacgac gactacgcct cctccgtgag aggtcgcgtg  1800
tcgatcaacg tggatacctc gaagaaccaa tatagcttgc aactgaacgc cgtgaccccct  1860
gaggataccg gagtgtacta ttgtgcgaga gtcaggctgc aagacggaaa ctcctggtcc  1920
gacgcattg atgtctgggg acagggtact atggtcacgg tgtcatctgg aggcggagga  1980
tcgcaaagcg ccctgactca gccggcttcg gctagcggtt caccggggca gtccgtgact  2040
atctcctgca ccgggacttc ctccgacgtg ggaggctaca attacgtgtc tggtaccag  2100
caacacccccg gcaaagcccc aaagctgatg atctacgacg tcagcaacag acccagcgga  2160
gtgtccaacc ggttcagcgg ctccaagtcc ggcaacaccg cctccctgac catcagcggg  2220
cttcaggccg aagatgaggc ggattactac tgctcctcgt acacctcaag ctcaactctg  2280
tacgtgttcg gcaccggtac tcagctcacc gtgctgacca ctacccccagc accgaggcca  2340
cccaccccgg ctcctaccat cgcctcccag cctctgtccc tgcgtccgga ggcatgtaga  2400
cccgcagctg gtggggccgt gcataccccgg ggtcttgact cgcctgcga tctacatt   2460
tgggcccctc tggctggtac ttgcggggtc ctgctgcttt cactcgtgat cactctttac  2520
tgtaagcgcg gtcggaagaa gctgctgtac atctttaagc aacccttcat gaggcctgtg  2580
cagactactc aagaggagga cggctgttca tgccggttcc cagaggagga ggaaggcgga  2640
tgcgaactgc gcgtgaaatt cagccgcagc gcagatgctc cagcctacca gcaggggcag  2700
aaccagctct acaacgaact caatcttggt cggagagagg agtacgacgt gctgacaag  2760
cggagaggac gggacccaga aatgggcggg aagccgcgca gaaagaatcc caagagggc  2820
ctgtacaacg agctccaaaa ggataagatg gcagaagcct atagcgagat tggtatgaaa  2880
gggaacgca aagaggcaa aggccacgac ggactgtacc agggactcag caccgccacc  2940
aaggacacct atgacgctct tcacatgcag gccctgccgc ctcgg                 2985

SEQ ID NO: 16            moltype = AA  length = 995
FEATURE                  Location/Qualifiers
REGION                   1..995
                         note = Synthetic polypeptide
source                   1..995
                         mol_type = protein
                         organism = synthetic construct
SEQUENCE: 16
MALPVTALLL  PLALLLHAAR  PEIVMTQSPA  TLSLSPGERA  TLSCRASQDI  SKYLNWYQQK   60
PGQAPRLLIY  HTSRLHSGIP  ARFSGSGSGT  DYTLTISSLQ  PEDFAVYFCQ  QGNTLPYTFG  120
QGTKLEIKGG  GGSGGGGSGG  GGSQVQLQES  GPGLVKPSET  LSLTCTVSGV  SLPDYGVSWI  180
RQPPGKGLEW  IGVIWGSETT  YYQSSLKSRV  TISKDNSKNQ  VSLKLSSVTA  ADTAVYYCAK  240
```

```
HYYYGGSYAM DYWGQGTLVT VSSTTTPAPR PPTPAPTIAS QPLSLRPEAC RPAAGGAVHT    300
RGLDFACDIY IWAPLAGTCG VLLLSLVITL YCKRGRKKLL YIFKQPFMRP VQTTQEEDGC    360
SCRFPEEEEG GCELRVKFSR SADAPAYQQG QNQLYNELNL GRREEYDVLD KRRGRDPEMG    420
GKPRRKNPQE GLYNELQKDK MAEAYSEIGM KGERRRGKGH DGLYQGLSTA TKDTYDALHM    480
QALPPRGSGA TNFSLLKQAG DVEENPGPMA LPVTALLLPL ALLLHAARPE VQLQQSGPGL    540
VKPSQTLSLT CAISGDSMLS NSDTWNWIRQ SPSRGLEWLG RTYHRSTWYD DYASSVRGRV    600
SINVDTSKNQ YSLQLNAVTP EDTGVYYCAR VRLQDGNSWS DAFDVWGQGT MVTVSSGGGG    660
SQSSALTQPAS ASGSPGQSVT ISCTGTSSDV GGYNYVSWYQ QHPGKAPKLM IYDVSNRPSG   720
VSNRFSGSKS GNTASLTISG LQAEDEADYY CSSYTSSSTL YVFGTGTQLT VLTTTPAPRP    780
PTPAPTIASQ PLSLRPEACR PAAGGAVHTR GLDFACDIYI WAPLAGTCGV LLLSLVITLY    840
CKRGRKKLLY IFKQPFMRPV QTTQEEDGCS CRFPEEEEGG CELRVKFSRS ADAPAYQQGQ    900
NQLYNELNLG RREEYDVLDK RRGRDPEMGG KPRRKNPQEG LYNELQKDKM AEAYSEIGMK    960
GERRRGKGHD GLYQGLSTAT KDTYDALHMQ ALPPR                              995

SEQ ID NO: 17           moltype = AA  length = 507
FEATURE                 Location/Qualifiers
REGION                  1..507
                        note = Synthetic polypeptide
source                  1..507
                        mol_type = protein
                        organism = synthetic construct
SEQUENCE: 17
MALPVTALLL PLALLLHAAR PEIVMTQSPA TLSLSPGERA TLSCRASQDI SKYLNWYQQK     60
PGQAPRLLIY HTSRLHSGIP ARFSGSGSGT DYTLTISSLQ PEDFAVYFCQ QGNTLPYTFG    120
QGTKLEIKGG GGSGGGGSGG GGSQVQLQES GPGLVKPSET LSLTCTVSGV SLPDYGVSWI    180
RQPPGKGLEW IGVIWGSETT YYQSSLKSRV TISKDNSKNQ VSLKLSSVTA ADTAVYYCAK    240
HYYYGGSYAM DYWGQGTLVT VSSTTTPAPR PPTPAPTIAS QPLSLRPEAC RPAAGGAVHT    300
RGLDFACDIY IWAPLAGTCG VLLLSLVITL YCKRGRKKLL YIFKQPFMRP VQTTQEEDGC    360
SCRFPEEEEG GCELRVKFSR SADAPAYQQG QNQLYNELNL GRREEYDVLD KRRGRDPEMG    420
GKPRRKNPQE GLYNELQKDK MAEAYSEIGM KGERRRGKGH DGLYQGLSTA TKDTYDALHM    480
QALPPRGSGA TNFSLLKQAG DVEENPG                                       507

SEQ ID NO: 18           moltype = AA  length = 488
FEATURE                 Location/Qualifiers
REGION                  1..488
                        note = Synthetic polypeptide
source                  1..488
                        mol_type = protein
                        organism = synthetic construct
SEQUENCE: 18
PMALPVTALL LPLALLLHAA RPEVQLQQSG PGLVKPSQTL SLTCAISGDS MLSNSDTWNW     60
IRQSPSRGLE WLGRTYHRST WYDDYASSVR GRVSINVDTS KNQYSLQLNA VTPEDTGVYY    120
CARVRLQDGN SWSDAFDVWG QGTMVTVSSG GGGSQSALTQ PASASGSPGQ SVTISCTGTS    180
SDVGGYNYVS WYQQHPGKAP KLMIYDVSNR PSGVSNRFSG SKSGNTASLT ISGLQAEDEA    240
DYYCSSYTSS STLYVFGTGT QLTVLTTTPA PRPPTPAPTI ASQPLSLRPE ACRPAAGGAV    300
HTRGLDFACD IYIWAPLAGT CGVLLLSLVI TLYCKRGRKK LLYIFKQPFM RPVQTTQEED    360
GCSCRFPEEE EGGCELRVKF SRSADAPAYQ QGQNQLYNEL NLGRREEYDV LDKRRGRDPE    420
MGGKPRRKNP QEGLYNELQK DKMAEAYSEI GMKGERRRGK GHDGLYQGLS TATKDTYDAL    480
HMQALPPR                                                            488

SEQ ID NO: 19           moltype = DNA  length = 2985
FEATURE                 Location/Qualifiers
misc_feature            1..2985
                        note = Synthetic polynucleotide
source                  1..2985
                        mol_type = other DNA
                        organism = synthetic construct
SEQUENCE: 19
atggcacttc ccgtcaccgc cctgctgctc ccactcgccc tccttctgca cgccgcccgc     60
cccgaagtgc agctgcagca gtcaggaccg ggcctggtca aaccttcgca gactctgtcc    120
ctgacttgcg ctataagcgg ggactccatg ctgagcaatt cggacacttg gaactggatt    180
cgccaaagcc ccagccgggg tctggaatgg ctgggaagga cctaccatcg ctctacttgg    240
tacgacgact acgccagctc cgtgcgagga cgcgtgtcca tcaacgtgga cacctccaag    300
aaccagtact cgcttcaact caacgcagtg accctgaagg ataccggagt ctactattgc    360
gcccgcgtgc ggctccagga cgggaactcc tggtcggacg ctttcgatgt ctggggacag    420
ggcactatgg tcaccgtcag ctccggcggg ggcggtagcc aatcggcgct gacacagccg    480
gcttccgcct cgggatcgcc tggacagtcg gtgaccatct cgtgcactgg aacctcctcc    540
gacgtggcg gctacaatta tgtgtcatgg taccagcagc acccgggaaa ggcccctaag    600
ctgatgatct acgacgtgtc caatagacct agcggggtgt caaacagatt ctccggatcc    660
aaatccggaa acactgcctc cctgaccatt tccggactgc aggccgagga cgaagccgat    720
tactactgct cctcttacac ctcctcatcc accctctacg tgtttgggac tgggacccag    780
ctgaccgtcc tcactaccac cccggcccg cggcccccta caccggcacc gactattgcc    840
agccagcctc tctcgctgcg gccggaggcc tgccgcccag ccgccggcgg agccgtgcac    900
accgggctc tggacttcgc gtgcgatatc tacatctggc ctcgggactg gcggacttgt    960
ggcgtgctgc tgctgtctct ggtcatcaca ctgtactgca agcgcggaag aaagaagctg   1020
ctctacatct tcaagcaacc cttcatgcgg cctgtgcaga ccacccagga agaggatggc   1080
tgctcctgcc ggttcccgga ggaagaagag ggcggatgcg aactgcgcgt gaagttcagc   1140
cgaagcgcc acgccccggc ctaccagcag ggccagaacc aactgtacaa cgaactcaac   1200
ctgggtcgga gagaagagta cgacgtgctg gacaaaagac gcggcaggga ccccgagatg   1260
```

-continued

```
ggcggaaagc ctcgccgcaa gaacccgcag gagggcctct acaacgagct gcagaaggac  1320
aagatggccg aagcctactc agagatcggc atgaaggggg agcggaggcg cgggaagggc  1380
cacgacggtt tgtaccaagg actttccact gcgaccaagg acacctacga tgccctccat  1440
atgcaagccc tgccgccccg gggttccgga gctaccaact tctcgctgtt gaagcaggcc  1500
ggagatgtcg aggaaaaccc gggacctatg gccctgccga tgaccgcgct cctgctgccc  1560
ctggctctgc tgcttcacgc ggcccggcct gagattgtga tgactcagag cccggcgacc  1620
ctgtccctgt cccccgggga gagagcaacc ctgtcgtgcc gggcctccca agacatctca  1680
aagtacctca attggtatca gcagaagcca ggacaggctc cacggttgct gatctaccac  1740
acttcgagac tgcactcagg aatcccccgcg cggttttccg gttccggctc cgggaccgac  1800
tacaccctga ccatcagctc gctccagcct gaggatttcg cagtgtactt ctgtcagcaa  1860
ggaaacaccc ttccatacac cttcggacag ggtaccaagc tggaaatcaa ggggaggaga  1920
ggatctgggg gcggtggttc cggaggcggt ggaagccaag tgcagctcca ggaaagcgga  1980
cccgggctgg tcaagccgag cgaaaccctc tcactgactt gtactgtgtc cggagtgtcc  2040
ctgcctgact atggagtgtc ctggatccga cagcccccg gaaagggtct ggagtggatt  2100
ggggtcatct ggggctccga aactacctac taccagagca gcctcaagag ccgggtcacc  2160
atttcaaagg ataactccaa gaatcaagtg tccctgaagc tgtcctcagt gacagccgca  2220
gacaccgccg tgtactactg cgccaagcac tactactacg gaggctccta cgcaatggac  2280
tactggggac aaggcacttt ggtcactgtg tcaagcacca ccacccctgc gcctcggctc  2340
cctaccccgg ctcccactat cgcgagccaa ccgctgagcc tgcggcctga ggcttgccga  2400
ccggccgctg gcggcgccgt gcatactcgg ggcctcgact ttgcctgtga catctacatc  2460
tgggccccc tggccggaac gtgcggagtg ctgctgctgt cgctggtcat taccctgtat  2520
tgcaaacgcg gaaggaagaa gctgttgtac attttcaagc agcccttcat gcgcccggtg  2580
caaactactc aggaggaaga tggctgttcc tgtcggttcc ccgaagagga agaaggcggc  2640
tgcgagttga gggtcaagtt ctcccggtcc gccgatgctc ccgcctacca acaggggcag  2700
aaccagcttt ataacgaact gaacctgggc aggagggagg aatatgatgt gttggataag  2760
cgccggcgcc gggacccaga aatgggggga aagcccagga gaaagaaccc tcaagaggga  2820
ctttacaacg aattgcagaa agacaaaatg gccgaggcct actccgagat tgggatgaag  2880
ggcgaaagac ggagaggaaa ggggcacgac gggctctacc agggactcag caccgccacc  2940
aaagatacct acgacgccct gcatatgcag gcgctgccgc cgcgc             2985
```

```
SEQ ID NO: 20           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 20
SNSDTWN                                                               7

SEQ ID NO: 21           moltype = AA  length = 18
FEATURE                 Location/Qualifiers
REGION                  1..18
                        note = Synthetic polypeptide
source                  1..18
                        mol_type = protein
                        organism = synthetic construct
SEQUENCE: 21
RTYHRSTWYD DYASSVRG                                                  18

SEQ ID NO: 22           moltype = AA  length = 15
FEATURE                 Location/Qualifiers
REGION                  1..15
                        note = Synthetic polypeptide
source                  1..15
                        mol_type = protein
                        organism = synthetic construct
SEQUENCE: 22
VRLQDGNSWS DAFDV                                                     15

SEQ ID NO: 23           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 23
GDSMLSNSD                                                             9

SEQ ID NO: 24           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 24
YHRSTWY                                                               7
```

```
SEQ ID NO: 25          moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 25
GDSMLSNSDT                                                                10

SEQ ID NO: 26          moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 26
TYHRSTWYD                                                                  9

SEQ ID NO: 27          moltype = AA  length = 17
FEATURE                Location/Qualifiers
REGION                 1..17
                       note = Synthetic polypeptide
source                 1..17
                       mol_type = protein
                       organism = synthetic construct
SEQUENCE: 27
ARVRLQDGNS WSDAFDV                                                        17

SEQ ID NO: 28          moltype = AA  length = 14
FEATURE                Location/Qualifiers
REGION                 1..14
                       note = Synthetic polypeptide
source                 1..14
                       mol_type = protein
                       organism = synthetic construct
SEQUENCE: 28
TGTSSDVGGY NYVS                                                           14

SEQ ID NO: 29          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 29
DVSNRPS                                                                    7

SEQ ID NO: 30          moltype = AA  length = 11
FEATURE                Location/Qualifiers
REGION                 1..11
                       note = Synthetic polypeptide
source                 1..11
                       mol_type = protein
                       organism = synthetic construct
SEQUENCE: 30
SSYTSSSTLY V                                                              11

SEQ ID NO: 31          moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 31
TSSDVGGYNY                                                                10

SEQ ID NO: 32          moltype =     length =
SEQUENCE: 32
000

SEQ ID NO: 33          moltype = AA  length = 8
FEATURE                Location/Qualifiers
REGION                 1..8
                       note = Synthetic polypeptide
```

```
source                        1..8
                              mol_type = protein
                              organism = synthetic construct
SEQUENCE: 33
YTSSSTLY                                                                    8

SEQ ID NO: 34                 moltype = AA  length = 9
FEATURE                       Location/Qualifiers
REGION                        1..9
                              note = Synthetic polypeptide
source                        1..9
                              mol_type = protein
                              organism = synthetic construct
SEQUENCE: 34
SSDVGGYNY                                                                   9

SEQ ID NO: 35                 moltype = AA  length = 10
FEATURE                       Location/Qualifiers
REGION                        1..10
                              note = Synthetic polypeptide
source                        1..10
                              mol_type = protein
                              organism = synthetic construct
SEQUENCE: 35
GVSLPDYGVS                                                                 10

SEQ ID NO: 36                 moltype = AA  length = 16
FEATURE                       Location/Qualifiers
REGION                        1..16
                              note = Synthetic polypeptide
source                        1..16
                              mol_type = protein
                              organism = synthetic construct
SEQUENCE: 36
VIWGSETTYY SSSLKS                                                          16

SEQ ID NO: 37                 moltype = AA  length = 16
FEATURE                       Location/Qualifiers
REGION                        1..16
                              note = Synthetic polypeptide
source                        1..16
                              mol_type = protein
                              organism = synthetic construct
SEQUENCE: 37
VIWGSETTYY QSSLKS                                                          16

SEQ ID NO: 38                 moltype = AA  length = 16
FEATURE                       Location/Qualifiers
REGION                        1..16
                              note = Synthetic polypeptide
source                        1..16
                              mol_type = protein
                              organism = synthetic construct
SEQUENCE: 38
VIWGSETTYY NSSLKS                                                          16

SEQ ID NO: 39                 moltype = AA  length = 12
FEATURE                       Location/Qualifiers
REGION                        1..12
                              note = Synthetic polypeptide
source                        1..12
                              mol_type = protein
                              organism = synthetic construct
SEQUENCE: 39
HYYYGGSYAM DY                                                              12

SEQ ID NO: 40                 moltype = AA  length = 11
FEATURE                       Location/Qualifiers
REGION                        1..11
                              note = Synthetic polypeptide
source                        1..11
                              mol_type = protein
                              organism = synthetic construct
SEQUENCE: 40
RASQDISKYL N                                                               11

SEQ ID NO: 41                 moltype = AA  length = 7
FEATURE                       Location/Qualifiers
REGION                        1..7
```

```
                        note = Synthetic polypeptide
source                  1..7
                        mol_type = protein
                        organism = synthetic construct
SEQUENCE: 41
HTSRLHS                                                                     7

SEQ ID NO: 42           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 42
QQGNTLPYT                                                                   9

SEQ ID NO: 43           moltype = DNA   length = 726
FEATURE                 Location/Qualifiers
misc_feature            1..726
                        note = Synthetic polynucleotide
source                  1..726
                        mol_type = other DNA
                        organism = synthetic construct
SEQUENCE: 43
gaaattgtga tgacccagtc acccgccact cttagccttt cacccggtga gcgcgcaacc           60
ctgtcttgca gagcctccca agacatctca aaatacctta attggtatca acagaagccc          120
ggacaggctc ctcgccttct gatctaccac accagccggc tccattctgg aatccctgcc          180
aggttcagcg gtagcggatc tgggaccgac tacaccctca ctatcagctc actgcagcca          240
gaggacttcg ctgtctattt ctgtcagcaa gggaacaccc tgccctacac ctttggacag          300
ggcaccaagc tcgagattaa aggtggaggt ggcagcggag gaggtgggtc cggcggtgga          360
ggaagccagg tccaactcca agaaagcgga ccgggtcttg tgaagccatc agaaactctt          420
tcactgactt gtactgtgag cggagtgtct ctccccgatt acggggtgtc ttggatcaga          480
cagccaccgg gaagggtct ggaatggatt ggagtgattt ggggctctga gactacttac          540
taccaatcat ccctcaagtc acgcgtcacc atctcaaagg acaactctaa gaatcaggtg          600
tcactgaaac tgtcatctgt gaccgcagcc gacaccgccg tgtactattg cgctaagcat          660
tactattatg gcggagcta cgcaatggat tactggggac agggtactct ggtcaccgtg          720
tccagc                                                                    726

SEQ ID NO: 44           moltype = AA   length = 242
FEATURE                 Location/Qualifiers
REGION                  1..242
                        note = Synthetic polypeptide
source                  1..242
                        mol_type = protein
                        organism = synthetic construct
SEQUENCE: 44
EIVMTQSPAT LSLSPGERAT LSCRASQDIS KYLNWYQQKP GQAPRLLIYH TSRLHSGIPA           60
RFSGSGSGTD YTLTISSLQP EDFAVYFCQQ GNTLPYTFGQ GTKLEIKGGG GSGGGGSGGG          120
GSQVQLQESG PGLVKPSETL SLTCTVSGVS LPDYGVSWIR QPPGKGLEWI GVIWGSETTY          180
YQSSLKSRVT ISKDNSKNQV SLKLSSVTAA DTAVYYCAKH YYYGGSYAMD YWGQGTLVTV          240
SS                                                                        242

SEQ ID NO: 45           moltype = DNA   length = 726
FEATURE                 Location/Qualifiers
misc_feature            1..726
                        note = Synthetic polynucleotide
source                  1..726
                        mol_type = other DNA
                        organism = synthetic construct
SEQUENCE: 45
gagattgtca tgactcagtc cccggccaca ctctccctgt cacccggaga aagagcaacc           60
ctgagctgca gggcgtccca ggacatctcg aagtacctga actggtacca gcagaagcct          120
ggacaagcac cccgcctcct gatctaccac acctcgcggc tgcattcggg aatccccgcc          180
agattctcag ggagcggatc aggaaccgac tacaccctga ctatctcgag cctgcaacca          240
gaggatttcg ccgtgtactt ctgccagcaa ggaaacaccc tgccctacac ctttggacag          300
ggaaccaagc tcgagattaa ggggggtggt ggatcgggag gggtggatc aggaggaggc          360
ggctcacaag tccagctgca agaatccggt ccgggacttg tgaagccgtc cgaaaccctg          420
tcactgactt gcactgtgtc cggggtgtca ttgcccgact acggcgtgag ctggattcgg          480
cagccccctg gaaagggatt ggaatggatc ggcgtgatct ggggttcgga aactacctac          540
tatcagtcct cactgaagtc ccgcgtgacc atcagcaagg ataattccaa aaaccaagtg          600
tctctgaagc tctccagcgt cactgccgcc gatactgccg tgtactactg cgccaagcac          660
tactattacg gcggttcgta cgccatggac tactggggcc aagggacact cgtgaccgtg          720
tcatcc                                                                    726

SEQ ID NO: 46           moltype = DNA   length = 726
FEATURE                 Location/Qualifiers
misc_feature            1..726
                        note = Synthetic polynucleotide
```

```
source                  1..726
                        mol_type = other DNA
                        organism = synthetic construct
SEQUENCE: 46
caagtccagc tgcaagaatc cggtccggga cttgtgaagc cgtccgaaac cctgtcactg   60
acttgcactg tgtccggggt gtcattgccc gactacggcg tgagctggat tcggcagccc  120
cctggaaagg gattggaatg gatcggcgtg atctggggtt cggaaactac ctactatcag  180
tcctcactga gtcccgcgt gaccatcagc aaggataatt ccaaaaacca agtgtctctg   240
aagctctcca gcgtcactgc cgccgatact gccgtgtact actgcgcaa gcactactat   300
tacggcggtt cgtacgccat ggactactgg ggacaaggca ctcttgtgac tgtgtcaagc  360
ggcggtggag ggagcggtgg gggcggttca ggaggaggcg gatcagagat cgtgatgacc  420
caatccccag ccaccctgtc cctcagccct ggagaaagag ccaccctgag ctgccgggcc  480
tcccaggata tcagcaagta cttgaactgg taccaacaaa agccggggca ggcgcccgg   540
ctcctgatct accacacctc gcgcctccac tcaggtatcc ccgccagatt ctcagggagc  600
ggctccggta ctgactacac cctgactatt tcctcactgc agccagagga ctttgccgtg  660
tacttctgcc agcagggaaa cactctgccg tacaccttcg ggcagggaac gaagcttgaa  720
attaag                                                             726

SEQ ID NO: 47           moltype = AA   length = 242
FEATURE                 Location/Qualifiers
REGION                  1..242
                        note = Synthetic polypeptide
source                  1..242
                        mol_type = protein
                        organism = synthetic construct
SEQUENCE: 47
QVQLQESGPG LVKPSETLSL TCTVSGVSLP DYGVSWIRQP PGKGLEWIGV IWGSETTYYQ   60
SSLKSRVTIS KDNSKNQVSL KLSSVTAADT AVYYCAKHYY YGGSYAMDYW GQGTLVTVSS  120
GGGGSGGGGS GGGGSEIVMT QSPATLSLSP GERATLSCRA SQDISKYLNW YQQKPGQAPR  180
LLIYHTSRLH SGIPARFSGS GSGTDYTLTI SSLQPEDFAV YFCQQGNTLP YTFGQGTKLE  240
IK                                                                 242

SEQ ID NO: 48           moltype = DNA   length = 726
FEATURE                 Location/Qualifiers
misc_feature            1..726
                        note = Synthetic polynucleotide
source                  1..726
                        mol_type = other DNA
                        organism = synthetic construct
SEQUENCE: 48
gagattgtga tgactcagag cccggcgacc ctgtccctgt cccccgggga gagagcaacc   60
ctgtcgtgcc gggcctccca agacatctca aagtacctca attggtatca gcagaagcca  120
ggacaggctc cacggttgct gatctaccac acttcgagac tgcactcagg aatccccgcg  180
cggttttccg gttccggctc cgggaccgac tacaccctga ccatcagctc gctccagcct  240
gaggatttcg cagtgtactt ctgtcagcaa ggaaacaccc ttccatacac cttcggacag  300
ggtaccaagc tggaaatcaa gggaggagga ggatctgggg gcggtggttc cggaggcggt  360
ggaagccaag tgcagctcca ggaaagcgga cccgggctgg tcaaccgga cgaaaccctc  420
tcactgactt gtactgtgtc cggagtgtcc ctgcctgact atggagtgtc ctggatccga  480
cagccccccg gaaagggtct ggagtggatt gggtcatct ggggctccga aactacctac   540
taccagagca gcctcaagag ccgggtcacc atttcaaagg ataactccaa gaatcaagtg  600
tccctgaagc tgtcctcagt gacagccgca gacaccgccg tgtactactg cgccaagcac  660
tactactacg gaggctccta cgcaatggac tactgggac aaggcacttt ggtcactgtg  720
tcaagc                                                             726

SEQ ID NO: 49           moltype = DNA   length = 729
FEATURE                 Location/Qualifiers
misc_feature            1..729
                        note = Synthetic polynucleotide
source                  1..729
                        mol_type = other DNA
                        organism = synthetic construct
SEQUENCE: 49
gaagtgcagc tgcagcagtc agggcctggc ctggtcaagc cgtcgcagac cctctccctg   60
acatgcgcca ttagcgggga ctccatgctg agcaactcgg acacctggaa ctggattcgg  120
cagtccccct tcccggggact cgagtggctc ggacgcacct accatcggag cacttggtac  180
gacgactacg cctcctccgt gagaggtcgc gtgtcgatca acgtggatac ctcgaagaac  240
cagtatagct tgcaactgaa cgccgtgacc cctgaggata ccgagtgta ctattgtgcg   300
agagtcaggc tgcaagacgg aaactcctgg tccgacgcat ttgatgtctg gggacagggt  360
actatggtca cggtgtcatc tggaggcgga ggatccgaaa gcccctgac tcagccgagct  420
tcggctagcg gttcaccggg gcagtccgtg actatctcct gcaccgggac ttcctccgac  480
gtgggaggct acaattacgt gtcctggtac cagcaacacc ccggcaaagc cccaaagctg  540
atgatctacg acgtcagcaa cagacccagc ggagtgccca accggttcag cggctccaag  600
tccggcaaca ccgcctccct gaccatcagc gggcttcagg ccgaagatga ggcggattac  660
tactgctcct cgtacacctc aagctcaact ctgtacgtgt tcggcaccgg tactcagctc  720
accgtgctg                                                          729

SEQ ID NO: 50           moltype = AA   length = 243
FEATURE                 Location/Qualifiers
REGION                  1..243
```

```
                        note = Synthetic polypeptide
source                  1..243
                        mol_type = protein
                        organism = synthetic construct
SEQUENCE: 50
EVQLQQSGPG LVKPSQTLSL TCAISGDSML SNSDTWNWIR QSPSRGLEWL GRTYHRSTWY    60
DDYASSVRGR VSINVDTSKN QYSLQLNAVT PEDTGVYYCA RVRLQDGNSW SDAFDVWGQG   120
TMVTVSSGGG GSQSALTQPA SASGSPGQSV TISCTGTSSD VGGYNYVSWY QQHPGKAPKL   180
MIYDVSNRPS GVSNRFSGSK SGNTASLTIS GLQAEDEADY YCSSYTSSST LYVFGTGTQL   240
TVL                                                                 243

SEQ ID NO: 51           moltype = DNA  length = 729
FEATURE                 Location/Qualifiers
misc_feature            1..729
                        note = Synthetic polynucleotide
source                  1..729
                        mol_type = other DNA
                        organism = synthetic construct
SEQUENCE: 51
gaagtgcagc tgcagcagtc aggaccgggc ctggtcaaac cttcgcagac tctgtccctg    60
acttgcgcta taagcgggga ctccatgctg agcaattcgg acacttggaa ctggattcgc   120
caaagcccca gccggggtct ggaatggctg gaaggacctc accatcgctc tacttggtac   180
gacgactacg ccagctccgt gcgaggacgc gtgtccatca acgtggacac ctccaagaac   240
cagtactcgc ttcaactcaa cgcagtgacc cctgaagata ccggagtcta ctattgcgcc   300
cgcgtgcggc tccaggacgg gaactcctgg tcggacgctt tcgatgtctg gggacagggc   360
actatggtca ccgtcagctc cggcggcggc ggtagcgctc agcagcctgc tagcgggtct   420
ccgcctcgg gatcgcctgg acagtcggtg accatctcgt gcactggaac ctcctccgac   480
gtgggcggct acaattatgt gtcatggtac cagcagcacc cgggaaaggc ccctaagctg   540
atgatctacg acgtgtccaa tagacctagc ggggtgtcaa acagattctc cggatccaaa   600
tccggaaaca ctgcctccct gaccatttcc ggactgcagg ccgaggacga agccgattac   660
tactgctcct cttacacctc ctcatccacc ctctacgtgt ttgggactgg gacccagctg   720
accgtcctc                                                           729

SEQ ID NO: 52           moltype = DNA  length = 759
FEATURE                 Location/Qualifiers
misc_feature            1..759
                        note = Synthetic polynucleotide
source                  1..759
                        mol_type = other DNA
                        organism = synthetic construct
SEQUENCE: 52
gaagtgcagc ttcaacaatc aggaccagga ctcgtcaaac catcacagac cctctccctc    60
acatgtgcca tctccgggga ctccatgttg agcaattccg acacttggaa ttggattaga   120
caaagcccgt cccgggggtct ggaatggttg gacgcacctc accaccggtc tacttggtac   180
gacgactacg cgtcatccgt gcggggaaga gtgtccatca acgtggacac ctccaagaac   240
cagtacagcc tgcagcttaa tgccgtgact cctgaggata cggcgtcta ctactgcgcc    300
cgcgtccgcc tgcaagacgg gaacagctgg agcgatgcat tcgatgtctg gggccagggsa   360
actatggtca ccgtgtcgtc tggggcggt ggatcgggtg gcgggggttc gggggggcggc   420
ggctctcagt ccgctcttac ccaaccggcc tcagcctcgg ggagcccggg ccagagcgtg   480
accatttcct gcaccggcac ttcatccgac gtgggcggct acaactacgt gtcctggtac   540
caacagcacc cgggaaaggc ccccaagctc atgatctacg acgtgtccaa caggccctcg   600
ggagtgtcca accggttctc gggttcgaaa tcgggaaaca cagccagcct gaccatcagc   660
ggactgcagg ctgaagatga agccgactac tactgctcct cctacacctc gtcatccacg   720
ctctacgtgt tcggcactgg aaactcagctg actgtgctg                         759

SEQ ID NO: 53           moltype = AA  length = 253
FEATURE                 Location/Qualifiers
REGION                  1..253
                        note = Synthetic polypeptide
source                  1..253
                        mol_type = protein
                        organism = synthetic construct
SEQUENCE: 53
EVQLQQSGPG LVKPSQTLSL TCAISGDSML SNSDTWNWIR QSPSRGLEWL GRTYHRSTWY    60
DDYASSVRGR VSINVDTSKN QYSLQLNAVT PEDTGVYYCA RVRLQDGNSW SDAFDVWGQG   120
TMVTVSSGGG GSGGGGSGGG GSQSALTQPA SASGSPGQSV TISCTGTSSD VGGYNYVSWY   180
QQHPGKAPKL MIYDVSNRPS GVSNRFSGSK SGNTASLTIS GLQAEDEADY YCSSYTSSST   240
LYVFGTGTQL TVL                                                      253

SEQ ID NO: 54           moltype = DNA  length = 729
FEATURE                 Location/Qualifiers
misc_feature            1..729
                        note = Synthetic polynucleotide
source                  1..729
                        mol_type = other DNA
                        organism = synthetic construct
SEQUENCE: 54
cagtccgctc ttacccaacc ggcctcagcc tcggggagcc ccggccagag cgtgaccatt    60
tcctgcaccg gcacttcatc cgacgtgggc ggctacaact acgtgtcctg gtaccaacag   120
```

```
caccccgggaa aggcccccaa gctcatgatc tacgacgtgt ccaacaggcc ctcgggagtg   180
tccaaccggt tctcgggttc gaaatcggga acacagcca gcctgaccat cagcggactg   240
caggctgaag atgaagccga ctactactgc tcctcctaca cctcgtcatc cacgctctac   300
gtgttcggca ctggaactca gctgactgtg ctgggcggag gaggctccga agtgcagctt   360
caacaatcag gaccaggact cgtcaaacca tcacagacca tctccctcac atgtgccatc   420
tccggggact ccatgttgag caattccgac acttggaatt ggattagaca aagcccgtcc   480
cggggtctgg aatggttggg acgcacctac caccggtcta cttggtacga cgactacgcg   540
tcatccgtgc ggggaagagt gtccatcaac gtggacacct ccaagaacca gtacagcctg   600
cagcttaatg ccgtgactcc tgaggatacg gcgtcactac tgcgcccg cgtccgcctg    660
caagacggga acagctggag cgatgcattc gatgtctggg gccagggaac tatggtcacc   720
gtgtcgtct                                                          729

SEQ ID NO: 55            moltype = AA  length = 243
FEATURE                  Location/Qualifiers
REGION                   1..243
                         note = Synthetic polypeptide
source                   1..243
                         mol_type = protein
                         organism = synthetic construct
SEQUENCE: 55
QSALTQPASA SGSPGQSVTI SCTGTSSDVG GYNYVSWYQQ HPGKAPKLMI YDVSNRPSGV    60
SNRFSGSKSG NTASLTISGL QAEDEADYYC SSYTSSSTLY VFGTGTQLTV LGGGSEVQL    120
QQSGPGLVKP SQTLSLTCAI SGDSMLSNSD TWNWIRQSPS RGLEWLGRTY HRSTWYDDYA   180
SSVRGRVSIN VDTSKNQYSL QLNAVTPEDT GVYYCARVRL QDGNSWSDAF DVWGQGTMVT   240
VSS                                                                243

SEQ ID NO: 56            moltype = DNA  length = 729
FEATURE                  Location/Qualifiers
misc_feature             1..729
                         note = Synthetic polynucleotide
source                   1..729
                         mol_type = other DNA
                         organism = synthetic construct
SEQUENCE: 56
cagtccgctc tgactcagcc ggcctcagct tcggggtccc ctggtcaaag cgtcactatt    60
tcctgtaccg gaacctcatc agacgtgggc ggctacaatt acgtgtcctg gtaccaacag   120
caccccggaa aggctcctaa gcttatgatc tacgacgtgt ccaaccggcc gtcaggagtg   180
tccaacagat tctccggctc caagagcgga aacactgcca gcttgaccat tagcggcttg   240
caggccgagg acgaagccga ctactactgc tctagctaca catcctcgtc taccctctac   300
gtgtttggaa cggggaccca gctgactgtg ctcgggggtg gaggatcaga ggtgcaactc   360
cagcagtccg gtcctggcct cgtgaaaccg tcccaaaccc tgtccctgac ttgcgccatc   420
tcgggcgact ccatgctgtc caattccgac acctggaact ggattagaca atcgcctagc   480
cggggactcg aatggctggg ccggacctac caccggtcca cgtggtatga cgactacgca   540
agctccgtcc ggggaagggt gtccattaac gtcgatacct ccaagaacca gtacagcctt   600
cagctgaacg ctgtgacccc cgaggatacc ggcgtctact actgtgcaag agtgcgattg   660
caggatggaa actcgtggtc ggacgcattc gatgtctggg gacagggaac tatggtgacc   720
gtgtcctcg                                                          729

SEQ ID NO: 57            moltype = DNA  length = 729
FEATURE                  Location/Qualifiers
misc_feature             1..729
                         note = Synthetic polynucleotide
source                   1..729
                         mol_type = other DNA
                         organism = synthetic construct
SEQUENCE: 57
cagtccgctc tgactcagcc ggcctcagct tcggggtccc ctggtcaaag cgtcactatt    60
tcctgtaccg gaacctcatc agacgtgggc ggctacaatt acgtgtcctg gtaccaacag   120
caccccggaa aggctcctaa gcttatgatc tacgacgtgt ccaaccggcc gtcaggagtg   180
tccaacagat tctccggctc caagagcgga aacactgcca gcttgaccat tagcggcttg   240
caggccgagg acgaagccga ctactactgc tctagctaca catcctcgtc taccctctac   300
gtgtttggaa cggggaccca gctgactgtg ctcgggggtg gaggatcaga ggtgcaactc   360
cagcagtccg gtcctggcct cgtgaaaccg tcccaaaccc tgtccctgac ttgcgccatc   420
tcgggcgact ccatgctgtc caattccgac acctggaact ggattagaca atcgcctagc   480
cggggactcg aatggctggg ccggacctac caccggtcca cgtggtatga cgactacgca   540
agctccgtcc ggggaagggt gtccattaac gtcgatacct ccaagaacca gtacagcctt   600
cagctgaacg ctgtgacccc cgaggatacc ggcgtctact actgtgcaag agtgcgattg   660
caggatggaa actcgtggtc ggacgcattc gatgtctggg gacagggaac tatggtcact   720
gtgtcctcc                                                          729

SEQ ID NO: 58            moltype = DNA  length = 63
FEATURE                  Location/Qualifiers
misc_feature             1..63
                         note = Synthetic polynucleotide
source                   1..63
                         mol_type = other DNA
                         organism = synthetic construct
SEQUENCE: 58
atggccctcc ctgtcaccgc cctgctgctt ccgctggctc ttctgctcca cgccgctcgg    60
```

```
ccc                                                                                63

SEQ ID NO: 59           moltype = AA   length = 21
FEATURE                 Location/Qualifiers
REGION                  1..21
                        note = Synthetic polypeptide
source                  1..21
                        mol_type = protein
                        organism = synthetic construct
SEQUENCE: 59
MALPVTALLL PLALLLHAAR P                                                            21

SEQ ID NO: 60           moltype = DNA   length = 63
FEATURE                 Location/Qualifiers
misc_feature            1..63
                        note = Synthetic polynucleotide
source                  1..63
                        mol_type = other DNA
                        organism = synthetic construct
SEQUENCE: 60
atggccctgc ccgtgactgc gctcctgctt ccgttggccc tgctcctgca tgccgccaga              60
cct                                                                                63

SEQ ID NO: 61           moltype = DNA   length = 63
FEATURE                 Location/Qualifiers
misc_feature            1..63
                        note = Synthetic polynucleotide
source                  1..63
                        mol_type = other DNA
                        organism = synthetic construct
SEQUENCE: 61
atggccttac cagtgaccgc cttgctcctg ccgctggcct tgctgctcca cgccgccagg              60
ccg                                                                                63

SEQ ID NO: 62           moltype = DNA   length = 63
FEATURE                 Location/Qualifiers
misc_feature            1..63
                        note = Synthetic polynucleotide
source                  1..63
                        mol_type = other DNA
                        organism = synthetic construct
SEQUENCE: 62
atggcacttc ccgtcaccgc cctgctgctc ccactcgccc tccttctgca cgccgcccgc              60
ccc                                                                                63

SEQ ID NO: 63           moltype = DNA   length = 63
FEATURE                 Location/Qualifiers
misc_feature            1..63
                        note = Synthetic polynucleotide
source                  1..63
                        mol_type = other DNA
                        organism = synthetic construct
SEQUENCE: 63
atggccctgc cagtgaccgc gctcctgctg ccsctggctc tgctgcttca cgcggcccgg              60
cct                                                                                63

SEQ ID NO: 64           moltype = DNA   length = 207
FEATURE                 Location/Qualifiers
misc_feature            1..207
                        note = Synthetic polynucleotide
source                  1..207
                        mol_type = other DNA
                        organism = synthetic construct
SEQUENCE: 64
accactaccc cagcaccgag gccacccacc ccggctccta ccatcgcctc ccagcctctg              60
tccctgcgtc cggaggcatg tagacccgca gctggtgggg ccgtgcatac ccggggtctt             120
gacttcgcct gcgatatcta catttgggcc cctctggctg gtacttgcgg ggtcctgctg             180
ctttcactcg tgatcactct ttactgt                                                    207

SEQ ID NO: 65           moltype = AA   length = 69
FEATURE                 Location/Qualifiers
REGION                  1..69
                        note = Synthetic polypeptide
source                  1..69
                        mol_type = protein
                        organism = synthetic construct
SEQUENCE: 65
TTTPAPRPPT PAPTIASQPL SLRPEACRPA AGGAVHTRGL DFACDIYIWA PLAGTCGVLL              60
LSLVITLYC                                                                          69
```

```
SEQ ID NO: 66           moltype = DNA  length = 207
FEATURE                 Location/Qualifiers
misc_feature            1..207
                        note = Synthetic polynucleotide
source                  1..207
                        mol_type = other DNA
                        organism = synthetic construct
SEQUENCE: 66
actaccaccc cggccccgcg gcccccctaca ccggcaccga ctattgccag ccagcctctc       60
tcgctgcggc cggaggcctg ccgcccagcc gccggcggag ccgtgcacac ccgcggtctg      120
gacttcgcgt gcgatatcta catctgggct ccgctggccg ggacttgtgg cgtgctgctg      180
ctgtctctgg tcatcacact gtactgc                                          207

SEQ ID NO: 67           moltype = DNA  length = 207
FEATURE                 Location/Qualifiers
misc_feature            1..207
                        note = Synthetic polynucleotide
source                  1..207
                        mol_type = other DNA
                        organism = synthetic construct
SEQUENCE: 67
accacgacgc cagcgccgcg accaccaaca ccggcgccca ccatcgcgtc gcagcccctg       60
tccctgcgcc cagaggcgtg ccggccagcg gcggggggcg cagtgcacac gaggggggctg    120
gacttcgcct gtgatatcta catctgggcg cccttggccg ggacttgtgg ggtccttctc     180
ctgtcactgg ttatcaccct ttactgc                                         207

SEQ ID NO: 68           moltype = DNA  length = 207
FEATURE                 Location/Qualifiers
misc_feature            1..207
                        note = Synthetic polynucleotide
source                  1..207
                        mol_type = other DNA
                        organism = synthetic construct
SEQUENCE: 68
accaccaccc ctgcgcctcg gcctcctacc ccggctccca ctatcgcgag ccagccgctg       60
agcctgcggc ctgaggcttg ccgaccggcc gctggcggcg ccgtgcatac tcggggcctc     120
gactttgcct gtgacatcta catctgggcc cccctggccg gaacgtgcgg agtgctgctg     180
ctgtcgctgg tcattaccct gtattgc                                         207

SEQ ID NO: 69           moltype = DNA  length = 126
FEATURE                 Location/Qualifiers
misc_feature            1..126
                        note = Synthetic polynucleotide
source                  1..126
                        mol_type = other DNA
                        organism = synthetic construct
SEQUENCE: 69
aagcgcggtc ggaagaagct gctgtacatc tttaagcaac ccttcatgag gcctgtgcag       60
actactcaag aggaggacgg ctgttcatgc cggttcccag aggaggagga aggcggctgc     120
gaactg                                                                126

SEQ ID NO: 70           moltype = AA   length = 42
FEATURE                 Location/Qualifiers
REGION                  1..42
                        note = Synthetic polypeptide
source                  1..42
                        mol_type = protein
                        organism = synthetic construct
SEQUENCE: 70
KRGRKKLLYI FKQPFMRPVQ TTQEEDGCSC RFPEEEEGGC EL                          42

SEQ ID NO: 71           moltype = DNA  length = 126
FEATURE                 Location/Qualifiers
misc_feature            1..126
                        note = Synthetic polynucleotide
source                  1..126
                        mol_type = other DNA
                        organism = synthetic construct
SEQUENCE: 71
aaacggggca gaaagaaact cctgtatata ttcaaacaac catttatgag accagtacaa       60
actactcaag aggaagatgg ctgtagctgc cgatttccag aagaagaaga aggaggatgt     120
gaactg                                                                126

SEQ ID NO: 72           moltype = DNA  length = 126
FEATURE                 Location/Qualifiers
misc_feature            1..126
                        note = Synthetic polynucleotide
source                  1..126
```

```
                        mol_type = other DNA
                        organism = synthetic construct
SEQUENCE: 72
aagcgcggaa gaaagaagct gctctacatc ttcaagcaac ccttcatgcg gcctgtgcag    60
accacccagg aagaggatgg ctgctcctgc cggttcccgg aggaagaaga gggcggatgc   120
gaactg                                                              126

SEQ ID NO: 73           moltype = DNA   length = 126
FEATURE                 Location/Qualifiers
misc_feature            1..126
                        note = Synthetic polynucleotide
source                  1..126
                        mol_type = other DNA
                        organism = synthetic construct
SEQUENCE: 73
aaacgcggaa ggaagaagct gttgtacatt ttcaagcagc ccttcatgcg cccggtgcaa    60
actactcagg aggaagatgg ctgttcctgt cggttcccccg aagaggaaga aggcggctgc  120
gagttg                                                              126

SEQ ID NO: 74           moltype = DNA   length = 336
FEATURE                 Location/Qualifiers
misc_feature            1..336
                        note = Synthetic polynucleotide
source                  1..336
                        mol_type = other DNA
                        organism = synthetic construct
SEQUENCE: 74
cgcgtgaaat tcagccgcag cgcagatgct ccagcctacc agcaggggca gaaccagctc    60
tacaacgaac tcaatcttgg tcggagagag gagtacgacg tgctggacaa gcggagagga   120
cgggacccag aaatgggcgg gaagccgcgc agaaagaatc cccaagagg cctgtacaac    180
gagctccaaa aggataagat ggcagactgtac tatgcgaga ttggtatgaa agggaacgc   240
agaagaggca aagccacga cggactgtac cagggactca gcaccgccac caaggacacc   300
tatgacgctc ttcacatgca ggccctgccg cctcgg                             336

SEQ ID NO: 75           moltype = AA   length = 112
FEATURE                 Location/Qualifiers
REGION                  1..112
                        note = Synthetic polypeptide
source                  1..112
                        mol_type = protein
                        organism = synthetic construct
SEQUENCE: 75
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 76           moltype = DNA   length = 336
FEATURE                 Location/Qualifiers
misc_feature            1..336
                        note = Synthetic polynucleotide
source                  1..336
                        mol_type = other DNA
                        organism = synthetic construct
SEQUENCE: 76
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336

SEQ ID NO: 77           moltype = DNA   length = 336
FEATURE                 Location/Qualifiers
misc_feature            1..336
                        note = Synthetic polynucleotide
source                  1..336
                        mol_type = other DNA
                        organism = synthetic construct
SEQUENCE: 77
cgcgtgaagt tcagccgaag cgccgacgcc ccggcctacc agcagggcca gaaccaactg    60
tacaacgaac tcaacctggg tcggagagaa gagtacgacg tgctggacaa agacgcggc   120
agggaccccg agatgggcgg aaagcctcgc cgcaagaacc cgcaggaggg cctctacaac   180
gagctgcaga aggacaagat ggccgaagcc tactcagaga tcggcatgaa gggggagcgg   240
aggcgcggga agggccacga cggttttgtac caaggacttt ccactgcgac caaggacacc   300
tacgatgccc tccatatgca agccctgccg ccccgg                             336

SEQ ID NO: 78           moltype = DNA   length = 336
FEATURE                 Location/Qualifiers
misc_feature            1..336
                        note = Synthetic polynucleotide
```

```
source                   1..336
                         mol_type = other DNA
                         organism = synthetic construct
SEQUENCE: 78
agggtcaagt tctcccggtc cgccgatgct cccgcctacc aacaggggca gaaccagctt    60
tataacgaac tgaacctggg caggagggag gaatatgatg tgttggataa gcgccggggc   120
cgggacccag aaatgggggg aaagcccaga agaaagaacc ctcaagaggg actttacaac   180
gaattgcaga aagacaaaat ggccgaggcc tactccgaga ttgggatgaa gggcgaaaga   240
cggagaggaa aggggcacga cgggctctac cagggactca gcaccgccac caaagatacc   300
tacgacgccc tgcatatgca ggcgctgccg ccgcgc                             336

SEQ ID NO: 79            moltype = DNA  length = 21
FEATURE                  Location/Qualifiers
misc_feature             1..21
                         note = Synthetic polynucleotide
source                   1..21
                         mol_type = other DNA
                         organism = synthetic construct
SEQUENCE: 79
ttggcagaag ccgccgcgaa a                                              21

SEQ ID NO: 80            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 80
LAEAAAK                                                               7

SEQ ID NO: 81            moltype = DNA  length = 45
FEATURE                  Location/Qualifiers
misc_feature             1..45
                         note = Synthetic polynucleotide
source                   1..45
                         mol_type = other DNA
                         organism = synthetic construct
SEQUENCE: 81
ggtggaggtg gcagcggagg aggtgggtcc ggcggtggag gaagc                    45

SEQ ID NO: 82            moltype = AA  length = 15
FEATURE                  Location/Qualifiers
REGION                   1..15
                         note = Synthetic polypeptide
source                   1..15
                         mol_type = protein
                         organism = synthetic construct
SEQUENCE: 82
GGGGSGGGGS GGGGS                                                     15

SEQ ID NO: 83            moltype = DNA  length = 45
FEATURE                  Location/Qualifiers
misc_feature             1..45
                         note = Synthetic polynucleotide
source                   1..45
                         mol_type = other DNA
                         organism = synthetic construct
SEQUENCE: 83
ggcggaggcg ggagcggagg aggaggctct ggcggaggag gaagc                    45

SEQ ID NO: 84            moltype = DNA  length = 45
FEATURE                  Location/Qualifiers
misc_feature             1..45
                         note = Synthetic polynucleotide
source                   1..45
                         mol_type = other DNA
                         organism = synthetic construct
SEQUENCE: 84
ggcggtggag gctcgggggg gggcggctca ggaggaggcg gctca                    45

SEQ ID NO: 85            moltype = DNA  length = 66
FEATURE                  Location/Qualifiers
misc_feature             1..66
                         note = Synthetic polynucleotide
source                   1..66
                         mol_type = other DNA
                         organism = synthetic construct
SEQUENCE: 85
```

```
ggaagcggag ctactaactt cagcctgctg aagcaggctg gagacgtgga ggagaaccct    60
ggacct                                                                66

SEQ ID NO: 86           moltype = AA  length = 22
FEATURE                 Location/Qualifiers
REGION                  1..22
                        note = Synthetic polypeptide
source                  1..22
                        mol_type = protein
                        organism = synthetic construct
SEQUENCE: 86
GSGATNFSLL KQAGDVEENP GP                                              22

SEQ ID NO: 87           moltype = DNA  length = 66
FEATURE                 Location/Qualifiers
misc_feature            1..66
                        note = Synthetic polynucleotide
source                  1..66
                        mol_type = other DNA
                        organism = synthetic construct
SEQUENCE: 87
ggttccggag ctaccaactt ctcgctgttg aagcaggccg gagatgtcga ggaaaacccg    60
ggacct                                                                66

SEQ ID NO: 88           moltype = DNA  length = 15
FEATURE                 Location/Qualifiers
misc_feature            1..15
                        note = Synthetic polynucleotide
source                  1..15
                        mol_type = other DNA
                        organism = synthetic construct
SEQUENCE: 88
ggtggaggtg gcagc                                                      15

SEQ ID NO: 89           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 89
GGGGS                                                                 5

SEQ ID NO: 90           moltype = AA  length = 284
FEATURE                 Location/Qualifiers
REGION                  1..284
                        note = Synthetic polypeptide
source                  1..284
                        mol_type = protein
                        organism = synthetic construct
SEQUENCE: 90
NWVNVISDLK KIEDLIQSMH IDATLYTESD VHPSCKVTAM KCFLLELQVI SLESGDASIH    60
DTVENLIILA NNSLSSNGNV TESGCKECEE LEEKNIKEFL QSFVHIVQMF INTSITCPPP   120
MSVEHADIWV KSYSLYSRER YICNSGFKRK AGTSSLTECV LNKATNVAHW TTPSLKCIRD   180
PALVHQRPAP PSTVTTAGVT PQPESLSPSG KEPAASSPSS NNTAATTAAI VPGSQLMPSK   240
SPSTGTTEIS SHESSHGTPS QTTAKNWELT ASASHQPPGV YPQG                    284
```

CD19 AND CD22 CHIMERIC ANTIGEN RECEPTORS AND USES THEREOF

CROSS-REFERENCE TO RELATED APPLICATIONS AND INCORPORATION OF SEQUENCE LISTING

This application is a divisional of U.S. patent application Ser. No. 17/104,961, filed Nov. 25, 2020, now U.S. Pat. No. 11,975,026, which claims priority to U.S. Provisional Patent Appln. No. 62/940,600 filed Nov. 26, 2019, which is incorporated into this application by reference in its entirety. The sequence listing that is contained in the filed named "PAT058691-US-DIV_ST26 SQL.xml," which is 152,375 bytes and was created on Mar. 25, 2024, is filed herewith and incorporated herein by reference.

FIELD OF THE INVENTION

The present invention relates generally to the use of T cells or natural killer (NK) cells engineered to express a Chimeric Antigen Receptor (CAR) comprising a Cluster of Differentiation 19 protein (CD19) binding domain and/or a Cluster of Differentiation 22 protein (CD22) binding domain to treat a disease associated with expression of CD19 and/or CD22.

BACKGROUND OF THE INVENTION

Many patients with B cell malignancies are incurable with standard therapy. In addition, traditional treatment options often have serious side effects. Attempts have been made in cancer immunotherapy, however, several obstacles render this a very difficult goal to achieve clinical effectiveness. Although hundreds of so-called tumor antigens have been identified, these are generally derived from self and thus are poorly immunogenic. Furthermore, tumors use several mechanisms to render themselves hostile to the initiation and propagation of immune attack.

Recent developments using chimeric antigen receptor (CAR) modified autologous T cell (CART) therapy, which relies on redirecting T cells to a suitable cell-surface molecule on cancer cells such as B cell malignancies, show promising results in harnessing the power of the immune system to treat B cell malignancies and other cancers (see, e.g., Sadelain et al., Cancer Discovery 3:388-398 (2013)). The clinical results of the murine derived CART19 (i.e., "CTL019") have shown promise in establishing complete remissions in patients suffering with CLL as well as in childhood ALL (see, e.g., Kalos et al., Sci Transl Med 3:95ra73 (2011), Porter et al., NEJM 365:725-733 (2011), Grupp et al., NEJM 368:1509-1518 (2013)). Besides the ability for the chimeric antigen receptor on the genetically modified T cells to recognize and destroy the targeted cells, a successful therapeutic T cell therapy needs to have the ability to proliferate and persist over time, in order to survey for leukemic relapse. The variable quality of T cells, resulting from anergy, suppression, or exhaustion, will have effects on CAR-transformed T cells' performance, over which skilled practitioners have limited control at this time. To be effective, CAR-transformed patient T cells need to persist and maintain the ability to proliferate in response to the cognate antigen.

SUMMARY

The disclosure features, inter alia, novel nucleic acid molecules encoding Chimeric Antigen Receptor (CAR) molecules which comprise a first CAR comprising a CD22 CAR and a second CAR comprising a CD19 CAR, e.g., dual CARs as described herein. In some embodiments, a CD22 CAR comprises a CD22 antigen binding domain, and a first transmembrane domain; a first co-stimulatory signaling domain; and/or a first primary signaling domain. In some embodiments, the CD19 CAR comprises a CD19 antigen binding domain, and a second transmembrane domain; a second co-stimulatory signaling domain; and/or a second primary signaling domain. In some embodiments of a CAR molecule disclosed herein, a CAR molecule comprises two identical polypeptide sequences, e.g., of a first and second transmembrane domain; a first and second co-stimulatory domain, and/or a first and second primary signaling domain, which polypeptide sequences are encoded by different nucleotide sequences. Also disclosed herein are methods of using said CAR molecules. Further disclosed herein are CARs comprising a bispecific antigen binding domain which comprises a CD22 antigen binding domain and a CD19 antigen binding domain, e.g., tandem CARs as described herein. Nucleic acids encoding the compositions, host cells, vectors, as well as methods of making and using, are also disclosed.

Dual CARs

In an aspect, the disclosure provides a nucleic acid molecule encoding a chimeric antigen receptor (CAR) molecule, wherein said CAR molecule comprises:
- (a) a first CAR comprising a first antigen binding domain which binds to CD22; a first transmembrane domain; a first co-stimulatory signaling domain; and/or a first primary signaling domain; and
- (b) a second CAR comprising a second antigen binding domain which binds to CD19; a second transmembrane domain; a second co-stimulatory signaling domain; and/or a second primary signaling domain, wherein:
- (i) the first transmembrane domain and the second transmembrane domain comprise the amino acid sequence of SEQ ID NO: 65 or an amino acid sequence with at least 90% identity thereto, optionally wherein a nucleotide sequence that encodes the first transmembrane domain and is comprised in the nucleic acid molecule is different from a nucleotide sequence that encodes the second transmembrane domain and is comprised in the nucleic acid molecule;
- (ii) the first co-stimulatory signaling domain and the second co-stimulatory signaling domain comprise the amino acid sequence of any one of SEQ ID NO: 70 or an amino acid sequence with at least 90% identity thereto, optionally wherein a nucleotide sequence that encodes the first co-stimulatory signaling domain and is comprised in the nucleic acid molecule is different from a nucleotide sequence that encodes the second co-stimulatory signaling domain and is comprised in the nucleic acid molecule; and/or
- (iii) the first primary signaling domain and the second primary signaling domain comprise the amino acid sequence of SEQ ID NO: 75 or an amino acid sequence with at least 90% identity thereto, optionally wherein a nucleotide sequence that encodes the primary signaling domain and is comprised in the nucleic acid molecule is different from a nucleotide sequence that encodes the second primary signaling domain and is comprised in the nucleic acid molecule.

In an embodiment, a first CAR comprises a first antigen binding domain which binds to CD22, a first transmembrane domain, and a first co-stimulatory signaling domain. In an embodiment, a first CAR comprises a first antigen binding domain which binds to CD22, a first transmembrane domain; and a first primary signaling domain. In an embodiment, the first CAR comprises a first antigen binding domain which binds to CD22, a first transmembrane domain, a first co-stimulatory signaling domain, and a first primary signaling domain.

In an embodiment, a second CAR comprises a second antigen binding domain which binds to CD19; a second transmembrane domain; and a second co-stimulatory signaling domain. In an embodiment, a second CAR comprises a second antigen binding domain which binds to CD19; a second transmembrane domain; and a second primary signaling domain. In an embodiment, a second CAR comprises a second antigen binding domain which binds to CD19; a second transmembrane domain; a second co-stimulatory signaling domain; and a second primary signaling domain.

In an embodiment, a CD22 antigen binding domain comprises one or more (e.g., all three) light chain complementarity determining region 1 (LC CDR1), light chain complementarity determining region 2 (LC CDR2), and light chain complementarity determining region 3 (LC CDR3) of a CD22 binding domain described herein, e.g., in Tables 1A, 2A or 3A; and/or one or more (e.g., all three) heavy chain complementarity determining region 1 (HC CDR1), heavy chain complementarity determining region 2 (HC CDR2), and heavy chain complementarity determining region 3 (HC CDR3) of a CD22 binding domain described herein, e.g., in Tables 1A, 2A or 3A. In an embodiment, a CD22 binding domain comprises the HC CDR1, HC CDR2, HC CDR3, LC CDR1, LC CDR2, LC CDR3 comprising the amino acid sequence of (i) SEQ ID NOs: 20, 21, 22, 28, 29, and 30, respectively; (ii) SEQ ID NOs: 23, 24, 22, 31, 32, and 33, respectively; or (iii) SEQ ID NOs: 25, 26, 27, 34, 32, and 30, respectively.

In an embodiment, a CD22 antigen binding domain comprises an scFv which comprises an amino acid sequence having at least one, two or three modifications (e.g., substitutions) but not more than 30, 20 or 10 modifications (e.g., substitutions) of a CD22 scFv sequence provided in Table 1A or 3A, e.g., SEQ ID NO: 50, 53, or 55. In an embodiment, the CD22 antigen binding domain comprises an scFv which comprises an amino acid sequence with at least 95% identity to a CD22 scFv sequence provided in Table 1A or 3A, e.g., SEQ ID NO: 50, 53, or 55. In an embodiment, the CD22 antigen binding domain comprises an scFv which comprises the amino acid sequence of a CD22 scFv sequence provided in Table 1A or 3A, e.g., SEQ ID NO: 50, 53, or 55.

In an embodiment, a CD22 antigen binding domain comprises an scFv which is encoded by a nucleotide sequence having at least 95%, 96%, 97%, 98%, 99%, or 100% identity to a CD22 scFv sequence provided in Table 1A or 3A, e.g., SEQ ID NO: 49, 51, 52, 54, 56, or 57. In an embodiment, the CD19 antigen binding domain comprises one or more (e.g., all three) light chain complementarity determining region 1 (LC CDR1), light chain complementarity determining region 2 (LC CDR2), and light chain complementarity determining region 3 (LC CDR3) of a CD19 antigen binding domain described herein, e.g., in Tables 1A, 2A, 3A, or 5A; and/or one or more (e.g., all three) heavy chain complementarity determining region 1 (HC CDR1), heavy chain complementarity determining region 2 (HC CDR2), and heavy chain complementarity determining region 3 (HC CDR3) of a CD19 antigen binding domain described herein, e.g., in Tables 1A, 2A, 3A, or 5A. In an embodiment, a CD19 binding domain comprises the HC CDR1, HC CDR2, HC CDR3, LC CDR1, LC CDR2, LC CDR3 comprising the amino acid sequence of (i) SEQ ID NOs: 35, 36, 39, 40, 41, and 42, respectively; (ii) SEQ ID NOs: 35, 37, 39, 40, 41, and 42, respectively; or (iii) SEQ ID NOs: 35, 38, 39, 40, 41, and 42, respectively. In an embodiment, a CD19 antigen binding domain comprises an scFv comprising an amino acid sequence having at least one, two or three modifications (e.g., substitutions) but not more than 30, 20 or 10 modifications (e.g., substitutions) of a CD19 scFv sequence provided in Tables 1A, 3A, or 5A, e.g., SEQ ID NO: 44 or 47. In an embodiment, a CD19 antigen binding domain comprises an scFv comprising an amino acid sequence with at least 95% identity to a CD19 scFv sequence provided in Tables 1A, 3A, or 5A, e.g., SEQ ID NO: 44 or 47. In an embodiment, a CD19 antigen binding domain comprises an scFv comprising the amino acid sequence of a CD19 scFv sequence provided in Tables 1A, 3A, or 5A, e.g., SEQ ID NO: 44 or 47. In an embodiment, the CD19 antigen binding domain comprises an scFv encoded by a nucleotide sequence having at least 95%, 96%, 97%, 98%, 99%, or 100% identity to a CD19 scFv sequence provided in Tables 1A, 3A, or 5A, e.g., SEQ ID NO: 43, 45, 46, or 48.

In an embodiment of a nucleic acid encoding a CAR molecule disclosed herein, the nucleotide sequence encoding the first transmembrane domain is at least 1%, 5%, 10%, 20%, 30%, 40%, 50%, 60%, 70%, 80%, 85%, 90%, 95%, or 100% different from the nucleotide sequence encoding the second transmembrane domain. In an embodiment, the nucleotide sequence encoding the first transmembrane domain differs by at least 1 nucleotide, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, 150 nucleotides, 200 nucleotides or all nucleotides from the nucleotide sequence encoding the second transmembrane domain.

In an embodiment of a nucleic acid encoding a CAR molecule disclosed herein, the nucleotide sequence encoding the first co-stimulatory signaling domain is at least 1%, 5%, 10%, 20%, 30%, 40%, 50%, 60%, 70%, 80%, 85%, 90%, 95%, or 100% different from the nucleotide sequence encoding the second co-stimulatory signaling domain. In an embodiment, the nucleotide sequence encoding the first co-stimulatory signaling domain differs by at least 1 nucleotide, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, 150 nucleotides, 200 nucleotides or all nucleotides from the nucleotide sequence encoding the second co-stimulatory signaling domain.

In an embodiment of a nucleic acid encoding a CAR molecule disclosed herein, the nucleotide sequence encoding the first primary signaling domain is at least 1%, 5%, 10%, 20%, 30%, 40%, 50%, 60%, 70%, 80%, 85%, 90%, 95%, or 100% different from the nucleotide sequence encoding the second primary signaling domain. In an embodiment, the nucleotide sequence encoding the first primary signaling domain differs by at least 1 nucleotide, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, 150 nucleotides, 200 nucleotides or all nucleotides from the nucleotide sequence encoding the second primary signaling domain.

In an aspect of a nucleic acid sequence encoding a CAR molecule disclosed herein, the CAR molecule is encoded by the nucleotide sequence of SEQ ID NO: 11, 15 or 19, or nucleotide sequence having at least 80%, 85%, 90%, 95%, 96%, 97%, 98%, or 99% identity thereto. In an aspect, a CAR molecule disclosed herein comprises the amino acid sequence of SEQ ID NO: 12 or 16, an amino acid sequence having at least 90% identity thereto.

In an aspect, the disclosure provides a cell (e.g., an immune effector cell) comprising a nucleic acid sequence encoding a chimeric antigen receptor (CAR) molecule, wherein said CAR molecule comprises:
(a) a first CAR comprising a first antigen binding domain which binds to CD22 and a first transmembrane domain; a first co-stimulatory signaling domain; and/or a first primary signaling domain; and
(b) a second CAR comprising a second antigen binding domain which binds to CD19 and a second transmembrane domain; a second co-stimulatory signaling domain; and/or a second primary signaling domain, wherein:
(i) the first transmembrane domain and the second transmembrane domain comprise the amino acid sequence of SEQ ID NO: 65 or an amino acid sequence with at least 90% identity thereto, optionally wherein a nucleotide sequence that encodes the first transmembrane domain and is comprised in the nucleic acid molecule is different from a nucleotide sequence that encodes the second transmembrane domain and is comprised in the nucleic acid molecule;
(ii) the first co-stimulatory signaling domain and the second co-stimulatory signaling domain comprise the amino acid sequence of SEQ ID NO: 70 or an amino acid sequence with at least 90% identity thereto, optionally wherein a nucleotide sequence that encodes the first co-stimulatory signaling domain and is comprised in the nucleic acid molecule is different from a nucleotide sequence that encodes the second co-stimulatory signaling domain and is comprised in the nucleic acid molecule; and/or
(iii) the first primary signaling domain and the second primary signaling domain comprise the amino acid sequence of SEQ ID NO: 75 or an amino acid sequence with at least 90% identity thereto, optionally wherein a nucleotide sequence that encodes the first primary signaling domain and is comprised in the nucleic acid molecule is different from a nucleotide sequence that encodes the second primary signaling domain and is comprised in the nucleic acid molecule.

In one aspect, the first primary signaling domain and the second primary signaling domain comprise the amino acid sequence of SEQ ID NO: 108 or an amino acid sequence with at least 90% identity thereto, optionally wherein a nucleotide sequence that encodes the first primary signaling domain and is comprised in the nucleic acid molecule is different from a nucleotide sequence that encodes the second primary signaling domain and is comprised in the nucleic acid molecule.

In another aspect, provided herein is a cell (e.g., an immune effector cell) comprising a chimeric antigen receptor (CAR) molecule, wherein said CAR molecule comprises:
(a) a first CAR comprising a first antigen binding domain which binds to CD22 and a first transmembrane domain; a first co-stimulatory signaling domain; and/or a first primary signaling domain; and
(b) a second CAR comprising a second antigen binding domain which binds to CD19 and a second transmembrane domain; a second co-stimulatory signaling domain; and/or a second primary signaling domain, wherein:
(i) the first transmembrane domain and the second transmembrane domain comprise the amino acid sequence of SEQ ID NO: 65 or an amino acid sequence with at least 90% identity thereto, optionally wherein a nucleotide sequence that encodes the first transmembrane domain and is comprised in a nucleic acid molecule is different from a nucleotide sequence that encodes the second transmembrane domain and is comprised in the nucleic acid molecule;
(ii) the first co-stimulatory signaling domain and the second co-stimulatory signaling domain comprise the amino acid sequence of SEQ ID NO: 70 or an amino acid sequence with at least 90% identity thereto, optionally wherein a nucleotide sequence that encodes the first co-stimulatory signaling domain and is comprised in a nucleic acid molecule is different from a nucleotide sequence that encodes the second co-stimulatory signaling domain and is comprised in the nucleic acid molecule; and/or
(iii) the first primary signaling domain and the second primary signaling domain comprise the amino acid sequence of SEQ ID NOs: 75 or an amino acid sequence with at least 90% identity thereto, optionally wherein a nucleotide sequence that encodes the first primary signaling domain and is comprised in a nucleic acid molecule is different from a nucleotide sequence that encodes the second primary signaling domain and is comprised in the nucleic acid molecule.

In an embodiment, the cell is an immune effector cell, e.g., T cell (e.g., CD3+, CD4+ or CD8+ T cell), or an NK cell. In an embodiment, the cell is a human cell.

In an aspect, provided herein is a method of providing anti-tumor immunity, comprising administering to a subject in need thereof, an effective amount of a cell, e.g., a population of immune effector cells, comprising, e.g., expressing, a CAR molecule disclosed herein, e.g., a dual CAR molecule disclosed herein.

In another aspect, the disclosure provides a method of treating a subject having a disease associated with an antigen (e.g., CD19 and/or CD22), comprising administering to the subject in need thereof, an effective amount of a cell, e.g., a population of immune effector cells, comprising, e.g., expressing, a CAR molecule disclosed herein, e.g., a dual CAR molecule disclosed herein.

Tandem CARs

In an aspect, the disclosure provides a bispecific antigen binding domain, comprising a first antigen binding domain which binds to CD22 and a second antigen binding domain which binds to CD19.

In another aspect, provided herein is a chimeric antigen receptor (CAR), comprising a bispecific antigen binding domain described herein.

In yet another aspect, the disclosure provides a nucleic acid encoding a chimeric antigen receptor (CAR), which comprises a bispecific antigen binding domain described herein.

In some embodiments of the bispecific antigen binding domain described herein, e.g., a CAR comprising the bispecific antigen binding domain, or nucleic acid encoding a CAR comprising the bispecific antigen binding domain, the first antigen binding domain can be upstream (e.g., in an N-terminal orientation) of the second antigen binding domain, or the first antigen binding domain can be downstream (e.g., in a C-terminal orientation) of the second antigen binding domain.

In some embodiments, each of the first antigen binding domain and second antigen binding domains comprise a scFv, e.g., a light chain variable (VL) domain and a heavy chain variable (VH) domain. In some embodiments, the first antigen binding domain comprises an scFv comprising a first VH (VH1) and a first VL (VL1). In some embodiments, the second antigen binding domain comprises an scFv comprising a second VH (VH2) and a second VL (VL2). In some embodiments, a bispecific antigen binding domain has any one of the following N terminal to C terminal configurations: VL1-VH1-VH2-VL2; VH1-VL1-VH2-VL2; VL1-VH1-VL2-VH2; VH1-VL1-VL2-VH2, VH2-VL2-VL1-VH1; VL2-VH2-VL1-VH1; VH2-VL2-VH1-VL1; or VL2-VH2-VH1-VL1.

In an aspect, a CAR comprising a bispecific antigen binding domain comprises the amino acid sequence of SEQ ID NO: 2 and is encoded by the nucleic acid sequence of SEQ ID NO: 1. In another aspect, a CAR comprising a bispecific antigen binding domain comprises the amino acid sequence of SEQ ID NO: 4 and is encoded by the nucleic acid sequence of SEQ ID NO: 3.

In another aspect, a CAR comprising a bispecific antigen binding domain comprises the amino acid sequence of SEQ ID NO: 6 and is encoded by the nucleic acid sequence of SEQ ID NO: 5. In another aspect, a CAR comprising a bispecific antigen binding domain comprises the amino acid sequence of SEQ ID NO: 8 and is encoded by the nucleic acid sequence of SEQ ID NO: 7. In another aspect, a CAR comprising a bispecific antigen binding domain comprises the amino acid sequence of SEQ ID NO: 10 and is encoded by the nucleic acid sequence of SEQ ID NO: 9. In an aspect, the disclosure provides a vector comprising a nucleic acid molecule encoding a CAR molecule disclosed herein, a nucleic acid encoding a bispecific antigen binding domain disclosed herein, or a nucleic acid encoding a CAR comprising a bispecific antigen binding domain disclosed herein.

In another aspect, provided herein is a pharmaceutical composition comprising a nucleic acid encoding a CAR molecule disclosed herein or a pharmaceutical composition comprising CAR molecule disclosed herein. In some embodiments, the pharmaceutical composition comprises an excipient, a carrier, a diluent and/or a stabilizer.

In yet another aspect, the disclosure provides a pharmaceutical composition comprising a bispecific antigen binding domain disclosed herein, a CAR comprising a bispecific antigen binding domain disclosed herein, or a CAR nucleic acid encoding a bispecific antigen binding domain disclosed herein. In some embodiments, the pharmaceutical composition comprises an excipient, a carrier, a diluent and/or a stabilizer.

In an aspect, provided herein is a method of providing anti-tumor immunity, comprising administering to a subject in need thereof, an effective amount of a cell, e.g., a population of immune effector cells, comprising, e.g., expressing, a CAR disclosed herein, e.g., a tandem CAR disclosed herein.

In another aspect, the disclosure provides a method of treating a subject having a disease associated with an antigen (e.g., CD19 and/or CD22), comprising administering to the subject in need thereof, an effective amount of a cell, e.g., a population of immune effector cells, comprising, e.g., expressing, a CAR disclosed herein, e.g., a tandem CAR disclosed herein. Those skilled in the art will recognize or be able to ascertain using no more than routine experimentation, many equivalents to the specific embodiments of the invention described herein. Such equivalents are intended to be encompassed by the following enumerated embodiments.

ENUMERATED EMBODIMENTS

1. A nucleic acid molecule encoding a chimeric antigen receptor (CAR) molecule, wherein said CAR molecule comprises:
   (a) a first CAR comprising a first antigen binding domain which binds to CD22; a first transmembrane domain; a first co-stimulatory signaling domain; and/or a first primary signaling domain; and
   (b) a second CAR comprising a second antigen binding domain which binds to CD19; a second transmembrane domain; a second co-stimulatory domain; and/or a second primary signaling domain,
   wherein:
   (i) the first transmembrane domain and the second transmembrane domain comprise the amino acid sequence of SEQ ID NO: 65 or an amino acid sequence with at least 90% identity thereto, optionally wherein a nucleotide sequence that encodes the first transmembrane domain and is comprised in the nucleic acid molecule is different from a nucleotide sequence that encodes the second transmembrane domain and is comprised in the nucleic acid molecule;
   (ii) the first co-stimulatory signaling domain and the second co-stimulatory signaling domain comprise the amino acid sequence of SEQ ID NO: 70 or an amino acid sequence with at least 90% identity thereto, optionally wherein a nucleotide sequence that encodes the first co-stimulatory signaling domain and is comprised in the nucleic acid molecule is different from a nucleotide sequence that encodes the second co-stimulatory signaling domain and is comprised in the nucleic acid molecule; and/or
   (iii) the first primary signaling domain and the second primary signaling domain comprise the amino acid sequence of SEQ ID NO: 75 or an amino acid sequence with at least 90% identity thereto, optionally wherein a nucleotide sequence that encodes the primary signaling domain and is comprised in the nucleic acid molecule is different from a nucleotide sequence that encodes the second primary signaling domain and is comprised in the nucleic acid molecule.

2. The nucleic acid molecule of embodiment 1, wherein the first CAR comprises:
   a first antigen binding domain which binds to CD22, a first transmembrane domain, and a first co-stimulatory signaling domain;
   a first antigen binding domain which binds to CD22, a first transmembrane domain; and a first primary signaling domain; or
   a first antigen binding domain which binds to CD22, a first transmembrane domain, a first co-stimulatory signaling domain, and a first primary signaling domain.

3. The nucleic acid molecule of embodiment 1 or 2, wherein the second CAR comprises:
   a second antigen binding domain which binds to CD19; a second transmembrane domain; and a second co-stimulatory signaling domain;
   a second antigen binding domain which binds to CD19; a second transmembrane domain; and a second primary signaling domain; or a second antigen binding domain which binds to CD19; a second transmembrane domain; a second co-stimulatory signaling domain; and a second primary signaling domain.

4. The nucleic acid molecule of any one of the preceding embodiments, wherein the CD22 antigen binding domain comprises:
   one or more (e.g., all three) light chain complementarity determining region 1 (LC CDR1), light chain complementarity determining region 2 (LC CDR2), and light chain complementarity determining region 3 (LC CDR3) of a CD22 binding domain described herein, e.g., in Tables 1A, 2A or 3A; and/or
   one or more (e.g., all three) heavy chain complementarity determining region 1 (HC CDR1), heavy chain complementarity determining region 2 (HC CDR2), and heavy chain complementarity determining region 3 (HC CDR3) of a CD22 binding domain described herein, e.g., in Tables 1A, 2A or 3A.

5. The nucleic acid molecule of embodiment 4, wherein the CD22 antigen binding domain comprises a LC CDR1, LC CDR2 and LC CDR3 of a CD22 binding domain described herein, e.g., in Table 1A, 2A or 3A; and/or a HC CDR1, HC CDR2 and HC CDR3 of a CD22 binding domain described herein, e.g., in Tables 1A, 2A or 3A.

6. The nucleic acid molecule of embodiment 4 or 5, wherein the CD22 antigen binding domain comprises a nucleotide sequence encoding LC CDR1 of SEQ ID NO: 28, 31, or 34, LC CDR2 of SEQ ID NO: 29 or 32; LC CDR3 of SEQ ID NO: 30 or 33; and/or HC CDR1 of SEQ ID NO: 20, 23, or 25, HC CDR2 or SEQ ID NO: 21, 24, or 26; HC CDR3 of SEQ ID NO: 22 or 27.

7. The nucleic acid molecule of any one of embodiments 4 to 6, wherein the CD22 antigen binding domain (e.g., an scFv) comprises a light chain variable (VL) region of a CD22 binding domain described herein, e.g., in Tables 1A or 3A; and/or a heavy chain variable (VH) region of a CD22 binding domain described herein, e.g., in Tables 1A or 3A.

8. The nucleic acid molecule of embodiment 7, wherein the CD22 antigen binding domain comprises a VL region:
   comprising an amino acid sequence having at least one, two or three modifications (e.g., substitutions) but not more than 30, 20 or 10 modifications (e.g., substitutions) of a CD22 VL region sequence provided in Table 1A or 3A;
   comprising an amino acid sequence with at least 95% identity to a CD22 VL region sequence provided in Table 1A or 3A; or
   which is encoded by a nucleotide sequence encoding the amino acid sequence of a CD22 VL region sequence provided in Table 1A or 3A.

9. The nucleic acid molecule of embodiment 7 or 8, wherein the CD22 antigen binding domain comprises a VH region:
   comprising an amino acid sequence having at least one, two or three modifications (e.g., substitutions) but not more than 30, 20 or 10 modifications (e.g., substitutions) of a CD22 VH region sequence provided in Table 1A or 3A;
   comprising an amino acid sequence with at least 95% identity to a CD22 VH region sequence provided in Table 1A or 3A; or
   which is encoded by a nucleotide sequence encoding the amino acid sequence of a CD22 VH region sequence provided in Table 1A or 3A.

10. The nucleic acid molecule of any one of embodiments 7 to 9, wherein the VH and VL regions of the CD22 antigen binding domain are connected by a linker, e.g., a linker with at least 95%, 96%, 97%, 98%, 99% or 100% identity to a linker described herein, e.g. a linker disclosed in Table 4A.

11. The nucleic acid molecule of any one of the preceding embodiments, wherein the CD22 antigen binding domain comprises an scFv which:
    comprises an amino acid sequence having at least one, two or three modifications (e.g., substitutions) but not more than 30, 20 or 10 modifications (e.g., substitutions) of a CD22 scFv sequence provided in Table 1A or 3A, e.g., SEQ ID NO: 50;
    comprises an amino acid sequence with at least 95% identity to a CD22 scFv sequence provided in Table 1A or 3A, e.g., SEQ ID NO: 50;
    comprises the amino acid sequence of a CD22 scFv sequence provided in Table 1A or 3A, e.g., SEQ ID NO: 50; or
    is encoded by a nucleotide sequence having at least 95%, 96%, 97%, 98%, 99%, or 100% identity to a CD22 scFv sequence provided in Table 1A or 3A, e.g., SEQ ID NO: 49 or 51.

12. The nucleic acid molecule of any one of the preceding embodiments, wherein the CD19 antigen binding domain comprises:
    one or more (e.g., all three) light chain complementarity determining region 1 (LC CDR1), light chain complementarity determining region 2 (LC CDR2), and light chain complementarity determining region 3 (LC CDR3) of a CD19 binding domain described herein, e.g., in Tables 1A, 2A, 3A, or 5A; and/or
    one or more (e.g., all three) heavy chain complementarity determining region 1 (HC CDR1), heavy chain complementarity determining region 2 (HC CDR2), and heavy chain complementarity determining region 3 (HC CDR3) of a CD19 binding domain described herein, e.g., in Tables 1A, 2A, 3A, or 5A.

13. The nucleic acid molecule of embodiment 12, wherein the CD19 antigen binding domain comprises a LC CDR1, LC CDR2 and LC CDR3 of a CD19 binding domain described herein, e.g., in Table 1A or 2A; and/or a HC CDR1, HC CDR2 and HC CDR3 of a CD19 binding domain described herein, e.g., in Table 1A, 2A or 3A.

14. The nucleic acid molecule of embodiment 12 or 13, wherein the CD19 antigen binding domain comprises a LC CDR1 of SEQ ID NO: 40, LC CDR2 of SEQ ID NO: 41; and LC CDR3 of SEQ ID NO: 42; and/or HC CDR1 of SEQ ID NO: 35, HC CDR2 of SEQ ID NO: 36-38; and HC CDR3 of SEQ ID NO: 39.

15. The nucleic acid molecule of any one of embodiments 12 to 14, wherein the CD19 antigen binding domain (e.g., an scFv) comprises a light chain variable (VL) region of a CD19 binding domain described herein, e.g., in Tables 1A, 3A, or 5A; and/or a heavy chain variable (VH) region of a CD19 binding domain described herein, e.g., in Tables 1A, 3A, or 5A.

16. The nucleic acid molecule of embodiment 15, wherein the CD19 antigen binding domain comprises a VL region comprising:
    an amino acid sequence having at least one, two or three modifications (e.g., substitutions) but not more than 30, 20 or 10 modifications (e.g., substitutions) of a CD19 VL region sequence provided in Tables 1A, 3A, or 5A;
an amino acid sequence with at least 95% identity to a CD19 VL region sequence provided in Tables 1A, 3A, or 5A; or
the amino acid sequence of a CD19 VL region sequence provided in Tables 1A, 3A, or 5A.

17. The nucleic acid molecule of embodiment 15 or 16, wherein the CD19 antigen binding domain comprises a VH region comprising:
an amino acid sequence having at least one, two or three modifications (e.g., substitutions) but not more than 30, 20 or 10 modifications (e.g., substitutions) of a CD19 VH region sequence provided in Tables 1A, 3A, or 5A;
an amino acid sequence with at least 95% identity to a CD19 VH region sequence provided in Tables 1A, 3A, or 5A; or
the amino acid sequence of a CD19 VH region sequence provided in Tables 1A, 3A, or 5A.

18. The nucleic acid molecule of any one of embodiments 15 to 17, wherein the VH and VL regions of the CD19 antigen binding domain are connected with a linker, e.g., a linker with at least 95%, 96%, 97%, 98%, 99% or 100% identity to a linker described herein, e.g. a linker disclosed in Table 4A.

19. The nucleic acid molecule of any one of the preceding embodiments, wherein the CD19 antigen binding domain comprises an scFv which:
comprises an amino acid sequence having at least one, two or three modifications (e.g., substitutions) but not more than 30, 20 or 10 modifications (e.g., substitutions) of a CD19 scFv sequence provided in Tables 1A, 3A, or 5A, e.g., SEQ ID NO: 44;
comprises an amino acid sequence with at least 95% identity to a CD19 scFv sequence provided in Tables 1A, 3A, or 5A, e.g., SEQ ID NO: 44;
comprises the amino acid sequence of a CD19 scFv sequence provided in Tables 1A, 3A, or 5A, e.g., SEQ ID NO: 44; or
is encoded by a nucleotide sequence having at least 95%, 96%, 97%, 98%, 99%, or 100% identity to a CD19 scFv sequence provided in Tables 1A, 3A, or 5A, e.g., SEQ ID NO: 43 or 48.

20. The nucleic acid molecule of any of the preceding embodiments, wherein the first transmembrane domain and the second transmembrane domain comprise an amino acid sequence with at least 90%, 95%, 96%, 97%, 98%, or 99% identity to the amino acid sequence of SEQ ID NO: 65.

21. The nucleic acid molecule of any of the preceding embodiments, wherein the first transmembrane domain and the second transmembrane domain comprise an amino acid sequence having one, two, three, four, five, six or seven modifications (e.g., substitutions) to the amino acid sequence of SEQ ID NO: 65.

22. The nucleic acid molecule of any of the preceding embodiments, wherein the first transmembrane domain and the second transmembrane domain comprise the amino acid sequence of SEQ ID NO: 65.

23. The nucleic acid molecule of any of the preceding embodiments, wherein the nucleotide sequence encoding the first transmembrane domain is at least 1%, 5%, 10%, 20%, 30%, 40%, 50%, 60%, 70%, 80%, 85%, 90%, 95%, or 100% different from the nucleotide sequence encoding the second transmembrane domain.

24. The nucleic acid molecule of any of the preceding embodiments, wherein the nucleotide sequence encoding the first transmembrane domain differs by at least 1 nucleotide, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, 150 nucleotides, 200 nucleotides or all nucleotides from the nucleotide sequence encoding the second transmembrane domain.

25. The nucleic acid molecule of any of the preceding embodiments, wherein the nucleotide sequence encoding the first transmembrane domain is chosen from a sequence having at least 95%, 96%, 97%, 98%, 99% or 100% identity to SEQ ID NO: 64 or 66.

26. The nucleic acid molecule of any of the preceding embodiments, wherein the nucleotide sequence encoding the second transmembrane domain is chosen from a sequence having at least 95%, 96%, 97%, 98%, 99% or 100% identity to SEQ ID NO: 67 or 68.

27. The nucleic acid molecule of any of the preceding embodiments, wherein the first co-stimulatory signaling domain and the second co-stimulatory signaling domain comprise an amino acid sequence with at least 90%, 95%, 96%, 97%, 98%, or 99% identity to the amino acid sequence of SEQ ID NO: 70.

28. The nucleic acid molecule of any of the preceding embodiments, wherein the first co-stimulatory signaling domain and the second co-stimulatory signaling domain comprise an amino acid sequence having one, two, three, four, or five modifications (e.g., substitutions) to the amino acid sequence of any one of SEQ ID NOs: 70.

29. The nucleic acid molecule of any of the preceding embodiments, wherein the first co-stimulatory signaling domain and the second co-stimulatory signaling domain comprise the amino acid sequence of any one of SEQ ID NOs: 70.

30. The nucleic acid molecule of any of the preceding embodiments, wherein the nucleotide sequence encoding the first co-stimulatory signaling domain is at least 1%, 5%, 10%, 20%, 30%, 40%, 50%, 60%, 70%, 80%, 85%, 90%, 95%, or 100% different from the nucleotide sequence encoding the second co-stimulatory signaling domain.

31. The nucleic acid molecule of any of the preceding embodiments, wherein the nucleotide sequence encoding the first co-stimulatory signaling domain differs by at least 1 nucleotide, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, 120 nucleotides, or all nucleotides from the nucleotide sequence encoding the second co-stimulatory signaling domain.

32. The nucleic acid molecule of any of the preceding embodiments, wherein the nucleotide sequence encoding the first co-stimulatory domain is chosen from a sequence having at least 95%, 96%, 97%, 98%, 99% or 100% identity to SEQ ID NO: 69 or 72.

33. The nucleic acid molecule of any of the preceding embodiments, wherein the nucleotide sequence encoding the second co-stimulatory domain is chosen from a sequence having at least 95%, 96%, 97%, 98%, 99% or 100% identity to SEQ ID NO: 71 or 73.

34. The nucleic acid molecule of any of the preceding embodiments, wherein the first primary signaling domain and the second primary signaling domain comprise an amino acid sequence with at least 90%, 95%, 96%, 97%, 98%, or 99% identity to the amino acid sequence of SEQ ID NO: 75.
35. The nucleic acid molecule of any of the preceding embodiments, wherein the first primary signaling domain and the second primary signaling domain comprise an amino acid sequence having one, two, three, four, five, six, seven, eight, nine, ten, eleven or twelve modifications (e.g., substitutions) to the amino acid sequence of SEQ ID NO: 75.
36. The nucleic acid molecule of any of the preceding embodiments, wherein the first primary signaling domain and the second primary signaling domain comprise the amino acid sequence of SEQ ID NO: 75.
37. The nucleic acid molecule of any of the preceding embodiments, wherein the nucleotide sequence encoding the first primary signaling domain is at least 1%, 5%, 10%, 20%, 30%, 40%, 50%, 60%, 70%, 80%, 85%, 90%, 95%, or 100% different from the nucleotide sequence encoding the second primary signaling domain.
38. The nucleic acid molecule of any of the preceding embodiments, wherein the nucleotide sequence encoding the first primary signaling domain differs by at least 1 nucleotide, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, 150 nucleotides, 200 nucleotides, 250 nucleotides, 300 nucleotides or all nucleotides from the nucleotide sequence encoding the second primary signaling domain.
39. The nucleic acid molecule of any of the preceding embodiments, wherein the nucleotide sequence encoding the first primary signaling domain is chosen from a sequence having at least 95%, 96%, 97%, 98%, 99% or 100% identity to SEQ ID NO: 74 or 77.
40. The nucleic acid molecule of any of the preceding embodiments, wherein the nucleotide sequence encoding the second primary signaling domain is chosen from a sequence having at least 95%, 96%, 97%, 98%, 99% or 100% identity to SEQ ID NO: 76 or 78.
41. The nucleic acid molecule of any of the preceding embodiments, wherein the first CAR and/or the second CAR comprises a signal peptide, e.g., a peptide comprising a stretch of hydrophobic amino acids, e.g., 5-16 residues.
42. The nucleic acid molecule of embodiment 41, wherein the signal peptide is chosen from a CD8alpha signal peptide, an interleukin 2 signal peptide, a human albumin signal peptide, a human chymotrypsinogen signal peptide, a human trypsinogen-2 signal peptide or other similar signal peptides disclosed in Stern B. et al. "Improving mammalian cell factories: The selection of signal peptide has a major impact on recombinant protein synthesis and secretion in mammalian cells." (2007).
43. The nucleic acid molecule of embodiment 41 or 42, wherein the signal peptide:
comprises a signal peptide provided in Table 4A;
comprises the amino acid of SEQ ID NOs: 59 or
is encoded by the nucleic acid of any one of SEQ ID NOs: 58, 60, 61, 62, or 63, or a nucleic acid having at least 95%, 96%, 97%, 98%, or 99% identity thereto.
44. The nucleic acid molecule of any of the preceding embodiments, wherein the nucleic acid molecule comprises in 5' to 3' direction the first CAR followed by the second CAR.
45. The nucleic acid molecule of any of embodiments 1 to 43, wherein the nucleic acid molecule comprises in 5' to 3' direction the second CAR followed by the first CAR.
46. The nucleic acid molecule of any of the preceding embodiments, further comprising a protease cleavage site (e.g., a T2A, P2A, E2A, or F2A cleavage site) or an internal ribosomal entry site.
47. The nucleic acid molecule of embodiment 46, wherein the protease cleavage site is a P2A site.
48. The nucleic acid molecule of embodiment 46 or 47, wherein the P2A site comprises: a nucleotide sequence encoding the amino acid sequence of SEQ ID NO: 86; or the nucleotide sequence of SEQ ID NO: 85 or 87.
49. The nucleic acid molecule of any one of embodiments 46 to 48, wherein the protease cleavage site or internal ribosomal entry site is situated between the first CAR and the second CAR.
50. The nucleic acid molecule of any one of embodiments 46 to 49, wherein the protease cleavage site is situated such that a cell can express a fusion protein comprising a first CAR and a second CAR, optionally wherein the fusion protein is processed into two peptides by proteolytic cleavage.
51. The nucleic acid molecule of any of the preceding embodiments, wherein the CAR molecule comprises the nucleotide sequence of SEQ ID NO: 11, or a nucleotide sequence having at least 80%, 85%, 90%, 95%, 96%, 97%, 98%, or 99% identity thereto.
52. The nucleic acid molecule of any of the preceding embodiments, wherein the CAR molecule comprises: a first CAR comprising the amino acid sequence of SEQ ID NO: 13 or an amino acid having at least 95%, 96%, 97%, 98%, or 99% identity thereto, and a second CAR comprising the amino acid sequence of SEQ ID NO: 14 or an amino acid having at least 95%, 96%, 97%, 98%, or 99% identity thereto.
53. The nucleic acid molecule of any of the preceding embodiments, wherein the CAR molecule comprises the amino acid sequence of SEQ ID NO: 12 or an amino acid having at least 95%, 96%, 97%, 98%, or 99% identity thereto.
54. The nucleic acid molecule of any of embodiments 1 to 50, wherein the CAR molecule is encoded by the nucleotide sequence of SEQ ID NO: 15 or a nucleotide sequence having at least 80%, 85%, 90%, 95%, 96%, 97%, 98%, or 99% identity thereto.
55. The nucleic acid molecule of any one of embodiments 1 to 50 or 54, wherein the CAR molecule comprises: a first CAR comprising the amino acid sequence of SEQ ID NO: 17 or an amino acid having at least 95%, 96%, 97%, 98%, or 99% identity thereto, and a second CAR comprising the amino acid sequence of SEQ ID NO: 18 or an amino acid having at least 95%, 96%, 97%, 98%, or 99% identity thereto.
56. The nucleic acid molecule of any one of embodiments 1 to 50, or 54 or 55, wherein the CAR molecule is encoded by a nucleic acid encoding the amino acid sequence of SEQ ID NO: 16 or an amino acid having at least 95%, 96%, 97%, 98%, or 99% identity thereto.
57. The nucleic acid molecule of any of embodiments 1 to 50, wherein the CAR molecule is encoded by the nucleotide sequence of SEQ ID NO: 19 or a nucleotide sequence having at least 80%, 85%, 90%, 95%, 96%, 97%, 98%, or 99% identity thereto.
58. The nucleic acid molecule of any one of embodiments 1 to 50 or 57, wherein the CAR molecule comprises: a first CAR comprising the amino acid sequence of SEQ ID NO: 13 or an amino acid having at least 95%, 96%, 97%, 98%, or 99% identity thereto, and a second CAR comprising the amino acid sequence of SEQ ID NO: 14 or an amino acid having at least 95%, 96%, 97%, 98%, or 99% identity thereto.
59. The nucleic acid molecule of any one of embodiments 1 to 50, or 57 or 58, wherein the CAR molecule comprises the amino acid sequence of SEQ ID NO: 12 or an amino acid having at least 95%, 96%, 97%, 98%, or 99% identity thereto.
60. A nucleic acid molecule encoding a chimeric antigen receptor (CAR) molecule, wherein said CAR molecule comprises in 5' to 3' orientation:
  (a) a first CAR comprising: a first signal peptide; a first antigen binding domain which binds to CD22; a first transmembrane domain; a first co-stimulatory signaling domain; and a first primary signaling domain;
  (b) a P2A protease cleavage site;
  (c) a second CAR comprising: a second signal peptide; a second antigen binding domain which binds to CD19; a second transmembrane domain; a second co-stimulatory domain; and a second primary signaling domain,
  wherein the CAR molecule is encoded by the nucleotide sequence of SEQ ID NO: 11; or a nucleic acid encoding the amino acid sequence of SEQ ID NO: 12.
61. A nucleic acid molecule encoding a chimeric antigen receptor (CAR) molecule, wherein said CAR molecule comprises in 5' to 3' orientation:
  (a) a second CAR comprising: a second signal peptide; a second antigen binding domain which binds to CD19; a second transmembrane domain; a second co-stimulatory domain; and a second primary signaling domain;
  (b) a P2A protease cleavage site;
  (c) a first CAR comprising: a first signal peptide; a first antigen binding domain which binds to CD22; a first transmembrane domain; a first co-stimulatory signaling domain; and a first primary signaling domain,
  wherein the CAR molecule is encoded by the nucleotide sequence of SEQ ID NO: 15; or a nucleic acid encoding the amino acid sequence of SEQ ID NO: 16.
62. A nucleic acid molecule encoding a chimeric antigen receptor (CAR) molecule, wherein said CAR molecule comprises in 5' to 3' orientation:
  (a) a first CAR comprising: a first signal peptide; a first antigen binding domain which binds to CD22; a first transmembrane domain; a first co-stimulatory signaling domain; and a first primary signaling domain;
  (b) a P2A protease cleavage site;
  (c) a second CAR comprising: a second signal peptide; a second antigen binding domain which binds to CD19; a second transmembrane domain; a second co-stimulatory domain; and a second primary signaling domain,
  wherein the CAR molecule is encoded by the nucleotide sequence of SEQ ID NO: 19; or a nucleic acid encoding the amino acid sequence of SEQ ID NO: 12.
63. The nucleic acid molecule of any of the preceding embodiments, further comprising a promoter sequence, e.g., EF1 promoter.
64. The nucleic acid molecule of any of the preceding embodiments, wherein the nucleotide sequence encoding the first CAR and the nucleotide sequence encoding the second CAR are disposed on a single nucleic acid construct.
65. The nucleic acid molecule of embodiment 64, wherein the nucleotide sequence encoding the first CAR and the nucleic acid encoding the second CAR are disposed on the same vector.
66. The nucleic acid molecule of any of the preceding embodiments, wherein the nucleotide sequence encoding the first CAR and the nucleotide sequence encoding the second CAR are disposed on different nucleic acid constructs, e.g., the nucleotide sequence encoding the first CAR is disposed on a first nucleic acid construct, and the nucleotide sequence encoding the second CAR is disposed on a second nucleic acid construct.
67. The nucleic acid molecule of embodiment 66, wherein the nucleotide sequence encoding the first CAR is disposed on a first vector.
68. The nucleic acid molecule of embodiment 66, wherein the nucleotide sequence encoding the second CAR is disposed on a second vector.
69. The nucleic acid molecule comprises a viral element, e.g., a viral packaging element.
70. A vector comprising the nucleic acid molecule of any of embodiments 1 to 69.
71. The vector of embodiment 70 wherein the vector is chosen from a DNA, a RNA, a plasmid, a lentivirus vector, adenoviral vector, or a retrovirus vector.
72. A cell (e.g., an immune effector cell) comprising the vector of embodiment 70 or 71, or the nucleic acid molecule of any of embodiments 1 to 69.
73. A cell (e.g., an immune effector cell) comprising a nucleic acid molecule encoding a chimeric antigen receptor (CAR) molecule, wherein said CAR molecule comprises:
  (a) a first CAR comprising a first antigen binding domain which binds to CD22 and a first transmembrane domain; a first co-stimulatory signaling domain; and/or a first primary signaling domain; and
  (b) a second CAR comprising a second antigen binding domain which binds to CD19 and a second transmembrane domain; a second co-stimulatory domain; and/or a second primary signaling domain,
  wherein:
  (i) the first transmembrane domain and the second transmembrane domain comprise the amino acid sequence of SEQ ID NO: 65 or an amino acid sequence with at least 90% identity thereto, optionally wherein a nucleotide sequence that encodes the first transmembrane domain and is comprised in the nucleic acid molecule is different from a nucleotide sequence that encodes the second transmembrane domain and is comprised in the nucleic acid molecule;
  (ii) the first co-stimulatory signaling domain and the second co-stimulatory signaling domain comprise the amino acid sequence of SEQ ID NO: 70 or an amino acid sequence with at least 90% identity thereto, optionally wherein a nucleotide sequence that encodes the first co-stimulatory signaling domain and is comprised in the nucleic acid molecule is different from a nucleotide sequence that encodes the second co-stimulatory signaling domain and is comprised in the nucleic acid molecule; and/or
  (iii) the first primary signaling domain and the second primary signaling domain comprise the amino acid sequence of any one of SEQ ID NO: 75 or an amino acid sequence with at least 90% identity thereto, optionally wherein a nucleotide sequence that encodes the primary signaling domain and is comprised in the nucleic acid molecule is different from a nucleotide sequence that encodes the second primary signaling domain and is comprised in the nucleic acid molecule.

74. A cell (e.g., an immune effector cell) comprising a chimeric antigen receptor (CAR) molecule, wherein said CAR molecule comprises:
   (a) a first CAR comprising a first antigen binding domain which binds to CD22 and a first transmembrane domain; a first co-stimulatory signaling domain; and/or a first primary signaling domain; and
   (b) a second CAR comprising a second antigen binding domain which binds to CD19 and a second transmembrane domain; a second co-stimulatory domain; and/or a second primary signaling domain,
   wherein:
   (i) the first transmembrane domain and the second transmembrane domain comprise the amino acid sequence of SEQ ID NO: 65 or an amino acid sequence with at least 90% identity thereto, optionally wherein a nucleotide sequence that encodes the first transmembrane domain and is comprised in a nucleic acid molecule is different from a nucleotide sequence that encodes the second transmembrane domain and is comprised in the nucleic acid molecule;
   (ii) the first co-stimulatory signaling domain and the second co-stimulatory signaling domain comprise the amino acid sequence of SEQ ID NO: 70 or an amino acid sequence with at least 90% identity thereto, optionally wherein a nucleotide sequence that encodes the first co-stimulatory signaling domain and is comprised in a nucleic acid molecule is different from a nucleotide sequence that encodes the second co-stimulatory signaling domain and is comprised in the nucleic acid molecule; and/or
   (iii) the first primary signaling domain and the second primary signaling domain comprise the amino acid sequence of SEQ ID NO: 75 or an amino acid sequence with at least 90% identity thereto, optionally wherein a nucleotide sequence that encodes the primary signaling domain and is comprised in a nucleic acid molecule is different from a nucleotide sequence that encodes the second primary signaling domain and is comprised in the nucleic acid molecule.

75. The cell of embodiment 74, wherein the cell comprises a nucleic acid encoding the CAR molecule.

76. The cell of embodiment 73 or 75, comprising the nucleic acid molecule of any of embodiments 1 to 69, or the vector of embodiment 70 or 71.

77. A cell comprising a chimeric antigen receptor (CAR) molecule, which comprises:
   (a) a first CAR comprising: a first signal peptide; a first antigen binding domain which binds to CD22; a first transmembrane domain; a first co-stimulatory signaling domain; and a first primary signaling domain;
   (b) a second CAR comprising: a second signal peptide; a second antigen binding domain which binds to CD19; a second transmembrane domain; a second co-stimulatory domain; and a second primary signaling domain,
   wherein the CAR molecule is encoded by the nucleotide sequence of SEQ ID NO: 11; or comprises the amino acid sequence of SEQ ID NO: 12.

78. A cell comprising a chimeric antigen receptor (CAR) molecule, which comprises:
   (a) a second CAR comprising: a second signal peptide; a second antigen binding domain which binds to CD19; a second transmembrane domain; a second co-stimulatory domain; and a second primary signaling domain;
   (b) a first CAR comprising: a first signal peptide; a first antigen binding domain which binds to CD22; a first transmembrane domain; a first co-stimulatory signaling domain; and a first primary signaling domain,
   wherein the CAR molecule is encoded by the nucleotide sequence of SEQ ID NO: 15; or comprises the amino acid sequence of SEQ ID NO: 16.

79. A cell comprising a chimeric antigen receptor (CAR) molecule, which comprises:
   (a) a first CAR comprising: a first signal peptide; a first antigen binding domain which binds to CD22; a first transmembrane domain; a first co-stimulatory signaling domain; and a first primary signaling domain;
   (b) a second CAR comprising: a second signal peptide; a second antigen binding domain which binds to CD19; a second transmembrane domain; a second co-stimulatory domain; and a second primary signaling domain,
   wherein the CAR molecule is encoded by the nucleotide sequence of SEQ ID NO: 19; or comprises the amino acid sequence of SEQ ID NO: 12.

80. The cell of any one of embodiments 72 to 79, wherein the cell is an immune effector cell, e.g., T cell (e.g., CD3+, CD4+ or CD8+ T cell), or an NK cell.

81. The cell of embodiment of any one of embodiments 72 to 80, wherein the cell is a human cell.

82. A method of making a cell (e.g., an immune effector cell) comprising transducing an immune effector cell, e.g., a T cell or NK cell, with a vector of embodiment 70 or 71.

83. A method of making a cell (e.g., an immune effector cell) comprising introducing a nucleic acid molecule of any one of embodiments 1 to 69, into an immune effector cell, e.g., a T cell or NK cell.

84. A method of generating a population of RNA-engineered cells comprising introducing an in vitro transcribed RNA or synthetic RNA into a cell, where the RNA comprises a nucleic acid molecule of any one of embodiments 1 to 69, 85. A bispecific antigen binding domain, comprising a first antigen binding domain which binds to CD22 and a second antigen binding domain which binds to CD19.

86. The bispecific antigen binding domain of embodiment 85, wherein the first antigen binding domain can be upstream (e.g., in an N-terminal orientation) of the second antigen binding domain, or the first antigen binding domain can be downstream (e.g., in a C-terminal orientation) of the second antigen binding domain.

87. The bispecific antigen binding domain of embodiment 85 or 86, wherein each of the first antigen binding domain and second antigen binding domains comprise a scFv, e.g., a light chain variable (VL) domain and a heavy chain variable (VH) domain.

88. The bispecific antigen binding domain of embodiment 87, wherein the VH can be upstream or downstream of the VL.

89. The bispecific antigen binding domain of embodiment 87 or 88, wherein the first antigen binding domain comprises an scFv comprising a first VH (VH1) and a first VL (VL1).
90. The bispecific antigen binding domain of any one of embodiments 87 to 89, wherein the second antigen binding domain comprises an scFv comprising a second VH (VH2) and a second VL (VL2).
91. The bispecific antigen binding domain of any one of embodiments 87 to 90, wherein first antigen binding domain is arranged with VH1 upstream of VL1.
92. The bispecific antigen binding domain of any one of embodiments 87 to 90, wherein first antigen binding domain is arranged with VL1 upstream of VH1.
93. The bispecific antigen binding domain of any one of embodiments 87 to 92, wherein the second antigen binding domain is arranged with VH2 upstream of VL2.
94. The bispecific antigen binding domain of any one of embodiments 87 to 92, wherein the second antigen binding domain is arranged with VL2 upstream of VH2.
95. The bispecific antigen binding domain of any one of embodiments 87 to 90, or 92 to 93 wherein the antigen binding domain has the following N terminal to C terminal configuration: VL1-VH1-VH2-VL2.
96. The bispecific antigen binding domain of any one of embodiments 87 to 90, 91 or 93, wherein the antigen binding domain has the following N terminal to C terminal configuration: VH1-VL1-VH2-VL2.
97. The bispecific antigen binding domain of any one of embodiments 87 to 90, 92, or 94, wherein the antigen binding domain has the following N terminal to C terminal configuration: VL1-VH1-VL2-VH2.
98. The bispecific antigen binding domain of any one of embodiments 87 to 90, 91, or 94, wherein the antigen binding domain has the following N terminal to C terminal configuration: VH1-VL1-VL2-VH2.
99. The bispecific antigen binding domain of any one of embodiments 85 to 98, wherein a linker is disposed between the first antigen binding domain and the second antigen binding domain.
100. The bispecific antigen binding domain of embodiment 99, wherein the linker is disposed between the scFv of the first antigen binding domain and the scFv of the second antigen binding domain.
101. The bispecific antigen binding domain of embodiment 100, wherein the linker is disposed between:
VH1 and VH2 if the construct has the configuration of: VL1-VH1-VH2-VL2;
VL1 and VH2 if the construct has the configuration of: VH1-VL1-VH2-VL2;
VH1 and VL2 if the construct has the configuration of VL1-VH1-VL2-VH2; or
VL1 and VL2 if the construct has the configuration of VH1-VL1-VL2-VH2.
102. The bispecific antigen binding domain of any one of embodiments 99 to 101, wherein the linker is long enough to avoid mispairing between the domains of the two scFvs.
103. The bispecific antigen binding domain of any one of embodiments 99 to 102, wherein the linker is a linker described herein, e.g., a linker provided in Table 1A or 4A.
104. The bispecific antigen binding domain of any one of embodiments 99 to 103, wherein the linker is a (Gly4-Ser)n linker, wherein n is 1, 2, 3, 4, 5, or 6.
105. The bispecific antigen binding domain of embodiment 104, wherein n=1, e.g., the linker has the amino acid sequence Gly4-Ser.
106. The bispecific antigen binding domain of embodiment 104, wherein n=3, e.g., SEQ ID NO: 82.
107. The bispecific antigen binding domain of any one of embodiments 99 to 103, wherein the linker comprises of the amino acid sequence: LAEAAAK, e.g., SEQ ID NO: 80.
108. The bispecific antigen binding domain of any one of embodiments 99 to 107, wherein a linker is disposed between the VL and VH of the scFv of the first antigen binding domain, e.g., a linker described herein.
109. The bispecific antigen binding domain of any one of embodiments 99 to 108, wherein a linker is disposed between the VL and VH of the scFv of the second antigen binding domain, e.g., a linker described herein.
110. The bispecific antigen binding domain of any one of embodiments 99 to 109, comprising an amino acid sequence of an antigen binding domain provided in Table 1A or 4A, e.g., any one of SEQ ID NOs: 2, 4, 6, 8, 10, 44, 47, 53, or 55, or an amino acid sequence having at least 95%, 96%, 97%, 98%, or 99% identity thereto.
112. The bispecific antigen binding domain of any one of embodiments 99 to 109, which is encoded by a nucleotide sequence of an antigen binding domain provided in Table 1A or 4a, e.g., any one of SEQ ID NOs: 1, 3, 5, 7, 9, 43, 45, 46, 52, 54, 56 or 57, or a nucleotide sequence having at least 80%, 85%, 90%, 95%, 96%, 97%, 98%, or 99% identity thereto.
113. A bispecific chimeric antigen receptor (CAR), comprising the bispecific antigen binding domain of any one of embodiments 85 to 112.
114. A nucleic acid construct encoding a bispecific chimeric antigen receptor (CAR), wherein the nucleic acid construct encodes the bispecific antigen binding domain of any one of embodiments 85 to 112.
115. A chimeric antigen receptor (CAR), comprising a bispecific antigen binding domain which comprises:
a first antigen binding domain which binds to CD22 and a second antigen binding domain which binds to CD19,
wherein the CAR comprises a transmembrane domain, a co-stimulatory domain and/or a primary signaling domain.
116. The CAR of embodiment 115, comprising the bispecific antigen binding domain of any one of embodiments 86 to 112.
117. The CAR of embodiment 115 or 116, comprising:
a bispecific antigen binding domain; a transmembrane domain; and a co-stimulatory signaling domain;
a bispecific antigen binding domain; a transmembrane domain; and a primary signaling domain; or
a bispecific antigen binding domain; a transmembrane domain; a co-stimulatory signaling domain; and a first primary signaling domain.
118. The CAR of any one of embodiments 115 to 117, wherein the CAR comprises a transmembrane domain, wherein the transmembrane domain is chosen from the alpha, beta or zeta chain of the T-cell receptor, CD28, CD3 epsilon, CD45, CD4, CD5, CD8, CD9, CD16, CD22, CD33, CD37, CD64, CD80, CD86, CD123, CD134, CD137 or CD154.

119. The CAR of embodiment 118, wherein the bispecific antigen binding domain is connected to the transmembrane domain by a hinge region, e.g., a hinge region described herein.

120. The CAR of any one of embodiments 115 to 119, wherein the CAR comprises a co-stimulatory domain, wherein the co-stimulatory domain comprises a signaling domain of OX40, CD2, CD27, CD28, CDS, ICAM-1, LFA-1 (CD11a/CD18), ICOS (CD278) or 4-1BB (CD137).

121. The CAR of any one of embodiments 115 to 120, wherein the co-stimulatory domain comprises a 4-1BB signaling domain.

122. The CAR of any one of embodiments 115 to 121, wherein the CAR comprise a primary signaling domain comprising a signaling domain of CD3 zeta.

123. The CAR of any one of embodiments 115 to 122, wherein the CAR comprises an amino acid sequence provided in Table 4A, e.g., any one of SEQ ID NOs: 2, 4, 6, 8, 10, or an amino acid sequence having at least 95%, 96%, 97%, 98%, or 99% identity thereto.

124. A chimeric antigen receptor (CAR), comprising a bispecific antigen binding domain which comprises a first antigen binding domain which binds to CD22 and a second antigen binding domain which binds to CD19, wherein:
   (i) the first and second antigen binding domains are each scFvs;
   (ii) the second antigen binding domain is oriented upstream of the first antigen binding domain; and
   (iii) a linker is disposed between the first antigen binding domain and the second antigen binding domain,
   wherein the CAR comprises a transmembrane domain, a co-stimulatory domain and a primary signaling domain, and
   wherein the CAR comprises the amino acid sequence of SEQ ID NO: 2 or a sequence with at least 95%, 96%, 97%, 98%, or 99% identity thereto.

125. A chimeric antigen receptor (CAR), comprising a bispecific antigen binding domain which comprises a first antigen binding domain which binds to CD22 and a second antigen binding domain which binds to CD19, wherein:
   (i) the first and second antigen binding domains are each scFvs;
   (ii) the first antigen binding domain is oriented upstream of the second antigen binding domain; and
   (iii) a linker is disposed between the first antigen binding domain and the second antigen binding domain,
   wherein the CAR comprises a transmembrane domain, a co-stimulatory domain and a primary signaling domain, and
   wherein the CAR comprises the amino acid sequence of SEQ ID NO: 4 or a sequence with at least 95%, 96%, 97%, 98%, or 99% identity thereto.

126. A chimeric antigen receptor (CAR), comprising a bispecific antigen binding domain which comprises a first antigen binding domain which binds to CD22 and a second antigen binding domain which binds to CD19, wherein:
   (i) the first and second antigen binding domains are each scFvs;
   (ii) the first antigen binding domain is oriented upstream of the second antigen binding domain; and
   (iii) a linker is disposed between the first antigen binding domain and the second antigen binding domain,
   wherein the CAR comprises a transmembrane domain, a co-stimulatory domain and a primary signaling domain, and
   wherein the CAR comprises the amino acid sequence of SEQ ID NO: 6 or a sequence with at least 95%, 96%, 97%, 98%, or 99% identity thereto.

127. A chimeric antigen receptor (CAR), comprising a bispecific antigen binding domain which comprises a first antigen binding domain which binds to CD22 and a second antigen binding domain which binds to CD19, wherein:
   (i) the first and second antigen binding domains are each scFvs;
   (ii) the first antigen binding domain is oriented upstream of the second antigen binding domain; and
   (iii) a linker is disposed between the first antigen binding domain and the second antigen binding domain,
   wherein the CAR comprises a transmembrane domain, a co-stimulatory domain and a primary signaling domain, and
   wherein the CAR comprises the amino acid sequence of SEQ ID NO: 8 or a sequence with at least 95%, 96%, 97%, 98%, or 99% identity thereto.

128. A chimeric antigen receptor (CAR), comprising a bispecific antigen binding domain which comprises a first antigen binding domain which binds to CD22 and a second antigen binding domain which binds to CD19, wherein:
   (i) the first and second antigen binding domains are each scFvs;
   (ii) the first antigen binding domain is oriented upstream of the second antigen binding domain; and
   (iii) a linker is disposed between the first antigen binding domain and the second antigen binding domain,
   wherein the CAR comprises a transmembrane domain, a co-stimulatory domain and a primary signaling domain, and
   wherein the CAR comprises the amino acid sequence of SEQ ID NO: 10 or a sequence with at least 95%, 96%, 97%, 98%, or 99% identity thereto.

129. A nucleic acid encoding a chimeric antigen receptor (CAR nucleic acid), wherein the CAR comprises a bispecific antigen binding domain which comprises:
   a first antigen binding domain which binds to CD22 and a second antigen binding domain which binds to CD19,
   wherein the CAR comprises a transmembrane domain, a co-stimulatory domain and/or a primary signaling domain.

130. The CAR nucleic acid of embodiment 129, comprising a nucleic acid encoding the bispecific antigen binding domain of any one of embodiments 86 to 112.

131. The CAR nucleic acid of embodiment 129 or 130, wherein the CAR comprises:
   a bispecific antigen binding domain; a transmembrane domain; and a co-stimulatory signaling domain;
   a bispecific antigen binding domain; a transmembrane domain; and a primary signaling domain; or
   a bispecific antigen binding domain; a transmembrane domain; a co-stimulatory signaling domain; and a first primary signaling domain.

132. The CAR nucleic acid of any one of embodiments 129 to 131, wherein the CAR comprises a transmembrane domain, wherein the transmembrane domain is chosen from the alpha, beta or zeta chain of the T-cell receptor, CD28, CD3 epsilon, CD45, CD4, CD5, CD8, CD9, CD16, CD22, CD33, CD37, CD64, CD80, CD86, CD123, CD134, CD137 or CD154.

133. The CAR nucleic acid of embodiment 132, wherein the bispecific antigen binding domain is connected to the transmembrane domain by a hinge region, e.g., a hinge region described herein.

134. The CAR nucleic acid of any one of embodiments 129 to 133, wherein the CAR comprises a co-stimulatory domain, wherein the co-stimulatory domain comprises a signaling domain of OX40, CD2, CD27, CD28, CDS, ICAM-1, LFA-1 (CD11a/CD18), ICOS (CD278) or 4-1BB (CD137).

135. The CAR nucleic acid of embodiment 134, wherein the co-stimulatory domain comprises a 4-1BB signaling domain.

136. The CAR nucleic acid of any one of embodiments 129 to 135, wherein the CAR comprises a primary signaling domain comprising a signaling domain of CD3 zeta.

137. The CAR nucleic acid of any one of embodiments 129 to 136, comprising the nucleotide sequence provided in Table 4A, e.g., any one of SEQ ID NOs: 1, 3, 5, 7, or 9 or a nucleotide sequence having at least 80%, 85%, 90%, 95%, 96%, 97%, 98%, or 99% identity thereto.

138. A nucleic acid encoding a chimeric antigen receptor (CAR nucleic acid), wherein the CAR comprises a bispecific antigen binding domain which comprises a first antigen binding domain which binds to CD22 and a second antigen binding domain which binds to CD19, wherein:
(i) the first and second antigen binding domains are each scFvs;
(ii) the second antigen binding domain is oriented upstream of the first antigen binding domain; and
(iii) a linker is disposed between the first antigen binding domain and the second antigen binding domain,
wherein the CAR comprises a transmembrane domain, a co-stimulatory domain and a primary signaling domain, and
wherein the CAR comprises the amino acid sequence of SEQ ID NO: 2, or a sequence with at least 80%, 85%, 90%, 95%, 96%, 97%, 98%, or 99% identity thereto.

139. A nucleic acid encoding a chimeric antigen receptor (CAR nucleic acid), wherein the CAR comprises a bispecific antigen binding domain which comprises a first antigen binding domain which binds to CD22 and a second antigen binding domain which binds to CD19, wherein:
(i) the first and second antigen binding domains are each scFvs;
(ii) the first antigen binding domain is oriented upstream of the second antigen binding domain; and
(iii) a linker is disposed between the first antigen binding domain and the second antigen binding domain,
wherein the CAR comprises a transmembrane domain, a co-stimulatory domain and a primary signaling domain, and
wherein the CAR comprises the amino acid sequence of SEQ ID NO: 4, or a sequence with at least 80%, 85%, 95%, 96%, 97%, 98%, or 99% identity thereto.

140. A nucleic acid encoding a chimeric antigen receptor (CAR nucleic acid), wherein the CAR comprises a bispecific antigen binding domain which comprises a first antigen binding domain which binds to CD22 and a second antigen binding domain which binds to CD19, wherein:
(i) the first and second antigen binding domains are each scFvs;
(ii) the first antigen binding domain is oriented upstream of the second antigen binding domain; and
(iii) a linker is disposed between the first antigen binding domain and the second antigen binding domain,
wherein the CAR comprises a transmembrane domain, a co-stimulatory domain and a primary signaling domain, and
wherein the CAR comprises the amino acid sequence of SEQ ID NO: 6, or a sequence with at least 80%, 85%, 90%, 95%, 96%, 97%, 98%, or 99% identity thereto.

141. A nucleic acid encoding a chimeric antigen receptor (CAR nucleic acid), wherein the CAR comprises a bispecific antigen binding domain which comprises a first antigen binding domain which binds to CD22 and a second antigen binding domain which binds to CD19, wherein:
(i) the first and second antigen binding domains are each scFvs;
(ii) the first antigen binding domain is oriented upstream of the second antigen binding domain; and
(iii) a linker is disposed between the first antigen binding domain and the second antigen binding domain,
wherein the CAR comprises a transmembrane domain, a co-stimulatory domain and a primary signaling domain, and
wherein the CAR comprises the amino acid sequence of SEQ ID NO: 8, or a sequence with at least 80%, 90%, 95%, 96%, 97%, 98%, or 99% identity thereto.

142. A nucleic acid encoding a chimeric antigen receptor (CAR nucleic acid), wherein the CAR comprises a bispecific antigen binding domain which comprises a first antigen binding domain which binds to CD22 and a second antigen binding domain which binds to CD19, wherein:
(i) the first and second antigen binding domains are each scFvs;
(ii) the first antigen binding domain is oriented upstream of the second antigen binding domain; and
(iii) a linker is disposed between the first antigen binding domain and the second antigen binding domain,
wherein the CAR comprises a transmembrane domain, a co-stimulatory domain and a primary signaling domain, and
wherein the CAR comprises the amino acid sequence of SEQ ID NO: 10, or a sequence with at least 95%, 96%, 97%, 98%, or 99% identity thereto.

143. A vector comprising the bispecific antigen binding domain of any one of embodiments 85-112, the CAR of any one of embodiments 113, or 115-128, or the CAR nucleic acid of any one of embodiments 114, or 129-142.

144. A cell (e.g., an immune effector cell), comprising the bispecific antigen binding domain of any one of embodiments 85-112, the CAR of any one of embodiments 113, or 115-128, the CAR nucleic acid of any one of embodiments 114, or 129-142, or the vector of embodiment 143.

145. A cell comprising a chimeric antigen receptor (CAR), wherein the CAR comprises a bispecific antigen binding domain comprising:
 a first antigen binding domain which binds to CD22 and a second antigen binding domain which binds to CD19,
 wherein the CAR comprises a transmembrane domain, a co-stimulatory domain and/or a primary signaling domain.

146. The cell of embodiment 145, comprising the CAR of any one of embodiments 116 to 123.

147. A method of making a cell (e.g., an immune effector cell) comprising:
 transducing an immune effector cell, e.g., a T cell or NK cell, with a vector of embodiment 143; or
 introducing a CAR nucleic acid molecule of any one of embodiments 129 to 142, into an immune effector cell, e.g., a T cell or NK cell.

148. A pharmaceutical composition comprising the nucleic acid encoding the CAR molecule of any one of embodiments 1 to 69, the bispecific antigen binding domain of any one of embodiments 85 to 112, the CAR of any one of embodiment 113, or 115 to 128, or the CAR nucleic acid of any one of embodiments 114, or 129 to 142, optionally wherein the pharmaceutical composition comprises an excipient, a carrier, a diluent and/or a stabilizer.

149. A method of providing anti-tumor immunity, comprising administering to a subject in need thereof, an effective amount of a cell, e.g., a population of immune effector cells, comprising, e.g., expressing, the nucleic acid encoding a CAR molecule of any one of embodiments 1 to 69, the bispecific antigen binding domain of any one of embodiments 85 to 112, the CAR of any one of embodiment 113, or 115 to 128, or the CAR nucleic acid of any one of embodiments 114, or 129 to 142.

150. A cell, e.g., a population of immune effector cells, comprising, e.g., expressing, the nucleic acid encoding a CAR molecule of any one of embodiments 1 to 69, the bispecific antigen binding domain of any one of embodiments 85 to 112, the CAR of any one of embodiment 113, or 115 to 128, or the CAR nucleic acid of any one of embodiments 114, or 129 to 142, for use in a method of providing anti-tumor immunity to a subject.

151. The method of embodiment 149 or the use of embodiment 150, wherein the cell is a T cell or an NK cell.

152. The method of embodiment 149 or 151 or the use of embodiment 150 or 151, wherein the cell is an autologous cell or an allogeneic cell.

153. The method of embodiment 149 or the use of embodiment 150, wherein the subject is a human.

154. A method of treating a subject having a disease associated with an antigen (e.g., CD19 and/or CD22), comprising administering to the subject in need thereof, an effective amount of a cell, e.g., a population of immune effector cells, comprising, e.g., expressing, the nucleic acid encoding a CAR molecule of any one of embodiments 1 to 69, the bispecific antigen binding domain of any one of embodiments 85 to 112, the CAR of any one of embodiment 113, or 115 to 128, or the CAR nucleic acid of any one of embodiments 114, or 129 to 142.

155. A cell, e.g., a population of immune effector cells, comprising, e.g., expressing, the nucleic acid encoding a CAR molecule of any one of embodiments 1 to 69, the bispecific antigen binding domain of any one of embodiments 85 to 112, the CAR of any one of embodiment 113, or 115 to 128, or the CAR nucleic acid of any one of embodiments 114, or 129 to 142, for use in a method of treating a subject having a disease associated with an antigen (e.g., CD19 and/or CD22).

156. The method of embodiment 154 or the use of embodiment 155, wherein the cell is a T cell or an NK cell.

157. The method of embodiment 154 or 155 or the use of embodiment 154 or 155, wherein the cell is an autologous cell or an allogeneic cell.

158. The method of embodiment 154 or the use of embodiment 155, wherein the subject is a human.

159. The method of any one of embodiments 154 or 155 to 158, or the use of any one of embodiments 155 to 158, wherein the disease associated with CD19 and/or CD22 is selected from a proliferative disease, e.g., a cancer or malignancy, a precancerous condition, e.g., a myelodysplasia, a myelodysplastic syndrome, or a preleukemia, or a non-cancer related indication associated with expression of CD19 and/or CD22.

160. The method, or use of embodiment 159, wherein the disease is a cancer, e.g., a hematological cancer.

161. The method of any one of embodiments 154 or 155 to 160, or the use of any one of embodiments 155 to 160, wherein the disease is a B cell malignancy.

162. The method, or use of embodiment 160 or 161, wherein the hematological cancer is chosen from acute myeloid leukemia (AML), B-cell acute lymphoblastic leukemia (BALL), small lymphocytic leukemia (SLL), acute lymphoblastic leukemia (ALL), chronic myelogenous leukemia (CML), chronic lymphocytic leukemia (CLL), mantle cell lymphoma (MCL), B cell prolymphocytic leukemia, blastic plasmacytoid dendritic cell neoplasm, Burkitt's lymphoma, diffuse large B cell lymphoma (DLBCL), follicular lymphoma, hairy cell leukemia, small cell-lymphoma, large cell-follicular lymphoma, a malignant lymphoproliferative condition, MALT lymphoma, Marginal zone lymphoma, multiple myeloma, myelodysplasia, or myelodysplastic syndrome, myeloproliferative neoplasm, non-Hodgkin's lymphoma, Hodgkin's lymphoma, plasmablastic lymphoma, plasmacytoid dendritic cell neoplasm, Waldenstrom macroglobulinemia, preleukemia, or a combination thereof.

163. The method of any one of embodiments 154 or 155 to 162, or the use of any one of embodiments 155 to 162, further comprising administering to the subject an agent that:
 increases the efficacy of a cell expressing a CAR molecule;
 ameliorates one or more side effects associated with administration of a cell expressing a CAR molecule; or
 treats the disease associated with CD19 and/or CD22.

BRIEF DESCRIPTION OF THE DRAWINGS

CAR and a CD19 CAR. FIG. 1A shows a dual CAR construct with a CD22 CAR followed by a CD19 CAR from N terminus to C terminus. FIG. 1B shows a different dual CAR construct with a CD22 CAR followed by a CD19 CAR from N terminus to C terminus.

FIG. 1C shows a dual CAR construct with a CD19 CAR followed by a CD22 CAR from N terminus to C terminus.

FIG. 3A is a graph depicting cytolytic activity (Cell killing) of the various constructs towards a CD22-negative ALL cell line (CD22KO Nalm6-Luc). FIG. 3B is a graph depicting cytolytic activity (Cell killing) of the various constructs towards a CD19-negative ALL cell line (CD19KO Nalm6-Luc). FIGS. 3C-3D are graphs showing IFNg cytokine production by the various CAR constructs in response to CD22 and/or CD19-expressing target cells.

FIG. 4A is a graph showing total flux (mean bioluminescence) for all treatment groups. FIG. 4B is a graph depicting expansion kinetics of the various CAR-T cells.

FIG. 5A and FIG. 5B depict results from small scale manufacturing process 72 h post-harvest and 144 h post-harvest, respectively. FIG. 5C depicts results from large scale manufacturing process.

FIG. 6A-6B show in vivo activity of mono and dual CAR T cells targeting CD19 and/or CD22 in a B-cell acute lymphoblastic leukemia xenograft model. FIG. 6A is a graph showing total flux (mean bioluminescence) for all treatment groups. FIG. 6B shows a direct comparison of the $0.3 \times 10^6$ (0.3 e6) dose groups.

DETAILED DESCRIPTION

Definitions

Figure 1A:
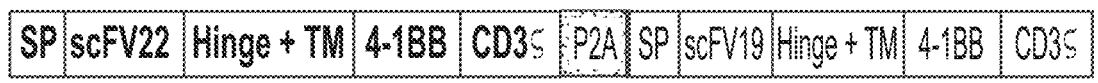
FIGS. 1A-1C are schematics of Dual CAR constructs disclosed herein. The dual CAR constructs include a CD22
Figure 1B:
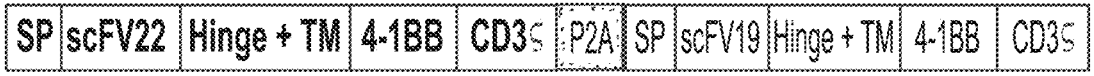
Figure 1C:
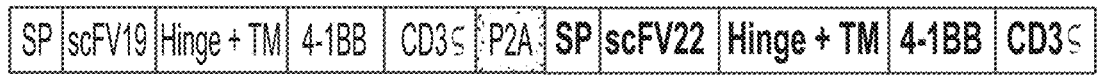
Figure 2:
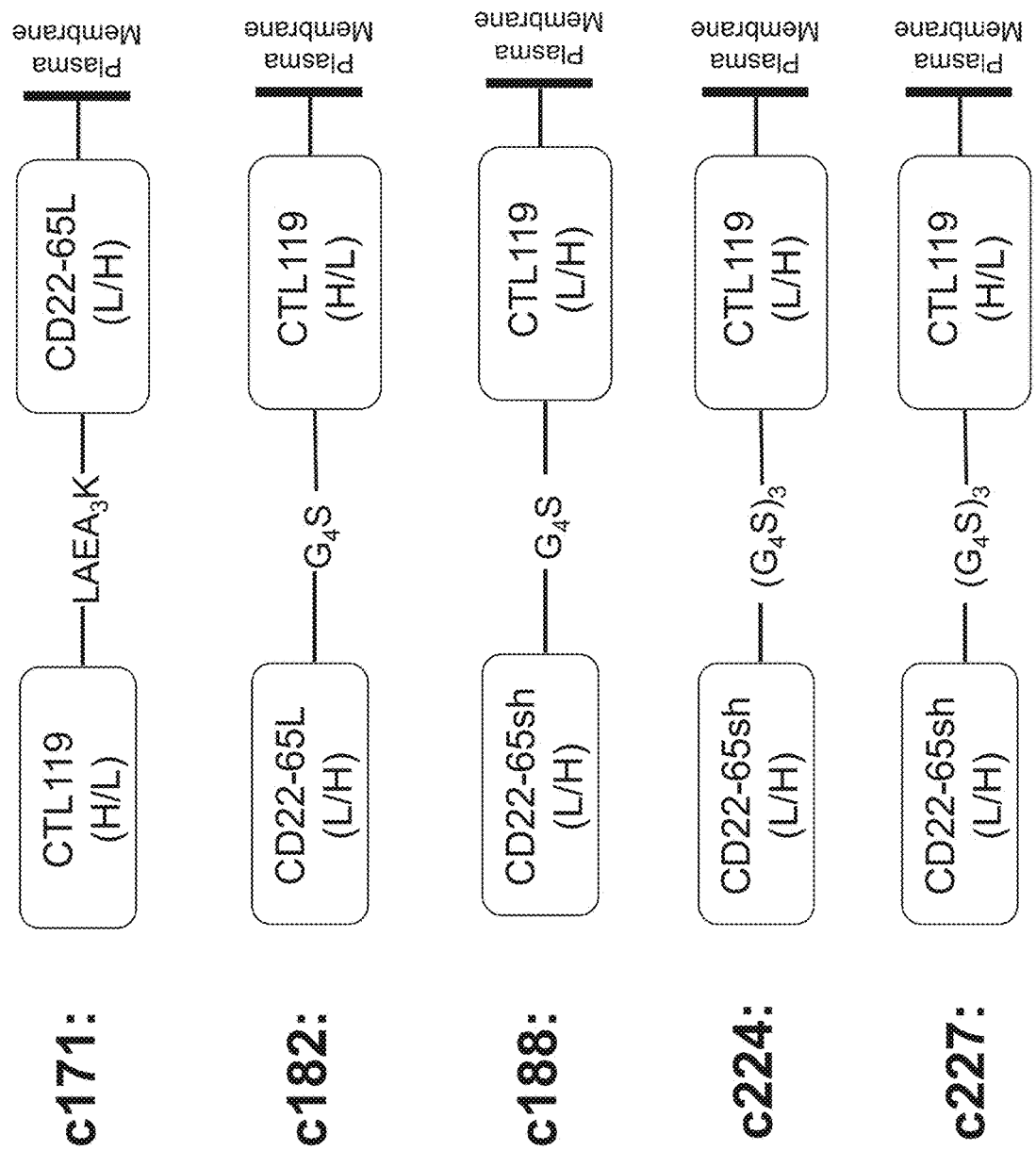
FIG. 2 is a schematic of the tandem CD19/CD22 CAR constructs of the present disclosure. Each tandem CAR comprises a bispecific antigen binding domain comprising a CD19 antigen binding domain and a CD22 antigen binding domain.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances±10%, or in some instances±5%, or in some instances±1%, or in some instances±0.1% from the specified value, as such variations are appropriate to perform the disclosed methods.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19.

The term "Chimeric Antigen Receptor," a "CAR," or a "CAR molecule" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with each other, e.g., are in the same polypeptide chain, e.g., comprise a chimeric fusion protein. In some embodiments, the set of polypeptides are not contiguous with each other, e.g., are in different polypeptide chains. In some embodiments, the set of polypeptides include a dimerization switch that, upon the presence of a dimerization molecule, can couple the polypeptides to one another, e.g., can couple an antigen binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from the costimulatory molecules described herein, e.g., 4-1BB (i.e., CD137), CD27 and/or CD28. In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In one aspect, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

The term "signaling domain" refers to the functional portion of a protein which acts by transmitting information within the cell to regulate cellular activity via defined signaling pathways by generating second messengers or functioning as effectors by responding to such messengers.

As used herein, the term "CD19" refers to the Cluster of Differentiation 19 protein, which is an antigenic determinant detectable on leukemia precursor cells. The human and murine amino acid and nucleic acid sequences can be found in a public database, such as GenBank, UniProt and Swiss-Prot. For example, the amino acid sequence of human CD19 can be found as UniProt/Swiss-Prot Accession No. P15391 and the nucleic acid sequence encoding of the human CD19 can be found at Accession No. NM_001178098. CD19 is expressed on most B lineage cancers, including, e.g., acute lymphoblastic leukaemia, chronic lymphocyte leukaemia and non-Hodgkin lymphoma. Other cells that express CD19 are provided below in the definition of "disease associated with expression of CD19." It is also an early marker of B cell progenitors. See, e.g., Nicholson et al. Mol. Immun. 34 (16-17): 1157-1165 (1997). In one aspect the antigen-binding portion of the CART recognizes and binds an antigen within the extracellular domain of the CD19 protein. In one aspect, the CD19 protein is expressed on a cancer cell. As used herein, "CD19" includes proteins comprising mutations, e.g., point mutations, fragments, insertions, deletions and splice variants of full length wild-type CD19.

As used herein, the terms "CD22," refers to an antigenic determinant known to be detectable on leukemia precursor cells. The human and murine amino acid and nucleic acid sequences can be found in a public database, such as GenBank, UniProt and Swiss-Prot. For example, the amino acid sequences of isoforms 1-5 human CD22 can be found at Accession Nos. NP 001762.2, NP 001172028.1, NP 001172029.1, NP 001172030.1, and NP 001265346.1, respectively, and the nucleic acid sequence encoding variants 1-5 of the human CD22 can be found at Accession No. NM 001771.3, NM 001185099.1, NM 001185100.1, NM 001185101.1, and NM 001278417.1, respectively. In one aspect, the antigen-binding portion of the CAR recognizes and binds an antigen within the extracellular domain of the CD22 protein. In one aspect, the CD22 protein is expressed on a cancer cell. As used herein, "CD22" includes proteins comprising mutations, e.g., point mutations, fragments, insertions, deletions and splice variants of full length wild-type CD22.

As used herein, the term "binding domain" (e.g., "CD22 binding domain") refers to a protein, e.g., an immunoglobulin chain or fragment thereof, comprising at least one immunoglobulin variable domain sequence. The term "binding domain" (also referred to herein as "antibody molecule") encompasses antibodies and antibody fragments. In an embodiment an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The term "antibody fragment" refers to at least one portion of an antibody, that retains the ability to specifically interact with (e.g., by binding, steric hinderance, stabilizing/destabilizing, spatial distribution) an epitope of an antigen. Examples of antibody fragments include, but are not limited to, Fab, Fab', F(ab')$_2$, Fv fragments, scFv antibody fragments, disulfide-linked Fvs (sdFv), a Fd fragment consisting of the VH and CHI domains, linear antibodies, single domain antibodies such as sdAb (either VL or VH), camelid VHH domains, multi-specific antibodies formed from antibody fragments such as a bivalent fragment comprising two Fab fragments linked by a disulfide brudge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies). The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "complementarity determining region" or "CDR," as used herein, refers to the sequences of amino acids within antibody variable regions which confer antigen specificity and binding affinity. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme) and ImMunoGenTics (IMGT) numbering (Lefranc, M. P., The Immunologist, 7, 132-136 (1999); Lefranc, M. P. et al., Dev. Comp. Immunol., 27, 55-77 (2003) ("IMGT" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia, the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT, the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "IMGT"). Under IMGT, the CDR regions of an antibody can be determined using the program IMGT/DomainGap Align.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleic acid sequence or a partial nucleic acid sequence encoding a protein that elicits an immune response therefore encodes an "antigen" as that term is used herein. Furthermore, one skilled in the art will understand that an antigen need not be encoded solely by a full length nucleic acid sequence of a gene. It is readily apparent that the present invention includes, but is not limited to, the use of partial nucleic acid sequences of more than one gene and that these nucleic acid sequences are arranged in various combinations to encode polypeptides that elicit the desired immune response. Moreover, a skilled artisan will understand that an antigen need not be encoded by a "gene" at all. It is readily apparent that an antigen can be generated, synthesized, or can be derived from a biological sample, or might be macromolecule besides a polypeptide. Such a biological sample can include, but is not limited to a tissue sample, a tumor sample, a cell or a fluid with other biological components.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies of the invention in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival. The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid tumors. As used herein, the term "cancer" or "tumor" includes premalignant, as well as malignant cancers and tumors.

The phrase "disease associated with expression of CD22" as used herein includes but is not limited to, a disease associated with expression of CD22 (e.g., wild-type or mutant CD22) or condition associated with cells which express, or at any time expressed, CD22 (e.g., wild-type or mutant CD22) including, e.g., a proliferative disease such as a cancer or malignancy or a precancerous condition such as a myelodysplasia, a myelodysplastic syndrome or a preleukemia; or a noncancer related indication associated with cells which express CD22 (e.g., wild-type or mutant CD22). For the avoidance of doubt, a disease associated with expression of CD22 may include a condition associated with cells which do not presently express CD22, e.g., because CD22 expression has been downregulated, e.g., due to treatment with a molecule targeting CD22, e.g., a CD22 CAR, but which at one time expressed CD22. In one aspect, a cancer associated with expression of CD22 is a hematological cancer. In one aspect, a hematological cancer includes but is not limited to AML, myelodysplastic syndrome, ALL, hairy cell leukemia, Prolymphocytic leukemia, Chronic myeloid leukemia, Hodgkin lymphoma, Blastic plasmacytoid dendritic cell neoplasm, and the like. Further disease associated with expression of CD22 expression include, but are not limited to, e.g., atypical and/or non-classical cancers, malignancies, precancerous conditions or proliferative diseases associated with expression of CD22. Non-cancer related indications associated with expression of CD22 may also be included. In some embodiments, the CD22-expressing cells express, or at any time expressed, CD22 Mrna. In an embodiment, the CD22-expressing cells produce a CD22 protein (e.g., wild-type or mutant), and the CD22 protein may be present at normal levels or reduced levels. In an embodiment, the CD22-expressing cells produced detectable levels of a CD22 protein at one point, and subsequently produced substantially no detectable CD22 protein.

The phrase "disease associated with expression of CD19" includes, but is not limited to, a disease associated with expression of CD19 (e.g., wild-type or mutant CD19) or condition associated with cells that express, or at any time expressed, CD19 (e.g., wild-type or mutant CD19) including, e.g., proliferative diseases such as a cancer or malignancy or a precancerous condition such as a myelodysplasia, a myelodysplastic syndrome or a preleukemia; or a noncancer related indication associated with cells which express CD19. For the avoidance of doubt, a disease associated with expression of CD19 may include a condition associated with cells that do not presently express CD19, e.g., because CD19 expression has been downregulated, e.g., due to treatment with a molecule targeting CD19, e.g., a CD19 CAR, but which at one time expressed CD19. In one aspect, a cancer associated with expression of CD19 is a hematological cancer. In one aspect, the hematological cancer is a leukemia or a lymphoma. In one aspect, a cancer associated with expression of CD19 includes cancers and malignancies including, but not limited to, e.g., one or more acute leukemias including but not limited to, e.g., B-cell acute Lymphoblastic Leukemia (BALL), T-cell acute Lymphoid Leukemia (TALL), acute lymphoblastic leukemia (ALL); one or more chronic leukemias including but not limited to, e.g., chronic myelogenous leukemia (CML), Chronic Lymphoid Leukemia (CLL). Additional cancers or hematologic conditions associated with expression of CD19 comprise, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma (MCL), Marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further, diseases associated with expression of CD19 expression include, but not limited to, e.g., atypical and/or non-classical cancers, malignancies, precancerous conditions or proliferative diseases associated with expression of CD19. Non-cancer related indications associated with expression of CD19 include, but are not limited to, e.g., autoimmune disease, (e.g., lupus), inflammatory disorders (allergy and asthma) and transplantation. In some embodiments, the CD19-expressing cells express, or at any time expressed, CD19 Mrna. In an embodiment, the CD19-expressing cells produce a CD19 protein (e.g., wild-type or mutant), and the CD19 protein may be present at normal levels or reduced levels. In an embodiment, the CD19-expressing cells produced detectable levels of a CD19 protein at one point, and subsequently produced substantially no detectable CD19 protein.

As used herein, unless otherwise specified, the terms "prevent," "preventing" and "prevention" refer to an action that occurs before the subject begins to suffer from the condition, or relapse of the condition. Prevention need not result in a complete prevention of the condition; partial prevention or reduction of the condition or a symptom of the condition, or reduction of the risk of developing the condition, is encompassed by this term.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. In one embodiment, the CAR-expressing cell is administered at a dose and/or dosing schedule described herein, and the B-cell inhibitor, or agent that enhances the activity of the CD19 CAR-expressing cell is administered at a dose and/or dosing schedule described herein.

"Derived from" as that term is used herein, indicates a relationship between a first and a second molecule. It generally refers to structural similarity between the first molecule and a second molecule and does not connote or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connote or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule," refers to a molecule expressed by an immune cell, e.g., T cell, NK cell, or B cell, that provides the cytoplasmic signaling sequence(s) that regulates activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In a specific CAR of the invention, the intracellular signaling domain in any one or more CARS of the invention comprises an intracellular signaling sequence, e.g., a primary signaling sequence of CD3-zeta. In a specific CAR of the invention, the primary signaling sequence of CD3-zeta is the sequence provided as SEQ ID NO: 96, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NK-T) cells, mast cells, and myeloid-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

An "intracellular signaling domain," as the term is used herein, refers to an intracellular portion of a molecule. The intracellular signaling domain generates a signal that promotes an immune effector function of the CAR containing cell, e.g., a CART cell or CAR-expressing NK cell. Examples of immune effector function, e.g., in a CART cell or CAR-expressing NK cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10 and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain or functional derivative thereof, that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO: 96.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that contribute to an efficient immune response. Costimulatory molecules include, but are not limited to an MHC class I molecule, TNF receptor proteins, Immunoglobulin-like proteins, cytokine receptors, integrins, 56 signalling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS 5 (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CSD, CD7, CD287, LIGHT, NKG2C, NKG2D, SLAMF7, NKp80, NKp30, NKp44, NKp46, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment or derivative thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank accno. AAA62478.2, or the equivalent residues from a non-human species, e.g., mouse, rodent, monkey, ape and the like. In one aspect, the "4-1BB costimulatory domain" is the sequence provided as SEQ ID NO: 70 or the equivalent residues from a non-human species, e.g., mouse, rodent, monkey, ape and the like.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleic acid sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleic acid sequence encoding an amino acid sequence" includes all nucleic acid sequences that are degenerate versions of each other and that encode the same amino acid sequence. The phrase nucleic acid sequence that encodes a protein or a RNA may also include introns to the extent that the nucleic acid sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleic acid sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleic acid sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17 (8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies), which contain minimal sequence derived from non-human immunoglobulin. For the most part, humanized antibodies and antibody fragments thereof are human immunoglobulins (recipient antibody or antibody fragment) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues that are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321:522-525, 1986; Reichmann et al., Nature, 332:323-329, 1988; Presta, Curr. Op. Struct. Biol., 2:593-596, 1992.

"Fully human" refers to an immunoglobulin, such as an antibody or antibody fragment, where the whole molecule is of human origin or consists of an amino acid sequence identical to a human form of the antibody or immunoglobulin.

"Murine" refers to mice or rats. For example, a murine antibody or fragment thereof contains the sequence of an antibody or fragment thereof that is isolated from a murine animal, e.g., mouse or rat.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementarity sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence that is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one that expresses the gene product in a tissue specific manner.

The term "constitutive" promoter refers to a nucleic acid sequence that, when operably linked with a polynucleotide that encodes or specifies a gene product, causes the gene product to be produced in a cell under most or all physiological conditions of the cell.

The term "inducible" promoter refers to a nucleic acid sequence that, when operably linked with a polynucleotide that encodes or specifies a gene product, causes the gene product to be produced in a cell substantially only when an inducer that corresponds to the promoter is present in the cell.

The term "tissue-specific" promoter refers to a nucleic acid sequence that, when operably linked with a polynucleotide that encodes or specifies a gene product, causes the gene product to be produced in a cell substantially only if the cell is a cell of the tissue type corresponding to the promoter.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser) (SEQ ID NO: 89), repeated n times where n is a positive integer equal to or greater than 1. For example, n=1, n=2, n=3. N=4, n=5 and n=6, n=7, n=8, n=9 and n=10. In one embodiment, the flexible polypeptide linker is $(Gly_4 Ser)_3$ (SEQ ID NO: 82). In another embodiment, the linkers include multiple repeats of $(Gly_2Ser)$, and (GlySer). In another embodiment, the polypeptide does not include a linker, e.g., (n=0). Also included within the scope of the invention are linkers described in WO2012/138475, incorporated herein by reference).

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNAses. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. Poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In some embodiments, the terms "treat", "treatment" and "treating"-refer to the inhibition of the progression of a proliferative disorder, either physically by, e.g., stabilization of a discernible symptom, physiologically by, e.g., stabilization of a physical parameter, or both. In some embodiments, the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, non-Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a binding partner (e.g., a stimulatory tumor antigen) protein present in a sample, but which antibody or ligand does not substantially recognize or bind other molecules in the sample.

"Refractory" as used herein refers to a disease, e.g., cancer, that does not respond to a treatment. In embodiments, a refractory cancer can be resistant to a treatment before or at the beginning of the treatment. In some embodiments, the refractory cancer can become resistant during a treatment. A refractory cancer is also called a resistant cancer.

A subject "responds" to treatment if a parameter of a cancer (e.g., a hematological cancer, e.g., cancer cell growth, proliferation and/or survival) in the subject is retarded or reduced by a detectable amount, e.g., about 5%, 10%, 20%, 30%, 40%, 50%, 60%, 70%, 80%, 90% or more as determined by any appropriate measure, e.g., by mass, cell count or volume. In one example, a subject responds to treatment if the subject experiences a life expectancy extended by about 5%, 10%, 20%, 30%, 40%, 50% or more beyond the life expectancy predicted if no treatment is administered. In another example, a subject responds to treatment, if the subject has an increased disease-free survival, overall survival or increased time to progression. Several methods can be used to determine if a patient responds to a treatment including, for example, criteria provided by NCCN Clinical Practice Guidelines in Oncology (NCCN Guidelines®). For example, in the context of B-ALL, a complete response or complete responder, may involve one or more of: <5% BM blast, >1000 neutrophil/ANC (/µL). >100,000 platelets (/µL) with no circulating blasts or extramedullary disease (no lymphadenopathy, splenomegaly, skin/gum infiltration/testicular mass/CNS involvement), Trilineage hematopoiesis, and no recurrence for 4 weeks. A partial responder may involve one or more of >50% reduction in BM blast, >1000 neutrophil/ANC (/µL). >100,000 platelets (/µL). A non-responder can show disease progression, e.g., >25% in BM blasts. In an embodiment, a complete responder is defined as having 7% or greater CD27+CD45RO− cells in the CD8+ population. In an embodiment, the percent of CAR+ cells at pre-harvest levels distinguish responders (e.g., complete responders and partial responders) from non-responders (NR).

The term "relapse" as used herein refers to reappearance of a cancer after an initial period of responsiveness (e.g., complete response or partial response). The initial period of responsiveness may involve the level of cancer cells falling below a certain threshold, e.g., below 20%, 1%, 10%, 5%, 4%, 3%, 2%, or 1%. The reappearance may involve the level of cancer cells rising above a certain threshold, e.g., above 20%, 1%, 10%, 5%, 4%, 3%, 2%, or 1%. For example, e.g., in the context of B-ALL, the reappearance may involve, e.g., a reappearance of blasts in the blood, bone marrow (>5%), or any extramedullary site, after a complete response. A complete response, in this context, may involve <5% BM blast. More generally, in an embodiment, a response (e.g., complete response or partial response) can involve the absence of detectable MRD (minimal residual disease). In an embodiment, the initial period of responsiveness lasts at least 1, 2, 3, 4, 5, or 6 days; at least 1, 2, 3, or 4 weeks; at least 1, 2, 3, 4, 6, 8, 10, or 12 months; or at least 1, 2, 3, 4, or 5 years.

"Regulatable chimeric antigen receptor (RCAR)," as that term is used herein, refers to a set of polypeptides, typically two in the simplest embodiments, which when in a RCARX cell, provides the RCARX cell with specificity for a target cell, typically a cancer cell, and with regulatable intracellular signal generation or proliferation, which can optimize an immune effector property of the RCARX cell. An RCARX cell relies at least in part, on an antigen binding domain to provide specificity to a target cell that comprises the antigen bound by the antigen binding domain. In an embodiment, an RCAR includes a dimerization switch that, upon the presence of a dimerization molecule, can couple an intracellular signaling domain to the antigen binding domain.

"Membrane anchor" or "membrane tethering domain", as that term is used herein, refers to a polypeptide or moiety, e.g., a myristoyl group, sufficient to anchor an extracellular or intracellular domain to the plasma membrane.

"Switch domain," as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term "low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating Mtor activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naïve T cells.

In an embodiment, the low, immune enhancing, dose of mTOR inhibitor results in one or more of the following:
an increase in the expression of one or more of the following markers: $CD62L^{high}$, $CD127^{high}$, $CD27^+$, and BCL2, e.g., on memory T cells, e.g., memory T cell precursors;
a decrease in the expression of KLRG1, e.g., on memory T cells, e.g., memory T cell precursors; and
an increase in the number of memory T cell precursors, e.g., cells with any one or combination of the following characteristics: increased $CD62L^{high}$, increased $CD127^{high}$, increased $CD27^+$, decreased KLRG1, and increased BCL2;
wherein any of the changes described above occurs, e.g., at least transiently, e.g., as compared to a non-treated subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Dual CARs

The disclosure features, at least in part, novel nucleic acid molecules encoding Chimeric Antigen Receptor (CAR) molecules comprising a first CAR comprising a CD22 CAR and a second CAR comprising a CD19 CAR, e.g., dual CARs as described herein. In some embodiments, the CD22 CAR comprises a CD22 antigen binding domain, and a first transmembrane domain; a first co-stimulatory signaling domain; and/or a first primary signaling domain. In some embodiments, the CD19 CAR comprises a CD19 antigen binding domain, and a second transmembrane domain; a second co-stimulatory signaling domain; and/or a second primary signaling domain. In some embodiments of a CAR molecule disclosed herein, the CAR molecule comprises two identical polypeptide sequences, e.g., of a first and second transmembrane domain; a first and second co-stimulatory domain; and/or a first and second primary signaling domain, the polypeptide sequences of which are encoded by different nucleotide sequences. Also disclosed herein are methods of using said CAR molecules.

Without wishing to be bound by theory, it is believed that in some embodiments, a nucleic acid molecule encoding a CAR molecule, e.g., a dual CAR molecule, is optimized, e.g., codon optimized, to prevent recombination, e.g., homologous recombination. In some embodiments, a CAR molecule, e.g., a dual CAR molecule, comprises two domains, e.g., a first transmembrane domain and a second transmembrane domain, each of which comprises a similar amino acid sequence but is encoded by a different nucleotide sequence.

In an aspect, a CAR molecule disclosed herein comprises a first CAR comprising a first antigen binding domain which binds to CD22; a first transmembrane domain; a first co-stimulatory signaling domain; and/or a first primary signaling domain.

In an embodiment, the CD22 antigen binding domain comprises one or more (e.g., all three) light chain complementarity determining region 1 (LC CDR1), light chain complementarity determining region 2 (LC CDR2), and light chain complementarity determining region 3 (LC CDR3) of a CD22 binding domain described herein, e.g., in Tables 1A, 2A or 3A; and/or one or more (e.g., all three) heavy chain complementarity determining region 1 (HC CDR1), heavy chain complementarity determining region 2 (HC CDR2), and heavy chain complementarity determining region 3 (HC CDR3) of a CD22 binding domain described herein, e.g., in Tables 1A, 2A or 3A. In an embodiment, the CD22 antigen binding domain comprises a LC CDR1, LC CDR2 and LC CDR3 of a CD22 binding domain described herein, e.g., in Table 1A, 2A or 3A; and/or a HC CDR1, HC CDR2 and HC CDR3 of a CD22 binding domain described herein, e.g., in Tables 1A, 2A or 3A.

In an embodiment, the CD22 binding domain comprises the LC CDR1 of SEQ ID NO: 28, the LC CDR2 of SEQ ID NO: 29 and the LC CDR3 of SEQ ID NO: 30. In an embodiment, the CD22 binding domain comprises the LC CDR1 of SEQ ID NO: 31, the LC CDR2 of SEQ ID NO: 32 and the LC CDR3 of SEQ ID NO: 33. In an embodiment, the CD22 binding domain comprises the LC CDR1 of SEQ ID NO: 34, the LC CDR2 of SEQ ID NO: 32 and the LC CDR3 of SEQ ID NO: 30.

In an embodiment, the CD22 binding domain comprises the HC CDR1 of SEQ ID NO: 20, the HC CDR2 of SEQ ID NO: 21 and the HC CDR3 of SEQ ID NO: 22. In an embodiment, the CD22 binding domain comprises the HC CDR1 of SEQ ID NO: 23, the HC CDR2 of SEQ ID NO: 24 and the HC CDR3 of SEQ ID NO: 22. In an embodiment, the CD22 binding domain comprises the HC CDR1 of SEQ ID NO: 25, the HC CDR2 of SEQ ID NO: 26 and the HC CDR3 of SEQ ID NO: 27.

In an embodiment, the CD22 binding domain comprises the LC CDR1 of SEQ ID NO: 28, the LC CDR2 of SEQ ID NO: 29 and the LC CDR3 of SEQ ID NO: 30; and the HC CDR1 of SEQ ID NO: 20, the HC CDR2 of SEQ ID NO: 21 and the HC CDR3 of SEQ ID NO: 22. In an embodiment, the CD22 binding domain comprises the LC CDR1 of SEQ ID NO: 31, the LC CDR2 of SEQ ID NO: 32 and the LC CDR3 of SEQ ID NO: 33; and the HC CDR1 of SEQ ID NO: 23, the HC CDR2 of SEQ ID NO: 24 and the HC CDR3 of SEQ ID NO: 22. In an embodiment, the CD22 binding domain comprises the LC CDR1 of SEQ ID NO: 34, the LC CDR2 of SEQ ID NO: 32 and the LC CDR3 of SEQ ID NO: 30; and the HC CDR1 of SEQ ID NO: 25, the HC CDR2 of SEQ ID NO: 26 and the HC CDR3 of SEQ ID NO: 27.

In an embodiment, the CD22 antigen binding domain (e.g., an scFv) comprises a light chain variable (VL) region of a CD22 binding domain described herein, e.g., in Tables 1A or 3A; and/or a heavy chain variable (VH) region of a CD22 binding domain described herein, e.g., in Tables 1A or 3A. In an embodiment, the CD22 antigen binding domain comprises a VL region comprising an amino acid sequence having at least one, two or three modifications (e.g., substitutions) but not more than 30, 20 or 10 modifications (e.g., substitutions) of a CD22 VL region sequence provided in Table 1A or 3A. In an embodiment, the CD22 antigen binding domain comprises a VL region comprising an amino acid sequence with at least 95% identity to a CD22 VL region sequence provided in Table 1A or 3A. In an embodiment, the CD22 antigen binding domain comprises a VL region comprising the amino acid sequence of a CD22 VL region sequence provided in Table 1A or 3A. In an embodiment, the CD22 antigen binding domain comprises a VH region comprising an amino acid sequence having at least one, two or three modifications (e.g., substitutions) but not more than 30, 20 or 10 modifications (e.g., substitutions) of a CD22 VH region sequence provided in Table 1A or 3A. In an embodiment, the CD22 antigen binding domain comprises a VH region comprising an amino acid sequence with at least 95% identity to a CD22 VH region sequence provided in Table 1A or 3A. In an embodiment, the CD22 antigen binding domain comprises a VH region comprising the amino acid sequence of a CD22 VH region sequence provided in Table 1A or 3A.

In an embodiment, the CD22 antigen binding comprises an scFv comprising an amino acid sequence having at least one, two or three modifications (e.g., substitutions) but not more than 30, 20 or 10 modifications (e.g., substitutions) of a CD22 scFv sequence provided in Table 1A or 3A, e.g., SEQ ID NO: 50. In an embodiment, the CD22 antigen binding comprises an scFv comprising an amino acid sequence with at least 95% identity to a CD22 scFv sequence provided in Table 1A or 3A, e.g., SEQ ID NO: 50. In an embodiment, the CD22 antigen binding comprises an scFv comprising the amino acid sequence of a CD22 scFv sequence provided in Table 1A or 3A, e.g., SEQ ID NO: 50. In an embodiment, the CD22 antigen binding comprises an scFv which is encoded by a nucleotide sequence having at least 95%, 96%, 97%, 98%, 99%, or 100% identity to a CD22 scFv sequence provided in Table 1A or 3A, e.g., SEQ ID NO: 49 or 51.

In an aspect, a CAR molecule disclosed herein comprises a second CAR comprising a second antigen binding domain which binds to CD19 and a second transmembrane domain; a second co-stimulatory domain; and/or a second primary signaling domain.

In some embodiments, the CD19 antigen binding domain comprises: one or more (e.g., all three) light chain complementarity determining region 1 (LC CDR1), light chain complementarity determining region 2 (LC CDR2), and light chain complementarity determining region 3 (LC CDR3) of a CD19 binding domain described herein, e.g., in Tables 1A, 2A, 3A, or 5A; and/or one or more (e.g., all three) heavy chain complementarity determining region 1 (HC CDR1), heavy chain complementarity determining region 2 (HC CDR2), and heavy chain complementarity determining region 3 (HC CDR3) of a CD19 binding domain described herein, e.g., in Tables 1A, 2A, 3A, or 5A. In some embodiments, the CD19 antigen binding domain comprises a LC CDR1, LC CDR2 and LC CDR3 of a CD19 binding domain described herein, e.g., in Table 1A or 2A; and/or a HC CDR1, HC CDR2 and HC CDR3 of a CD19 binding domain described herein, e.g., in Table 1A, 2A or 3A. In some embodiments, the CD19 antigen binding domain comprises a LC CDR1 of SEQ ID NO: 40, LC CDR2 of SEQ ID NO: 41; and LC CDR3 of SEQ ID NO: 42; and/or HC CDR1 of SEQ ID NO: 35, HC CDR2 of SEQ ID NO: 36-38; and HC CDR3 of SEQ ID NO: 39.

In some embodiments, the CD19 antigen binding domain (e.g., an scFv) comprises a light chain variable (VL) region of a CD19 binding domain described herein, e.g., in Tables 1A, 3A, or 5A; and/or a heavy chain variable (VH) region of a CD19 binding domain described herein, e.g., in Tables 1A, 3A, or 5A. In some embodiments, the CD19 antigen binding domain comprises a VL region comprising an amino acid sequence having at least one, two or three modifications (e.g., substitutions) but not more than 30, 20 or 10 modifications (e.g., substitutions) of a CD19 VL region sequence provided in Tables 1A, 3A, or 5A. In some embodiments, the CD19 antigen binding domain comprises a VL region comprising an amino acid sequence with at least 95% identity to a CD19 VL region sequence provided in Tables 1A, 3A, or 5A. In some embodiments, the CD19 antigen binding domain comprises a VL region comprising the amino acid sequence of a CD19 VL region sequence provided in Tables 1A, 3A, or 5A. In some embodiments, the CD19 antigen binding domain comprises a VH region comprising an amino acid sequence having at least one, two or three modifications (e.g., substitutions) but not more than 30, 20 or 10 modifications (e.g., substitutions) of a CD19 VH region sequence provided in Tables 1A, 3A, or 5A. In some embodiments, the CD19 antigen binding domain comprises a VH region comprising an amino acid sequence with at least 95% identity to a CD19 VH region sequence provided in Tables 1A, 3A, or 5A. In some embodiments, the CD19 antigen binding domain comprises a VH region comprising the amino acid sequence of a CD19 VH region sequence provided in Tables 1A, 3A, or 5A.

In other embodiments, the CD19 antigen binding domain comprises an scFv comprising an amino acid sequence having at least one, two or three modifications (e.g., substitutions) but not more than 30, 20 or 10 modifications (e.g., substitutions) of a CD19 scFv sequence provided in Tables 1A, 3A, or 5A, e.g., SEQ ID NO: 44. In other embodiments, the CD19 antigen binding domain comprises an scFv comprising an amino acid sequence with at least 95% identity to a CD19 scFv sequence provided in Tables 1A, 3A, or 5A, e.g., SEQ ID NO: 44. In other embodiments, the CD19 antigen binding domain comprises an scFv comprising the amino acid sequence of a CD19 scFv sequence provided in Tables 1A, 3A, or 5A, e.g., SEQ ID NO: 44. In other embodiments, the CD19 antigen binding domain comprises an scFv which is encoded by a nucleotide sequence having at least 95%, 96%, 97%, 98%, 99%, or 100% identity to a CD19 scFv sequence provided in Tables 1A, 3A, or 5A, e.g., SEQ ID NO: 43 or 48.

In an aspect, a CAR molecule disclosed herein comprises a first CAR comprising a first transmembrane domain and a second CAR comprising a second transmembrane domain. In an embodiment, the first transmembrane domain and the second transmembrane domain comprise the same amino acid sequence, e.g., as disclosed herein. In an embodiment, the first transmembrane domain and the second transmembrane domain are encoded by a first nucleotide sequence and a second nucleotide sequence, respectively. In some embodiments, the first nucleotide sequence and the second nucleotide sequence differ by at least one nucleotide. In some embodiments, the first transmembrane domain and the second transmembrane domain are the same transmembrane domain, e.g., chosen from the alpha, beta or zeta chain of the T-cell receptor, CD28, CD3 epsilon, CD45, CD4, CD5, CD8, CD9, CD16, CD22, CD33, CD37, CD64, CD80, CD86, CD123, CD134, CD137 or CD154.

In some embodiments, the first transmembrane domain and the second transmembrane domain are different transmembrane domains, e.g., chosen from the alpha, beta or zeta chain of the T-cell receptor, CD28, CD3 epsilon, CD45, CD4, CD5, CD8, CD9, CD16, CD22, CD33, CD37, CD64, CD80, CD86, CD123, CD134, CD137 or CD154.

In an aspect, a nucleic acid molecule encoding a CAR molecule described herein comprises a first CAR comprising a first transmembrane domain and a second CAR comprising a second transmembrane domain. In some embodiments, the first transmembrane domain and the second transmembrane domain comprise the CD8 alpha transmembrane domain. In some embodiments, the first transmembrane domain and the second transmembrane domain comprise the amino acid sequence of SEQ ID NO: 65 or an amino acid sequence with at least 90% identity thereto. In some embodiments, a nucleotide sequence that encodes the first transmembrane domain and is comprised in the nucleic acid molecule is different from a nucleotide sequence that encodes the second transmembrane domain and is comprised in the nucleic acid molecule.

In an aspect, a CAR molecule disclosed herein comprises a first CAR comprising a first co-stimulatory domain and a second CAR comprising a second co-stimulatory domain. In an embodiment, the first co-stimulatory domain and the second co-stimulatory domain comprise the same amino acid sequence, e.g., as disclosed herein. In an embodiment, the first co-stimulatory domain and the second co-stimulatory domain are encoded by a first nucleotide sequence and a second nucleotide sequence, respectively. In some embodiments, the first nucleotide sequence and the second nucleotide sequence differ by at least one nucleotide.

In some embodiments, the first co-stimulatory domain and the second co-stimulatory domain are the same co-stimulatory domain, e.g., chosen from a signaling domain of OX40, CD2, CD27, CD28, CDS, ICAM-1, LFA-1 (CD11a/CD18), ICOS (CD278) or 4-1BB (CD137).

In some embodiments, the first co-stimulatory domain and the second co-stimulatory domain are different co-stimulatory domains, e.g., chosen from a signaling domain of OX40, CD2, CD27, CD28, CDS, ICAM-1, LFA-1 (CD11a/CD18), ICOS (CD278) or 4-1BB (CD137).

In an aspect, a nucleic acid molecule encoding a CAR molecule described herein comprises a first CAR comprising a first co-stimulatory domain and a second CAR comprising a second co-stimulatory domain. In some embodiments, the first co-stimulatory domain and the second co-stimulatory domain comprise a 4-1BB co-stimulatory domain. In some embodiments, the first co-stimulatory domain and the second co-stimulatory domain comprise the amino acid sequence of SEQ ID NO: 65 or an amino acid sequence with at least 90% identity thereto.

In some embodiments, a nucleotide sequence that encodes the first co-stimulatory domain and is comprised in the nucleic acid molecule is different from a nucleotide sequence that encodes the second co-stimulatory domain and is comprised in the nucleic acid molecule.

In some aspects, the present disclosure provides a nucleic acid molecule encoding a CAR molecule, e.g., comprising (i) a first CAR comprising a CD22 antigen binding domain and (ii) a second CAR comprising a CD19 antigen binding domain. In embodiments, the nucleic acid comprises RNA or DNA. In embodiments, the nucleic acid sequences encoding (i) and (ii) are situated in the same orientation, e.g., transcription of the nucleic acid sequences encoding (i) and (ii) proceeds in the same direction. In embodiments, the nucleic acid sequences encoding (i) and (ii) are situated in different orientations. In embodiments, a single promoter controls expression of the nucleic acid sequences encoding (i) and (ii). In embodiments, a nucleic acid encoding a protease cleavage site (such as a T2A, P2A, E2A, or F2A cleavage site) is situated between the nucleic acid sequences encoding (i) and (ii). In embodiments, the protease cleavage site is placed such that a cell can express a fusion protein comprising (i) and (ii), which protein is subsequently processed into two peptides by proteolytic cleavage. In some embodiments, the nucleic acid sequences encoding (i) is upstream of the nucleic acid sequences encoding (ii), or the nucleic acid sequences encoding (ii) is upstream of the nucleic acid sequences encoding (i). In embodiments, a first promoter controls expression of the nucleic acid sequence encoding (i) and a second promoter controls expression of the nucleic acid sequence encoding (ii). In embodiments, the nucleic acid is a plasmid. In embodiments, the nucleic acid comprises a viral packaging element. In some aspects, the present disclosure provides a cell, e.g., an immune effector cell, comprising the nucleic acid described herein, e.g., a nucleic acid comprising (i) and (ii) as described above. The cell may comprise a protease (e.g., endogenous or exogenous) that cleaves a T2A, P2A, E2A, or F2A cleavage site.

Exemplary nucleotide and amino acid sequences of a CAR molecule, e.g., dual CAR molecule disclosed herein is provided in Table 1A.

TABLE 1A

Dual and tandem CD19-CD22 CAR sequences

| Identifier | SEQ ID NO | Sequence |
|---|---|---|
| | | Tandem CD19-CD22 CARs |
| CG#c171 | 1 | atggccctccctgtcaccgccctgctgcttccgctggctcttctgctccacgccgctcggcccg<br>aaattgtgatgacccagtcacccgccactcttagcctttcacccggtgagcgcgcaaccctgtc<br>ttgcagagcctcccaagacatctcaaaatacc ttaattggtatcaacagaagcccggacaggc<br>tcctcgccttctgatctaccacaccagccggctccattctggaatccctgccaggttcagcggt<br>agcggatctgggaccgactacaccctcactatcagctcactgcagccagaggacttcgctgtc<br>tatttctgtcagcaaggg aacaccctgccctacacctttggacagggcaccaagctcgagatt<br>aaaggtggaggtggcagcggaggaggtgggtccggcggtggaggaagccaggtccaact<br>ccaagaaagcggaccgggtcttgtgaagccatcagaaactctttcactgacttgtactgtgagc<br>ggagtgtctctccccgattacggggtgtcttggatcagacagccaccggggaagggtctgga<br>atggattggagtgatttggggctctgagactacttactaccaatcatccctcaagtcacgcgtca<br>ccatctcaaaggacaactctaagaatcaggtgtcactgaaactgtcatctgtgaccgcagccg<br>acaccgccgtgtactattgcgctaagcattactattatgcgggagctacgcaatggattactg<br>gggacagggtactctggtcaccgtgtccagcttggcagaagccgccgcgaaagaagtgcag<br>cttcaacaatcaggaccaggactcgtcaaaccatcacagaccctctccctcacatgtgccatct<br>ccggggactccatgttgagcaattccgacacttggaattggattagacaaagcccgtcccggg<br>gtctggaatggttgggacgcacctaccaccggtctacttggtacgacgactacgcgtcatccg<br>tgcggggaagagtgtccatcaacgtggacacctccaagaaccagtacagcctgcagcttaat<br>gccgtgactcctgaggatacggcgctctactactgcgcccgcgtccgcctgcaagacggga<br>acagctggagcgatgcattcgatgtctggggccagggaactatggtcaccgtgtcgtctggg<br>ggcggtggatcgggtggcggggttcggggggcggcggctctcagtccgctcttacccaac<br>cggcctcagcctcggggagcccggccagagcgtgaccatttcctgcaccggcacttcatcc<br>gacgtgggcggctacaactacgtgtcctggtaccaacagcacccgggaaaggccccaag<br>ctcatgatctacgacgtgtccaacaggccctcgggagtgtccaaccggttctcgggttcgaaa<br>tcgggaaacacagccagcctgaccatcagcggactgcaggctgaagatgaagccgactact<br>actgctcctcctacacctcgtcatccacgctctacgtgttcggcactggaactcagctgactgtg<br>ctgaccactaccccagcaccgaggccacccaccccggctcctaccatcgcctcccagcctct<br>gtccctgcgtccggaggcatgtagacccgcagctggtggggccgtgcataccgggtctt<br>gacttcgcctgcgatatctacatttgggccctctggctggtacttgcggggtcctgctgctttca<br>ctcgtgatcactcttttactgtaagcgcggtcggaagaagctgctgtacatctttaagcaaccctt<br>catgaggcctgtgcagactactcaagaggaggacggctgttcatgccggttcccagaggag<br>gaggaaggcggctgcgaactgcgcgtgaaattcagccgcagcgcagatgctccagcctac<br>cagcaggggcagaaccagctctacaacgaactcaatcttggtcggagagaggagtacgacg<br>tgctggacaagcggagaggacgggacccagaaatgggcgggaagccgcgcagaaagaa<br>tccccaagagggcctgtacaacgagtccaaaaggataagatggcagaagcctatagcgag<br>attggtatgaaaggggaacgcagaagaggcaaaggccacgacggactgtaccagggactc<br>agcaccgccaccaaggacacctatgacgctcttcacatgcaggccctgccgcctcgg |
| | 2 | MALPVTALLLPLALLLHAARPEIVMTQSPATLSLSPGERAT<br>LSCRASQDISKYLNWYQQKPGQAPRLLIYHTSRLHSGIPAR<br>FSGSGSGTDYTLTISSLQPEDFAVYFCQQGNTLPYTFGQGT<br>KLEIKGGGGSGGGGSGGGGSQVQLQESGPGLVKPSETLSLT<br>CTVSGVSLPDYGVSWIRQPPGKGLEWIGVIWGSETTYYQSS<br>LKSRVTISKDNSKNQVSLKLSSVTAADTAVYYCAKHYYYG<br>GSYAMDYWGQGTLVTVSSLAEAAAKEVQLQQSGPGLVKP<br>SQTLSLTCAISGDSMLSNSDTWNWIRQSPSRGLEWLGRTY<br>HRSTWYDDYASSVRGRVSINVDTSKNQYSLQLNAVTPEDT<br>GVYYCARVRLQDGNSWSDAFDVWGQGTMVTVSSGGGGS<br>GGGGSGGGGSQSALTQPASASGSPGQSVTISCTGTSSDVGG<br>YNYVSWYQQHPGKAPKLMIYDVSNRPSGVSNRFSGSKSG<br>NTASLTISGLQAEDEADYYCSSYTSSSTLYVFGTGTQLTVL<br>TTTPAPRPPTPAPTIASQPLSLRPEACRPAAGGAVHTRGLDF<br>ACDIYIWAPLAGTCGVLLLSLVITLYCKRGRKKLLYIFKQPF<br>MRPVQTTQEEDGCSCRFPEEEEGGCELRVKFSRSADAPAY<br>QQGQNQLYNELNLGRREEYDVLDKRRGRDPEMGGKPRRK<br>NPQEGLYNELQKDKMAEAYSEIGMKGERRRGKGHDGLYQ<br>GLSTATKDTYDALHMQALPPR |
| CG#c182 | 3 | atggccctccctgtcaccgccctgctgcttccgctggctcttctgctccacgccgctcggcccg<br>aagtgcagcttcaacaatcaggaccaggactcgtcaaaccatcacagaccctctccctcacat<br>gtgccatctccggggactccatgttgagcaattccgacacttggaattggattagacaaagccc<br>gtcccggggtctggaatggttgggacgcacctaccaccggtctacttggtacgacgactacg<br>cgtcatccgtgcggggaagagtgtccatcaacgtggacacctccaagaaccagtacagcctg |

TABLE 1A -continued

Dual and tandem CD19-CD22 CAR sequences

| Identifier | SEQ ID NO | Sequence |
|---|---|---|
| | | cagcttaatgccgtgactcctgaggatacgggcgtctactactgcgcccgcgtccgcctgcaa<br>gacgggaacagctggagcgatgcattcgatgtctggggccaggaactatggtcaccgtgtc<br>gtctggggggggtggatcgggtggcggggggttcggggggcggcggctctcagtccgctctt<br>acccaaccggcctcagcctcggggagccccggccagagcgtgaccatttcctgcaccggc<br>acttcatccgacgtgggcggctacaactacgtgtcctggtaccaacagcacccgggaaggc<br>ccccaagctcatgatctacgacgtgtccaacaggccctcggagtgtccaaccggttctcgg<br>gttcgaaatcgggaaacacagccagcctgaccatcagcggactgcaggctgaagatgaagc<br>cgactactactgctcctcctacacctcgtcatccacgctctacgtgttcggcactggaactcagc<br>tgactgtgctggggggggagggagtgaaattgtgatgacccagtcacccgccactcttagc<br>cttcacccggtgagcgcgcaacccgtcttgcagagcctcccaagacatctcaaaataccttta<br>attggtatcaacagaagcccggacaggctcctcgcccttctgatctaccacaccagccggctcc<br>attctggaatccctgccaggttcagcggtagcggatctgggaccgactacaccctcactatca<br>gctcactgcagccagaggacttcgctgtctatttctgtcagcaagggaacaccctgccctaca<br>cctttggacagggcaccaagctcgagattaaaggtggaggtggcagcggaggaggtgggt<br>ccggcggtggaggaagccaggtccaactccaagaaagcggacccggggtcttgtgaagccat<br>cagaaactctttcactgacttgtactgtgagcggagtgtctctccccgattacgggggtgtcttgg<br>atcagacagccaccggggaagggtctgaatggattggagtgatttggggctctgagactac<br>ttactaccaatcatccctcaagtcacgcgtcaccatctcaaaggacaactctaagaatcaggtg<br>tcactgaaactgtcatctgtgaccgcagccgacaccgccgtgtactattgcgctaagcattact<br>attatggcgggagctacgcaatgattactggggacaggggtactctggtcaccgtgtccagca<br>ccactaccccagcaccgaggccacccaccccggctcctaccatcgcctcccagcctctgtcc<br>ctgcgtccggaggcatgtagaccgcagctggtggggccgtgcatacccgggggtcttgactt<br>cgcctgcgatatctacatttgggcccctctggctggtacttgcggggtcctgctgctttcactcgt<br>gatcactcttttactgtaagcgcggtcggaagaagctgctgtacatctcttaagcaaccttcatga<br>ggcctgtgcagactactcaagaggaggcggctgttcatgccggttcccagaggaggagga<br>aggcggctgcgaactcgcgtgaaattcagccgcagcgcagatgctccagcctaccagcag<br>gggcagaaccagctctacaacgaactcaatcttggtcggagagaggagtacgacgtgctgg<br>acaagcggagaggacgggacccagaaatgggcgggaagccgcgcagaaagaatcccca<br>agagggcctgtacaacgagctccaaaaggataagatggcagaagcctatagcgagattggt<br>atgaaaggggaacgcagaagaggcaaaggccacgacggactgtaccaggggactcagcac<br>cgccaccaaggacacctatgacgctcttcacatgcaggccctgccgcctcgg |
| | 4 | MALPVTALLLPLALLLHAARPEVQLQQSGPGLVKPSQTLSL<br>TCAISGDSMLSNSDTWNWIRQSPSRGLEWLGRTYHRSTWY<br>DDYASSVRGRVSINVDTSKNQYSLQLNAVTPEDTGVYYCA<br>RVRLQDGNSWSDAFDVWGQGTMVTVSSGGGGSGGGGSG<br>GGGSQSALTQPASASGSPGQSVTISCTGTSSDVGGYNYVS<br>WYQQHPGKAPKLMIYDVSNRPSGVSNRFSGSKSGNTASLT<br>ISGLQAEDEADYYCSSYTSSSTLYVFGTGTQLTVLGGGGSE<br>IVMTQSPATLSLSPGERATLSCRASQDISKYLNWYQQKPGQ<br>APRLLIYHTSRLHSGIPARFSGSGSGTDYTLTISSLQPEDFAV<br>YFCQQGNTLPYTFGQGTKLEIKGGGGSGGGGSGGGGSQVQ<br>LQESGPGLVKPSETLSLTCTVSGVSLPDYGVSWIRQPPGKG<br>LEWIGVIWGSETTYYQSSLKSRVTISKDNSKNQVSLKLSSV<br>TAADTAVYYCAKHYYYGGSYAMDYWGQGTLVTVSSTTT<br>PAPRPPTPAPTIASQPLSLRPEACRPAAGGAVHTRGLDFAC<br>DIYIWAPLAGTCGVLLLSLVITLYCKRGRKKLLYIFKQPFM<br>RPVQTTQEEDGCSCRFPEEEEGGCELRVKFSRSADAPAYQQ<br>GQNQLYNELNLGRREEYDVLDKRRGRDPEMGGKPRRKNP<br>QEGLYNELQKDKMAEAYSEIGMKGERRRGKGHDGLYQGL<br>STATKDTYDALHMQALPPR |
| CG#c188 | 5 | atggccctccctgtcaccgccctgctgcttccgctggctcttctgctccacgccgctcggcccc<br>agtccgctcttacccaaccggcctcagcctcggggagccccggccagagcgtgaccatttcc<br>tgcaccggcacttcatccgacgtgggcggctacaactacgtgtcctggtaccaacagcaccc<br>gggaaaggccccaagctcatgatctacgacgtgtccaacaggccctcggagtgtccaac<br>cggttctcgggttcgaaatcgggaaacacagccagcctgaccatcagcggactgcaggctg<br>aagatgaagccgactactactgctcctcctacacctcgtcatccacgctctacgtgttcggcact<br>ggaactcagctgactgtgctggggcggaggaggctccgaagtgcagcttcaacaatcaggac<br>caggactcgtcaaaccatcacagaccctctccctcacatgtgccatctccgggactccatgtt<br>gagcaattccgacacttggaattggattagacaaagcccgtcccggggtctggaatggttggg<br>acgcacctaccaccggtctacttggtacgacgactacgcgtcatccgtgcgggaagagtgt<br>ccatcaacgtggacacctccaagaaccagtacagcctgcagcttaatgccgtgactcctgag<br>gatacgggcgtctactactgcgcccgcgtccgcctgcaagacgggaacagctggagcgatg<br>cattcgatgtctggggccaggaactatggtcaccgtgtcgtctggggggggggggagtgaa<br>attgtgatgacccagtcacccgccactcttagccttcacccggtgagcgcgcaacccgtcttt<br>gcagagcctcccaagacatctcaaaataccttaattggtatcaacagaagcccggacaggctc<br>ctcgcccttctgatctaccacaccagccggctccattctggaatccctgccaggttcagcggtag<br>cggatctgggaccgactacaccctcactatcagctcactgcagccagaggacttcgctgtcta<br>tttctgtcagcaagggaacaccctgccctacacctttggacagggcaccaagctcgagattaa<br>aggtggaggtggcagcggaggaggtgggtccggcggtggaggaagccaggtccaactcc<br>aagaaagcggacccggggtcttgtgaagccatcagaaactctttcactgacttgtactgtgagcg<br>gagtgtctctccccgattacggggtgtcttggatcagacagccaccggggaagggtctggaa<br>tggattggagtgatttggggctctgagactacttactaccaatcatccctcaagtcacgcgtcac<br>catctcaaaggacaactctaagaatcaggtgtcactgaaactgtcatctgtgaccgcagccga |

TABLE 1A -continued

Dual and tandem CD19-CD22 CAR sequences

| Identifier | SEQ ID NO | Sequence |
|---|---|---|
| | | caccgccgtgtactattgcgctaagcattactattatggcgggagctacgcaatggattactgg<br>ggacagggtactctggtcaccgtgtccagcaccactacccccagcaccgaggccacccacc<br>cggctcctaccatcgcctcccagcctctgtccctgcgtccggaggcatgtagacccgcagct<br>ggtggggccgtgcatacccggggtcttgacttcgcctgcgatatctacatttgggcccctctgg<br>ctggtacttgcggggtcctgctgctttcactcgtgatcactctttactgtaagcgcggtcggaag<br>aagctgctgtacatctttaagcaacccttcatgaggcctgtgcagactactcaagaggaggac<br>ggctgttcatgccggttcccagaggaggaggaaggcggctgcgaactgcgcgtgaaattca<br>gccgcagcgcagatgctccagcctaccagcaggggcagaaccagctctacaacgaactca<br>atcttggtcggagagaggagtacgacgtgctggacaagcggagaggacgggacccagaaa<br>tgggcgggaagccgcgcagaaagaatccccaagagggcctgtacaacgagctccaaaag<br>gataagatggcagaagcctatagcgagattggtatgaaggggaacgcagaagaggcaaa<br>ggccacgacggactgtaccagggactcagcaccgccaccaaggacacctatgacgctcttc<br>acatgcaggccctgccgcctcgg |
| | 6 | MALPVTALLLPLALLLHAARPQSALTQPASASGSPGQSVTI<br>SCTGTSSDVGGYNYVSWYQQHPGKAPKLMIYDVSNRPSG<br>VSNRFSGSKSGNTASLTISGLQAEDEADYYCSSYTSSSTLY<br>VFGTGTQLTVLGGGGSEVQLQQSGPGLVKPSQTLSLTCAIS<br>GDSMLSNSDTWNWIRQSPSRGLEWLGRTYHRSTWYDDYA<br>SSVRGRVSINVDTSKNQYSLQLNAVTPEDTGVYYCARVRL<br>QDGNSWSDAFDVWGQGTMVTVSSGGGGSEIVMTQSPATL<br>SLSPGERATLSCRASQDISKYLNWYQQKPGQAPRLLIYHTS<br>RLHSGIPARFSGSGSGTDYTLTISSLQPEDFAVYFCQQGNTL<br>PYTFGQGTKLEIKGGGGSGGGGSGGGGSQVQLQESGPGLV<br>KPSETLSLTCTVSGVSLPDYGVSWIRQPPGKGLEWIGVIWG<br>SETTYYQSSLKSRVTISKDNSKNQVSLKLSSVTAADTAVYY<br>CAKHYYYGGSYAMDYWGQGTLVTVSSTTTPAPRPPTPAPT<br>IASQPLSLRPEACRPAAGGAVHTRGLDFACDIYIWAPLAGT<br>CGVLLLSLVITLYCKRGRKKLLYIFKQPFMRPVQTTQEEDG<br>CSCRFPEEEEGGCELRVKFSRSADAPAYQQGQNQLYNELN<br>LGRREEYDVLDKRRGRDPEMGGKPRRKNPQEGLYNELQK<br>DKMAEAYSEIGMKGERRRGKGHDGLYQGLSTATKDTYDA<br>LHMQALPPR |
| CG#c224 | 7 | atggccctgccgtgactgcgctcctgcttccgttggccctgctcctgcatgccgccagacctc<br>agtccgctctgactcagccggcctcagcttcggggtcccctggtcaaagcgtcactatttcctg<br>taccggaacctcatcagacgtgggcggctacaattacgtgtcctggtaccaacagcacccg<br>gaaaggctcctaagcttatgatctacgacgtgtccaaccggccgtcaggagtgtccaacagat<br>tctccggctccaagagcggaaacactgccagcttgaccattagcggcttgcaggccgagga<br>cgaagccgactactactgctctagctacacatcctcgtctaccctacgtgtttggaacgggg<br>acccagctgactgtgctcggggtggaggatcagaggtgcaactccagcagtccggtcctg<br>gcctcgtgaaaccgtcccaaaccctgtccctgacttgcgccatctcgggcgactccatgctgt<br>ccaattccgacacctggaactggattagacaatcgcctagccggggactcgaatggctgggc<br>cggacctaccaccggtccacgtggtatgacgactacgcaagctccgtccggggaagggtgt<br>ccattaacgtcgatacctccaagaaccagtacagccttcagctgaacgctgtgaccccgag<br>gataccggcgtctactactgtgcaagagtgcgattgcaggatggaaactcgtggtcggacgc<br>attcgatgtctggggacagggaactatggtgaccgtgtcctcgggcggaggcgggagcgga<br>ggaggaggctctggcggaggaggaagcgagattgtcatgactcagtcccggccacactct<br>ccctgtcacccggagaaagagcaaccctgagctgcagggcgtcccaggacatctcgaagta<br>cctgaactggtaccagcagaagcctggacaagcaccccgcctcctgatctaccacacctcgc<br>ggctgcattcgggaatccccgccagattctcagggagcggatcaggaaccgactacaccct<br>gactatctcgagcctgcaaccagaggatttcgccgtgtacttctgccagcaaggaaacaccct<br>gccctacacctttggacagggaaccaagctcgagattaaggggggtggtggatcggaggg<br>ggtggatcaggaggaggcggctcacaagtccagctgcaagaatccggtccgggacttgtga<br>agccgtccgaaaccctgtcactgacttgcactgtgtccggggtgtcattgcccgactacggcg<br>tgagctggattcggcagccccctggaaagggattggaatggatcggcgtgatctggggttcg<br>gaaactacctactatcagtcctcactgaagtcccgcgtgaccatcagcaaggataattccaaaa<br>accaagtgtctctgaagctctccagcgtcactgccgccgatactgccgtgtactactgcgca<br>agcactactattacgcggttcgtacgccatggactactggggcaagggacactcgtgacc<br>gtgtcatccaccactaccccagcaccgaggccacccaccccggctcctaccatcgcctcca<br>gcctctgtccctgcgtccggaggcatgtagacccgcagctggtggggccgtgcatacccgg<br>ggtcttgacttcgcctgcgatatctacatttgggcccctctggtacttgcggggtcctgctgct<br>gctttcactcgtgatcactctttactgtaagcgcggtcggaagaagctgctgtacatctttaagca<br>acccttcatgaggcctgtgcagactactcaagaggaggacggctgttcatgccggttcccaga<br>ggaggaggaaggcggctgcgaactgcgcgtgaaattcagccgcagcgcagatgctccagc<br>ctaccagcaggggcagaaccagctctacaacgaactcaatcttggtcggagagaggagtac<br>gacgtgctggacaagcggagaggacgggacccagaaatgggcgggaagccgcgcagaa<br>agaatccccaagagggcctgtacaacgagctccaaaaggataagatggcagaagcctatag<br>cgagattggtatgaaggggaacgcagaagaggcaaaggccacgacggactgtaccagg<br>gactcagcaccgccaccaaggacacctatgacgctcttcacatgcaggccctgccgcctcgg |
| | 8 | MALPVTALLLPLALLLHAARPQSALTQPASASGSPGQSVTI<br>SCTGTSSDVGGYNYVSWYQQHPGKAPKLMIYDVSNRPSG<br>VSNRFSGSKSGNTASLTISGLQAEDEADYYCSSYTSSSTLY<br>VFGTGTQLTVLGGGGSEVQLQQSGPGLVKPSQTLSLTCAIS |

TABLE 1A -continued

Dual and tandem CD19-CD22 CAR sequences

| Identifier | SEQ ID NO | Sequence |
|---|---|---|
| | | GDSMLSNSDTWNWIRQSPSRGLEWLGRTYHRSTWYDDYA<br>SSVRGRVSINVDTSKNQYSLQLNAVTPEDTGVYYCARVRL<br>QDGNSWSDAFDVWGQGTMVTVSSGGGGSGGGGSGGGGS<br>EIVMTQSPATLSLSPGERATLSCRASQDISKYLNWYQQKPG<br>QAPRLLIYHTSRLHSGIPARFSGSGSGTDYTLTISSLQPEDFA<br>VYFCQQGNTLPYTFGQGTKLEIKGGGGSGGGGSGGGGSQV<br>QLQESGPGLVKPSETLSLTCTVSGVSLPDYGVSWIRQPPGK<br>GLEWIGVIWGSETTYYQSSLKSRVTISKDNSKNQVSLKLSS<br>VTAADTAVYYCAKHYYYGGSYAMDYWGQGTLVTVSSTT<br>TPAPRPPTPAPTIASQPLSLRPEACRPAAGGAVHTRGLDFAC<br>DIYIWAPLAGTCGVLLLSLVITLYCKRGRKKLLYIFKQPFM<br>RPVQTTQEEDGCSCRFPEEEEGGCELRVKFSRSADAPAYQQ<br>GQNQLYNELNLGRREEYDVLDKRRGRDPEMGGKPRRKNP<br>QEGLYNELQKDKMAEAYSEIGMKGERRRGKGHDGLYQGL<br>STATKDTYDALHMQALPPR |
| CG#c227 | 9 | atggccctgccgtgactgcgctcctgcttccgttggccctgctcctgcatgccgccagacctc<br>agtccgctctgactcagccggcctcagcttcggggtcccctggtcaaagcgtcactatttcctg<br>taccggaacctcatcagacgtgggcggctacaattacgtgtcctggtaccaacagcaccccg<br>gaaaggctcctaagcttatgatctacgatgtgtccaaccggccgtcaggagtgtccaacagat<br>tctccggctccaagagcggaaacactgccagcttgaccattagcggcttgcaggccgagga<br>cgaagccgactactactgctctagctacacatcctcgtctaccctctacgtgtttggaacgggg<br>acccagctgactgtgctcgggggtggaggatcagaggtgcaactccagcagtccggtcctg<br>gcctcgtgaaaccgtcccaaaccctgtccctgacttgcgccatctcgggcgactccatgctgt<br>ccaattccgacacctggaactggattagacaatcgcctagccggggactcgaatggctgggc<br>cggacctaccaccggtccacgtggtatgacgactacgcaagctccgtccggggaagggtgt<br>ccattaacgtcgatacctccaagaaccagtacagccttcagctgaacgctgtgaccccgag<br>gataccggcgtctactactgtgcaagagtgcgattgcaggatgaaactcgtggtcggacgc<br>attcgatgtctggggacagggaactatggtcactgtgtcctccggcggtggaggctcgggg<br>ggggcggctcaggaggaggcggctcacaagtccagctgcaagaatccggtccgggacttg<br>tgaagccgtccgaaaccctgtcactgacttgcactgtgtccggggtgtcattgcccgactacg<br>gcgtgagctggattcggcagcccctggaaagggattggaatggatcggcgtgatctgggt<br>tcggaaactacctactatcagtcctcactgaagtcccgcgtgaccatcagcaaggataattcca<br>aaaaccaagtgtctctgaagctctccagcgtcactgccgccgatactgccgtgtactactgcg<br>ccaagcactactattacggcggttcgtacgccatggactactggggacaaggcactcttgtga<br>ctgtctcaagcggcggtggagggagcggtgggggcggttcaggaggaggcggatcagag<br>atcgtgatgacccaatccccagccaccctgtccctcagccctggagaaagagccaccctgag<br>ctgcagggcctcccaggatatcagcaagtacttgaactggtaccaacaaaagccggggcag<br>gcgcccccggctcctgatctaccacacctcgcgcctccactcaggtatccccgccagattctca<br>gggagcggctccggtactgactacaccctgactatttcctcactgcagccagaggactttgcc<br>gtgtacttctgccagcagggaaacactctgccgtacaccttcgggcagggaacgaagcttga<br>aattaagaccactaccccagcaccgaggccacccacccccggctcctaccatcgcctcccag<br>cctctgtccctgcgtccgaggcatgtagacccgcagctggtggggccgtgcatacccggg<br>gtcttgacttcgcctgcgatatctacatttgggcccctctggctggtacttgcgggtcctgctg<br>ctttcactcgtgatcactctttactgtaagcgcggtcggaagaagctgctgtacatctttaagcaa<br>cccttcatgaggcctgtgcagactactcaagaggaggacggctgttcatgccggttcccaga<br>ggaggaggaaggcggctgcgaactgcgcgtgaaattcagccgcagcgcagatgctccagc<br>ctaccagcaggggcagaaccagtctctacaacgaactcaatcttggtcggagagaggagtac<br>gacgtgctggacaagcggagaggacgggacccagaaatgggcgggaagccgcgcagaa<br>agaatccccaagagggcctgtacaacgagctccaaaaggataagatggcagaagcctatag<br>cgagattggtatgaaggggaacgcagaagaggcaaaggccacgacggactgtaccagg<br>gactcagcaccgccaccaaggacacctatgacgctcttcacatgcaggccctgccgcctcgg |
| | 10 | MALPVTALLLPLALLLHAARPQSALTQPASASGSPGQSVTI<br>SCTGTSSDVGGYNYVSWYQQHPGKAPKLMIYDVSNRPSG<br>VSNRFSGSKSGNTASLTISGLQAEDEADYYCSSYTSSSTLY<br>VFGTGTQLTVLGGGGSEVQLQQSGPGLVKPSQTLSLTCAIS<br>GDSMLSNSDTWNWIRQSPSRGLEWLGRTYHRSTWYDDYA<br>SSVRGRVSINVDTSKNQYSLQLNAVTPEDTGVYYCARVRL<br>QDGNSWSDAFDVWGQGTMVTVSSGGGGSGGGGSGGGGS<br>QVQLQESGPGLVKPSETLSLTCTVSGVSLPDYGVSWIRQPP<br>GKGLEWIGVIWGSETTYYQSSLKSRVTISKDNSKNQVSLKL<br>SSVTAADTAVYYCAKHYYYGGSYAMDYWGQGTLVTVSS<br>GGGGSGGGGSGGGGSEIVMTQSPATLSLSPGERATLSCRAS<br>QDISKYLNWYQQKPGQAPRLLIYHTSRLHSGIPARFSGSGS<br>GTDYTLTISSLQPEDFAVYFCQQGNTLPYTFGQGTKLEIKTT<br>TPAPRPPTPAPTIASQPLSLRPEACRPAAGGAVHTRGLDFAC<br>DIYIWAPLAGTCGVLLLSLVITLYCKRGRKKLLYIFKQPFM<br>RPVQTTQEEDGCSCRFPEEEEGGCELRVKFSRSADAPAYQQ<br>GQNQLYNELNLGRREEYDVLDKRRGRDPEMGGKPRRKNP<br>QEGLYNELQKDKMAEAYSEIGMKGERRRGKGHDGLYQGL<br>STATKDTYDALHMQALPPR |

TABLE 1A -continued

Dual and tandem CD19-CD22 CAR sequences

| Identifier | SEQ ID NO | Sequence |
|---|---|---|

Dual CD19-CD22 CARs
CG#c201

| Full length CD19-CD22 Dual CAR nucleic acid | 11 | atggccctccctgtcaccgccctgctgcttccgctggctcttctgctccacgccgctcggcccg
aagtgcagctgcagcagtcagggcctggcctggtcaagccgtcgcagaccctctccctgac
atgcgccattagcggggactccatgctgagcaactcggacacctggaactggattcggcagt
cccttcccggggactcgagtggctcggacgcacctaccatcggagcacttggtacgacga
ctacgcctcctccgtgagaggtcgcgtgtcgatcaacgtggatacctcgaagaaccagtatag
cttgcaactgaacgccgtgaccctgaggataccggagtgtactattgtgcgagagtcaggct
gcaagacggaaactcctggtccgacgcatttgatgtctggggacagggtactatggtcacggt
gtcatctgaggcggaggatcgcaaagcgccctgactcagccggcttcggctagcggttca
ccggggcagtccgtgactatctcctgcaccgggacttcctccgacgtggggaggctacaattac
gtgtcctggtaccagcaacaccccggcaaagccccaaagctgatgatctacgacgtcagcaa
cagacccagcggagtgtccaaccggttcagcggctccaagtccggcaacaccgcctccctg
accatcagcgggcttcaggccgaagatgaggcggattactgctcctcgtacacctcaag
ctcaactctgtacgtgttcggcaccggtactcagctcaccgtgctgaccactaccccagcacc
gaggccacccaccccggctcctaccatcgcctcccagcctctgtccctgcgtccggaggcat
gtagacccgcagctggtggggccgtgcatacccggggtcttgacttcgcctgcgatatctaca
tttgggcccctctggctgacttgcggggtcctgctgcttcactcgtgatcactcttttactgtaa
gcgcggtcggaagaagctgctgtacatctttaagcaacccttcatgaggcctgtgcagactac
tcaagaggaggacggctgttcatgccggttcccagaggaggaggaaggcggctgcgaact
gcgcgtgaaattcagccgcagcgcagatgctccagcctaccagcaggggcagaaccagct
ctacaacgaactcaatcttggtcggagagaggagtacgacgtgctggacaagcggagagga
cgggacccagaaatgggcggggaagccgcgcagaaagaatccccaagagggcctgtacaa
cgagctccaaaaggataagatggcagaagcctatagcgagattggtatgaaagggaacgc
agaagaggcaaaggccacgacggactgtaccagggactcagcaccgccaccaaggacac
ctatgacgctcttcacatgcaggccctgccgcctcggggaagcggagctactaacttcagcct
gctgaagcaggctgggacgtggaggagaaccctggacctatggccttaccagtgaccgcc
ttgctcctgccgctggccttgctgctccacgccgccaggccggaaattgtgatgacccagtca
cccgccactcttagcctttcaccggtgagcgcgcaaccctgtcttgcagagcctcccaagac
atctcaaaatacttaattggtatcaacagaagcccggacaggctcctcgccttctgatctacca
caccagccggctccattctggaatccctgccaggttcagcggtagcggatctgggaccgact
acacctctcactatcagctcactgcagccagaggacttcgctgtctattctgtcagcaaggaa
cacccctgccctacacctttggacagggcaccaagctcgagattaaaggtggaggtggcagc
ggaggaggtgggtccggcggtggaggaagccaggtccaactccaagaaagcggaccgg
gtcttgtgaagccatcagaaaactcttcactgacttgtactgtgagcggagtgtctctccccgatt
acggggtgtcttggatcagacagccaccggggaagggtctggaatggattggagtgatttgg
ggctctgagactacttactaccaatcatccctcaagtcacgcgtcaccatctcaaaggacaact
ctaagaatcaggtgtcactgaaactgtcatctgtgaccgcagccgacaccgccgtgtactattg
cgctaagcattactattatggcgggagctacgcaatggattactgggcagggtactctggt
caccgtgtccagcaccacgacgccagcgccgcgaccaccaacaccggcgcccaccatcg
cgtcgcagcccctgtccctgcgcccagaggcgtgccggccagcggcgggggcgcagtg
cacacgaggggctggacttcgcctgtgatatctacatctgggcgcccttggccgggacttgt
ggggtccttctcctgtcactggttatcaccctttactgcaaacggggcagaaagaaactcctgt
atatattcaaacaaccatttatgagaccagtacaaactactcaagaggaagatggctgtagctg
ccgatttccagaagaagaagaaggaggatgtgaactgagagtgaagttcagcaggagcgca
gacgcccccgcgtaccagcagggccagaaccagctctataacgagctcaatctaggacgaa
gagaggagtacgatgtttgacaagagacgtggccgggaccctgagatgggggaaagc
cgagaaggaagaaccctcaggaaggcctgtacaatgaactgcagaaagataagatggcgg
aggcctacagtgagattgggatgaaggcgagcgccggaggggcaaggggcacgatggc
ctttaccagggtctcagtacagccaccaaggacacctacgacgcccttcacatgcaggccct
gccccctcgc |
| Full length CD19-CD22 Dual CAR amino acid | 12 | MALPVTALLLPLALLLHAARPEVQLQQSGPGLVKPSQTLSL
TCAISGDSMLSNSDTWNWIRQSPSRGLEWLGRTYHRSTWY
DDYASSVRGRVSINVDTSKNQYSLQLNAVTPEDTGVYYCA
RVRLQDGNSWSDAFDVWGQGTMVTVSSGGGGSQSALTQP
ASASGSPGQSVTISCTGTSSDVGGYNYVSWYQQHPGKAPK
LMIYDVSNRPSGVSNRFSGSKSGNTASLTISGLQAEDEADY
YCSSYTSSSTLYVFGTGTQLTVLTTTPAPRPPTPAPTIASQPL
SLRPEACRPAAGGAVHTRGLDFACDIYIWAPLAGTCGVLL
LSLVITLYCKRGRKKLLYIFKQPFMRPVQTTQEEDGCSCRF
PEEEEGGCELRVKFSRSADAPAYQQGQNQLYNELNLGRRE
EYDVLDKRRGRDPEMGGKPRRKNPQEGLYNELQKDKMA
EAYSEIGMKGERRRGKGHDGLYQGLSTATKDTYDALHMQ
ALPPRGSGATNFSLLKQAGDVEENPGPMALPVTALLLPLAL
LLHAARPEIVMTQSPATLSLSPGERATLSCRASQDISKYLN
WYQQKPGQAPRLLIYHTSRLHSGIPARFSGSGSGTDYTLTIS
SLQPEDFAVYFCQQGNTLPYTFGQGTKLEIKGGGGSGGGG
SGGGGSQVQLQESGPGLVKPSETLSLTCTVSGVSLPDYGVS
WIRQPPGKGLEWIGVIWGSETTYYQSSLKSRVTISKDNSKN
QVSLKLSSVTAADTAVYYCAKHYYYGGSYAMDYWGQGT
LVTVSSTTTPAPRPPTPAPTIASQPLSLRPEACRPAAGGAVH
TRGLDFACDIYIWAPLAGTCGVLLLSLVITLYCKRGRKKLL |

TABLE 1A -continued

Dual and tandem CD19-CD22 CAR sequences

| Identifier | SEQ ID NO | Sequence |
|---|---|---|
| | | YIFKQPFMRPVQTTQEEDGCSCRFPEEEEGGCELRVKFSRS ADAPAYQQGQNQLYNELNLGRREEYDVLDKRRGRDPEM GGKPRRKNPQEGLYNELQKDKMAEAYSEIGMKGERRRGK GHDGLYQGLSTATKDTYDALHMQALPPR |
| CD22 CAR (with P2A site) | 13 | MALPVTALLLPLALLLHAARPEVQLQQSGPGLVKPSQTLSL TCAISGDSMLSNSDTWNWIRQSPSRGLEWLGRTYHRSTWY DDYASSVRGRVSINVDTSKNQYSLQLNAVTPEDTGVYYCA RVRLQDGNSWSDAFDVWGQGTMVTVSSGGGGSQSALTQP ASASGSPGQSVTISCTGTSSDVGGYNYVSWYQQHPGKAPK LMIYDVSNRPSGVSNRFSGSKSGNTASLTISGLQAEDEADY YCSSYTSSSTLYVFGTGTQLTVLTTTPAPRPPTPAPTIASQPL SLRPEACRPAAGGAVHTRGLDFACDIYIWAPLAGTCGVLL LSLVITLYCKRGRKKLLYIFKQPFMRPVQTTQEEDGCSCRF PEEEEGGCELRVKFSRSADAPAYQQGQNQLYNELNLGRRE EYDVLDKRRGRDPEMGGKPRRKNPQEGLYNELQKDKMA EAYSEIGMKGERRRGKGHDGLYQGLSTATKDTYDALHMQ ALPPRGSGATNFSLLKQAGDVEENPG |
| CD19 CAR | 14 | PMALPVTALLLPLALLLHAARPEIVMTQSPATLSLSPGERA TLSCRASQDISKYLNWYQQKPGQAPRLLIYHTSRLHSGIPA RFSGSGSGTDYTLTISSLQPEDFAVYFCQQGNTLPYTFGQG TKLEIKGGGGSGGGGSGGGGSQVQLQESGPGLVKPSETLSL TCTVSGVSLPDYGVSWIRQPPGKGLEWIGVIWGSETTYYQS SLKSRVTISKDNSKNQVSLKLSSVTAADTAVYYCAKHYYY GGSYAMDYWGQGTLVTVSSTTTPAPRPPTPAPTIASQPLSL RPEACRPAAGGAVHTRGLDFACDIYIWAPLAGTCGVLLLS LVITLYCKRGRKKLLYIFKQPFMRPVQTTQEEDGCSCRFPE EEEGGCELRVKFSRSADAPAYQQGQNQLYNELNLGRREEY DVLDKRRGRDPEMGGKPRRKNPQEGLYNELQKDKMAEA YSEIGMKGERRRGKGHDGLYQGLSTATKDTYDALHMQAL PPR |

CG#c203

| | | |
|---|---|---|
| Full length CD19-CD22 Dual CAR nucleic acid | 15 | atggccttaccagtgaccgccttgctcctgccgctggccttgctgctccacgccgccaggccg gaaattgtgatgacccagtcacccgccactcttagcctttcacccggtgagcgcgcaaccctg tcttgcagagcctcccaagacatctcaaataccttaattggtatcaacagaagcccggacag gctcctcgcctt ctgatctaccacaccagccggctccattctgaatccctgccaggttcagcg gtagcggatctgggaccgactacaccctcactatcagctcactgcagccagaggacttcgct gtctatttctgtcagcaagggaacaccctgccctacaccttggacagggcaccagctcgag attaaaggtggaggtggcagcggaggaggtgggtccggcggtggaggaagccaggtcca actccaag aaagcggaccgggtcttgtgaagccatcagaaactctttcactgacttgtactgtg agcggagtgtctctccccgattacggggtgtcttggatcagacagccaccggggaagggtct ggaatggattggagtgatttgggctctgagactacttactaccaatcatccctcaagtcacgc gtcaccatctcaaaggacaactctaagaatcaggtgtcactgaaactgtcatctgtgaccgcag ccgacaccgccgtgtactattgcgctaagcattactattatggcggagctacgcaatggatta ctggggacagggtactctggtcaccgtgtccagcaccacgacgccagcgccgcgaccacc aacaccggcgcccaccatcgcgtcgcagccctgtccctgcgcccagaggcgtgccggcc agcggcggggggcgcagtgcacacgaggggggctggacttcgcctgtgatatctacatctgg gcgcccttggccgggacttgtggggtcctttctcctgtcactggttatcacccttactgcaaacg gggcagaaagaaactcctgtatatattcaaacaaccatttatgagaccagtacaaactactcaa gaggaagatggctgtagctgccgatttccagaagaagaagaaggaggatgtgaactgagag tgaagttcagcaggagcgagacgccccccgcgtaccagcagggccagaaccagctctata acgagctcaatctaggacgaagagaggagtacgatgtttttggacaagagacgtggcccgga ccctgagatgggggaaagccgagaaggaagaaccctcaggaaggcctgtacaatgaact gcagaaagataagatggcggaggcctacagtgagattgggatgaaaggcgagcgccgga ggggcaaggggcacgatggccttaccagggtctcagtacagccaccaaggacacctacga cgcccttcacatgcaggccctgccccctcgcggaagcggagctactaacttcagcctgctga agcaggctggagacgtggaggagaaccctggacctatgccctccctgtcaccgccctgct gcttccgctggctcttctgctccacgccgctcggcccgaagtgcagctgcagcagtcaggggc ctggcctgtcaagccgtcgcagaccctctccctgacatgccattagcggggcattccatg ctgagcaactcggacacctggaactggattcggcagtccccttcccggggactcgagtggt cggacgcacctaccatcggagcacttggtacgacgactacgcctcctccgtgagaggtcgc gtgtcgatcaacgtggatacctcgaagaaccagtatagcttgcaactgaacgccgtgacccct gaggataccggagtgtactattgtgcgagagtcaggctgcaagacggaaactcctggtccga cgcatttgatgtctggggacagggtactatggtcacggtgtcatctggaggcggaggatcgca aagcgccctgactcagccggcttcggctagcggttcaccggggcagtccgtgactatctcct gcaccgggacttcctccgacgtgggaggctacaattacgtgtcctggtaccagcaacaccc ggcaaagccccaaagctgatgatctacgacgtcagcaacagacccagcggagtgtccaac cggttcagcggctccaagtccggcaacaccgcctcctgaccatcagcggcttcaggccga agatgaggcggattactactgctcctcgtacacctcaagctcaactctgtacgtgttcggcacc ggtactcagctcaccgtgctgaccactacccagcaccgaggccacccaccccggctccta ccatcgcctcccagcctctgtcctcgctccggaggcatgtagaccccgcagctggtgggcc gtgcataccgggggtcttgacttcgcctgcgatatctacatttgggcccctctggctggtacttg |

TABLE 1A -continued

Dual and tandem CD19-CD22 CAR sequences

| Identifier | SEQ ID NO | Sequence |
|---|---|---|
| | | cggggtcctgctgctttcactcgtgatcactctttactgtaagcgcggtcggaagaagctgctgt<br>acatctttaagcaacccttcatgaggcctgtgcagactactaagaggaggacggctgttcatg<br>ccggttcccagaggaggaggaaggcggctgcgaactgcgcgtgaaattcagccgcagcgc<br>agatgctccagcctaccagcaggggcagaaccagctctacaacgaacttcaatcttggtcgga<br>gagaggagtacgacgtgctggacaagcggagaggacgggacccagaaatgggcgggaa<br>gccgcgcagaaagaatccccaagagggcctgtacaacgagctccaaaaggataagatggc<br>agaagcctatagcgagattggtatgaaggggaacgcagaagaggcaaaggccacgacg<br>gactgtaccagggactcagcaccgccaccaaggacacctatgacgctcttcacatgcaggcc<br>ctgccgcctcgg |
| Full length CD19-CD22 Dual CAR amino acid | 16 | MALPVTALLLPLALLLHAARPEIVMTQSPATLSLSPGERAT<br>LSCRASQDISKYLNWYQQKPGQAPRLLIYHTSRLHSGIPAR<br>FSGSGSGTDYTLTISSLQPEDFAVYFCQQGNTLPYTFGQGT<br>KLEIKGGGGSGGGGSGGGGSQVQLQESGPGLVKPSETLSLT<br>CTVSGVSLPDYGVSWIRQPPGKGLEWIGVIWGSETTYYQSS<br>LKSRVTISKDNSKNQVSLKLSSVTAADTAVYYCAKHYYYG<br>GSYAMDYWGQGTLVTVSSTTTPAPRPPTPAPTIASQPLSLR<br>PEACRPAAGGAVHTRGLDFACDIYIWAPLAGTCGVLLLSL<br>VITLYCKRGRKKLLYIFKQPFMRPVQTTQEEDGCSCRFPEE<br>EEGGCELRVKFSRSADAPAYQQGQNQLYNELNLGRREEY<br>DVLDKRRGRDPEMGGKPRRKNPQEGLYNELQKDKMAEA<br>YSEIGMKGERRRGKGHDGLYQGLSTATKDTYDALHMQAL<br>PPRGSGATNFSLLKQAGDVEENPGPMALPVTALLLPLALLL<br>HAARPEVQLQQSGPGLVKPSQTLSLTCAISGDSMLSNSDT<br>WNWIRQSPSRGLEWLGRTYHRSTWYDDYASSVRGRVSIN<br>VDTSKNQYSLQLNAVTPEDTGVYYCARVRLQDGNSWSDA<br>FDVWGQGTMVTVSSGGGGSQSALTQPASASGSPGQSVTIS<br>CTGTSSDVGGYNYVSWYQQHPGKAPKLMIYDVSNRPSGV<br>SNRFSGSKSGNTASLTISGLQAEDEADYYCSSYTSSSTLYVF<br>GTGTQLTVLTTTPAPRPPTPAPTIASQPLSLRPEACRPAAGG<br>AVHTRGLDFACDIYIWAPLAGTCGVLLLSLVITLYCKRGRK<br>KLLYIFKQPFMRPVQTTQEEDGCSCRFPEEEEGGCELRVKF<br>SRSADAPAYQQGQNQLYNELNLGRREEYDVLDKRRGRDP<br>EMGGKPRRKNPQEGLYNELQKDKMAEAYSEIGMKGERRR<br>GKGHDGLYQGLSTATKDTYDALHMQALPPR |
| CD19 CAR (with P2A site) | 17 | MALPVTALLLPLALLLHAARPEIVMTQSPATLSLSPGERAT<br>LSCRASQDISKYLNWYQQKPGQAPRLLIYHTSRLHSGIPAR<br>FSGSGSGTDYTLTISSLQPEDFAVYFCQQGNTLPYTFGQGT<br>KLEIKGGGGSGGGGSGGGGSQVQLQESGPGLVKPSETLSLT<br>CTVSGVSLPDYGVSWIRQPPGKGLEWIGVIWGSETTYYQSS<br>LKSRVTISKDNSKNQVSLKLSSVTAADTAVYYCAKHYYYG<br>GSYAMDYWGQGTLVTVSSTTTPAPRPPTPAPTIASQPLSLR<br>PEACRPAAGGAVHTRGLDFACDIYIWAPLAGTCGVLLLSL<br>VITLYCKRGRKKLLYIFKQPFMRPVQTTQEEDGCSCRFPEE<br>EEGGCELRVKFSRSADAPAYQQGQNQLYNELNLGRREEY<br>DVLDKRRGRDPEMGGKPRRKNPQEGLYNELQKDKMAEA<br>YSEIGMKGERRRGKGHDGLYQGLSTATKDTYDALHMQAL<br>PPRGSGATNFSLLKQAGDVEENPG |
| CD22 CAR | 18 | PMALPVTALLLPLALLLHAARPEVQLQQSGPGLVKPSQTLS<br>LTCAISGDSMLSNSDTWNWIRQSPSRGLEWLGRTYHRSTW<br>YDDYASSVRGRVSINVDTSKNQYSLQLNAVTPEDTGVYYC<br>ARVRLQDGNSWSDAFDVWGQGTMVTVSSGGGGSQSALT<br>QPASASGSPGQSVTISCTGTSSDVGGYNYVSWYQQHPGKA<br>PKLMIYDVSNRPSGVSNRFSGSKSGNTASLTISGLQAEDEA<br>DYYCSSYTSSSTLYVFGTGTQLTVLTTTPAPRPPTPAPTIAS<br>QPLSLRPEACRPAAGGAVHTRGLDFACDIYIWAPLAGTCG<br>VLLLSLVITLYCKRGRKKLLYIFKQPFMRPVQTTQEEDGCS<br>CRFPEEEEGGCELRVKFSRSADAPAYQQGQNQLYNELNLG<br>RREEYDVLDKRRGRDPEMGGKPRRKNPQEGLYNELQKDK<br>MAEAYSEIGMKGERRRGKGHDGLYQGLSTATKDTYDALH<br>MQALPPR |
| | | CG#c230 |
| Full length CD19-CD22 Dual CAR nucleic acid | 19 | atggcacttcccgtcaccgccctgctgctcccactcgccctccttctgcacgccgcccgcccc<br>gaagtgcagctgcagcagtcaggaccgggcctggtcaaaccttcgcagactctgtccctgac<br>ttgcgctataagcggggactccatgctgagcaattcggacacttggaactggattcgccaaag<br>cccagccggggtctggaatggctgggaaggacctaccatcgctcgctctacttggtacgacgact<br>acgccagctccgtgcgaggacgcgtgtccatcaacgtggacacctccaagaaccagtactc<br>gcttcaactcaacgcagtgaccctgaagataccggagtctactattgcgcccgctgcggct<br>ccaggacgggaactcctggtcggacgcttcgatgtctggggacagggcactatggtcaccg<br>tcagctccggcggcggcgtagccaatcggcgctgacacagccggcttccgcctcgggatc<br>gcctggacagtcggtgaccatctcgtgcactggaacctcctccgacgtgggcggctacaatta |

TABLE 1A -continued

Dual and tandem CD19-CD22 CAR sequences

| Identifier | SEQ ID NO | Sequence |
|---|---|---|
| | | tgtgtcatggtaccagcagcacccgggaaaggcccctaagctgatgatctacgacgtgtcca<br>atagacctagcggggtgtcaaacagattctccggatccaaatccggaaacactgcctccctga<br>ccatttccggactgcaggccgaggacgaagccgattactactgctcctcttacacctcctcatc<br>caccctctacgtgtttgggactgggacccagctgaccgtcctcactaccaccccggccccgc<br>ggcccctacaccggcaccgactattgccagcagcctctctcgctgcggccggaggcctg<br>ccgcccagccgccggcggagccgtgcacacccgcggtctggacttcgcgtgcgatatctac<br>atctgggctccgctggccgggacttgtggcgtgctgctgctgtctctggtcatcacactgtact<br>gcaagcgcggaagaaagaagctgctctacatcttcaagcaacccttcatgcggcctgtgcag<br>accacccaggaagaggatggctgctcctgccggttcccggaggaagaagagggcggatgc<br>gaactgcgcgtgaagttcagccgaagcgccgacgccccggcctaccagcagggccagaa<br>ccaactgtacaacgaactcaacctgggtcggagagaagagtacgacgtgctggacaaaaga<br>cgcggcagggaccccgagatgggcggaaagcctcgccgcaagaacccgcaggagggcc<br>tctacaacgagctgcagaaggacaagatggccgaagcctactcagagatcggcatgaaggg<br>ggagcggaggcgcggggaagggccacgacggtttgtaccaaggactttccactgcgaccaa<br>ggacacctacgatgccctccatatgcaagccctgccgccccggggttccggagctaccaact<br>tctcgctgttgaagcaggccggagatgtcgaggaaaaccccggacctatggcctgccagt<br>gaccgcgctcctgctgcccctggctctgctgcttcacgcggccccggcctgagattgtgatgac<br>tcagagcccggcgaccctgtccctgtcccccggggagagagcaaccctgtcgtgccgggc<br>ctcccaagacatctcaaagtacctcaattggtatcagcagaagccaggacaggctccacggtt<br>gctgatctaccacacttcgagactgcactcaggaatccccgcgcggtttccggttccggctcc<br>gggaccgactacaccctgaccatcagctcgctccagcctgaggatttcgcagtgtacttctgtc<br>agcaaggaaacaccccttccatacaccttcggacagggtaccaagctggaaatcaagggagg<br>aggaggatctggggcggtggttccggaggcggtggaagccaagtgcagctccaggaaa<br>gcggacccgggctggtcaagccgagcgaaacccctctcactgacttgtactgtgtccggagtg<br>tccctgcctgactatggagtgtcctggatccgacagccccccggaaagggtctggagtggatt<br>ggggtcatctgggctccgaaactacctactaccagagcagcctcaagagccgggtcaccat<br>ttcaaaggataactccaagaatcaagtgccctgaagctgtcctcagtgacagccgcagacac<br>cgccgtgtactactgcgcaagcactactactacggaggctcctacgcaatggactactggg<br>gacaaggcacttttggtcactgtgtcaagcaccaccacccctgcgcctcggcctcctaccccg<br>gctcccactatcgcgagccagccgctgagcctgcggcctgaggcttgccgaccggccgctg<br>gcggcgccgtgcatactcggggcctcgactttgcctgtgacatctacatctgggccccctgg<br>ccggaacgtgcggagtgctgctgctgtcgctggtcattaccctgtattgcaaacgcggaagga<br>agaagctgttgtacattttcaagcagccctcatgcgcccggtgcaaactactcaggaggaag<br>atggctgttcctgtcggttccccgaagaggaagaaggcggctgcgagttgagggtcaagttct<br>cccggtccgccgatgctcccgcctaccaacaggggcagaaccagctttataacgaactgaac<br>ctgggcaggagggaggaataatgatgtgttggataagcgccgggccgggacccagaaatg<br>gggggaaagcccagaagaaagaaccctcaagagggactttacaacgaattgcagaaagac<br>aaaatggccgaggcctactccgagattgggatgaagggcgaaagacggagaggaaggg<br>gcacgacgggctctaccagggactcagcaccgccaccaaagatacctacgacgccctgcat<br>atgcaggcgctgccgccgcgc |
| Full length CD 19-CD22 Dual CAR amino acid | 12 | MALPVTALLLPLALLLHAARPEVQLQQSGPGLVKPSQTLSL<br>TCAISGDSMLSNSDTWNWIRQSPSRGLEWLGRTYHRSTWY<br>DDYASSVRGRVSINVDTSKNQYSLQLNAVTPEDTGVYYCA<br>RVRLQDGNSWSDAFDVWGQGTMVTVSSGGGGSQSALTQP<br>ASASGSPGQSVTISCTGTSSDVGGYNYVSWYQQHPGKAPK<br>LMIYDVSNRPSGVSNRFSGSKSGNTASLTISGLQAEDEADY<br>YCSSYTSSSTLYVFGTGTQLTVLTTTPAPRPPTPAPTIASQPL<br>SLRPEACRPAAGGAVHTRGLDFACDIYIWAPLAGTCGVLL<br>LSLVITLYCKRGRKKLLYIFKQPFMRPVQTTQEEDGCSCRF<br>PEEEEGGCELRVKFSRSADAPAYQQGQNQLYNELNLGRRE<br>EYDVLDKRRGRDPEMGGKPRRKNPQEGLYNELQKDKMA<br>EAYSEIGMKGERRRGKGHDGLYQGLSTATKDTYDALHMQ<br>ALPPRGSGATNFSLLKQAGDVEENPGPMALPVTALLLPLAL<br>LLHAARPEIVMTQSPATLSLSPGERATLSCRASQDISKYLN<br>WYQQKPGQAPRLLIYHTSRLHSGIPARFSGSGSGTDYTLTIS<br>SLQPEDFAVYFCQQGNTLPYTFGQGTKLEIKGGGGSGGGG<br>SGGGGSQVQLQESGPGLVKPSETLSLTCTVSGVSLPDYGVS<br>WIRQPPGKGLEWIGVIWGSETTYYQSSLKSRVTISKDNSKN<br>QVSLKLSSVTAADTAVYYCAKHYYYGGSYAMDYWGQGT<br>LVTVSSTTTPAPRPPTPAPTIASQPLSLRPEACRPAAGGAVH<br>TRGLDFACDIYIWAPLAGTCGVLLLSLVITLYCKRGRKKLL<br>YIFKQPFMRPVQTTQEEDGCSCRFPEEEEGGCELRVKFSRS<br>ADAPAYQQGQNQLYNELNLGRREEYDVLDKRRGRDPEM<br>GGKPRRKNPQEGLYNELQKDKMAEAYSEIGMKGERRRGK<br>GHDGLYQGLSTATKDTYDALHMQALPPR |
| CD22 CAR (with P2A site) | 13 | MALPVTALLLPLALLLHAARPEVQLQQSGPGLVKPSQTLSL<br>TCAISGDSMLSNSDTWNWIRQSPSRGLEWLGRTYHRSTWY<br>DDYASSVRGRVSINVDTSKNQYSLQLNAVTPEDTGVYYCA<br>RVRLQDGNSWSDAFDVWGQGTMVTVSSGGGGSQSALTQP<br>ASASGSPGQSVTISCTGTSSDVGGYNYVSWYQQHPGKAPK |

TABLE 1A-continued

Dual and tandem CD19-CD22 CAR sequences

| Identifier | SEQ ID NO | Sequence |
|---|---|---|
| | | LMIYDVSNRPSGVSNRFSGSKSGNTASLTISGLQAEDEADY<br>YCSSYTSSSTLYVFGTGTQLTVLTTTPAPRPPTPAPTIASQPL<br>SLRPEACRPAAGGAVHTRGLDFACDIYIWAPLAGTCGVLL<br>LSLVITLYCKRGRKKLLYIFKQPFMRPVQTTQEEDGCSCRF<br>PEEEEGGCELRVKFSRSADAPAYQQGQNQLYNELNLGRRE<br>EYDVLDKRRGRDPEMGGKPRRKNPQEGLYNELQKDKMA<br>EAYSEIGMKGERRRGKGHDGLYQGLSTATKDTYDALHMQ<br>ALPPRGSGATNFSLLKQAGDVEENPG |
| CD19 CAR | 14 | PMALPVTALLLPLALLLHAARPEIVMTQSPATLSLSPGERA<br>TLSCRASQDISKYLNWYQQKPGQAPRLLIYHTSRLHSGIPA<br>RFSGSGSGTDYTLTISSLQPEDFAVYFCQQGNTLPYTFGQG<br>TKLEIKGGGGSGGGGSGGGGSQVQLQESGPGLVKPSETLSL<br>TCTVSGVSLPDYGVSWIRQPPGKGLEWIGVIWGSETTYYQS<br>SLKSRVTISKDNSKNQVSLKLSSVTAADTAVYYCAKHYYY<br>GGSYAMDYWGQGTLVTVSSTTTPAPRPPTPAPTIASQPLSL<br>RPEACRPAAGGAVHTRGLDFACDIYIWAPLAGCGVLLLS<br>LVITLYCKRGRKKLLYIFKQPFMRPVQTTQEEDGCSCRFPE<br>EEEGGCELRVKFSRSADAPAYQQGQNQLYNELNLGRREEY<br>DVLDKRRGRDPEMGGKPRRKNPQEGLYNELQKDKMAEA<br>YSEIGMKGERRRGKGHDGLYQGLSTATKDTYDALHMQAL<br>PPR |

CD22 and CD19 CDRs of a dual CAR or tandem CAR of the disclosure are provided in Table 2A.

TABLE 2A

CD22 and CD19 CDR sequences

| Identifier | SEQ ID NO | Sequence |
|---|---|---|
| CD22 CDRs | | |
| HCDR1 (Kabat) | 20 | SNSDTWN |
| HCDR2 (Kabat) | 21 | RTYHRSTWYDDYASSVRG |
| HCDR3 (Kabat) | 22 | VRLQDGNSWSDAFDV |
| HCDR1 (Chothia) | 23 | GDSMLSNSD |
| HCDR2 (Chothia) | 24 | YHRSTWY |
| HCDR3 (Chothia) | 22 | VRLQDGNSWSDAFDV |
| HCDR1 (IMGT) | 25 | GDSMLSNSDT |
| HCDR2 (IMGT) | 26 | TYHRSTWYD |
| HCDR3 (IMGT) | 27 | ARVRLQDGNSWSDAFDV |
| LCDR1 (Kabat) | 28 | TGTSSDVGGYNYVS |
| LCDR2 (Kabat) | 29 | DVSNRPS |
| LCDR3 (Kabat) | 30 | SSYTSSSTLYV |
| LCDR1 (Chothia) | 31 | TSSDVGGYNY |
| LCDR2 (Chothia) | 32 | DVS |
| LCDR3 (Chothia) | 33 | YTSSSTLY |
| LCDR1 (IMGT) | 34 | SSDVGGYNY |
| LCDR2 (IMGT) | 32 | DVS |
| LCDR3 (IMGT) | 30 | SSYTSSSTLYV |
| CD19 CDRs | | |
| HCDR1 (Kabat) | 35 | GVSLPDYGVS |
| HCDR2 (Kabat) | 36 | VIWGSETTYYSSSLKS |
| | 37 | VIWGSETTYYQSSLKS |
| | 38 | VIWGSETTYYNSSLKS |
| HCDR3 (Kabat) | 39 | HYYYGGSYAMDY |
| LCDR1 | 40 | RASQDISKYLN |
| LCDR2 | 41 | HTSRLHS |
| LCDR3 | 42 | QQGNTLPYT |

Table 3A provides nucleotide and amino acid sequence for CD19 and CD22 binding domains of a dual CAR or a tandem CAR disclosed herein.

TABLE 3A

CD19 and CD22 binding domains

| Identifier | SEQ ID NO | Sequence |
|---|---|---|
| scFv CAR19 in c201, c203 and tandem CARs c171, c182, c188 | 43 | gaaattgtgatgacccagtcacccgccactcttagcctttcacccggtgagcgcgcaaccctgt cttgcagagcctcccaagacatctcaaaataccttaattggtatcaacagaagcccggacaggc tcctcgccttctgatctaccacaccagccggctccattctggaatccctgccaggttcagcggta gcggatctgggaccgactacaccctcactatcagctcactgcagccagaggacttcgctgtcta tttctgtcagcaagggaacaccctgccctacacctttggacagggcaccaagctcgagattaaa ggtggaggtggcagcggagaggtgggtccggcggtggaggaagccaggtccaactccaa gaaagcggaccgggtcttgtgaagccatcagaaactcttcactgacttgtactgtgagcggag tgtctctccccgattacggggtgtcttggatcagacagccaccggggaagggtctggaatggat tggagtgatttgggctctgagactacttactaccaatcatccctcaagtcacgcgtcaccatctc aaaggacaactctaagaatcaggtgtcactgaaactgtcatctgtgaccgcagccgacaccgc cgtgtactattgcgctaagcattactattatggcgggagctacgcaatggattactggggacagg gtactctggtcaccgtgtccagc |
|  | 44 | EIVMTQSPATLSLSPGERATLSCRASQDISKYLNWYQQKPG QAPRLLIYHTSRLHSGIPARFSGSGSGTDYTLTISSLQPEDFA VYFCQQGNTLPYTFGQGTKLEIKGGGGSGGGGSGGGGSQV QLQESGPGLVKPSETLSLTCTVSGVSLPDYGVSWIRQPPGKG LEWIGVIWGSETTYYQSSLKSRVTISKDNSKNQVSLKLSSVT AADTAVYYCAKHYYYGGSYAMDYWGQGTLVTVSS |
| scFv CAR19 in c224 | 45 | gagattgtcatgactcagtccccggccacactctccctgtcaccggagaaagagcaaccctg agctgcagggcgtcccaggacatctcgaagtacctgaactggtaccagcagaagcctggaca agcaccccgcctcctgatctaccacacctcgcggctgcattcggggaatccccgccagattctca gggagcggatcaggaaccgactacaccctgactatctcgagcctgcaaccagaggatttcgc cgtgtacttctgccagcaaggaaacaccctgccctacacctttggacagggaaccaagctcga gattaaggggggtggtggatcgggagggggtggatcaggaggaggcggctcacaagtcca gctgcaagaatccggtccgggacttgtgaagccgtccgaaaccctgtcactgacttgcactgtg tccggggtgtcattgcccgactacggcgtgagctggattcggcagccccctggaaagggattg gaatggatcggcgtgatctgggggttcggaaactacctactatcagtcctcactgaagtcccgcg tgaccatcagcaaggataattccaaaaaccaagtgtctctgaagctctccagcgtcactgccgc cgatactgccgtgtactactgcgccaagcactactattacggcggttcgtacgccatggactact ggggccaagggacactcgtgaccgtgtcatcc |
|  | 44 | EIVMTQSPATLSLSPGERATLSCRASQDISKYLNWYQQKPG QAPRLLIYHTSRLHSGIPARFSGSGSGTDYTLTISSLQPEDFA VYFCQQGNTLPYTFGQGTKLEIKGGGGSGGGGSGGGGSQV QLQESGPGLVKPSETLSLTCTVSGVSLPDYGVSWIRQPPGKG LEWIGVIWGSETTYYQSSLKSRVTISKDNSKNQVSLKLSSVT AADTAVYYCAKHYYYGGSYAMDYWGQGTLVTVSS |
| scFv CAR19 in c227 | 46 | caagtccagctgcaagaatccggtccgggacttgtgaagccgtccgaaaccctgtcactgactt gcactgtgtccggggtgtcattgcccgactacggcgtgagctggattcggcagccccctggaa agggattggaatggatcggcgtgatctgggggttcggaaactacctactatcagtcctcactgaa gtcccgcgtgaccatcagcaaggataattccaaaaaccaagtgtctctgaagctctccagcgtc actgccgccgatactgccgtgtactactgcgccaagcactactattacggcggttcgtacgccat ggactactggggacaaggcactcttgtgactgtgtcaagcggcggtggagggagcggtggg ggcggttcaggaggaggcggatcagagatcgtgatgacccaatccccagccaccctgtccct cagccctggagaaagagccaccctgagctgccgggcctcccaggatatcagcaagtacttga actggtaccaacaaagccggggcaggcgccccggctcctgatctaccacacctcgcgcctc cactcaggtatccccgccagattctcagggagcggctccggtactgactacaccctgactatttc ctcactgcagccagaggactttgccgtgtacttctgccagcagggaaacactctgccgtacacc ttcgggcagggaacgaagcttgaaattaag |
|  | 47 | QVQLQESGPGLVKPSETLSLTCTVSGVSLPDYGVSWIRQPPG KGLEWIGVIWGSETTYYQSSLKSRVTISKDNSKNQVSLKLSS VTAADTAVYYCAKHYYYGGSYAMDYWGQGTLVTVSSGG GGSGGGGSGGGGSEIVMTQSPATLSLSPGERATLSCRASQDI SKYLNWYQQKPGQAPRLLIYHTSRLHSGIPARFSGSGSGTD YTLTISSLQPEDFAVYFCQQGNTLPYTFGQGTKLEIK |
| scFv CAR19 in c230 | 48 | gagattgtgatgactcagagcccggcgaccctgtccctgtccccggggagagagcaaccct gtcgtgccgggcctcccaagacatctcaaagtacctcaattggtatcagcagaagccaggaca ggctccacggttgctgatctaccacacttcgagactgcactcaggaatcccgcgcggttttcc ggttccggctccgggaccgactacaccctgaccatcagctcgctccagcctgaggatttcgca gtgtacttctgtcagcaaggaaacaccttccatacaccttcggacagggtaccaagctggaaa tcaagggaggaggaggatctggggcggtggttccggaggcggtggaagccaagtgcagc tccaggaaagcggacccggctggtcaagccgagcgaaaccctctcactgacttgtactgtgt ccggagtgtccctgcctgactatggagtgtcctggatccgacagccccccggaaagggtctgg agtggattgggtcatctgggggctccgaaactacctactaccagagcagcctcaagagccgg gtcaccatttcaaaggataactccaagaatcaagtgtccctgaagctgtcctcagtgacagccg cagacaccgccgtgtactactgcgccaagcactactactacggaggctcctacgcaatggact actgggacaaggcactttggtcactgtgtcaagc |

TABLE 3A-continued

CD19 and CD22 binding domains

| Identifier | SEQ ID NO | Sequence |
|---|---|---|
| | 44 | EIVMTQSPATLSLSPGERATLSCRASQDISKYLNWYQQKPG<br>QAPRLLIYHTSRLHSGIPARFSGSGSGTDYTLTISSLQPEDFA<br>VYFCQQGNTLPYTFGQGTKLEIKGGGGSGGGGSGGGGSQV<br>QLQESGPGLVKPSETLSLTCTVSGVSLPDYGVSWIRQPPGKG<br>LEWIGVIWGSETTYYQSSLKSRVTISKDNSKNQVSLKLSSVT<br>AADTAVYYCAKHYYYGGSYAMDYWGQGTLVTVSS |
| ScFVCAR2 2 in c201 and c203 | 49 | gaagtgcagctgcagcagtcagggcctggcctggtcaagccgtcgcagaccctctccctgac<br>atgcgccattagcggggactccatgctgagcaactcggacacctggaactggattcggcagtc<br>cccttcccggggactcgagtggctcggacgcacctaccatcggagcacttggtacgacgacta<br>cgcctcctccgtgagaggtcgcgtgtcgatcaacgtggatacctcgaagaaccagtatagcttg<br>caactgaacgccgtgaccectgaggataccggagtctactattgtgcgagagtcaggctgcaa<br>gacggaaactcctggtccgacgcatttgatgtctggggacagggtactatggtcacggtgtcat<br>ctggaggcgaggatcgcaaagcgccctgactcagccggcttcggctagcggttcaccggg<br>gcagtccgtgactatctcctgcaccgggacttcctccgacgtgggaggctacaattacgtgtcct<br>ggtaccagcaacaccccggcaaagcccaaagctgatgatctacgacgtcagcaacagacc<br>cagcggagtgtccaaccggttcagcggctccaagtccggcaacaccgcctccctgaccatca<br>gcgggcttcaggccgaagatgaggcggattactactgctcctcgtacacctcaagctcaactct<br>gtacgtgttcggcaccggtactcagctcaccgtgctg |
| | 50 | EVQLQQSGPGLVKPSQTLSLTCAISGDSMLSNSDTWNWIRQ<br>SPSRGLEWLGRTYHRSTWYDDYASSVRGRVSINVDTSKNQ<br>YSLQLNAVTPEDTGVYYCARVRLQDGNSWSDAFDVWGQG<br>TMVTVSSGGGGSQSALTQPASASGSPGQSVTISCTGTSSDVG<br>GYNYVSWYQQHPGKAPKLMIYDVSNRPSGVSNRFSGSKSG<br>NTASLTISGLQAEDEADYYCSSYTSSSTLYVFGTGTQLTVL |
| ScFVCAR2 2 in 230 | 51 | gaagtgcagctgcagcagtcaggaccgggcctggtcaaaccttcgcagactctgtccctgact<br>tgcgctataagcggggactccatgctgagcaattcggacacttggaactggattcgccaaagc<br>cccagccggggtctggaatggctgggaaggacctaccatcgctctacttggtacgacgactac<br>gccagctccgtgcgaggacgcgtgtccatcaacgtggacacctccaagaaccagtactcgctt<br>caactcaacgcagtgaccectgaagataccggagtctactattgcgcccgcgtgcggctccag<br>gacgggaactcctggtcggacgctttcgatgtctggggacagggcactatggtcaccgtcagc<br>tccggcggcggcggtagccaatcggcgctgacacagccggcttccgcctcgggatcgcctg<br>gacagtcggtgaccatctcgtgcactggaacctcctccgacgtgggcggctacaattatgtgtc<br>atggtaccagcagcacccgggaaaggcccctaagctgatgatctacgacgtgtccaatagacc<br>tagcggggtgtcaaacagattctccggatccaaatccggaaacactgcctccctgaccattccc<br>ggactgcaggccgaggacgaagccgattactactgctcctcttacacctcctcatccaccctcta<br>cgtgtttgggactgggacccagctgaccgtcctc |
| | 50 | EVQLQQSGPGLVKPSQTLSLTCAISGDSMLSNSDTWNWIRQ<br>SPSRGLEWLGRTYHRSTWYDDYASSVRGRVSINVDTSKNQ<br>YSLQLNAVTPEDTGVYYCARVRLQDGNSWSDAFDVWGQG<br>TMVTVSSGGGGSQSALTQPASASGSPGQSVTISCTGTSSDVG<br>GYNYVSWYQQHPGKAPKLMIYDVSNRPSGVSNRFSGSKSG<br>NTASLTISGLQAEDEADYYCSSYTSSSTLYVFGTGTQLTVL |
| ScFVCAR2 2 in 171, c182 | 52 | gaagtgcagcttcaacaatcaggaccaggactcgtcaaaccatcacagaccctctccctcacat<br>gtgccatctccggggactccatgttgagcaattccgacacttggaattggattagacaaagccc<br>gtcccggggtctggaatggttgggacgcacctaccaccggtctacttggtacgacgactacgc<br>gtcatccgtgcggggaagagtgtccatcaacgtggacacctccaagaaccagtacagcctgc<br>agcttaatgccgtgactcctgaggatacgggcgtctactactgcgcccgcgtccgctccaag<br>acgggaacagctggagcgatgcattcgatgtctggggccagggaactatggtcaccgtgtcgt<br>ctggggcggtggcggtgggcgggggttcggggggcggcggctctcagtccgctcttac<br>ccaaccggcctcagcctcggggagcccggccagagcgtgaccatttcctgcaccggcactt<br>catccgacgtgggcggctacaactacgtgtcctggtaccaacagcacccgggaaaggcccc<br>aagctcatgatctacgacgtgtccaacaggccctcgggagtgtccaaccggttctcggggttcga<br>atcgggaaacacagccagcctgaccatcagcggactgcaggctgaagatgaagccgacta<br>ctactgctcctcctacacctcgtcatccacgctctacgtgttcggcactggaactcagctgactgt<br>gctg |
| | 53 | EVQLQQSGPGLVKPSQTLSLTCAISGDSMLSNSDTWNWIRQ<br>SPSRGLEWLGRTYHRSTWYDDYASSVRGRVSINVDTSKNQ<br>YSLQLNAVTPEDTGVYYCARVRLQDGNSWSDAFDVWGQG<br>TMVTVSSGGGGSGGGGSGGGGSQSALTQPASASGSPGQSV<br>TISCTGTSSDVGGYNYVSWYQQHPGKAPKLMIYDVSNRPSG<br>VSNRFSGSKSGNTASLTISGLQAEDEADYYCSSYTSSSTLYV<br>FGTGTQLTVL |
| ScFVCAR2 2 in c188 | 54 | cagtccgctcttacccaaccggcctcagcctcggggagcccggccagagcgtgaccatttcc<br>tgcaccggcacttcatccgacgtgggcggctacaactacgtgtcctggtaccaacagcacccg<br>ggaaaggcccccaagctcatgatctacgacgtgtccaacaggccctcgggagtgtccaaccg<br>gttctcggggttcgaaatcgggaaacacagccagcctgaccatcagcggactgcaggctgaag<br>atgaagccgactactactgctcctcctacacctcgtcatccacgctctacgtgttcggcactgga<br>actcagctgactgtgctgggcggaggaggctccgaagtgcagcttcaacaatcaggaccagg<br>actcgtcaaaccatcacagaccctctccctcacatgtgccatctccggggactccatgttgagca<br>attccgacacttggaattggattagacaaagcccgtcccggggtctggaatggttgggacgca<br>cctaccaccggtctacttggtacgacgactacgcgtcatccgtgcggggaagagtgtccatcaa |

TABLE 3A-continued

CD19 and CD22 binding domains

| Identifier | SEQ ID NO | Sequence |
|---|---|---|
| | | cgtggacacctccaagaaccagtacagcctgcagcttaatgccgtgactcctgaggatacggg<br>cgtctactactgcgcccgcgtccgcctgcaagacgggaacagctggagcgatgcattcgatgt<br>ctggggccagggaactatggtcaccgtgtcgtct |
| | 55 | QSALTQPASASGSPGQSVTISCTGTSSDVGGYNYVSWYQQH<br>PGKAPKLMIYDVSNRPSGVSNRFSGSKSGNTASLTISGLQAE<br>DEADYYCSSYTSSSTLYVFGTGTQLTVLGGGGSEVQLQQSG<br>PGLVKPSQTLSLTCAISGDSMLSNSDTWNWIRQSPSRGLEW<br>LGRTYHRSTWYDDYASSVRGRVSINVDTSKNQYSLQLNAV<br>TPEDTGVYYCARVRLQDGNSWSDAFDVWGQGTMVTVSS |
| ScFVCAR22 in c224 | 56 | cagtccgctctgactcagccggcctcagcttcggggtccctggtcaaagcgtcactatttcctg<br>taccggaacctcatcagacgtgggcggctacaattacgtgtcctggtaccaacagcacccgg<br>aaaggctcctaagcttatgatctacgacgtgtccaaccggccgtcaggagtgtccaacagattct<br>ccggctccaagagcggaaacactgccagcttgaccattagcggcttgcaggccgaggacga<br>agccgactactactgctctagctacacatcctcgtctaccctctacgtgtttggaacggggaccc<br>agctgactgtgctcgggggtggaggatcagaggtgcaactccagcagtccggtcctggcctc<br>gtgaaaccgtcccaaaccctgtccctgacttgcgccatctcgggcgactccatgctgtccaattc<br>cgacacctggaactggattagacaatcgcctagccggggactcgaatggctgggccggacct<br>accaccggtccacgtggtatgacgactacgcaagctccgtccggggaagggtgtccattaacg<br>tcgatacctccaagaaccagtacagccttcagctgaacgctgtgaccccgaggataccggcg<br>tctactactgtgcaagagtgcgattgcaggatggaaactcgtggtcggacgcattcgatgtctg<br>gggacagggaactatggtgaccgtgtcctcg |
| | 55 | QSALTQPASASGSPGQSVTISCTGTSSDVGGYNYVSWYQQH<br>PGKAPKLMIYDVSNRPSGVSNRFSGSKSGNTASLTISGLQAE<br>DEADYYCSSYTSSSTLYVFGTGTQLTVLGGGGSEVQLQQSG<br>PGLVKPSQTLSLTCAISGDSMLSNSDTWNWIRQSPSRGLEW<br>LGRTYHRSTWYDDYASSVRGRVSINVDTSKNQYSLQLNAV<br>TPEDTGVYYCARVRLQDGNSWSDAFDVWGQGTMVTVSS |
| ScFVCAR22 in c227 | 57 | cagtccgctctgactcagccggcctcagcttcggggtccctggtcaaagcgtcactatttcctg<br>taccggaacctcatcagacgtgggcggctacaattacgtgtcctggtaccaacagcacccgg<br>aaaggctcctaagcttatgatctacgacgtgtccaaccggccgtcaggagtgtccaacagattct<br>ccggctccaagagcggaaacactgccagcttgaccattagcggcttgcaggccgaggacga<br>agccgactactactgctctagctacacatcctcgtctaccctctacgtgtttggaacggggaccc<br>agctgactgtgctcgggggtggaggatcagaggtgcaactccagcagtccggtcctggcctc<br>gtgaaaccgtcccaaaccctgtccctgacttgcgccatctcgggcgactccatgctgtccaattc<br>cgacacctggaactggattagacaatcgcctagccggggactcgaatggctgggccggacct<br>accaccggtccacgtggtatgacgactacgcaagctccgtccggggaagggtgtccattaacg<br>tcgatacctccaagaaccagtacagccttcagctgaacgctgtgaccccgaggataccggcg<br>tctactactgtgcaagagtgcgattgcaggatggaaactcgtggtcggacgcattcgatgtctg<br>gggacagggaactatggtcactgtgtcctcc |
| | 55 | QSALTQPASASGSPGQSVTISCTGTSSDVGGYNYVSWYQQH<br>PGKAPKLMIYDVSNRPSGVSNRFSGSKSGNTASLTISGLQAE<br>DEADYYCSSYTSSSTLYVFGTGTQLTVLGGGGSEVQLQQSG<br>PGLVKPSQTLSLTCAISGDSMLSNSDTWNWIRQSPSRGLEW<br>LGRTYHRSTWYDDYASSVRGRVSINVDTSKNQYSLQLNAV<br>TPEDTGVYYCARVRLQDGNSWSDAFDVWGQGTMVTVSS |

Table 4A provides nucleotide and amino acid sequences for additional CAR components, e.g., signal peptide, linkers and P2A sites.

TABLE 4A

Additional CAR components

| Identifier | SEQ ID NO | Sequence |
|---|---|---|
| Signal peptide for CAR22 in c201, c203, and tandem CARs c171, c182, c188 | 58<br>59 | atggccctccctgtcaccgccctgctgcttccgctggctcttctgctccacgccgctcggccc<br>MALPVTALLLPLALLLHAARP |
| Signal peptide in tandem CARs c224, c227 | 60<br>59 | atggccctgcccgtgactgcgctcctgcttccgttggccctgctcctgcatgccgccagacct<br>MALPVTALLLPLALLLHAARP |

TABLE 4A-continued

Additional CAR components

| Identifier | SEQ ID NO | Sequence |
|---|---|---|
| Signal peptide CAR19 in c201 and c203 | 61 | atggccttaccagtgaccgccttgctcctgccgctggccttgctgctccacgccgccaggccg |
| | 59 | MALPVTALLLPLALLLHAARP |
| Signal peptide CAR22 in c230 | 62 | atggcacttcccgtcaccgccctgctgctcccactcgccctccttctgcacgccgcccgccc |
| | 59 | MALPVTALLLPLALLLHAARP |
| Signal peptide CAR19 in c230 | 63 | atggccctgccagtgaccgcgctcctgctgccccctggctctgctgcttcacgcggcccggct |
| | 59 | MALPVTALLLPLALLLHAARP |
| CD8 hinge and transmembrane CAR22 in c201 and c203, and in tandem CARs c171, c182, c188, c224, c227 | 64 | accactaccccagcaccgaggccacccaccccggctcctaccatcgcctcccagcctctgtccctgcgtccggaggcatgtagacccgcagctggtggggccgtgcatacccggggtcttgacttcgcctgcgatatctacatttgggccccctctggctggtacttgcggggtcctgctgctttcactcgtgatcactctttactgt |
| | 65 | TTTPAPRPPTPAPTIASQPLSLRPEACRPAAGGAVHTRGLDFACDIYIWAPLAGTCGVLLLSLVITLYC |
| CD8 hinge and transmembrane CAR22 In c230 | 66 | actaccaccccggccccgcggcccccctacaccggcaccgactattgccagccagcctctctcgctgcggccggaggcctgccgcccagccgccggcggagccgtgcacacccgcggtctggacttcgcgtgcgatatctacatctgggctccgctggccgggacttgtggcgtgctgctgctgtctctggtcatcacactgtactgc |
| | 65 | TTTPAPRPPTPAPTIASQPLSLRPEACRPAAGGAVHTRGLDFACDIYIWAPLAGTCGVLLLSLVITLYC |
| CD8 hinge and transmembrane CAR19 in c201 and c203 | 67 | accacgacgccagccgccgcgaccaccaacaccggcgcccaccatcgcgtcgcagcccctgtccctgcgcccagaggcgtgccggccagcggcgggggcgcagtgcacacgaggggctggacttcgcctgtgatatctacatctgggcgcccttggccgggacttgtggggtccttctcctgtcactggttatcacccttactgc |
| | 65 | TTTPAPRPPTPAPTIASQPLSLRPEACRPAAGGAVHTRGLDFACDIYIWAPLAGTCGVLLLSLVITLYC |
| CD8 hinge and transmembrane CAR19 In c230 | 68 | accaccaccccctgcgcctcggcctcctaccccggctcccactatcgcgagccagccgctgagcctgcggcctgaggcttgccgaccggccgctggcggcgccgtgcatactcggggcctcgactttgcctgtgacatctacatctgggcccccctggccggaacgtgcggagtgctgctgctgtcgctggtcattaccctgtattgc |
| | 65 | TTTPAPRPPTPAPTIASQPLSLRPEACRPAAGGAVHTRGLDFACDIYIWAPLAGTCGVLLLSLVITLYC |
| 4-1BB CAR22 in c201 and c203, and tandem CARs c171, c182, c188, c224, c227 | 69 | aagcgcggtcggaagaagctgctgtacatctttaagcaacccttcatgaggcctgtgcagactactcaagaggaggacggctgttcatgccggttcccagaggaggaggaaggcggctgcgaactg |
| | 70 | KRGRKKLLYIFKQPFMRPVQTTQEEDGCSCRFPEEEEGGCEL |
| 4-1BB CAR19 in c201 and c203 | 71 | aaacggggcagaaagaaactcctgtatatattcaaacaaccatttatgagaccagtacaaactactcaagaggaagatggctgtagctgccgatttccagaagaagaagaagaaggaggatgtgaactg |
| | 70 | KRGRKKLLYIFKQPFMRPVQTTQEEDGCSCRFPEEEEGGCEL |
| 4-1BB CAR22 in c230 | 72 | aagcgcggaagaaagaagctgctctacatcttcaagcaacccttcatgcggcctgtgcagaccacccaggaagaggatggctgctcctgccggttcccggaggaagaagagggcggatgcgaactg |
| | 70 | KRGRKKLLYIFKQPFMRPVQTTQEEDGCSCRFPEEEEGGCEL |
| 4-1BB CAR19 in c230 | 73 | aaacgcggaaggaagaagctgttgtacattttcaagcagcccttcatgcgcccggtgcaaactactcaggaggaagatggctgttcctgtcggttccccgaagaggaagaaggcggctgcgagttg |
| | 70 | KRGRKKLLYIFKQPFMRPVQTTQEEDGCSCRFPEEEEGGCEL |
| CD3zeta CAR22 in c201 and | 74 | cgcgtgaaattcagccgcagcgcagatgctccagcctaccagcaggggcagaaccagctctacaacgaactcaatcttggtcggagagaggagtacgacgtgctggacaagcggagaggacgggacccagaaatgggcgggaagccgcgcagaaagaatcccaagagggcctgtaca |

TABLE 4A-continued

Additional CAR components

| Identifier | SEQ ID NO | Sequence |
|---|---|---|
| c203, and tandem CARs 171, c182, c188, c224, c227 | 75 | acgagctccaaaaggataagatggcagaagcctatagcgagattggtatgaaaggggaac gcagaagaggcaaaggccacgacggactgtaccagggactcagcaccgccaccaagga cacctatgacgctcttcacatgcaggccctgccgcctcgg RVKFSRSADAPAYQQGQNQLYNELNLGRREEYDVLDKRR GRDPEMGGKPRRKNPQEGLYNELQKDKMAEAYSEIGMK GERRRGKGHDGLYQGLSTATKDTYDALHMQALPPR |
| CD3zeta CAR19 in c201 and c203 | 76 | agagtgaagttcagcaggagcgcagacgcccccgcgtaccagcagggccagaaccagct ctataacgagctcaatctaggacgaagagaggagtacgatgttttggacaagagacgtggc cgggaccctgagatgggggaaagccgagaaggaagaaccctcaggaaggcctgtaca atgaactgcagaaagataagatggcggaggcctacagtgagattgggatgaaaggcgagc gccggaggggcaaggggcacgatggcctttaccagggtctcagtacagccaccaaggac acctacgacgcccttcacatgcaggccctgccccctcgc |
|  | 75 | RVKFSRSADAPAYQQGQNQLYNELNLGRREEYDVLDKRR GRDPEMGGKPRRKNPQEGLYNELQKDKMAEAYSEIGMK GERRRGKGHDGLYQGLSTATKDTYDALHMQALPPR |
| CD3zeta CAR22 in c230 | 77 | cgcgtgaagttcagccgaagcgccgacgcccccggcctaccagcagggccagaaccaact gtacaacgaactcaacctgggtcggagagaagagtacgacgtgctggacaaaagacgcg gcagggaccccgagatgggcggaaagcctcgccgcaagaacccgcaggagggcctcta caacgagctgcagaaggacaagatggccgaagcctactcagagatcggcatgaagggg agcggaggcgcgggaagggccacgacggtttgtaccaaggactttccactgcgaccaag gacacctacgatgccctccatatgcaagccctgccgccccgg |
|  | 75 | RVKFSRSADAPAYQQGQNQLYNELNLGRREEYDVLDKRR GRDPEMGGKPRRKNPQEGLYNELQKDKMAEAYSEIGMK GERRRGKGHDGLYQGLSTATKDTYDALHMQALPPR |
| CD3zeta CAR19 in c230 | 78 | agggtcaagttctcccggtccgccgatgctccgcctaccaacaggggcagaaccagctttt ataacgaactgaacctgggcaggagggaggaatatgatgtgttggataagcgccggggcc gggacccagaaatggggggaaagcccagaagaaagaaccctcaagagggactttacaac gaattgcagaaagacaaaatggccgaggcctactccgagattgggatgaagggcgaaaga cggagaggaaaggggcacgacgggctctaccagggactcagcaccgccaccaaagata cctacgacgccctgcatatgcaggcgctgccgccgcgc |
|  | 75 | RVKFSRSADAPAYQQGQNQLYNELNLGRREEYDVLDKRR GRDPEMGGKPRRKNPQEGLYNELQKDKMAEAYSEIGMK GERRRGKGHDGLYQGLSTATKDTYDALHMQALPPR |
| Linker between scFVs in c171 | 79 | ttggcagaagccgccgcgaaa |
|  | 80 | LAEAAAK |
| Linker between scFVs in c182, c188 | 81 | ggtggaggtggcagcggaggaggtgggtccggcggtggaggaagc |
|  | 82 | GGGGSGGGGSGGGGS |
| Linker between scFVs in c224 | 83 | ggcggaggcgggagcggaggaggaggctctggcggaggaggaagc |
|  | 82 | GGGGSGGGGSGGGGS |
| Linker between scFVs in c227 | 84 | ggcggtggaggctcggggggggcggctcaggaggaggcggctca |
|  | 82 | GGGGSGGGGSGGGGS |
| P2A in c201, c203 | 85 | ggaagcggagctactaacttcagcctgctgaagcaggctggagacgtggaggagaaccct ggacct |
|  | 86 | GSGATNFSLLKQAGDVEENPGP |
| P2A in c230 | 87 | ggttccggagctaccaacttctcgctgttgaagcaggccggagatgtcgaggaaacccgg gacct |
|  | 86 | GSGATNFSLLKQAGDVEENPGP |
| Gly4Ser linker | 88 | Ggtggaggtggcagc |
|  | 89 | GGGGS |

TABLE 5A

| Identifier | SEQ ID NO | Sequence |
|---|---|---|
| CAR19-1 scFv domain | 90 | EIVMTQSPATLSLSPGERATLSCRASQDISKYLNWYQQKPG QAPRLLIYHTSRLHSGIPARFSGSGSGTDYTLTISSLQPEDFA VYFCQQGNTLPYTFGQGTKLEIKGGGGSGGGGSGGGGSQ VQLQESGPGLVKPSETLSLTCTVSGVSLPDYGVSWIRQPPG KGLEWIGVIWGSETTYYSSSLKSRVTISKDNSKNQVSLKLS SVTAADTAVYYCAKHYYYGGSYAMDYWGQGTLVTVSS |
| CAR19-2 scFv domain | 91 | MALPVTALLLPLALLLHAARPEIVMTQSPATLSLSPGERAT LSCRASQDISKYLNWYQQKPGQAPRLLIYHTSRLHSGIPAR FSGSGSGTDYTLTISSLQPEDFAVYFCQQGNTLPYTFGQGT KLEIKGGGGSGGGGSGGGGSQVQLQESGPGLVKPSETLSL TCTVSGVSLPDYGVSWIRQPPGKGLEWIGVIWGSETTYYQ SSLKSRVTISKDNSKNQVSLKLSSVTAADTAVYYCAKHYY YGGSYAMDYWGQGTLVTVSSHHHHHHHH |
| CAR19-2 full CAR (with signal peptide) | 92 | MALPVTALLLPLALLLHAARPEIVMTQSPATLSLSPGERAT LSCRASQDISKYLNWYQQKPGQAPRLLIYHTSRLHSGIPAR FSGSGSGTDYTLTISSLQPEDFAVYFCQQGNTLPYTFGQGT KLEIKGGGGSGGGGSGGGGSQVQLQESGPGLVKPSETLSL TCTVSGVSLPDYGVSWIRQPPGKGLEWIGVIWGSETTYYQ SSLKSRVTISKDNSKNQVSLKLSSVTAADTAVYYCAKHYY YGGSYAMDYWGQGTLVTVSSTTTPAPRPPTPAPTIASQPLS LRPEACRPAAGGAVHTRGLDFACDIYIWAPLAGTCGVLLL SLVITLYCKRGRKKLLYIFKQPFMRPVQTTQEEDGCSCRFP EEEEGGCELRVKFSRSADAPAYKQGQNQLYNELNLGRREE YDVLDKRRGRDPEMGGKPRRKNPQEGLYNELQKDKMAE AYSEIGMKGERRRGKGHDGLYQGLSTATKDTYDALHMQA LPPR |
| CAR19-2 full CAR | 93 | EIVMTQSPATLSLSPGERATLSCRASQDISKYLNWYQQKPG QAPRLLIYHTSRLHSGIPARFSGSGSGTDYTLTISSLQPEDFA VYFCQQGNTLPYTFGQGTKLEIKGGGGSGGGGSGGGGSQ VQLQESGPGLVKPSETLSLTCTVSGVSLPDYGVSWIRQPPG KGLEWIGVIWGSETTYYQSSLKSRVTISKDNSKNQVSLKLS SVTAADTAVYYCAKHYYYGGSYAMDYWGQGTLVTVSST TTPAPRPPTPAPTIASQPLSLRPEACRPAAGGAVHTRGLDFA CDIYIWAPLAGTCGVLLLSLVITLYCKRGRKKLLYIFKQPF MRPVQTTQEEDGCSCRFPEEEEGGCELRVKFSRSADAPAY KQGQNQLYNELNLGRREEYDVLDKRRGRDPEMGGKPRRK NPQEGLYNELQKDKMAEAYSEIGMKGERRRGKGHDGLYQ GLSTATKDTYDALHMQALPPR |
| CAR19-3 scFv domain | 94 | QVQLQESGPGLVKPSETLSLTCTVSGVSLPDYGVSWIRQPP GKGLEWIGVIWGSETTYYSSSLKSRVTISKDNSKNQVSLKL SSVTAADTAVYYCAKHYYYGGSYAMDYWGQGTLVTVSS GGGGSGGGGSGGGGSEIVMTQSPATLSLSPGERATLSCRAS QDISKYLNWYQQKPGQAPRLLIYHTSRLHSGIPARFSGSGS GTDYTLTISSLQPEDFAVYFCQQGNTLPYTFGQGTKLEIK |
| CAR19-5 scFv domain | 95 | EIVMTQSPATLSLSPGERATLSCRASQDISKYLNWYQQKPG QAPRLLIYHTSRLHSGIPARFSGSGSGTDYTLTISSLQPEDFA VYFCQQGNTLPYTFGQGTKLEIKGGGGSGGGGSGGGGSG GGGSQVQLQESGPGLVKPSETLSLTCTVSGVSLPDYGVSWI RQPPGKGLEWIGVIWGSETTYYSSSLKSRVTISKDNSKNQV SLKLSSVTAADTAVYYCAKHYYYGGSYAMDYWGQGTLV TVSS |
| CAR19-6 scFv domain | 96 | EIVMTQSPATLSLSPGERATLSCRASQDISKYLNWYQQKPG QAPRLLIYHTSRLHSGIPARFSGSGSGTDYTLTISSLQPEDFA VYFCQQGNTLPYTFGQGTKLEIKGGGGSGGGGSGGGGSG GGGSQVQLQESGPGLVKPSETLSLTCTVSGVSLPDYGVSWI RQPPGKGLEWIGVIWGSETTYYQSSLKSRVTISKDNSKNQV SLKLSSVTAADTAVYYCAKHYYYGGSYAMDYWGQGTLV TVSS |
| CAR19-7 scFv domain | 97 | QVQLQESGPGLVKPSETLSLTCTVSGVSLPDYGVSWIRQPP GKGLEWIGVIWGSETTYYSSSLKSRVTISKDNSKNQVSLKL SSVTAADTAVYYCAKHYYYGGSYAMDYWGQGTLVTVSS GGGGSGGGGSGGGGSGGGGSEIVMTQSPATLSLSPGERAT LSCRASQDISKYLNWYQQKPGQAPRLLIYHTSRLHSGIPAR FSGSGSGTDYTLTISSLQPEDFAVYFCQQGNTLPYTFGQGT KLEIK |

TABLE 5A-continued

Additional CD19 binding domains and other sequences

| Identifier | SEQ ID NO | Sequence |
|---|---|---|
| CAR19-8 scFv domain | 98 | QVQLQESGPGLVKPSETLSLTCTVSGVSLPDYGVSWIRQPP GKGLEWIGVIWGSETTYYQSSLKSRVTISKDNSKNQVSLKL SSVTAADTAVYYCAKHYYYGGSYAMDYWGQGTLVTVSS GGGGSGGGGSGGGGSGGGGSEIVMTQSPATLSLSPGERAT LSCRASQDISKYLNWYQQKPGQAPRLLIYHTSRLHSGIPAR FSGSGSGTDYTLTISSLQPEDFAVYFCQQGNTLPYTFGQGT KLEIK |
| CAR19-9 scFv domain | 99 | EIVMTQSPATLSLSPGERATLSCRASQDISKYLNWYQQKPG QAPRLLIYHTSRLHSGIPARFSGSGSGTDYTLTISSLQPEDFA VYFCQQGNTLPYTFGQGTKLEIKGGGGSGGGGSGGGGSGG GGSQVQLQESGPGLVKPSETLSLTCTVSGVSLPDYGVSWIR QPPGKGLEWIGVIWGSETTYYNSSLKSRVTISKDNSKNQVS LKLSSVTAADTAVYYCAKHYYYGGSYAMDYWGQGTLVT VSS |
| CAR19-10 scFv domain | 100 | QVQLQESGPGLVKPSETLSLTCTVSGVSLPDYGVSWIRQPP GKGLEWIGVIWGSETTYYNSSLKSRVTISKDNSKNQVSLKL SSVTAADTAVYYCAKHYYYGGSYAMDYWGQGTLVTVSS GGGGSGGGGSGGGGSGGGGSEIVMTQSPATLSLSPGERAT LSCRASQDISKYLNWYQQKPGQAPRLLIYHTSRLHSGIPAR FSGSGSGTDYTLTISSLQPEDFAVYFCQQGNTLPYTFGQGT KLEIK |
| CAR19-11 scFv domain | 101 | EIVMTQSPATLSLSPGERATLSCRASQDISKYLNWYQQKPG QAPRLLIYHTSRLHSGIPARFSGSGSGTDYTLTISSLQPEDFA VYFCQQGNTLPYTFGQGTKLEIKGGGGSGGGGSGGGGSQV QLQESGPGLVKPSETLSLTCTVSGVSLPDYGVSWIRQPPGK GLEWIGVIWGSETTYYNSSLKSRVTISKDNSKNQVSLKLSS VTAADTAVYYCAKHYYYGGSYAMDYWGQGTLVTVSS |
| CAR19-12 scFv domain | 102 | QVQLQESGPGLVKPSETLSLTCTVSGVSLPDYGVSWIRQPP GKGLEWIGVIWGSETTYYNSSLKSRVTISKDNSKNQVSLKL SSVTAADTAVYYCAKHYYYGGSYAMDYWGQGTLVTVSS GGGGSGGGGSGGGGSEIVMTQSPATLSLSPGERATLSCRAS QDISKYLNWYQQKPGQAPRLLIYHTSRLHSGIPARFSGSGS GTDYTLTISSLQPEDFAVYFCQQGNTLPYTFGQGTKLEIK |
| CAR19-A full CAR | 103 | MLLLVTSLLLCELPHPAFLLIPDIQMTQTTSSLSASLGDRVTI SCRASQDISKYLNWYQQKPDGTVKLLIYHTSRLHSGVPSRF SGSGSGTDYSLTISNLEQEDIATYFCQQGNTLPYTFGGGTK LEITGSTSGSGKPGSGEGSTKGEVKLQESGPGLVAPSQSLSV TCTVSGVSLPDYGVSWIRQPPRKGLEWLGVIWGSETTYYN SALKSRLTIIKDNSKSQVFLKMNSLQTDDTAIYYCAKHYYY GGSYAMDYWGQGTSVTVSSAAAIEVMYPPPYLDNEKSNG TIIHVKGKHLCPSPLFPGPSKPFWVLVVVGGVLACYSLLVT VAFIIFWVRSKRSRLLHSDYMNMTPRRPGPTRKHYQPYAPP RDFAAYRSRVKFSRSADAPAYQQGQNQLYNELNLGRREE YDVLDKRRGRDPEMGGKPRRKNPQEGLYNELQKDKMAE AYSEIGMKGERRRGKGHDGLYQGLSTATKDTYDALHMQA LPPR |
| CAR19-A scFv domain | 104 | DIQMTQTTSSLSASLGDRVTISCRASQDISKYLNWYQQKPD GTVKLLIYHTSRLHSGVPSRFSGSGSGTDYSLTISNLEQEDI ATYFCQQGNTLPYTFGGGTKLEITGSTSGSGKPGSGEGSTK GEVKLQESGPGLVAPSQSLSVTCTVSGVSLPDYGVSWIRQP PRKGLEWLGVIWGSETTYYNSALKSRLTIIKDNSKSQVFLK MNSLQTDDTAIYYCAKHYYYGGSYAMDYWGQGTSVTVS S |
| CAR19-B full CAR | 105 | MLLLVTSLLLCELPHPAFLLIPDIQMTQTTSSLSASLGDRVTI SCRASQDISKYLNWYQQKPDGTVKLLIYHTSRLHSGVPSRF SGSGSGTDYSLTISNLEQEDIATYFCQQGNTLPYTFGGGTK LEITGSTSGSGKPGSGEGSTKGEVKLQESGPGLVAPSQSLSV TCTVSGVSLPDYGVSWIRQPPRKGLEWLGVIWGSETTYYN SALKSRLTIIKDNSKSQVFLKMNSLQTDDTAIYYCAKHYYY GGSYAMDYWGQGTSVTVSSESKYGPPCPPCPMFWVLVVV GGVLACYSLLVTVAFIIFWVKRGRKKLLYIFKQPFMRPVQT TQEEDGCSCRFPEEEGGCELRVKFSRSADAPAYQQGQNQ LYNELNLGRREEYDVLDKRRGRDPEMGGKPRRKNPQEGL YNELQKDKMAEAYSEIGMKGERRRGKGHDGLYQGLSTAT KDTYDALHMQALPPR |

TABLE 5A-continued

Additional CD19 binding domains and other sequences

| Identifier | SEQ ID NO | Sequence |
|---|---|---|
| CAR19-B scFv domain | 106 | DIQMTQTTSSLSASLGDRVTISCRASQDISKYLNWYQQKPD GTVKLLIYHTSRLHSGVPSRFSGSGSGTDYSLTISNLEQEDI ATYFCQQGNTLPYTFGGGTKLEITGSTSGSGKPGSGEGSTK GEVKLQESGPGLVAPSQSLSVTCTVSGVSLPDYGVSWIRQP PRKGLEWLGVIWGSETTYYNSALKSRLTIIKDNSKSQVFLK MNSLQTDDTAIYYCAKHYYYGGSYAMDYWGQGTSVTVS S |
| Signal peptide | 107 | MLLLVTSLLLCELPHPAFLLIP |
| CD3zeta | 108 | RVKFSRSADAPAYKQGQNQLYNELNLGRREEYDVLDKRR GRDPEMGGKPRRKNPQEGLYNELQKDKMAEAYSEIGMKG ERRRGKGHDGLYQGLSTATKDTYDALHMQALPPR |

Tandem CARs

In an aspect, disclosed herein are CARs comprising a bispecific antigen binding domain, e.g., tandem CARs. In some embodiments, a bispecific antigen binding domain comprises two antigen binding domains, e.g., a first antigen binding domain and a second antigen binding 818182898.1 domain. In some embodiments, a tandem CAR comprises a bispecific antigen binding domain comprising a CD22 antigen binding domain and a CD19 antigen binding domain.

In some embodiments of the bispecific antigen binding domain, the first antigen binding domain is an antibody molecule, e.g., an antibody binding domain (e.g., a scFv). In some embodiments of the bispecific antigen binding domain, the second antigen binding domain is an antibody molecule, e.g., an antibody binding domain (e.g., a scFv). Within each antibody molecule, e.g., scFv, of the bispecific antigen binding domain, the VH can be upstream or downstream of the VL.

In some embodiments, the upstream antibody or antibody fragment (e.g., scFv) is arranged with its VH (VH1) upstream of its VL (VL1) and the downstream antibody or antibody fragment (e.g., scFv) is arranged with its VL (VL2) upstream of its VH (VH2), such that the overall bispecific antibody molecule has the arrangement VH1-VL1-VL2-VH2, from an N- to C-terminal orientation.

In some embodiments, the upstream antibody or antibody fragment (e.g., scFv) is arranged with its VL (VL1) upstream of its VH (VH1) and the downstream antibody or antibody fragment (e.g., scFv) is arranged with its VH (VH2) upstream of its VL (VL2), such that the overall bispecific antibody molecule has the arrangement VL1-VH1-VH2-VL2, from an N- to C-terminal orientation.

In some embodiments, the upstream antibody or antibody fragment (e.g., scFv) is arranged with its VL (VL1) upstream of its VH (VH1) and the downstream antibody or antibody fragment (e.g., scFv) is arranged with its VL (VL2) upstream of its VH (VH2), such that the overall bispecific antibody molecule has the arrangement VL1-VH1-VL2-VH2, from an N- to C-terminal orientation.

In yet some embodiments, the upstream antibody or antibody fragment (e.g., scFv) is arranged with its VH (VH1) upstream of its VL (VL1) and the downstream antibody or antibody fragment (e.g., scFv) is arranged with its VH (VH2) upstream of its VL (VL2), such that the overall bispecific antibody molecule has the arrangement VH1-VL1-VH2-VL2, from an N- to C-terminal orientation.

In any of the aforesaid configurations, optionally, a linker is disposed between the two antibodies or antibody fragments (e.g., scFvs), e.g., between VL1 and VL2 if the construct is arranged as VH1-VL1-VL2-VH2; between VH1 and VH2 if the construct is arranged as VL1-VH1-VH2-VL2; between VH1 and VL2 if the construct is arranged as VL1-VH1-VL2-VH2; or between VL1 and VH2 if the construct is arranged as VH1-VL1-VH2-VL2. In general, the linker between the two scFvs should be long enough to avoid mispairing between the domains of the two scFvs. The linker may be a linker as described herein. In some embodiments, the linker is a (Gly4-Ser) n linker, wherein n is 1, 2, 3, 4, 5, or 6. In some embodiments, the linker is (Gly4-Ser) n, wherein n=1, e.g., the linker has the amino acid sequence Gly4-Ser. In some embodiments, the linker is (Gly4-Ser) n, wherein n=4 (SEQ ID NO: 82). In some embodiments, the linker comprises, e.g., consists of, the amino acid sequence: LAEAAAK (e.g., SEQ ID NO: 80).

In any of the aforesaid configurations, optionally, a linker is disposed between the VL and VH of the first scFv. Optionally, a linker is disposed between the VL and VH of the second scFv. In constructs that have multiple linkers, any two or more of the linkers can be the same or different. Accordingly, in some embodiments, a bispecific CAR comprises VLs, VHs, and optionally one or more linkers in an arrangement as described herein.

In some embodiments, each antibody molecule, e.g., each antigen binding domain (e.g., each scFv) comprises a linker between the VH and the VL regions. In some embodiments, the linker between the VH and the VL regions is a (Gly4-Ser) n linker, wherein n is 1, 2, 3, 4, 5, or 6. In some embodiments, the linker is (Gly4-Ser) n, wherein n=1, e.g., the linker has the amino acid sequence Gly4-Ser. In some embodiments, the linker is (Gly4-Ser) n, wherein n=4 (SEQ ID NO: 82). In some embodiments, the VH and VL regions are connected without a linker.

Split CAR

In some embodiments, the CAR-expressing cell uses a split CAR. The split CAR approach is described in more detail in PCT publications WO2014/055442 and WO2014/055657, incorporated herein by reference. Briefly, a split CAR system comprises a cell expressing a first CAR having a first antigen binding domain and a costimulatory domain (e.g., 4-1BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length. RNA so produced can efficiently transfect different kinds of cells. In one aspect, the template includes sequences for the CAR.

In one aspect the CAR, e.g., dual CAR or tandem CAR, is encoded by a messenger RNA (mRNA). In one aspect the mRNA encoding the CAR, e.g., dual CAR or tandem CAR, is introduced into an immune effector cell, e.g., a T cell or a NK cell, for production of a CAR-expressing cell, e.g., a CART cell or a CAR NK cell.

In one embodiment, the in vitro transcribed RNA of a CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementarity to regions of the DNA to be used as a template for the PCR. "Substantially complementarity," as used herein, refers to sequences of nucleotides where a majority or all of the bases in the primer sequence are complementarity, or one or more bases are non-complementarity, or mismatched. Substantially complementarity sequences are able to anneal or hybridize with the intended DNA target under annealing conditions used for PCR. The primers can be designed to be substantially complementarity to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementarity to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementarity to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In some embodiments, the 5' UTR can be 5'UTR of an RNA virus whose RNA genome is stable in cells. In some embodiments, various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleic acid sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12 (8): 861-70 (2001).

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. Sec, e.g., Aronovich et al. Hum. Mol. Genet. 20.R1 (2011): R14-20; Singh et al. Cancer Res. 15 (2008): 2961-2971; Huang et al. Mol. Ther. 16 (2008): 580-589; Grabundzija et al. Mol. Ther. 18 (2010): 1200-1209; Kebriaci et al. Blood. 122.21 (2013): 166; Williams. Molecular Therapy 16.9 (2008): 1515-16; Bell et al. Nat. Protoc. 2.12 (2007): 3153-65; and Ding et al. Cell. 122.3 (2005): 473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al.

Exemplary transposons include a pT2-based transposon. See, e.g., Grabundzija et al. Nucleic Acids Res. 41.3 (2013): 1829-47; and Singh et al. Cancer Res. 68.8 (2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). Sec, e.g., Aronovich et al.; Kebriaci et al.; and Grabundzija et al., all of which are incorporated herein by reference.

Use of the SBTS permits efficient integration and expression of a transgene, e.g., a nucleic acid encoding a CAR described herein. Provided herein are methods of generating a cell, e.g., T cell or NK cell, that stably expresses a CAR described herein, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In some embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Nucleic Acid Constructs Encoding a CAR

The present invention also provides nucleic acid molecules encoding one or more CAR constructs described herein. In one aspect, the nucleic acid molecule is provided as a messenger RNA transcript. In one aspect, the nucleic acid molecule is provided as a DNA construct.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, crisper, CAS9, and zinc finger nucleases. See below June et al. 2009 *Nature Reviews Immunology* 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1α, ubiquitin C, or phosphoglycerokinase (PGK) promoters.

An example of a promoter that is capable of expressing a CAR transgene in a mammalian T cell is the EF-1 alpha (EF1a) promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17 (8): 1453-1464 (2009). In one aspect, the EF1a promoter comprises the sequence as known in the art.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479:79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5:505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell or NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells or NK cells. In one aspect, the mammalian T cell is a human T cell.

Methods of Manufacture/Production

The present invention also provides methods of making a cell disclosed herein, e.g., methods of engineering a T cell or NK cell to express a nucleic acid molecule encoding one or more CAR constructs described herein. In some embodiments, the manufacturing methods disclosed herein are used to manufacture a cell comprising a nucleic acid molecule encoding two CARs disclosed herein (e.g., a CD19/CD22 tandem and/or dual CAR disclosed herein). In some embodiments, the manufacturing methods disclosed herein are used to manufacture a cell comprising a nucleic acid molecule encoding a diabody CAR disclosed herein, e.g., an anti-CD22/anti-CD19 diabody CAR disclosed herein. In some embodiments, the manufacturing methods disclosed herein are used to manufacture a cell comprising two nucleic acid molecules, each of which encodes a CAR disclosed herein (e.g., one nucleic acid molecule encoding an anti-CD22 CAR and one nucleic acid molecule encoding an anti-CD19 CAR). In some embodiments, provided herein is a population of cells (for example, immune effector cells, for example, T cells or NK cells) made by any of the manufacturing processes described herein.

Activation Process

In some embodiments, the methods disclosed herein may manufacture immune effector cells engineered to express one or more CARs in less than 24 hours. Without wishing to be bound by theory, the methods provided herein preserve the undifferentiated phenotype of T cells, such as naïve T cells, during the manufacturing process. These CAR-expressing cells with an undifferentiated phenotype may persist longer and/or expand better in vivo after infusion. In some embodiments, CART cells produced by the manufacturing methods provided herein comprise a higher percentage of stem cell memory T cells, compared to CART cells produced by the traditional manufacturing process, e.g., as measured using single-cell or bulk RNA-seq or flow cytometry using markers known in the art. In some embodiments, CART cells produced by the manufacturing methods provided herein comprise a lower percentage of effector T cells, compared to CART cells produced by the traditional manufacturing process, e.g., as measured using single-cell RNA-seq. In some embodiments, CART cells produced by the manufacturing methods provided herein better preserve the stemness of T cells, compared to CART cells produced by the traditional manufacturing process, e.g., as measured using scRNA-seq. In some embodiments, CART cells produced by the manufacturing methods provided herein show a lower level of hypoxia, compared to CART cells produced by the traditional manufacturing process, e.g., as measured using scRNA-seq. In some embodiments, CART cells produced by the manufacturing methods provided herein show a lower level of autophagy, compared to CART cells produced by the traditional manufacturing process, e.g., as measured using scRNA-seq. In some embodiments, the immune effector cells are engineered to comprise a nucleic acid molecule encoding a tandem or dual CAR disclosed herein (e.g., a CD19/CD22 tandem or dual CAR disclosed herein). In some embodiments, the immune effector cells are engineered to comprise a nucleic acid molecule encoding a tandem or dual CAR disclosed herein, e.g., an anti-CD22/anti-CD19 tandem or dual CAR disclosed herein. In some embodiments, the immune effector cells are engineered to comprise two nucleic acid molecules, each of which encodes a CAR disclosed herein (e.g., one nucleic acid molecule encoding an anti-CD22 CAR and one nucleic acid molecule encoding an anti-CD19 CAR). In other embodiments, the immune effector cells are engineered to comprise one nucleic acid molecule which encodes one or two CARs disclosed herein (e.g., one nucleic acid molecule encoding an anti-CD22/anti-CD19 tandem or anti-CD22/anti-CD19 CARs).

In some embodiments, the methods disclosed herein do not involve using a bead, such as Dynabeads® (for example, CD3/CD28 Dynabeads®), and do not involve a de-beading step. In some embodiments, the CART cells manufactured by the methods disclosed herein may be administered to a subject with minimal ex vivo expansion, for example, less than 2 days, less than 1 day, less than 12 hours, less than 8 hours, less than 6 hours, less than 4 hours, less than 3 hours, less than 2 hours, less than 1 hour, or no ex vivo expansion. Accordingly, the methods described herein provide a fast manufacturing process of making improved CAR-expressing cell products for use in treating a disease in a subject.

In some embodiments, the present disclosure provides methods of making a population of cells (for example, T cells) that express a chimeric antigen receptor (CAR) (e.g., one or more CARs, e.g., two CARs) comprising: (i) contacting a population of cells (for example, T cells, for example, T cells isolated from a frozen or fresh leukapheresis product) with an agent that stimulates a CD3/TCR complex and/or an agent that stimulates a costimulatory molecule on the surface of the cells; (ii) contacting the population of cells (for example, T cells) with a nucleic acid molecule(s) (for example, a DNA or RNA molecule) encoding the CAR(s), thereby providing a population of cells (for example, T cells) comprising the nucleic acid molecule, and (iii) harvesting the population of cells (for example, T cells) for storage (for example, reformulating the population of cells in cryopreservation media) or administration, wherein: (a) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 26 hours after the beginning of step (i), for example, no later than 22, 23, or 24 hours after the beginning of step (i), for example, no later than 24 hours after the beginning of step (i); (b) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 30 hours after the beginning of step (ii), for example, no later than 22, 23, 24, 25, 26, 27, 28, 29, or 30 hours after the beginning of step (ii); and/or (c) the population of cells from step (iii) are not expanded, or expanded by no more than 5%, 10%, 15%, 20%, 25%, 30%, 35%, or 40%, for example, no more than 10%, as assessed by the number of living cells compared to the population of cells at the beginning of step (i); or d) the population of cells from step (iii) are fewer, or less by 5%, 10%, 15%, 20%, 25%, 30%, 35%, 40%, 45%, 50%, 55%, 60%, 65%, or 70%, for example, as assessed by the number of living cells compared to the population of cells at the beginning of step (i). In some embodiments, the nucleic acid molecule in step (ii) is a DNA molecule. In some embodiments, the nucleic acid molecule in step (ii) is an RNA molecule. In some embodiments, the nucleic acid molecule in step (ii) is on a viral vector, for example, a viral vector chosen from a lentivirus vector, an adenoviral vector, or a retrovirus vector. In some embodiments, the nucleic acid molecule in step (ii) is on a non-viral vector. In some embodiments, the nucleic acid molecule in step (ii) is on a plasmid. In some embodiments, the nucleic acid molecule in step (ii) is not on any vector. In some embodiments, step (ii) comprises transducing the population of cells (for example, T cells) a viral vector(s) comprising a nucleic acid molecule encoding the CAR(s).

In some embodiments of the aforementioned methods, the methods further comprise adding an adjuvant or a transduction enhancement reagent in the cell culture medium to enhance transduction efficiency. In some embodiments, the adjuvant or transduction enhancement reagent comprises a cationic polymer. In some embodiments, the adjuvant or transduction enhancement reagent is selected from: LentiBOOST™ (Sirion Biotech), vectofusin-1, F108 (Poloxamer 338 or Pluronic® F-38), hexadimethrine bromide (Polybrene), PEA, Pluronic F68, Pluronic F127, Protamine Sulfate, Synperonic or LentiTrans™. In some embodiments, the adjuvant is LentiBOOST™ (Sirion Biotech). In other embodiments, the adjuvant is F108 (Poloxamer 338 or Pluronic® F-38).

In some embodiments, the population of cells (for example, T cells) is collected from an apheresis sample (for example, a leukapheresis sample) from a subject.

In some embodiments, the apheresis sample (for example, a leukapheresis sample) is collected from the subject and shipped as a frozen sample (for example, a cryopreserved sample) to a cell manufacturing facility. Then the frozen apheresis sample is thawed, and T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the activation process described herein. In some embodiments, the selected T cells (for example, CD4+ T cells and/or CD8+ T cells) undergo one or more rounds of freeze-thaw before being seeded for CART manufacturing.

In some embodiments, the apheresis sample (for example, a leukapheresis sample) is collected from the subject and shipped as a fresh product (for example, a product that is not frozen) to a cell manufacturing facility. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the activation process described herein. In some embodiments, the selected T cells (for example, CD4+ T cells and/or CD8+ T cells) undergo one or more rounds of freeze-thaw before being seeded for CART manufacturing. In some embodiments, the apheresis sample (for example, a leukapheresis sample) is collected from the subject. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then shipped as a frozen sample (for example, a cryopreserved sample) to a cell manufacturing facility. The selected T cells (for example, CD4+ T cells and/or CD8+ T cells) are later thawed and seeded for CART manufacturing using the activation process described herein.

In some embodiments, cells (for example, T cells) are contacted with anti-CD3 and anti-CD28 antibodies and, for example, immediately followed by transduction with a vector (for example, a lentiviral vector) (e.g. one or more vectors) encoding a CAR (e.g. one or more CARs). 24 hours after culture initiation, the cells are washed and formulated for storage or administration. Without wishing to be bound by theory, brief CD3 and CD28 stimulation may promote efficient transduction of self-renewing T cells. Compared to traditional CART manufacturing approaches, the activation process provided herein does not involve prolonged ex vivo expansion. Similar to the cytokine process, the activation process provided herein also preserves undifferentiated T cells during CART manufacturing.

In some embodiments, cells (for example, T cells) are contacted with anti-CD3 and anti-CD28 antibodies for, for example, 12 hours, followed by transduction with a vector (for example, a lentiviral vector) (e.g. one or more vectors) encoding a CAR (e.g. one or more CARs). 24 hours after culture initiation, the cells are washed and formulated for storage or administration. Without wishing to be bound by theory, brief CD3 and CD28 stimulation may promote efficient transduction of self-renewing T cells. Compared to traditional CART manufacturing approaches, the activation process provided herein does not involve prolonged ex vivo expansion. Similar to the cytokine process, the activation process provided herein also preserves undifferentiated T cells during CART manufacturing.

In some embodiments, the population of cells is contacted with an agent that stimulates a CD3/TCR complex and/or an agent that stimulates a costimulatory molecule on the surface of the cells.

In some embodiments, T cells are selected using anti-CD4 and anti-CD8 beads by positive selection, using, for example, a cell sorting machine (for example, a CliniMACS® Prodigy® device).

In some embodiments, T cells are selected using anti-CD45RA and anti-CCR7 beads by positive selection, using, for example, a cell sorting machine (for example, a CliniMACS® Prodigy® device).

In some embodiments, T cells are selected using anti-CD45RA and anti-CD27 beads by positive selection, using, for example, a cell sorting machine (for example, a CliniMACS® Prodigy® device).

In some embodiments, T cells are selected using anti-CD3 and anti-CD28 beads by positive selection, using, for example, a cell sorting machine (for example, a CliniMACS® Prodigy® device).

In some embodiments, T cells are selected using anti-lineage beads (except for T cell) by negative selection, using, for example, a cell sorting machine (for example, a CliniMACS® Prodigy® device).

In some embodiments, the agent that stimulates a CD3/TCR complex is an agent that stimulates CD3. In some embodiments, the agent that stimulates a costimulatory molecule is an agent that stimulates CD28, ICOS, CD27, HVEM, LIGHT, CD40, 4-1BB, OX40, DR3, GITR, CD30, TIM1, CD2, CD226, or any combination thereof. In some embodiments, the agent that stimulates a costimulatory molecule is an agent that stimulates CD28. In some embodiments, the agent that stimulates a CD3/TCR complex is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand). In some embodiments, the agent that stimulates a CD3/TCR complex is an antibody. In some embodiments, the agent that stimulates a CD3/TCR complex is an anti-CD3 antibody. In some embodiments, the agent that stimulates a costimulatory molecule is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand). In some embodiments, the agent that stimulates a costimulatory molecule is an antibody. In some embodiments, the agent that stimulates a costimulatory molecule is an anti-CD28 antibody. In some embodiments, the agent that stimulates a CD3/TCR complex or the agent that stimulates a costimulatory molecule does not comprise a bead. In some embodiments, the agent that stimulates a CD3/TCR complex comprises an anti-CD3 antibody covalently attached to a colloidal polymeric nanomatrix. In some embodiments, the agent that stimulates a costimulatory molecule comprises an anti-CD28 antibody covalently attached to a colloidal polymeric nanomatrix. In some embodiments, the agent that stimulates a CD3/TCR complex and the agent that stimulates a costimulatory molecule comprise T Cell TransAct™.

In some embodiments, the matrix comprises or consists of a polymeric, for example, biodegradable or biocompatible inert material, for example, which is non-toxic to cells. In some embodiments, the matrix is composed of hydrophilic polymer chains, which obtain maximal mobility in aqueous solution due to hydration of the chains. In some embodiments, the mobile matrix may be of collagen, purified proteins, purified peptides, polysaccharides, glycosaminoglycans, or extracellular matrix compositions. A polysaccharide may include for example, cellulose ethers, starch, gum arabic, agarose, dextran, chitosan, hyaluronic acid, pectins, xanthan, guar gum or alginate. Other polymers may include polyesters, polyethers, polyacrylates, polyacrylamides, polyamines, polyethylene imines, polyquaternium polymers, polyphosphazenes, polyvinylalcohols, polyvinylacetates, polyvinylpyrrolidones, block copolymers, or polyurethanes. In some embodiments, the mobile matrix is a polymer of dextran. In some embodiments, the population of cells is contacted with a nucleic acid molecule (e.g. one or more nucleic acid molecules) encoding a CAR (e.g. one or more CARs). In some embodiments, the population of cells is transduced with a DNA molecule (e.g. one or more DNA molecules) encoding a CAR (e.g. one or more CARs).

In some embodiments, contacting the population of cells with the nucleic acid molecule(s) encoding the CAR(s) occurs simultaneously with contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0.5 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 20 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 19 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 18 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 17 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 16 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 15 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 14 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 14 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 13 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 12 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 11 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 10 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 9 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 8 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 7 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 6 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 5 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 4 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 3 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR(s) occurs no later than 2 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 1 hour after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 30 minutes after the beginning of contacting the population of cells with the agent that stimulates a CD3/TCR complex and/or the agent that stimulates a costimulatory molecule on the surface of the cells described above.

In some embodiments, the population of cells is harvested for storage or administration.

In some embodiments, the population of cells is harvested for storage or administration no later than 72, 60, 48, 36, 32, 31, 30, 29, 28, 27, 26, 25, 24, 23, 22, 21, 20, 19, or 18 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 26 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 25 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 24 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 23 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 22 hours after the beginning of contacting the population of cells with the agent that stimulates a CD3/TCR complex and/or the agent that stimulates a costimulatory molecule on the surface of the cells described above.

In some embodiments, the population of cells is not expanded ex vivo.

In some embodiments, the population of cells is expanded by no more than 5, 6, 7, 8, 9, 10, 11, 12, 13, 14, 15, 16, 17, 18, 19, 20, 25, 30, 35, 40, 45, 50, 55, or 60%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 5%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 10%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 15%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 20%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 25%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 30%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 35%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 40%, for example, as assessed by the number of living cells, compared to the population of cells before it is contacted with the agent that stimulates a CD3/TCR complex and/or the agent that stimulates a costimulatory molecule on the surface of the cells described above.

In some embodiments, the population of cells is expanded by no more than 1, 1.5, 2, 2.5, 3, 3.5, 4, 4.5, 5, 6, 7, 8, 9, 10, 11, 12, 16, 20, 24, 36, or 48 hours, for example, as assessed by the number of living cells, compared to the population of cells before it is contacted with the one or more cytokines described above.

In some embodiments, the activation process is conducted in serum free cell media. In some embodiments, the activation process is conducted in cell media comprising one or more cytokines chosen from: IL-2, IL-15 (for example, hetIL-15 (IL15/sIL-15Ra)), or IL-6 (for example, IL-6/sIL-6Ra). In some embodiments, hetIL-15 comprises the amino acid sequence of NWVNVISDLKKIEDLIQSMHIDAT-LYTESDVHPSCKVTAMKCFLLELQVISLESGDASIH DTVENLIILANNSLSSNGNVTESGCKECEELEEKNI-KEFLQSFVHIVQMFINTSITCPPPMS VEHADIWVK-SYSLYSRERYICNSGFKRKAGTSSLTECVLNKATN-VAHWTTPSLKCIRDP ALVHQRPAPPSTVTTAGVTPQPESL-SPSGKEPAASSPSSNNTAATTAAIVPGSQLMPSKSP STGTTEISSHESSHGTPSQTTAKNWEL-TASASHQPPGVYPQG (SEQ ID NO: 109). In some embodiments, hetIL-15 comprises an amino acid sequence having at least about 70, 75, 80, 85, 90, 95, or 99% identity to SEQ ID NO: 109. In some embodiments, the activation process is conducted in cell media comprising a LSD1 inhibitor. In some embodiments, the activation process is conducted in cell media comprising a MALT1 inhibitor. In some embodiments, the serum free cell media comprises a serum replacement. In some embodiments, the serum replacement is CTS™ Immune Cell Serum Replacement (ICSR). In some embodiments, the level of ICSR can be, for example, up to 5%, for example, about 1%, 2%, 3%, 4%, or 5%. Without wishing to be bound by theory, using cell media, for example, Rapid Media, comprising ICSR, for example, 2% ICSR, may improve cell viability during a manufacture process described herein.

In some embodiments, the present disclosure provides methods of making a population of cells (for example, T cells) that express a chimeric antigen receptor (CAR) comprising: (a) providing an apheresis sample (for example, a fresh or cryopreserved leukapheresis sample) collected from a subject; (b) selecting T cells from the apheresis sample (for example, using negative selection, positive selection, or selection without beads); (c) seeding isolated T cells at, for example, $1 \times 10^6$ to $1 \times 10^7$ cells/mL; (d) contacting T cells with an agent that stimulates T cells, for example, an agent that stimulates a CD3/TCR complex and/or an agent that stimulates a costimulatory molecule on the surface of the cells (for example, contacting T cells with anti-CD3 and/or anti-CD28 antibody, for example, contacting T cells with TransAct); (c) contacting T cells with a nucleic acid molecule(s) (for example, a DNA or RNA molecule) encoding the CAR(s) (for example, contacting T cells with a virus comprising a nucleic acid molecule(s) encoding the CAR(s)) for, for example, 6-48 hours, for example, 20-28 hours; and (f) washing and harvesting T cells for storage (for example, reformulating T cells in cryopreservation media) or administration. In some embodiments, step (f) is performed no later than 30 hours after the beginning of step (d) or (c), for example, no later than 22, 23, 24, 25, 26, 27, 28, 29, or 30 hours after the beginning of step (d) or (c).

In some embodiments, provided herein is a population of cells (for example, immune effector cells, for example, T cells or NK cells) made by any of the manufacturing processes described herein (e.g., the Activation Process described herein).

In some embodiments, the percentage of naïve cells, for example, naïve T cells, for example, CD45RA+ CD45RO− CCR7+ T cells, in the population of cells at the end of the manufacturing process (for example, at the end of the cytokine process or the activation process described herein) (1) is the same as, (2) differs, for example, by no more than 4, 5, 6, 7, 8, 9, 10, 11, 12, 13, 14, or 15%, from, or (3) is increased, for example, by at least 5, 6, 7, 8, 9, 10, 11, 12, 13, 14, 15, 16, 17, 18, 19, 20, 21, 22, 23, 24, or 25%, as compared to, the percentage of naïve cells, for example, naïve T cells, for example, CD45RA+ CD45RO− CCR7+ cells, in the population of cells at the beginning of the manufacturing process (for example, at the beginning of the cytokine process or the activation process described herein). In some embodiments, the population of cells at the end of the manufacturing process (for example, at the end of the cytokine process or the activation process described herein) shows a higher percentage of naïve cells, for example, naïve T cells, for example, CD45RA+ CD45RO− CCR7+ T cells (for example, at least 5, 6, 7, 8, 9, 10, 11, 12, 13, 14, 15, 16, 17, 18, 19, 20, 25, 30, 35, 40, 45, or 50% higher), compared with cells made by an otherwise similar method which lasts, for example, more than 26 hours (for example, which lasts more than 5, 6, 7, 8, 9, 10, 11, or 12 days) or which involves expanding the population of cells in vitro for, for example, more than 3 days (for example, expanding the population of cells in vitro for 3, 4, 5, 6, 7, 8, 9, 10, 11, 12, 13, 14, or 15 days).

In some embodiments, the percentage of naïve cells, for example, naïve T cells, for example, CD45RA+ CD45RO− CCR7+ T cells, in the population of cells at the end of the manufacturing process (for example, at the end of the cytokine process or the activation process described herein) is not less than 20, 25, 30, 35, 40, 45, 50, 55, or 60%.

In some embodiments, the percentage of central memory cells, for example, central memory T cells, for example, CD95+ central memory T cells, CD45RO+ central memory T cells, and/or CCR7+ central memory T cells, in the population of cells at the end of the manufacturing process (for example, at the end of the cytokine process or the activation process described herein) (1) is the same as, (2) differs, for example, by no more than 4, 5, 6, 7, 8, 9, 10, 11, 12, 13, 14, or 15% from, or (3) is decreased, for example, by at least 5, 6, 7, 8, 9, 10, 11, 12, 13, 14, 15, 16, 17, 18, 19, 20, 21, 22, 23, 24, or 25%, as compared to, the percentage of central memory cells, for example, central memory T cells, for example, CD95+ central memory T cells, in the population of cells at the beginning of the manufacturing process (for example, at the beginning of the cytokine process or the activation process described herein). In some embodiments, the population of cells at the end of the manufacturing process (for example, at the end of the cytokine process or the activation process described herein) shows a lower percentage of central memory cells, for example, central memory T cells, for example, CD95+ central memory T cells (for example, at least 5, 6, 7, 8, 9, 10, 11, 12, 13, 14, 15, 16, 17, 18, 19, 20, 25, 30, 35, 40, 45, or 50% lower), compared with cells made by an otherwise similar method which lasts, for example, more than 26 hours (for example, which lasts more than 5, 6, 7, 8, 9, 10, 11, or 12 days) or which involves expanding the population of cells in vitro for, for example, more than 3 days (for example, expanding the population of cells in vitro for 3, 4, 5, 6, 7, 8, 9, 10, 11, 12, 13, 14, or 15 days).

In some embodiments, the percentage of central memory cells, for example, central memory T cells, for example, CD95+ central memory T cells, in the population of cells at the end of the manufacturing process (for example, at the end of the cytokine process or the activation process described herein) is no more than 40, 45, 50, 55, 60, 65, 70, 75, or 80%.

In some embodiments, the population of cells at the end of the manufacturing process (for example, at the end of the cytokine process or the activation process described herein) after being administered in vivo, persists longer or expands at a higher level (for example, at least 20, 25, 30, 35, 40, 45, 50, 55, 60, 65, 70, 75, 80, 85, or 90% higher), compared with cells made by an otherwise similar method which lasts, for example, more than 26 hours (for example, which lasts more than 5, 6, 7, 8, 9, 10, 11, or 12 days) or which involves expanding the population of cells in vitro for, for example, more than 3 days (for example, expanding the population of cells in vitro for 3, 4, 5, 6, 7, 8, 9, 10, 11, 12, 13, 14, or 15 days).

In some embodiments, the population of cells has been enriched for IL6R-expressing cells (for example, cells that are positive for IL6Rα and/or IL6Rβ) prior to the beginning of the manufacturing process (for example, prior to the beginning of the cytokine process or the activation process described herein). In some embodiments, the population of cells comprises, for example, no less than 30, 35, 40, 45, 50, 55, 60, 65, 70, 75, or 80% of IL6R-expressing cells (for example, cells that are positive for IL6Rα and/or IL6Rβ) at the beginning of the manufacturing process (for example, at the beginning of the cytokine process or the activation process described herein).

Cytokine Process

In some embodiments, the present disclosure provides methods of making a population of cells (for example, T cells) that express a chimeric antigen receptor (CAR) (e.g., one or more CARs, e.g., two CARs) comprising: (1) contacting a population of cells with a cytokine chosen from IL-2, IL-7, IL-15, IL-21, IL-6, or a combination thereof, (2) contacting the population of cells (for example, T cells) with a nucleic acid molecule(s) (for example, a DNA or RNA molecule) encoding the CAR(s), thereby providing a population of cells (for example, T cells) comprising the nucleic acid molecule, and (3) harvesting the population of cells (for example, T cells) for storage (for example, reformulating the population of cells in cryopreservation media) or administration, wherein: (a) step (2) is performed together with step (1) or no later than 5 hours after the beginning of step (1), for example, no later than 1, 2, 3, 4, or 5 hours after the beginning of step (1), and step (3) is performed no later than 26 hours after the beginning of step (1), for example, no later than 22, 23, or 24 hours after the beginning of step (1), for example, no later than 24 hours after the beginning of step (1), or (b) the population of cells from step (3) are not expanded, or expanded by no more than 5, 10, 15, 20, 25, 30, 35, or 40%, for example, no more than 10%, for example, as assessed by the number of living cells, compared to the population of cells at the beginning of step (1). In some embodiments, the nucleic acid molecule in step (2) is a DNA molecule. In some embodiments, the nucleic acid molecule in step (2) is an RNA molecule. In some embodiments, the nucleic acid molecule in step (2) is on a viral vector, for example, a viral vector chosen from a lentivirus vector, an adenoviral vector, or a retrovirus vector. In some embodiments, the nucleic acid molecule in step (2) is on a non-viral vector. In some embodiments, the nucleic acid molecule in step (2) is on a plasmid. In some embodiments, the nucleic acid molecule in step (2) is not on any vector. In some embodiments, step (2) comprises transducing the population of cells (for example, T cells) with a viral vector comprising a nucleic acid molecule(s) encoding the CAR(s). In some embodiments, the cells are engineered to comprise a nucleic acid molecule encoding a tandem or dual CAR disclosed herein (e.g., a CD19/CD22 tandem or dual CAR disclosed herein). In some embodiments, the cells are engineered to comprise a nucleic acid molecule encoding a diabody CAR disclosed herein, e.g., an anti-CD22/anti-CD19 diabody CAR disclosed herein. In some embodiments, the cells are engineered to comprise two nucleic acid molecules, each of which encodes a CAR disclosed herein (e.g., one nucleic acid molecule encoding an anti-CD22 CAR and one nucleic acid molecule encoding an anti-CD19 CAR).

In some embodiments, the population of cells (for example, T cells) is collected from an apheresis sample (for example, a leukapheresis sample) from a subject.

In some embodiments, the apheresis sample (for example, a leukapheresis sample) is collected from the subject and shipped as a frozen sample (for example, a cryopreserved sample) to a cell manufacturing facility. The frozen apheresis sample is then thawed, and T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the cytokine process described herein. In some embodiments, at the end of the cytokine process, the CAR T cells are cryopreserved and later thawed and administered to the subject. In some embodiments, the selected T cells (for example, CD4+ T cells and/or CD8+ T cells) undergo one or more rounds of freeze-thaw before being seeded for CART manufacturing.

In some embodiments, the apheresis sample (for example, a leukapheresis sample) is collected from the subject and shipped as a fresh product (for example, a product that is not frozen) to a cell manufacturing facility. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the cytokine process described herein. In some embodiments, the selected T cells (for example, CD4+ T cells and/or CD8+ T cells) undergo one or more rounds of freeze-thaw before being seeded for CART manufacturing.

In some embodiments, the apheresis sample (for example, a leukapheresis sample) is collected from the subject. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then shipped as a frozen sample (for example, a cryopreserved sample) to a cell manufacturing facility. The selected T cells (for example, CD4+ T cells and/or CD8+ T cells) are later thawed and seeded for CART manufacturing using the cytokine process described herein.

In some embodiments, after cells (for example, T cells) are seeded, one or more cytokines (for example, one or more cytokines chosen from IL-2, IL-7, IL-15 (for example, hetIL-15 (IL15/sIL-15Ra)), IL-21, or IL-6 (for example, IL-6/sIL-6R)) as well as a vector (for example, a lentiviral vector) (e.g. one or more vectors) encoding a CAR (e.g., one or more CARs) are added to the cells. After incubation for 20-24 hours, the cells are washed and formulated for storage or administration.

Different from traditional CART manufacturing approaches, the cytokine process provided herein does not involve CD3 and/or CD28 stimulation, or ex vivo T cell expansion. T cells that are contacted with anti-CD3 and anti-CD28 antibodies and expanded extensively ex vivo tend to show differentiation towards a central memory phenotype. Without wishing to be bound by theory, the cytokine process provided herein preserves or increases the undifferentiated phenotype of T cells during CART manufacturing, generating a CART product that may persist longer after being infused into a subject.

In some embodiments, the population of cells is contacted with one or more cytokines (for example, one or more cytokines chosen from IL-2, IL-7, IL-15 (for example, hetIL-15 (IL15/sIL-15Ra)), IL-21, or IL-6 (for example, IL-6/sIL-6Ra).

In some embodiments, the population of cells is contacted with IL-2. In some embodiments, the population of cells is contacted with IL-7. In some embodiments, the population of cells is contacted with IL-15 (for example, hetIL-15 (IL15/sIL-15Ra)). In some embodiments, the population of cells is contacted with IL-21. In some embodiments, the population of cells is contacted with IL-6 (for example, IL-6/sIL-6Ra). In some embodiments, the population of cells is contacted with IL-2 and IL-7. In some embodiments, the population of cells is contacted with IL-2 and IL-15 (for example, hetIL-15 (IL15/sIL-15Ra)). In some embodiments, the population of cells is contacted with IL-2 and IL-21. In some embodiments, the population of cells is contacted with IL-2 and IL-6 (for example, IL-6/sIL-6Ra). In some embodiments, the population of cells is contacted with IL-7 and IL-15 (for example, hetIL-15 (IL15/sIL-15Ra)). In some embodiments, the population of cells is contacted with IL-7 and IL-21. In some embodiments, the population of cells is contacted with IL-7 and IL-6 (for example, IL-6/sIL-6Ra). In some embodiments, the population of cells is contacted with IL-15 (for example, hetIL-15 (IL15/sIL-15Ra)) and IL-21. In some embodiments, the population of cells is contacted with IL-15 (for example, hetIL-15 (IL15/sIL-15Ra)) and IL-6 (for example, IL-6/sIL-6Ra). In some embodiments, the population of cells is contacted with IL-21 and IL-6 (for example, IL-6/sIL-6Ra). In some embodiments, the population of cells is contacted with IL-7, IL-15 (for example, hetIL-15 (IL15/sIL-15Ra)), and IL-21. In some embodiments, the population of cells is further contacted with a LSD1 inhibitor. In some embodiments, the population of cells is further contacted with a MALT1 inhibitor.

In some embodiments, the population of cells is contacted with 20, 30, 40, 50, 60, 70, 80, 90, 100, 110, 120, 130, 140, 150, 160, 170, 180, 190, 200, 210, 220, 230, 240, 250, 260, 270, 280, 290, or 300 U/ml of IL-2. In some embodiments, the population of cells is contacted with 1, 2, 3, 4, 5, 6, 7, 8, 9, 10, 11, 12, 13, 14, 15, 16, 17, 18, 19, or 20 ng/ml of IL-7. In some embodiments, the population of cells is contacted with 1, 2, 3, 4, 5, 6, 7, 8, 9, 10, 11, 12, 13, 14, 15, 16, 17, 18, 19, or 20 ng/ml of IL-15.

In some embodiments, the population of cells is contacted with a nucleic acid molecule (e.g. one or more nucleic acid molecules) encoding a CAR (e.g., one or more CARs). In some embodiments, the population of cells is transduced with a DNA molecule (e.g. one or more DNA molecules) encoding a CAR (e.g. one or more CARs).

In some embodiments, contacting the population of cells with the nucleic acid molecule encoding the CAR(s) occurs simultaneously with contacting the population of cells with the one or more cytokines described above. In some embodiments, contacting the population of cells with the nucleic acid molecule encoding the CAR(s) occurs no later than 1, 1.5, 2, 2.5, 3, 3.5, 4, 4.5, 5, 5.5, 6, 6.5, 7, 7.5, 8, 8.5, 9, 9.5 or 10 hours after the beginning of contacting the population of cells with the one or more cytokines described above. In some embodiments, contacting the population of cells with the nucleic acid molecule encoding the CAR(s) occurs no later than 5 hours after the beginning of contacting the population of cells with the one or more cytokines described above. In some embodiments, contacting the population of cells with the nucleic acid molecule encoding the CAR(s)

occurs no later than 4 hours after the beginning of contacting the population of cells with the one or more cytokines described above. In some embodiments, contacting the population of cells with the nucleic acid molecule encoding the CAR(s) occurs no later than 3 hours after the beginning of contacting the population of cells with the one or more cytokines described above. In some embodiments, contacting the population of cells with the nucleic acid molecule encoding the CAR(s) occurs no later than 2 hours after the beginning of contacting the population of cells with the one or more cytokines described above. In some embodiments, contacting the population of cells with the nucleic acid molecule encoding the CAR(s) occurs no later than 1 hour after the beginning of contacting the population of cells with the one or more cytokines described above.

In some embodiments, the population of cells is harvested for storage or administration. In some embodiments, the population of cells is harvested for storage or administration no later than 72, 60, 48, 36, 32, 31, 30, 29, 28, 27, 26, 25, 24, 23, 22, 21, 20, 19, or 18 hours after the beginning of contacting the population of cells with the one or more cytokines described above. In some embodiments, the population of cells is harvested for storage or administration no later than 26 hours after the beginning of contacting the population of cells with the one or more cytokines described above. In some embodiments, the population of cells is harvested for storage or administration no later than 25 hours after the beginning of contacting the population of cells with the one or more cytokines described above. In some embodiments, the population of cells is harvested for storage or administration no later than 24 hours after the beginning of contacting the population of cells with the one or more cytokines described above. In some embodiments, the population of cells is harvested for storage or administration no later than 23 hours after the beginning of contacting the population of cells with the one or more cytokines described above. In some embodiments, the population of cells is harvested for storage or administration no later than 22 hours after the beginning of contacting the population of cells with the one or more cytokines described above.

In some embodiments, the population of cells is not expanded ex vivo.

In some embodiments, the population of cells is expanded by no more than 5, 6, 7, 8, 9, 10, 11, 12, 13, 14, 15, 16, 17, 18, 19, 20, 25, 30, 35, 40, 45, 50, 55, or 60%, for example, as assessed by the number of living cells, compared to the population of cells before it is contacted with the one or more cytokines described above. In some embodiments, the population of cells is expanded by no more than 5%, for example, as assessed by the number of living cells, compared to the population of cells before it is contacted with the one or more cytokines described above. In some embodiments, the population of cells is expanded by no more than 10%, for example, as assessed by the number of living cells, compared to the population of cells before it is contacted with the one or more cytokines described above. In some embodiments, the population of cells is expanded by no more than 15%, for example, as assessed by the number of living cells, compared to the population of cells before it is contacted with the one or more cytokines described above. In some embodiments, the population of cells is expanded by no more than 20%, for example, as assessed by the number of living cells, compared to the population of cells before it is contacted with the one or more cytokines described above. In some embodiments, the population of cells is expanded by no more than 25%, for example, as assessed by the number of living cells, compared to the population of cells before it is contacted with the one or more cytokines described above. In some embodiments, the population of cells is expanded by no more than 30%, for example, as assessed by the number of living cells, compared to the population of cells before it is contacted with the one or more cytokines described above. In some embodiments, the population of cells is expanded by no more than 35%, for example, as assessed by the number of living cells, compared to the population of cells before it is contacted with the one or more cytokines described above. In some embodiments, the population of cells is expanded by no more than 40%, for example, as assessed by the number of living cells, compared to the population of cells before it is contacted with the one or more cytokines described above.

In some embodiments, the population of cells is expanded by no more than 1, 1.5, 2, 2.5, 3, 3.5, 4, 4.5, 5, 6, 7, 8, 9, 10, 11, 12, 16, 20, 24, 36, or 48 hours, for example, as assessed by the number of living cells, compared to the population of cells before it is contacted with the one or more cytokines described above.

In some embodiments, the population of cells is not contacted in vitro with an agent that stimulates a CD3/TCR complex (for example, an anti-CD3 antibody) and/or an agent that stimulates a costimulatory molecule on the surface of the cells (for example, an anti-CD28 antibody), or if contacted, the contacting step is less than 1, 1.5, 2, 2.5, 3, 3.5, 4, 4.5, or 5 hours. In some embodiments, the population of cells is contacted in vitro with an agent that stimulates a CD3/TCR complex (for example, an anti-CD3 antibody) and/or an agent that stimulates a costimulatory molecule on the surface of the cells (for example, an anti-CD28 antibody) for 20, 21, 22, 23, 24, 25, 26, 27, or 28 hours.

In some embodiments, the population of cells manufactured using the cytokine process provided herein shows a higher percentage of naïve cells among CAR-expressing cells (for example, at least 5, 6, 7, 8, 9, 10, 11, 12, 13, 14, 15, 16, 17, 18, 19, 20, 25, 30, 35, 40, 45, 50, 55, or 60% higher), compared with cells made by an otherwise similar method which further comprises contacting the population of cells with, for example, an agent that binds a CD3/TCR complex (for example, an anti-CD3 antibody) and/or an agent that binds a costimulatory molecule on the surface of the cells (for example, an anti-CD28 antibody).

In some embodiments, the cytokine process provided herein is conducted in cell media comprising no more than 0, 0.5, 1, 1.5, 2, 2.5, 3, 3.5, 4, 4.5, 5, 5.5, 6, 6.5, 7, 7.5, or 8% serum. In some embodiments, the cytokine process provided herein is conducted in cell media comprising a LSD1 inhibitor, a MALT1 inhibitor, or a combination thereof.

Additional Exemplary Manufacturing Methods

In some embodiments, cells, e.g., T cells or NK cells are activated, e.g., using anti-CD3/anti-CD28 antibody coated Dynabeads®, contacted with one or more nucleic acid molecules encoding a CAR (e.g. one or more CARs) and then expanded in vitro for, for example, 7, 8, 9, 10, or 11 days. In some embodiments, the cells, e.g., T cells or NK cells are selected from a fresh or cryopreserved leukapheresis sample, e.g., using positive or negative selection. In some embodiments, the cells are contacted with a nucleic acid molecule (e.g. one or more nucleic acid molecules) encoding a CAR (e.g. one or more CARs). In some embodiments, the cells are contacted with a nucleic acid molecule encoding a tandem or dual CAR disclosed herein (e.g., a CD19/CD22 tandem or dual CAR). In some embodiments, the cells are contacted with two nucleic acid molecules, one expressing a first CAR (e.g., an anti-CD22 CAR) and the other expressing a second CAR (e.g., an anti-CD19 CAR). In some embodiments, the cells are contacted with a nucleic acid molecule encoding a diabody CAR (e.g., an anti-CD22/anti-CD19 diabody CAR disclosed herein).

Elutriation

In some embodiments, the methods described herein feature an elutriation method that removes unwanted cells, for example, monocytes and blasts, thereby resulting in an improved enrichment of desired immune effector cells suitable for CAR expression. In some embodiments, the elutriation method described herein is optimized for the enrichment of desired immune effector cells suitable for CAR expression from a previously frozen sample, for example, a thawed sample. In some embodiments, the elutriation method described herein provides a preparation of cells with improved purity as compared to a preparation of cells collected from the elutriation protocols known in the art. In some embodiments, the elutriation method described herein includes using an optimized viscosity of the starting sample, for example, cell sample, for example, thawed cell sample, by dilution with certain isotonic solutions (for example, PBS), and using an optimized combination of flow rates and collection volume for each fraction collected by an elutriation device. Exemplary elutriation methods that could be applied in the present invention are described on pages 48-51 of WO 2017/117112, herein incorporated by reference in its entirety.

Density Gradient Centrifugation

Manufacturing of adoptive cell therapeutic product requires processing the desired cells, for example, immune effector cells, away from a complex mixture of blood cells and blood elements present in peripheral blood apheresis starting materials. Peripheral blood-derived lymphocyte samples have been successfully isolated using density gradient centrifugation through Ficoll solution. However, Ficoll is not a preferred reagent for isolating cells for therapeutic use, as Ficoll is not qualified for clinical use. In addition, Ficoll contains glycol, which has toxic potential to the cells. Furthermore, Ficoll density gradient centrifugation of thawed apheresis products after cryopreservation yields a suboptimal T cell product, for example, as described in the Examples herein. For example, a loss of T cells in the final product, with a relative gain of non-T cells, especially undesirable B cells, blast cells and monocytes was observed in cell preparations isolated by density gradient centrifugation through Ficoll solution.

Without wishing to be bound by theory, it is believed that immune effector cells, for example, T cells, dehydrate during cryopreservation to become denser than fresh cells. Without wishing to be bound by theory, it is also believed that immune effector cells, for example, T cells, remain denser longer than the other blood cells, and thus are more readily lost during Ficoll density gradient separation as compared to other cells. Accordingly, without wishing to be bound by theory, a medium with a density greater than Ficoll is believed to provide improved isolation of desired immune effector cells in comparison to Ficoll or other mediums with the same density as Ficoll, for example, 1.077 g/mL.

In some embodiments, the density gradient centrifugation method described herein includes the use of a density gradient medium comprising iodixanol. In some embodiments, the density gradient medium comprises about 60% iodixanol in water.

In some embodiments, the density gradient centrifugation method described herein includes the use of a density gradient medium having a density greater than Ficoll. In some embodiments, the density gradient centrifugation method described herein includes the use of a density gradient medium having a density greater than 1.077 g/mL, for example, greater than 1.077 g/mL, greater than 1.1 g/mL, greater than 1.15 g/mL, greater than 1.2 g/mL, greater than 1.25 g/mL, greater than 1.3 g/mL, greater than 1.31 g/mL. In some embodiments, the density gradient medium has a density of about 1.32 g/mL.

Additional embodiments of density gradient centrifugation are described on pages 51-53 of WO 2017/117112, herein incorporated by reference in its entirety.

Enrichment by Selection

Provided herein are methods for selection of specific cells to improve the enrichment of the desired immune effector cells suitable for CAR expression. In some embodiments, the selection comprises a positive selection, for example, selection for the desired immune effector cells. In some embodiments, the selection comprises a negative selection, for example, selection for unwanted cells, for example, removal of unwanted cells. In embodiments, the positive or negative selection methods described herein are performed under flow conditions, for example, by using a flow-through device, for example, a flow-through device described herein. Exemplary positive and negative selections are described on pages 53-57 of WO 2017/117112, herein incorporated by reference in its entirety. Selection methods can be performed under flow conditions, for example, by using a flow-through device, also referred to as a cell processing system, to further enrich a preparation of cells for desired immune effector cells, for example, T cells, suitable for CAR expression. Exemplary flow-through devices are described on pages 57-70 of WO 2017/117112, herein incorporated by reference in its entirety. Exemplary cell separation and debeading methods are described on pages 70-78 of WO 2017/117112, herein incorporated by reference in its entirety.

Selection procedures are not limited to ones described on pages 57-70 of WO 2017/117112. Negative T cell selection via removal of unwanted cells with CD19, CD14 and CD26 Miltenyi beads in combination with column technology (CliniMACS® Plus or CliniMACS® Prodigy®) or positive T cell selection with a combination of CD4 and CD8 Miltenyi beads and column technology (CliniMACS® Plus or CliniMACS® Prodigy®) can be used. Alternatively, column-free technology with releasable CD3 beads (GE Healthcare) can be used.

In addition, bead-free technologies such as ThermoGenesis X-series devices can be utilized as well.

Methods of making a cell disclosed herein include those known in the art, e.g., as described in CN 108103105, CN 108085342, CN 108018312, CN 107287164, WO 18052947, WO 17123956, WO 17114497, WO 17103596, WO 17068421, WO 17023803, WO 17015427, WO 16196388, WO 16168595, WO 14186469, WO 17165245, WO 18106732, WO 17015490, WO 18075813, WO 18102761, WO 17127755, WO 17214333, WO 18059549, WO 17190100, WO 16180778, WO 18057823, and/or CN 106957822, each one of which is hereby incorporated by reference in its entirety.

Sources of Cells

Prior to expansion and genetic modification or other modification, a source of cells, e.g., T cells or natural killer (NK) cells, can be obtained from a subject. The term "subject" is intended to include living organisms in which an immune response can be elicited (e.g., mammals). Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present invention disclosure, immune effector cells, e.g., T cells, can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one aspect, T cells are isolated from peripheral blood lymphocytes by lysing the red blood cells and depleting the monocytes, for example, by centrifugation through a PERCOLL™ gradient or by counterflow centrifugal elutriation.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-C25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Militenyi™. In one embodiment, the ratio of cells to CD25 depletion reagent is 1 e7 cells to 20 uL, or 1 e7 cells to 15 uL, or 1 e7 cells to 10 uL, or 1 e7 cells to 5 uL, or 1 e7 cells to 2.5 uL, or 1 e7 cells to 1.25 uL.

In one embodiment, the population of immune effector cells to be depleted includes about $6 \times 10^9$ CD25+ T cells. In other aspects, the population of immune effector cells to be depleted include about $1 \times 10^9$ to $1 \times 10^{10}$ CD25+ T cell, and any integer value in between. In one embodiment, the resulting population T regulatory depleted cells has $2 \times 10^9$ T regulatory cells, e.g., CD25+ cells, or less (e.g., $1 \times 10^9$, $5 \times 10^8$, $1 \times 10^8$, $5 \times 10^7$, $1 \times 10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include B7-H1, B&-1, CD160, P1H, 2B4, PD1, TIM3, CEACAM (e.g., CEACAM-1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-C25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In some embodiments, the removal of T regulatory cells, e.g., CD25+ cells, and the removal of the check point inhibitor expressing cells is sequential, and can occur, e.g., in either order.

Methods described herein can include a positive selection step. For example, T cells can be isolated by incubation with anti-CD3/anti-CD28 (e.g., 3×28)-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of about 10 billion cells/ml, 9 billion/ml, 8 billion/ml, 7 billion/ml, 6 billion/ml, or 5 billion/ml is used. In one aspect, a concentration of 1 billion cells/ml is used. In one aspect, a concentration of cells from 75, 80, 85, 90, 95, or 100 million cells/ml is used. In further aspects, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5 \times 10^6$/ml. In other aspects, the concentration used can be from about $1 \times 10^5$/ml to $1 \times 10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells or NK cells, to be engineered to express a CAR, are harvested after a sufficient time, or after sufficient dosing of the low, immune enhancing, dose of an mTOR inhibitor, such that the level of PD1 negative immune effector cells, e.g., T cells or NK cells, or the ratio of PD1 negative immune effector cells, e.g., T cells/NK cells/PD1 positive immune effector cells, e.g., T cells or NK cells, in the subject or harvested from the subject has been, at least transiently, increased.

In some embodiments, population of immune effector cells, e.g., T cells or NK cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/NK cells/PD1 positive immune effector cells, e.g., T cells or NK cells.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Allogenic CART

In embodiments described herein, the immune effector cell can be an allogenic immune effector cell, e.g., T cell or NK cell. For example, the cell can be an allogenic T cell, e.g., an allogenic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host. Such cells can be created through the use of one or more gene editing systems as described herein. In embodiments, the gene editing system targets a sequence encoding a component of the TCR, for example a sequence in the TCR alpha constant chain gene (TRAC) or its regulatory elements. In embodiments, the gene editing system targets a sequence encoding a component of the TCR, for example a sequence in the TCR beta constant chain gene (TRBC) or its regulatory elements.

A T cell described herein can be, e.g., engineered such that it does not express a functional HLA on its surface. For example, a T cell described herein, can be engineered such that cell surface expression HLA, e.g., HLA class 1 and/or HLA class II, is downregulated. Such cells can be created through the use of one or more gene editing systems as described herein. In embodiments, the gene editing system targets a sequence encoding a component of one or more HLA molecules. In embodiments, the gene editing system targets a sequence encoding a factor which affects the expression of one or more HLA molecules. In embodiments, the gene editing system targets a regulator of MHC class I expression, for example a sequence encoding beta-2 microglobulin (B2M). In embodiments, the gene editing system targets a sequence encoding a regulator of MHC class II molecule expression, for example, CIITA. In embodiments, gene editing systems targeting both a regulator of MHC class I expression (for example, B2M) and a regulator of MHC class II molecule expression (e.g., CIITA) are introduced into the cells, such that at least MHC class I molecule and at least one MHC class II molecule expression is downregulated.

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not express or expresses at low levels an inhibitory molecule, e.g. by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGF beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit, e.g., TCR or HLA

In some embodiments, TCR expression and/or HLA expression can be inhibited using siRNA or shRNA that targets a nucleic acid encoding a TCR and/or HLA in a T cell.

Expression of siRNA and shRNAs in T cells can be achieved using any conventional expression system, e.g., such as a lentiviral expression system.

Exemplary shRNAs that downregulate expression of components of the TCR are described, e.g., in US Publication No.: 2012/0321667. Exemplary siRNA and shRNA that downregulate expression of HLA class I and/or HLA class II genes are described, e.g., in U.S. publication No.: US 2007/0036773.

CRISPR to Inhibit, e.g., TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene.

Naturally-occurring CRISPR/Cas systems are found in approximately 40% of sequenced eubacteria genomes and 90% of sequenced archaca. Grissa et al. (2007) BMC Bioinformatics 8:172. This system is a type of prokaryotic immune system that confers resistance to foreign genetic elements such as plasmids and phages and provides a form of acquired immunity. Barrangou et al. (2007) *Science* 315:1709-1712; Marragini et al. (2008) *Science* 322:1843-1845.

The CRISPR/Cas system has been modified for use in gene editing (silencing, enhancing or changing specific genes) in eukaryotes such as mice or primates. Wiedenheft et al. (2012) *Nature* 482:331-8. This is accomplished by introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) *Science* 327:167-170; Makarova et al. (2006) *Biology Direct* 1:7. The spacers thus serve as templates for RNA molecules, analogously to siRNAs. Pennisi (2013) *Science* 341:833-836. As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J. Mol. Evol.* 60:174-182; Bolotin et al. (2005) *Microbiol.* 151:2551-2561; Pourcel et al. (2005) *Microbiol.* 151:653-663; and Stern et al. (2010) *Trends. Genet.* 28:335-340. For example, the Cse (Cas subtype, *E. coli*) proteins (e.g., CasA) form a functional complex, Cascade, that processes CRISPR RNA transcripts into spacer-repeat units that Cascade retains. Brouns et al. (2008) *Science* 321:960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in *Pyrococcus furiosus* and other prokaryotes form a functional complex with small CRISPR RNAs that recognizes and cleaves complementarity target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) *Science* 341:833-836.

The CRISPR/Cas system can thus be used to edit a TCR and/or HLA gene (adding or deleting one or more base pairs), or introducing a premature stop which thus decreases expression of a target gene or chromosomal sequence such as a TCR and/or HLA. The CRISPR/Cas system can alternatively be used like RNA interference, turning off TCR and/or HLA gene in a reversible fashion. In a mammalian cell, for example, the RNA can guide the Cas protein, e.g., a Cas protein lacking nuclease activity (e.g., dCas9), to a TCR and/or HLA promoter, sterically blocking RNA polymerases.

Artificial CRISPR/Cas systems can be generated which inhibit, for example, TCR and/or HLA, using technology known in the art, e.g., that described in U.S. Publication No. 20140068797. CRISPR systems which may be useful in the inventions described herein include those described in, for example, PCT application publication WO2017/093969, the contents of which are incorporated herein by reference in their entirety.

TALEN to Inhibit, e.g., TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene.

TALENs are produced artificially by fusing a TAL effector DNA binding domain to a DNA cleavage domain. Transcription activator-like effects (TALEs) can be engineered to bind any desired DNA sequence, including a portion of the HLA or TCR gene. By combining an engineered TALE with a DNA cleavage domain, a restriction enzyme can be produced which is specific to any desired DNA sequence, including a HLA or TCR sequence. These can then be introduced into a cell, wherein they can be used for genome editing. Boch (2011) *Nature Biotech.* 29:135-6; and Boch et al. (2009) *Science* 326:1509-12; Moscou et al. (2009) *Science* 326:3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. (2011) *Nucl. Acids Res.* 39: e82; Miller et al. (2011) *Nature Biotech.* 29:143-8; Hockemeyer et al. (2011) *Nature Biotech.* 29:731-734; Wood et al. (2011) *Science* 333:307; Doyon et al. (2010) *Nature Methods* 8:74-79; Szczepek et al. (2007) *Nature Biotech.* 25:786-793; and Guo et al. (2010) *J. Mol. Biol.* 200:96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) *Nature Biotech.* 29:143-8.

A HLA or TCR TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the HLA or TCR gene or introduce such a defect into a wt HLA or TCR gene, thus decreasing expression of HLA or TCR.

TALENs specific to sequences in HLA or TCR can be constructed using any method known in the art, including various schemes using modular components. Zhang et al. (2011) *Nature Biotech.* 29:149-53; Geibler et al. (2011) *PLoS ONE* 6: e19509.

Zinc Finger Nuclease to Inhibit, e.g., HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene.

Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) *Genetics Society of America* 188:773-782; and Kim et al. (1996) *Proc. Natl. Acad. Sci. USA* 93:1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) *Proc. Natl. Acad. Sci. USA* 95:10570-5.

Also like a TALEN, a ZFN can create a double-stranded break in the DNA, which can create a frame-shift mutation if improperly repaired, leading to a decrease in the expression and amount of HLA and/or TCR in a cell. ZFNs can also be used with homologous recombination to mutate in the HLA or TCR gene.

ZFNs specific to sequences in HLA AND/OR TCR can be constructed using any method known in the art. Cathomen et al. (2008) *Mol. Ther.* 16:1200-7; and Guo et al. (2010) *J. Mol. Biol.* 400:96.

Activation and Expansion of Immune Effector Cells (e.g., T Cells)

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, invention population of immune effector cells may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30 (8): 3975-3977, 1998; Haanen et al., J. Exp. Med. 190 (9): 13191328, 1999; Garland et al., J. Immunol Meth. 227 (1-2): 53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. patent application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle:cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects of the present invention, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, 104 to 109 T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 10 billion cells/ml, 9 billion/ml, 8 billion/ml, 7 billion/ml, 6 billion/ml, or 5 billion/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a cell comprising, e.g., expressing, a dual CAR or a tandem CAR described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a CD19 CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells comprising, e.g., expressing, a dual CAR or a tandem CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells comprising, e.g., expressing, a dual CAR or a tandem CAR described herein, are expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

In one aspect of the present invention, the mixture may be cultured for several hours (about 3 hours) to about 14 days or any hourly integer value in between. In one aspect, the mixture may be cultured for 21 days. In one aspect of the invention the beads and the T cells are cultured together for about eight days. In one aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence IL-15 and/or IL-7 (e.g., IL-15 and IL-7).

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a CAR, e.g., a dual CAR or a tandem CAR, is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a CAR, e.g., a dual CAR or a tandem CAR, are described in further detail below.

Western blot analysis of CAR expression in primary T cells can be used to detect the presence of monomers and dimers. Sec, e.g., Milone et al., Molecular Therapy 17 (8): 1453-1464 (2009). Very briefly, T cells (1:1 mixture of CD4+ and CD8+ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of CAR+ T cells following antigen stimulation can be measured by flow cytometry. For example, a mixture of CD4+ and CD8+ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the CD4+ and/or CD8+ T cell subsets by flow cytometry. See, e.g., Milone et al., Molecular Therapy 17 (8): 1453-1464 (2009). Alternatively, a mixture of CD4+ and CD8+ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either CD19+ K562 cells (K562-CD19), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/ml. GFP+ T cells are enumerated by flow cytometry using bead-based counting. See, e.g., Milone et al., Molecular Therapy 17 (8): 1453-1464 (2009). Similar assays can be performed using anti-CD20 T cells (see, e.g. Gill et al Blood 2014; 123:2343) or with anti-CD20 CAR T cells.

Sustained CAR+ T cell expansion in the absence of re-stimulation can also be measured. See, e.g., Milone et al., Molecular Therapy 17 (8): 1453-1464 (2009). Briefly, mean T cell volume (fl) is measured on day 8 of culture using a Coulter Multisizer III particle counter, a Nexcelom Cellometer Vision, or Millipore Scepter following stimulation with αCD3/αCD28 coated magnetic beads on day 0, and transduction with the indicated CAR on day 1.

Animal models can also be used to measure a CART activity. For example, xenograft model using human CD19-specific CAR+ T cells to treat a primary human pre-B ALL in immunodeficient mice can be used. Sec, e.g., Milone et al., Molecular Therapy 17 (8): 1453-1464 (2009). Very briefly, after establishment of ALL, mice are randomized as to treatment groups. Different numbers of αCD19-ζ and αCD19-BB-ζ engineered T cells are coinjected at a 1:1 ratio into NOD-SCID-γ$^{-/-}$ mice bearing B-ALL. The number of copies of αCD19-ζ and αCD19-BB-ζ vector in spleen DNA from mice is evaluated at various times following T cell injection. Animals are assessed for leukemia at weekly intervals. Peripheral blood CD19+ B-ALL blast cell counts are measured in mice that are injected with αCD19-ζ CAR+ T cells or mock-transduced T cells. Survival curves for the groups are compared using the log-rank test. In addition, absolute peripheral blood CD4+ and CD8+ T cell counts 4 weeks following T cell injection in NOD-SCID-γ$^{-/-}$ mice can also be analyzed. Mice are injected with leukemic cells and 3 weeks later are injected with T cells engineered to express CAR by a bicistronic lentiviral vector that encodes the CAR linked to eGFP. T cells are normalized to 45-50% input GFP+ T cells by mixing with mock-transduced cells prior to injection, and confirmed by flow cytometry. Animals are assessed for leukemia at 1-week intervals. Survival curves for the CAR+ T cell groups are compared using the log-rank test. Similar experiments can be done with dual CARTs or tandem CARTs.

Dose dependent CAR treatment response can be evaluated. See, e.g., Milone et al., Molecular Therapy 17 (8): 1453-1464 (2009). For example, peripheral blood is obtained 35-70 days after establishing leukemia in mice injected on day 21 with CAR T cells, an equivalent number of mock-transduced T cells, or no T cells. Mice from each group are randomly bled for determination of peripheral blood CD19+ ALL blast counts and then killed on days 35 and 49. The remaining animals are evaluated on days 57 and 70. Similar experiments can be done with dual CARTs or tandem CARTs.

Assessment of cell proliferation and cytokine production has been previously described, e.g., at Milone et al., Molecular Therapy 17 (8): 1453-1464 (2009). Briefly, assessment of CAR-mediated proliferation is performed in microtiter plates by mixing washed T cells with K562 cells expressing CD19 (K19) or CD32 and CD137 (KT32-BBL) for a final T-cell:K562 ratio of 2:1. K562 cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8+ T cell expansion ex vivo. T cells are enumerated in cultures using CountBright™ fluorescent beads (Invitrogen, Carlsbad, CA) and flow cytometry as described by the manufacturer. CAR$^+$ T cells are identified by GFP expression using T cells that are engineered with eGFP-2A linked CAR-expressing lentiviral vectors. For CAR$^+$ T cells not expressing GFP, the CAR$^+$ T cells are detected with biotinylated recombinant CD19 protein and a secondary avidin-PE conjugate. CD4+ and CD8$^+$ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, CA) according the manufacturer's instructions or using a Luminex 30-plex kit (Invitrogen). Fluorescence is assessed using a BD Fortessa flow cytometer, and data is analyzed according to the manufacturer's instructions. Similar experiments can be done with dual CARTs or tandem CARTs.

Cytotoxicity can be assessed by a standard 51Cr-release assay. See, e.g., Milone et al., Molecular Therapy 17 (8): 1453-1464 (2009). Briefly, target cells (K562 lines and primary pro-B-ALL cells) are loaded with 51Cr (as NaCrO4, New England Nuclear, Boston, MA) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released 51Cr is then measured using a gamma particle counter (Packard Instrument Co., Waltham, MA). Each condition is performed in at least triplicate, and the percentage of lysis is calculated using the formula: % Lysis=(ER−SR)/(TR−SR), where ER represents the average 51Cr released for each experimental condition.

Imaging technologies can be used to evaluate specific trafficking and proliferation of CARs in tumor-bearing animal models. Such assays have been described, for example, in Barrett et al., Human Gene Therapy 22:1575-1586 (2011). Briefly, NOD/SCID/γc$^{−/−}$ (NSG) mice are injected IV with Nalm-6 cells followed 7 days later with T cells 4 hour after electroporation with the CAR constructs. The T cells are stably transfected with a lentiviral construct to express firefly luciferase, and mice are imaged for bioluminescence. Alternatively, therapeutic efficacy and specificity of a single injection of CAR$^+$ T cells in Nalm-6 xenograft model can be measured as the following: NSG mice are injected with Nalm-6 transduced to stably express firefly luciferase, followed by a single tail-vein injection of T cells electroporated with a CAR 7 days later. Animals are imaged at various time points post injection. For example, photon-density heat maps of firefly luciferase positive leukemia in representative mice at day 5 (2 days before treatment) and day 8 (24 hr post CAR$^+$ PBLs) can be generated.

Other assays, including those described in the Example section herein as well as those that are known in the art can also be used to evaluate the dual CART or tandem CART constructs disclosed herein.

Therapeutic Application

The present invention provides, among other things, compositions and methods for treating a cancer or a disease associated with expression of CD19 and/or CD22 or condition associated with cells which express CD19 and/or CD22. In some embodiments, the cancer or disease includes, e.g., a proliferative disease such as a cancer or malignancy or a precancerous condition such as a myelodysplasia, a myelodysplastic syndrome or a preleukemia; or a noncancer related indication associated with cells which express CD19 and/or CD22. In one aspect, a cancer or disease associated with expression of CD22 is a hematological cancer. In one aspect, a hematological cancer includes but is not limited to a B-cell malignancy. In one aspect, the hematological cancer is a leukemia or a lymphoma. In one aspect, a cancer, e.g., a cancer associated with expression of CD19 and/or CD22, includes cancers and malignancies including, but not limited to, e.g., one or more acute leukemias including but not limited to B-cell acute lymphoblastic leukemia (BALL), e.g., pediatric BALL and/or adult BALL, T-cell acute lymphoid leukemia (TALL), small lymphocytic leukemia (SLL), acute lymphoblastic leukemia (ALL); one or more chronic leukemias including but not limited to chronic myelogenous leukemia (CML), chronic lymphocytic leukemia (CLL); additional hematologic cancers or hematologic conditions including, but not limited to mantle cell lymphoma (MCL), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, Marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and "preleukemia" (which is a diverse collection of hematological conditions united by ineffective production (or dysplasia) of myeloid blood cells). In some embodiments, to the disease associated with CD19 and/or CD22 expression includes, but not limited to, atypical and/or non-classical cancers, malignancies, precancerous conditions or proliferative diseases expressing CD19 and/or CD22, and any combination thereof.

Non-cancer related indications associated with expression of CD22 may also be included. Non-cancer related indications associated with expression of CD22 include, but are not limited to, e.g., autoimmune disease, (e.g., lupus, rheumatoid arthritis, multiple sclerosis autoimmune hemolytic anemia, pure red cell aplasia, idiopathic thrombocytopeniaurpura, Evans syndrome, vasculitis, bullous skin disorders, type 1 diabetes mellitus, Sjogren's syndrome, anti-NMDA receptor encephalitis and Devic's disease, Graves' ophthalmopathy, and autoimmune pancreatitis), inflammatory disorders (allergy and asthma) and transplantation.

In one aspect, the invention provides methods for treating a disease associated with CD19 and/or CD22 expression. In one aspect, the invention provides methods for treating a disease wherein part of the tumor is negative for CD19 and/or CD22 and part of the tumor is positive for CD19 and/or CD22. For example, the CAR of the invention is useful for treating subjects that have undergone treatment for a disease associated with expression of CD19 and/or CD22, wherein the subject that has undergone treatment related to expression of CD19 and/or CD22 exhibits a disease associated with expression of CD19 and/or CD22.

In one aspect, the invention pertains to a vector comprising CAR as described herein operably linked to promoter for expression in mammalian T cells or NK cells. In one aspect, the invention provides a recombinant T cell expressing the CAR for use in treating CD19 and/or CD22-expressing tumors, wherein the recombinant T cell expressing the CD19 CAR and CD22 CAR is termed a dual CART. In one aspect, the invention provides a recombinant T cell expressing the CAR for use in treating CD19 and/or CD22-expressing tumors, wherein the recombinant T cell expressing the CD19 antigen binding domain and CD22 antigen binding domain is termed a tandem CART. In one aspect, dual CART or tandem CART of the invention is capable of contacting a tumor cell with at least one CD19 CAR or CD22 CAR of the invention expressed on its surface such that the CART targets the tumor cell and growth of the tumor is inhibited.

In one aspect, the invention pertains to a method of inhibiting growth of a CD19 and/or CD22-expressing tumor cell, comprising contacting the tumor cell with a CAR-expressing cell, e.g., a dual CAR or tandem CAR-expressing, NK cell of the present invention such that the CAR-expressing cell is activated in response to the antigen and targets the cancer cell, wherein the growth of the tumor is inhibited.

In one aspect, the invention pertains to a method of treating cancer in a subject. The method comprises administering to the subject a CAR-expressing cell, e.g., a dual CAR or tandem CAR-expressing cell of the present invention such that the cancer is treated in the subject. An example of a cancer that is treatable by the CAR-expressing cell, e.g., dual CAR or tandem CAR-expressing cell of the invention is a cancer associated with expression of CD22. An example of a cancer that is treatable by the CAR-expressing cell, e.g., dual CAR or tandem CAR-expressing cell of the invention includes but is not limited to a hematological cancer described herein. The invention includes a type of cellular therapy where cells are genetically modified to express a chimeric antigen receptor (CAR) and the CAR-expressing cell is infused to a recipient in need thereof. The infused cell is able to kill tumor cells in the recipient. Unlike antibody therapies, CAR-modified cells are able to replicate in vivo resulting in long-term persistence that can lead to sustained tumor control. In various aspects, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the cell to the patient.

The invention also includes a type of cellular therapy where immune effector cells, e.g., NK cells or T cells are modified, e.g., by in vitro transcribed RNA, to transiently express a chimeric antigen receptor (CAR) and the CAR-expressing (e.g., CART or CAR-expressing NK) cell is infused to a recipient in need thereof. The infused cell is able to kill cancer cells in the recipient. Thus, in various aspects, the CAR-expressing cells, e.g., T or NK cells, administered to the patient, is present for less than one month, e.g., three weeks, two weeks, one week, after administration of the CAR-expressing cell, e.g., T or NK cell, to the patient.

In one aspect, the CAR-modified cells of the invention, e.g., fully human CAR-expressing cells, may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified cells of the invention are used in the treatment of diseases, disorders and conditions associated with expression of CD22 and/or CD19. In certain aspects, the cells of the invention are used in the treatment of patients at risk for developing diseases, disorders and conditions associated with expression of CD22 and/or CD19. Thus, the present invention provides methods for the treatment or prevention of diseases, disorders and conditions associated with expression of CD22 and/or CD19 comprising administering to a subject in need thereof, a therapeutically effective amount of the CAR-modified cells of the invention.

In one aspect the CAR-expressing cells of the inventions may be used to treat a proliferative disease such as a cancer or malignancy or is a precancerous condition such as a myelodysplasia, a myelodysplastic syndrome or a preleukemia. In one aspect, a cancer associated with expression of CD22 and/or CD19 is a hematological cancer preleukemia, hyperproliferative disorder, hyperplasia or a dysplasia, which is characterized by abnormal growth of cells.

In one aspect, the CAR-expressing cells of the invention are used to treat a cancer, wherein the cancer is a hematological cancer. Hematological cancer conditions are the types of cancer such as leukemia and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoblastic leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

Lymphoma is a group of blood cell tumors that develop from lymphocytes. Exemplary lymphomas include non-Hodgkin lymphoma and Hodgkin lymphoma.

In one aspect, the compositions and CAR-expressing cells of the present invention are particularly useful for treating B cell malignancies, such as non-Hodgkin lymphomas, e.g., DLBCL, Follicular lymphoma, or CLL.

Non-Hodgkin lymphoma (NHL) is a group of cancers of lymphocytes, formed from either B or T cells. NHLs occur at any age and are often characterized by lymph nodes that are larger than normal, weight loss, and fever. Different types of NHLs are categorized as aggressive (fast-growing) and indolent (slow-growing) types. B-cell non-Hodgkin lymphomas include Burkitt lymphoma, chronic lymphocytic leukemia/small lymphocytic lymphoma (CLL/SLL), diffuse large B-cell lymphoma (DLBCL), follicular lymphoma, immunoblastic large cell lymphoma, precursor B-lymphoblastic lymphoma, and mantle cell lymphoma. Examples of T-cell non-Hodgkin lymphomas include mycosis fungoides, anaplastic large cell lymphoma, and precursor T-lymphoblastic lymphoma. Lymphomas that occur after bone marrow or stem cell transplantation are typically B-cell non-Hodgkin lymphomas. See, e.g., Maloney. NEJM. 366.21 (2012): 2008-16.

Diffuse large B-cell lymphoma (DLBCL) is a form of NHL that develops from B cells. DLBCL is an aggressive lymphoma that can arise in lymph nodes or outside of the lymphatic system, e.g., in the gastrointestinal tract, testes, thyroid, skin, breast, bone, or brain. Three variants of cellular morphology are commonly observed in DLBCL: centroblastic, immunoblastic, and anaplastic. Centroblastic morphology is most common and has the appearance of medium-to-large-sized lymphocytes with minimal cytoplasm. There are several subtypes of DLBCL. For example, primary central nervous system lymphoma is a type of DLBCL that only affects the brain is called and is treated differently than DLBCL that affects areas outside of the brain. Another type of DLBCL is primary mediastinal B-cell lymphoma, which often occurs in younger patients and grows rapidly in the chest. Symptoms of DLBCL include a painless rapid swelling in the neck, armpit, or groin, which is caused by enlarged lymph nodes. For some subjects, the swelling may be painful. Other symptoms of DLBCL include night sweats, unexplained fevers, and weight loss. Although most patients with DLBCL are adults, this disease sometimes occurs in children. Treatment for DLBCL includes chemotherapy (e.g., cyclophosphamide, doxorubicin, vincristine, prednisone, etoposide), antibodies (e.g., Rituxan), radiation, or stem cell transplants.

Follicular lymphoma a type of non-Hodgkin lymphoma and is a lymphoma of follicle center B-cells (centrocytes and centroblasts), which has at least a partially follicular pattern. Follicular lymphoma cells express the B-cell markers CD10, CD19, CD20, and CD22. Follicular lymphoma cells are commonly negative for CD5. Morphologically, a follicular lymphoma tumor is made up of follicles containing a mixture of centrocytes (also called cleaved follicle center cells or small cells) and centroblasts (also called large noncleaved follicle center cells or large cells). The follicles are surrounded by non-malignant cells, mostly T-cells. The follicles contain predominantly centrocytes with a minority of centroblasts. The World Health Organization (WHO) morphologically grades the disease as follows: grade 1 (<5 centroblasts per high-power field (hpf); grade 2 (6-15 centroblasts/hpf); grade 3 (>15 centroblasts/hpf). Grade 3 is further subdivided into the following grades: grade 3A (centrocytes still present); grade 3B (the follicles consist almost entirely of centroblasts). Treatment of follicular lymphoma includes chemotherapy, e.g., alkylating agents, nucleoside analogs, anthracycline-containing regimens, e.g., a combination therapy called CHOP-cyclophosphamide, doxorubicin, vincristine, prednisone/prednisolone, antibodies (e.g., rituximab), radioimmunotherapy, and hematopoietic stem cell transplantation.

CLL is a B-cell malignancy characterized by neoplastic cell proliferation and accumulation in bone morrow, blood, lymph nodes, and the spleen. The median age at time of diagnosis of CLL is about 65 years. Current treatments include chemotherapy, radiation therapy, biological therapy, or bone marrow transplantation. Sometimes symptoms are treated surgically (e.g., splenectomy removal of enlarged spleen) or by radiation therapy (e.g., de-bulking swollen lymph nodes). Chemotherapeutic agents to treat CLL include, e.g., fludarabine, 2-chlorodeoxyadenosine (cladribine), chlorambucil, vincristine, pentostatin, cyclophosphamide, alemtuzumab (Campath-1H), doxorubicin, and prednisone. Biological therapy for CLL includes antibodies, e.g., alemtuzumab, rituximab, and ofatumumab; as well as tyrosine kinase inhibitor therapies. A number of criteria can be used to classify stage of CLL, e.g., the Rai or Binet system. The Rai system describes CLL has having five stages: stage 0 where only lymphocytosis is present; stage I where lymphadenopathy is present; stage II where splenomegaly, lymphadenopathy, or both are present; stage III where anemia, organomegaly, or both are present (progression is defined by weight loss, fatigue, fever, massive organomegaly, and a rapidly increasing lymphocyte count); and stage IV where anemia, thrombocytopenia, organomegaly, or a combination thereof are present. Under the Binet staging system, there are three categories: stage A where lymphocytosis is present and less than three lymph nodes are enlarged (this stage is inclusive of all Rai stage 0 patients, one-half of Rai stage I patients, and one-third of Rai stage II patients); stage B where three or more lymph nodes are involved; and stage C wherein anemia or thrombocytopenia, or both are present. These classification systems can be combined with measurements of mutation of the immunoglobulin genes to provide a more accurate characterization of the state of the disease. The presence of mutated immunoglobulin genes correlates to improved prognosis.

In another embodiment, the CAR-expressing cells of the present invention are used to treat cancers or leukemias, e.g., with leukemia stem cells. For example, the leukemia stem cells are $CD34^+/CD38^-$ leukemia cells.

The present invention provides, among other things, compositions and methods for treating cancer. In one aspect, the cancer is a hematologic cancer including but is not limited to one or more acute leukemias including but not limited to B-cell acute lymphoblastic leukemia (BALL), e.g., pediatric BALL and/or adult BALL, T-cell acute lymphoid leukemia (TALL), small lymphocytic leukemia (SLL), acute lymphoblastic leukemia (ALL); one or more chronic leukemias including but not limited to chronic myelogenous leukemia (CML), chronic lymphocytic leukemia (CLL); additional hematologic cancers or hematologic conditions including, but not limited to mantle cell lymphoma (MCL), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, Marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and "preleukemia" which is a diverse collection of hematological conditions united by ineffective production (or dysplasia) of myeloid blood cells, and to disease associated with CD22 expression include, but not limited to atypical and/or non-classical cancers, malignancies, precancerous conditions or proliferative diseases expressing CD22; and any combination thereof.

The CAR-modified cells of the present invention may be administered either alone, or as a pharmaceutical composition in combination with diluents and/or with other components such as IL-2 or other cytokines or cell populations.

In another aspect, the CAR-expressing cell, e.g., dual CAR or tandem CAR-expressing cells, of the invention may be used for treatment of a subject previously treated with a CD19 CAR-expressing cell. In some embodiments, the CAR-expressing cell of the invention is administered post-relapse of a cancer or other condition previously treated with CD19 CAR-expressing cell.

In some embodiments, the cancer or other condition is CD19 expressing. In some embodiments, the cancer or other condition is CD22 expressing. In some embodiments, the cancer or other condition is CD19 and CD22 expressing.

In some embodiments, the cancer or other condition has not previously been responsive to CD19 CAR-expressing cell. In some embodiments, the subject cancer or other condition is responsive to treatment with CD19 CAR-expressing cell. In some embodiments, the cancer or other condition was more responsive to treatment with CD19 CAR-expressing cell than it is presently. In some embodiments, the cancer or other condition was responsive to treatment with CD19 CAR-expressing cell. In some embodiments, the cancer or other condition was responsive to treatment with CD19 CAR-expressing cell and is no longer responsive to CD19 CAR-expressing cell.

In some embodiments, the CAR, e.g., dual CAR or tandem CAR (e.g., as described herein) is administered due to a reduction or loss of responsiveness to CD19 CAR-expressing cell. In some embodiments, CD19 CAR-expressing cell therapy has been discontinued. In some embodiments, CD19 CAR therapy has been discontinued due to a reduction or loss of responsiveness to CD19 CAR-expressing cell.

In some embodiments, the CAR, e.g., dual CAR or tandem CAR (e.g., as described herein) is administered due to a reduction or loss of responsiveness to CD22 CAR-expressing cell. In some embodiments, CD22 CAR-expressing cell therapy has been discontinued. In some embodiments, CD22 CAR therapy has been discontinued due to a reduction or loss of responsiveness to CD22 CAR-expressing cell.

The present invention also provides methods for preventing, treating and/or managing a disease associated with CD22-expressing cells (e.g., a hematologic cancer or atypical cancer expressing CD22), the methods comprising administering to a subject in need a CD22 CAR-expressing cell of the invention that binds to the CD22-expressing cell. In one aspect, the subject is a human. Non-limiting examples of disorders associated with CD22-expressing cells include autoimmune diseases, (e.g., lupus, rheumatoid arthritis, multiple sclerosis autoimmune hemolytic anemia, pure red cell aplasia, idiopathic thrombocytopenia purpura, Evans syndrome, vasculitis, bullous skin disorders, type 1 diabetes mellitus, Sjogren's syndrome, anti-NMDA receptor encephalitis and Devic's disease, Graves' ophthalmopathy, and autoimmune pancreatitis), inflammatory disorders (allergy and asthma), transplantation, and cancers (such as hematological cancers or atypical cancers expressing CD22).

The present invention also provides methods for preventing, treating and/or managing a disease associated with CD22-expressing cells, the methods comprising administering to a subject in need of a dual CAR or a tandem CAR-expressing cell of the invention that binds to the CD22-expressing cell. In one aspect, the subject is a human.

In some embodiments, the subject is a non-responder to CD19 CAR therapy. In some embodiments, the subject is a partial responder to CD19 CAR therapy. In some embodiments, the subject is a complete responder to CD19 CAR therapy. In some embodiments, the subject is a non-relapser to CD19 CAR therapy. In some embodiments, the subject is a relapser to CD19 CAR therapy.

In some embodiments, a cancer or other condition that was previously responsive to treatment with CD19 CAR-expressing cells does not express CD19. In some embodiments, a cancer or other condition that was previously responsive to treatment with CD19 CAR-expressing cells has a 10%, 20%, 30%, 40%, 50% or more reduction in CD19 expression levels relative to when the cancer or other condition was responsive to treatment with CD19 CAR-expressing cells. In some embodiments, a cancer or other condition that was previously responsive to treatment with CD19 CAR-expressing cells expresses CD22.

In some embodiments, the CAR-expressing cell, e.g., dual CAR or tandem CAR-expressing cell of the invention is administered post-relapse of a cancer or other condition previously treated with a CD19 CAR-expressing cell.

Bone Marrow Ablation

In one aspect, the present invention provides compositions and methods for bone marrow ablation. For example, in one aspect, the invention provides compositions and methods for eradication of at least a portion of existing bone marrow in a subject. It is described herein that, in certain instances, the CAR-expressing cell, e.g., dual CAR or tandem CAR-expressing cells comprising a CD22 CAR and a CD19 CAR of the present invention eradicates CD19 and/or CD22 positive bone marrow myeloid progenitor cells.

In one aspect, the invention provides a method of bone marrow ablation comprising administering a CAR-expressing cell, e.g., a dual CAR or tandem CAR-expressing cell, of the invention to a subject in need of bone marrow ablation. For example, the present method may be used to eradicate some or all of the existing bone marrow of a subject having a disease or disorder in which bone marrow transplantation or bone marrow reconditioning is a beneficial treatment strategy. In one aspect, the bone marrow ablation method of the invention, comprising the administration of a CAR-expressing cell, e.g., a dual CAR or tandem CAR-expressing cell, described elsewhere herein, is performed in a subject prior to bone marrow transplantation. Thus, in one aspect, the method of the invention provides a cellular conditioning regimen prior to bone marrow or stem cell transplantation. In one aspect, bone marrow transplantation comprises transplantation of a stem cell. The bone marrow transplantation may comprise transplantation of autologous or allogeneic cells.

The present invention provides a method of treating a disease or disorder comprising administering a CAR-expressing cell, e.g., a dual CAR or tandem CAR-expressing cell, of the invention to eradicate at least a portion of existing bone marrow. The method may be used as at least a portion of a treatment regimen for treating any disease or disorder where bone marrow transplantation is beneficial. That is, the present method may be used in any subject in need of a bone marrow transplant. In one aspect, bone marrow ablation comprising administration of a CAR-expressing cell, e.g., a dual CAR or tandem CAR-expressing cell, is useful in the treatment of AML. In certain aspects, bone marrow ablation by way of the present method is useful in treating a hematological cancer, a solid tumor, a hematologic disease, a metabolic disorder, HIV, HTLV, a lysosomal storage disorder, and an immunodeficiency.

Compositions and methods disclosed herein may be used to eradicate at least a portion of existing bone marrow to treat hematological cancers including, but not limited to cancers described herein, e.g., leukemia, lymphoma, myeloma, ALL, AML, CLL, CML, Hodgkin lymphoma, Non-Hodgkin lymphoma (e.g., DLBCL or follicular lymphoma), and multiple myeloma.

Compositions and methods disclosed herein may be used to treat hematologic diseases including, but not limited to myelodysplasia, anemia, paroxysmal nocturnal hemoglobinuria, aplastic anemia, acquired pure red cell anemia, Diamon-Blackfan anemia, Fanconi anemia, cytopenia, amegakaryotic thrombocytopenia, myeloproliferative disorders, polycythemia vera, essential thrombocytosis, myelofibrosis, hemoglobinopathies, sickle cell disease, β thalassemia major, among others.

In one aspect, the present invention provides a method of treating cancer comprising bone marrow conditioning, where at least a portion of bone marrow of the subject is eradicated by the CAR-expressing cell, e.g., dual CAR or tandem CAR-expressing cell, of the invention. For example, in certain instances, the bone marrow of the subject comprises a malignant precursor cell that can be targeted and eliminated by the activity of the CAR-expressing cell, e.g., the dual CAR or tandem CAR-expressing cell. In one aspect, a bone marrow conditioning therapy comprises administering a bone marrow or stem cell transplant to the subject following the eradication of native bone marrow. In one aspect, the bone marrow reconditioning therapy is combined with one or more other anti-cancer therapies, including, but not limited to anti-tumor CAR therapies, chemotherapy, radiation, and the like.

In one aspect, eradication of the administered CAR expressing cell may be required prior to infusion of bone marrow or stem cell transplant. Eradication of the CAR-expressing cell may be accomplished using any suitable strategy or treatment, including, but not limited to, use of a suicide gene, limited CAR persistence using RNA encoded CARs, or anti-T cell modalities including antibodies or chemotherapy.

CD22 Associated Diseases and/or Disorders

The present disclosure provides, among other things, compositions and methods for treating a disease associated with expression of CD22 or condition associated with cells which express CD22 including, e.g., a proliferative disease such as a cancer or malignancy or a precancerous condition; or a noncancer related indication associated with cells which express CD22. In one aspect, a cancer associated with expression of CD22 is a hematological cancer. In one aspect, a hematological cancer includes but is not limited to a B-cell malignancy. In one aspect, the hematological cancer is a leukemia or a lymphoma. In one aspect, a cancer associated with expression of CD22 includes cancers and malignancies including, but not limited to, e.g., one or more acute leukemias including but not limited to B-cell acute lymphoblastic leukemia (BALL), e.g., pediatric BALL and/or adult BALL, T-cell acute lymphoid leukemia (TALL), small lymphocytic leukemia (SLL), acute lymphoblastic leukemia (ALL); one or more chronic leukemias including but not limited to chronic lymphocytic leukemia (CLL); additional hematologic cancers or hematologic conditions including, but not limited to mantle cell lymphoma (MCL), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, Marginal zone lymphoma, non-Hodgkin lymphoma, Hodgkin lymphoma, plasmablastic lymphoma, plasmacytoid dendritic cell neoplasm, and Waldenstrom macroglobulinemia. In another embodiment, the disease associated with CD22 expression includes, but not limited to, atypical and/or non-classical cancers, malignancies, precancerous conditions or proliferative diseases expressing CD22; and any combination thereof.

Non-cancer related indications associated with expression of CD22 may also be included. Non-cancer related indications associated with expression of CD22 include, but are not limited to, e.g., autoimmune disease, (e.g., lupus, rheumatoid arthritis, multiple sclerosis autoimmune hemolytic anemia, pure red cell aplasia, idiopathic thrombocytopeniaurpura, Evans syndrome, vasculitis, bullous skin disorders, type 1 diabetes mellitus, Sjogren's syndrome, anti-NMDA receptor encephalitis and Devic's disease, Graves' ophthalmopathy, and autoimmune pancreatitis), inflammatory disorders (allergy and asthma) and solid-organ or hematopoietic cell transplantation.

In one aspect, the disclosure provides methods for treating a disease associated with CD22 expression. In one aspect, the disclosure provides methods for treating a disease wherein part of the tumor is negative for CD22 and part of the tumor is positive for CD22. For example, the CAR of the disclosure is useful for treating subjects that have undergone treatment for a disease associated with expression of CD22, wherein the subject that has undergone treatment related to expression of CD22 exhibits a disease associated with expression of CD22.

In one aspect, the disclosure pertains to a vector comprising a CAR, e.g., a dual CAR or a tandem CAR, operably linked to promoter for expression in mammalian cells (e.g., T cells or NK cells). In one aspect, the disclosure provides a recombinant T cell expressing the CAR, e.g., dual CAR or tandem CAR, for use in treating CD22-expressing tumors. In one aspect, the CAR expressing T cell or NK cell of the disclosure is capable of contacting a tumor cell with at least one CAR of the disclosure expressed on its surface such that the CAR expressing T cell or NK cell targets the tumor cell and growth of the tumor is inhibited.

In one aspect, the disclosure pertains to a method of inhibiting growth of a CD22-expressing tumor cell, comprising contacting the tumor cell with a CAR cell (e.g., T cell or NK cell) of the present disclosure such that the CART is activated in response to the antigen and targets the cancer cell, wherein the growth of the tumor is inhibited.

In one aspect, the disclosure pertains to a method of treating cancer in a subject. The method comprises administering to the subject a CAR expressing cell (e.g., T cell or NK cell) of the present disclosure such that the cancer is treated in the subject. An example of a cancer that is treatable by the CAR expressing cell (e.g., T cell or NK cell) of the disclosure is a cancer associated with expression of CD22. An example of a cancer that is treatable by the CAR expressing cell (e.g., T cell or NK cell) of the disclosure includes but is not limited to a hematological cancer described herein.

The disclosure includes a type of cellular therapy where cells (e.g., T cells or NK cells) are genetically modified to express a chimeric antigen receptor (CAR) and the CAR expressing cell (e.g., T cell or NK cells) is infused to a recipient in need thereof. The infused cell is able to kill tumor cells in the recipient. Unlike antibody therapies, CAR-modified cells (e.g., T cells or NK cells) are able to replicate in vivo resulting in long-term persistence that can lead to sustained tumor control. In various aspects, the cells (e.g., T cells or NK cells) administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

The disclosure also includes a type of cellular therapy where immune effector cells, e.g., NK cells or T cells are modified, e.g., by in vitro transcribed RNA, to transiently express a chimeric antigen receptor (CAR) and the CAR-expressing (e.g., CART or CAR expressing NK cell) cell is infused to a recipient in need thereof. The infused cell is able to kill cancer cells in the recipient. Thus, in various aspects, the CAR-expressing cells, e.g., T cells or NK cells, are administered to the patient, is present for less than one month, e.g., three weeks, two weeks, one week, after administration of the CAR-expressing cell, e.g., T cells or NK cell, to the patient.

Without wishing to be bound by any particular theory, the anti-tumor immunity response elicited by the CAR-modified cells (e.g., T cells or NK cells) may be an active or a passive immune response, or alternatively may be due to a direct vs indirect immune response. In one aspect, the CAR trans-duced cells (e.g., T cells or NK cells) exhibit specific proinflammatory cytokine secretion and potent cytolytic activity in response to human cancer cells expressing CD22, resist soluble CD22 inhibition, mediate bystander killing and mediate regression of an established human tumor. For example, antigen-less tumor cells within a heterogeneous field of CD22-expressing tumor may be susceptible to indirect destruction by CD22-redirected T cells that has previously reacted against adjacent antigen-positive cancer cells.

In one aspect, the CAR cells (e.g., T cells or NK cells) of the disclosure, e.g., fully human CAR-expressing cells, may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR cell can be administered to a mammalian recipient to provide a therapeutic benefit. The mammalian recipient may be a human and the CAR cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present disclosure. Other suitable methods are known in the art, therefore the present disclosure is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present disclosure also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified cells (e.g., T cells or NK cells) of the disclosure are used in the treatment of diseases, disorders and conditions associated with expression of CD22. In certain aspects, the cells of the disclosure are used in the treatment of patients at risk for developing diseases, disorders and conditions associated with expression of CD22. Thus, the present disclosure provides methods for the treatment or prevention of diseases, disorders and conditions associated with expression of CD22 comprising administering to a subject in need thereof, a therapeutically effective amount of the CAR cells (e.g., T cells or NK cells) of the disclosure.

In one aspect the CAR expressing cells of the disclosures may be used to treat a proliferative disease such as a cancer or malignancy or is a precancerous condition. In one aspect, a cancer associated with expression of CD22 is a hematological cancer preleukemia, hyperproliferative disorder, hyperplasia or a dysplasia, which is characterized by abnormal growth of cells.

In one aspect, the CAR expressing cells of the disclosure are used to treat a cancer, wherein the cancer is a hematological cancer. Hematological cancer conditions are the types of cancer such as leukemia and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoblastic leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

Lymphoma is a group of blood cell tumors that develop from lymphocytes. Exemplary lymphomas include non-Hodgkin lymphoma and Hodgkin lymphoma.

In one aspect, the compositions and CART cells or CAR expressing NK cells of the present disclosure are particularly useful for treating B cell malignancies, such as non-Hodgkin lymphomas, e.g., DLBCL, Follicular lymphoma, or CLL.

Non-Hodgkin lymphoma (NHL) is a group of cancers of lymphocytes, formed from either B or T cells. NHLs occur at any age and are often characterized by lymph nodes that are larger than normal, weight loss, and fever. Different types of NHLs are categorized as aggressive (fast-growing) and indolent (slow-growing) types. B-cell non-Hodgkin lymphomas include Burkitt lymphoma, chronic lymphocytic leukemia/small lymphocytic lymphoma (CLL/SLL), diffuse large B-cell lymphoma (DLBCL), follicular lymphoma, immunoblastic large cell lymphoma, precursor B-lymphoblastic lymphoma, and mantle cell lymphoma. Examples of T-cell non-Hodgkin lymphomas include mycosis fungoides, anaplastic large cell lymphoma, and precursor T-lymphoblastic lymphoma. Lymphomas that occur after bone marrow or stem cell transplantation are typically B-cell non-Hodgkin lymphomas. See, e.g., Maloney. NEJM. 366.21 (2012): 2008-16.

Diffuse large B-cell lymphoma (DLBCL) is a form of NHL that develops from B cells. DLBCL is an aggressive lymphoma that can arise in lymph nodes or outside of the lymphatic system, e.g., in the gastrointestinal tract, testes, thyroid, skin, breast, bone, or brain. Three variants of cellular morphology are commonly observed in DLBCL: centroblastic, immunoblastic, and anaplastic. Centroblastic morphology is most common and has the appearance of medium-to-large-sized lymphocytes with minimal cytoplasm. There are several subtypes of DLBCL. For example, primary central nervous system lymphoma is a type of DLBCL that only affects the brain is called and is treated differently than DLBCL that affects areas outside of the brain. Another type of DLBCL is primary mediastinal B-cell lymphoma, which often occurs in younger patients and grows rapidly in the chest. Symptoms of DLBCL include a painless rapid swelling in the neck, armpit, or groin, which is caused by enlarged lymph nodes. For some subjects, the swelling may be painful. Other symptoms of DLBCL include night sweats, unexplained fevers, and weight loss. Although most patients with DLBCL are adults, this disease sometimes occurs in children. Treatment for DLBCL includes chemotherapy (e.g., cyclophosphamide, doxorubicin, vincristine, prednisone, etoposide), antibodies (e.g., Rituxan), radiation, or stem cell transplants.

Follicular lymphoma a type of non-Hodgkin lymphoma and is a lymphoma of follicle center B-cells (centrocytes and centroblasts), which has at least a partially follicular pattern. Follicular lymphoma cells express the B-cell markers CD10, CD19, CD20, and CD22. Follicular lymphoma cells are commonly negative for CD5. Morphologically, a follicular lymphoma tumor is made up of follicles containing a mixture of centrocytes (also called cleaved follicle center cells or small cells) and centroblasts (also called large noncleaved follicle center cells or large cells). The follicles are surrounded by non-malignant cells, mostly T-cells. The follicles contain predominantly centrocytes with a minority of centroblasts. The World Health Organization (WHO) morphologically grades the disease as follows: grade 1 (<5 centroblasts per high-power field (hpf); grade 2 (6-15 centroblasts/hpf); grade 3 (>15 centroblasts/hpf). Grade 3 is further subdivided into the following grades: grade 3A (centrocytes still present); grade 3B (the follicles consist almost entirely of centroblasts). Treatment of follicular lymphoma includes chemotherapy, e.g., alkylating agents, nucleoside analogs, anthracycline-containing regimens, e.g., a combination therapy called CHOP—cyclophosphamide, doxorubicin, vincristine, prednisone/prednisolone, antibodies (e.g., rituximab), radioimmunotherapy, and hematopoietic stem cell transplantation.

CLL is a B-cell malignancy characterized by neoplastic cell proliferation and accumulation in bone morrow, blood, lymph nodes, and the spleen. The median age at time of diagnosis of CLL is about 65 years. Current treatments include chemotherapy, radiation therapy, biological therapy, or bone marrow transplantation. Sometimes symptoms are treated surgically (e.g., splenectomy removal of enlarged spleen) or by radiation therapy (e.g., de-bulking swollen lymph nodes). Chemotherapeutic agents to treat CLL include, e.g., fludarabine, 2-chlorodeoxyadenosine (cladribine), chlorambucil, vincristine, pentostatin, cyclophosphamide, alemtuzumab (Campath-1H), doxorubicin, and prednisone. Biological therapy for CLL includes antibodies, e.g., alemtuzumab, rituximab, and ofatumumab; as well as tyrosine kinase inhibitor therapies. A number of criteria can be used to classify stage of CLL, e.g., the Rai or Binet system. The Rai system describes CLL has having five stages: stage 0 where only lymphocytosis is present; stage I where lymphadenopathy is present; stage II where splenomegaly, lymphadenopathy, or both are present; stage III where anemia, organomegaly, or both are present (progression is defined by weight loss, fatigue, fever, massive organomegaly, and a rapidly increasing lymphocyte count); and stage IV where anemia, thrombocytopenia, organomegaly, or a combination thereof are present. Under the Binet staging system, there are three categories: stage A where lymphocytosis is present and less than three lymph nodes are enlarged (this stage is inclusive of all Rai stage 0 patients, one-half of Rai stage I patients, and one-third of Rai stage II patients); stage B where three or more lymph nodes are involved; and stage C wherein anemia or thrombocytopenia, or both are present. These classification systems can be combined with measurements of mutation of the immunoglobulin genes to provide a more accurate characterization of the state of the disease. The presence of mutated immunoglobulin genes correlates to improved prognosis.

In another embodiment, the CAR expressing cells of the present disclosure are used to treat cancers or leukemias, e.g., with leukemia stem cells. For example, the leukemia stem cells are $CD34^+/CD38^-$ leukemia cells.

The present disclosure provides, among other things, compositions and methods for treating cancer. In one aspect, the cancer is a hematologic cancer including but is not limited to one or more acute leukemias including but not limited to B-cell acute lymphoblastic leukemia (BALL), e.g., pediatric BALL and/or adult BALL, T-cell acute lymphoid leukemia (TALL), small lymphocytic leukemia (SLL), acute lymphoblastic leukemia (ALL); one or more chronic leukemias including but not limited chronic lymphocytic leukemia (CLL); additional hematologic cancers or hematologic conditions including, but not limited to mantle cell lymphoma (MCL), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, Marginal zone lymphoma, non-Hodgkin lymphoma, Hodgkin lymphoma, plasmablastic lymphoma, plasmacytoid dendritic cell neoplasm, Waldenstrom macroglobulinemia, and to disease associated with CD22 expression include, but not limited to atypical and/or non-classical cancers, malignancies, precancerous conditions or proliferative diseases expressing CD22; and any combination thereof.

The CAR cells of the present disclosure may be administered either alone, or as a pharmaceutical composition in combination with diluents and/or with other components such as IL-2 or other cytokines or cell populations.

The present disclosure also provides methods for inhibiting the proliferation or reducing a CD22-expressing cell population, the methods comprising contacting a population of cells comprising a CD22-expressing cell with a CAR expressing cell of the disclosure that binds to the CD22-expressing cell. In an aspect, the present disclosure provides methods for inhibiting the proliferation or reducing the population of cancer cells expressing CD22, the methods comprising contacting the CD22-expressing cancer cell population with a CAR expressing cell of the disclosure that binds to the CD22-expressing cell. In one aspect, the present disclosure provides methods for inhibiting the proliferation or reducing the population of cancer cells expressing CD22, the methods comprising contacting the CD22-expressing cancer cell population with a CART of the disclosure that binds to the CD22-expressing cell. In certain aspects, the CAR expressing cell of the disclosure reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for B-cell malignancy or another cancer associated with CD22-expressing cells relative to a negative control. In one aspect, the subject is a human.

The present disclosure also provides methods for preventing, treating and/or managing a disease associated with CD22-expressing cells (e.g., a hematologic cancer or atypical cancer expressing CD22), the methods comprising administering to a subject in need a CAR expressing cell of the disclosure that binds to the CD22-expressing cell. In one aspect, the subject is a human. Non-limiting examples of disorders associated with CD22-expressing cells include autoimmune diseases, (e.g., lupus, rheumatoid arthritis, multiple sclerosis autoimmune hemolytic anemia, pure red cell aplasia, idiopathic thrombocytopeniarpura, Evans syndrome, vasculitis, bullous skin disorders, type 1 diabetes mellitus, Sjogren's syndrome, anti-NMDA receptor encephalitis and Devic's disease, Graves' ophthalmopathy, and autoimmune pancreatitis), inflammatory disorders (allergy and asthma), transplantation, and cancers (such as hematological cancers or atypical cancers expressing CD22).

The present disclosure also provides methods for preventing, treating and/or managing a disease associated with CD22-expressing cells, the methods comprising administering to a subject in need a CAR expressing cell of the disclosure that binds to the CD22-expressing cell. In one aspect, the subject is a human.

The present disclosure provides methods for preventing relapse of cancer associated with CD22-expressing cells, the methods comprising administering to a subject in need thereof a CAR expressing cell of the disclosure that binds to the CD22-expressing cell. In one aspect, the methods comprise administering to the subject in need thereof an effective amount of a CAR expressing cell described herein that binds to the CD22-expressing cell in combination with an effective amount of another therapy.

In some embodiments, the CD22 expressing cell expresses CD19, CD123, FLT-3, ROR-1, CD79b, CD179b, CD79a, CD10, CD34, and/or CD20. In certain embodiments, the CD22 expressing cell expresses CD19. In some embodiments, the CD22-expressing cell does not express CD19.

In some embodiments, the subject is a non-responder to CD19 CAR therapy. In some embodiments, the subject is a partial responder to CD19 CAR therapy. In some embodiments, the subject is a complete responder to CD19 CAR therapy. In some embodiments, the subject is a non-relapser to CD19 CAR therapy. In some embodiments, the subject is a partial relapser to CD19 CAR therapy. In some embodiments, the subject is a complete relapser to CD19 CAR therapy.

In some embodiments, a cancer or other condition that was previously responsive to treatment with CD19 CAR-expressing cells does not express CD19. In some embodiments, a cancer or other condition that was previously responsive to treatment with CD19 CAR-expressing cells has a 10%, 20%, 30%, 40%, 50% or more reduction in CD19 expression levels relative to when the cancer or other condition was responsive to treatment with CD19 CAR-expressing cells. In some embodiments, a cancer or other condition that was previously responsive to treatment with CD19 CAR-expressing cells expresses CD22.

In some embodiments, the CAR-expressing cell of the disclosure is administered post-relapse of a cancer or other condition previously treated with CD19 CAR-expressing cell.

CD19 CAR T Cells for Use in Treating Multiple Myeloma

Even with current regimens of chemotherapy, targeted therapies, and autologous stem cell transplant, myeloma is considered an incurable disease. In one study (not disclosed), treatment of multiple myeloma (MM) with autologous T cells directed to CD19 with a chimeric antigen receptor (lentivirus/CD19:4-1BB:CD3zeta; also known as "CART19" or CTL019) is described. This example demonstrates that CD19-directed CAR therapies have the potential to establish deep, long-term durable remissions based on targeting the myeloma stem cell and/or tumor cells that express very low (undetectable by most methods) levels of CD19.

CAR19 T Cell Therapy for Hodgkin Lymphoma

CAR 19 T cell therapy can also be used to treat Hodgkin lymphoma (HL). Hodgkin lymphoma is characterized by the presence of malignant Hodgkin Reed-Sternberg (HRS) cells that are derived from clonal germinal center B cells. There are several factors that indicate the therapeutic efficacy of CAR 19 T cell therapy for HL. CD19 staining of HL tumors shows CD19-expressing (CD19$^+$) cells within the tumor and tumor microenvironment. A study has shown that a clonal B cell population (CD20$^+$CD27$^+$ALDH$^+$) that expresses CD19 is responsible for the generation and maintenance of Hodgkin lymphoma cell lines, and also circulates in the blood of most HL patients (Jones et al., Blood, 2009, 113 (23): 5920-5926). This clonal B cell population has also been suggested to give rise to or contribute to the generation of the malignant HRS cells. Thus, CART19 therapy would deplete this B cell population that contributes to tumorigenesis or maintenance of tumor cells. Another study showed that B cell depletion retards solid tumor growth in multiple murine models (Kim et al., J Immunotherapy, 2008, 31 (5): 446-57). In support of the idea that depletion of B cells in the HL tumor microenvironment results in some anti-tumor effect, current therapies, such as rituxan, are being clinically tested for targeting and depletion of tumoral B cells in HL (Younes et al., Blood, 2012, 119 (18): 4123-8). De novo carcinogenesis related to chronic inflammation has also been shown to be B-cell dependent (de Visser, et al., Cancer Cell, 2005, 7 (5): 411-23). The results from these studies indicate that targeting of the B cell population, particularly in the HL tumor microenvironment, would be useful for treating HL, by reducing or inhibiting disease progression or tumor growth.

Non-Responder Subset of CLL Patients Exhibit Increased Expression of Immune Checkpoint Inhibitor Molecules In one study (data not published), CART19 cells from clinical manufacture from 34 CLL patients were assessed for expression of immune checkpoint inhibitor molecules, such as PD-1, LAG3, and TIM3. The response of this cohort to CART19 was known and hence a correlation between response and biomarker expression patterns could be assessed.

Effects of mTOR Inhibition on Immunosenescence in the Elderly

The efficacy of mTOR inhibition on immunosenescence is described, e.g., in Example 1 of International Application WO/2015/073644, and the entirety of the application is herein incorporated by reference.

Enhancement of Immune Response to Vaccine in Elderly Subjects

The efficacy of mTOR inhibition on enhancing an immune response is described, e.g., in Example 2 of International Application WO/2015/073644, and the entirety of the application is herein incorporated by reference.

Low Dose mTOR Inhibition Increases Energy and Exercise;

The effect of mTOR inhibition on energy and exercise is described, e.g., in Example 3 of 20 International Application WO/2015/073644, and the entirety of the application is herein incorporated by reference.

P70 S6 Kinase Inhibition with RAD001

The effect of mTOR inhibition on P70 S6 kinase inhibition is described, e.g., in Example 4 of International Application WO/2015/073644, and the entirety of the application is herein incorporated by reference.

Exogenous IL-7 Enhances the Function of CAR T Cells

After adoptive transfer of CAR T cells, some patients experience limited persistence of the CAR T cells, which can result in suboptimal levels of anti-tumor activity. In this example, the effects of administration of exogenous human IL-7 is assessed in mouse xenograft models where an initial suboptimal response to CAR T cells has been observed.

Combination Therapies

A CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In some embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

The CAR therapy and/or other therapeutic agents, procedures or modalities can be administered during periods of active disorder, or during a period of remission or less active disease. The CAR therapy can be administered before the other treatment, concurrently with the treatment, post-treatment, or during remission of the disorder.

When administered in combination, the CAR therapy and the additional agent (e.g., second or third agent), or all, can be administered in an amount or dose that is higher, lower or the same than the amount or dosage of each agent used individually, e.g., as a monotherapy. In certain embodiments, the administered amount or dosage of the CAR therapy, the additional agent (e.g., second or third agent), or all, is lower (e.g., at least 20%, at least 30%, at least 40%, or at least 50%) than the amount or dosage of each agent used individually, e.g., as a monotherapy. In some embodiments, the amount or dosage of the CAR therapy, the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In further aspects, a CAR-expressing cell described herein may be used in a treatment regimen in combination with surgery, cytokines, radiation, or chemotherapy such as cytoxan, fludarabine, histone deacetylase inhibitors, demethylating agents, or peptide vaccine, such as that described in Izumoto et al. 2008 J Neurosurg 108:963-971.

In certain instances, compounds of the present invention are combined with other therapeutic agents, such as other anti-cancer agents, anti-allergic agents, anti-nausea agents (or anti-emetics), pain relievers, cytoprotective agents, and combinations thereof.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the compounds of the present invention include: antitumor antibiotics; tyrosine kinase inhibitors; alkylating agents; anti-microtubule or anti-mitotic agents; or oncolytic viruses.

Exemplary tyrosine kinase inhibitors include but are not limited to Erlotinib hydrochloride (Tarceva®); Linifanib (N-[4-(3-amino-1H-indazol-4-yl)phenyl]-N'-(2-fluoro-5-methylphenyl) urea, also known as ABT 869, available from Genentech); Sunitinib malate (Sutent®); Bosutinib (4-[(2,4-dichloro-5-methoxyphenyl)amino]-6-methoxy-7-[3-(4-methylpiperazin-1-yl) propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); and Imatinib or Imatinib mesylate (Gilvec® and Gleevec®).

Exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BICNU®); Bendamustine (Treanda®); Busulfan (Busulfex® and Myleran®); Carboplatin (Paraplatin®); Lomustine (also known as CCNU, CecNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednimustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anti-tumor antibiotics include, e.g., Doxorubicin (Adriamycin® and Rubex®); Bleomycin (Lenoxane®); Daunorubicin (daunorubicin hydrochloride, daunomycin, and rubidomycin hydrochloride, Cerubidine®); Daunorubicin liposomal (daunorubicin citrate liposome, DaunoXome®); Mitoxantrone (DHAD, Novantrone®); Epirubicin (Ellence™); Idarubicin (Idamycin®, Idamycin PFS®); Mitomycin C (Mutamycin®); Geldanamycin; Herbimycin; Ravidomycin; and Desacetylravidomycin.

Exemplary anti-microtubule or anti-mitotic agents include, without limitation, *Vinca* Alkaloids (such as Vinorelbine tartrate (Navelbine®), Vincristine (Oncovin®), and Vindesine (Eldisine®)); Taxanes (such as paclitaxel and docetaxel); and Estramustine (Emcyl® or Estracyt®).

In some embodiments, a CAR-expressing cell described herein is administered in combination with an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In some embodiments, the oncolytic virus is a virus, e.g., recombinant oncolytic virus, described in US2010/0178684 A1, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684 A1, incorporated herein by reference in its entirety. In embodiments, the recombinant oncolytic virus, e.g., oncolytic NDV, comprises a pro-apoptotic protein (e.g., apoptin), a cytokine (e.g., GM-CSF, interferon-gamma, interleukin-2 (IL-2), tumor necrosis factor-alpha), an immunoglobulin (e.g., an antibody against ED-B fibronectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3 (2012): 347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18 (2000): 723-27. In some embodiments, an oncolytic adenovirus comprises one described in Table 1 on page 725 of Alemany et al., incorporated herein by reference in its entirety.

Exemplary oncolytic viruses include but are not limited to the following:

Group B Oncolytic Adenovirus (ColoAd1) (PsiOxus Therapeutics Ltd.) (see, e.g., Clinical Trial Identifier: NCT02053220);

ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);

VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);

Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Català d'Oncologia) (see, e.g., Clinical Trial Identifier: NCT01864759);

Celyvir, which comprises bone marrow-derived autologous mesenchymal stem cells (MSCs) infected with ICOVIR5, an oncolytic adenovirus (Hospital Infantil Universitario Niño Jesús, Madrid, Spain/Ramon Alemany) (see, e.g., Clinical Trial Identifier: NCT01844661);

CG0070, which is a conditionally replicating oncolytic serotype 5 adenovirus (Ad5) in which human E2F-1 promoter drives expression of the essential Ela viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intra-arterial, intravenous, intramuscular, intrathecal, or intraperitoneal injection. In embodiments, an oncolytic virus described herein is administered intratumorally, transdermally, transmucosally, orally, intranasally, or via pulmonary administration.

In one embodiment, a CAR expressing cell described herein are administered to a subject in combination with a molecule targeting GITR and/or modulating GITR functions, such as a GITR agonist and/or a GITR antibody that depletes regulatory T cells (Tregs). In one embodiment, the GITR binding molecules and/or molecules modulating GITR functions (e.g., GITR agonist and/or Treg depleting GITR antibodies) are administered prior to the CAR-expressing cell. For example, in one embodiment, the GITR agonist can be administered prior to apheresis of the cells. In one embodiment, the subject has CLL. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, a CAR expressing cell described herein is administered to a subject in combination with an mTOR inhibitor, e.g., an mTOR inhibitor described herein, e.g., a rapalog such as everolimus. In one embodiment, the mTOR inhibitor is administered prior to the CAR-expressing cell. For example, in one embodiment, the mTOR inhibitor can be administered prior to apheresis of the cells.

In one embodiment, a CAR expressing cell described herein is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells.

In one embodiment, a CAR expressing cell described herein is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor.

In one embodiment, a CAR-expressing cell described herein can be used in combination with a kinase inhibitor.

In an embodiment this approach can be used to optimize the performance of CAR cells described herein in the subject. While not wishing to be bound by theory, it is believed that, in an embodiment, the performance of endogenous, non-modified immune effector cells, e.g., T cells or NK cells, is improved. While not wishing to be bound by theory, it is believed that, in an embodiment, the performance of a CAR expressing cell is improved. In some embodiments, cells, e.g., T cells or NK cells, which have, or will be engineered to express a CAR, can be treated ex vivo by contact with an amount of an mTOR inhibitor that increases the number of PD1 negative immune effector cells, e.g., T cells/NK cells or increases the ratio of PD1 negative immune effector cells, e.g., T cells/NK cells/PD1 positive immune effector cells, e.g., T cells or NK cells.

In an embodiment, administration of a low, immune enhancing, dose of an mTOR inhibitor, e.g., an allosteric inhibitor, e.g., RAD001, or a catalytic inhibitor, is initiated prior to administration of an CAR expressing cell described herein, e.g., T cells or NK cells. In an embodiment, the CAR cells are administered after a sufficient time, or sufficient dosing, of an mTOR inhibitor, such that the level of PD1 negative immune effector cells, e.g., T cells/NK cells, or the ratio of PD1 negative immune effector cells, e.g., T cells/NK cells/PD1 positive immune effector cells, e.g., T cells or NK cells, has been, at least transiently, increased.

In an embodiment, the cell, e.g., T cell or NK cell, to be engineered to express a CAR, is harvested after a sufficient time, or after sufficient dosing of the low, immune enhancing, dose of an mTOR inhibitor, such that the level of PD1 negative immune effector cells, e.g., T cells or NK cells, or the ratio of PD1 negative immune effector cells, e.g., T cells/NK cells/PD1 positive immune effector cells, e.g., T cells or NK cells, in the subject or harvested from the subject has been, at least transiently, increased.

In some embodiments, the mTOR inhibitor is administered for an amount of time sufficient to decrease the proportion of PD-1 positive T cells, increase the proportion of PD-1 negative T cells, or increase the ratio of PD-1 negative T cells/PD-1 positive T cells, in the peripheral blood of the subject, or in a preparation of T cells isolated from the subject.

In some embodiments, the dose of an mTOR inhibitor is associated with mTOR inhibitor of at least 5 but no more than 90%, e.g., as measured by p70 S6K inhibition. In some embodiments, the dose of an mTOR inhibitor is associated with mTOR inhibition of at least 10% but no more than 40%, e.g., as measured by p70 S6K inhibition.

In one embodiment, the kinase inhibitor is a CDK4 inhibitor, e.g., a CDK4 inhibitor described herein, e.g., a CD4/6 inhibitor, such as, e.g., 6-Acetyl-8-cyclopentyl-5-methyl-2-(5-piperazin-1-yl-pyridin-2-ylamino)-8H-pyrido [2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo[3,4-d] pyrimidine. The MNK inhibitor can be, e.g., a MNK1a, MNK1b, MNK2a and/or MNK2b inhibitor. In one embodiment, the kinase inhibitor is a DGK inhibitor, e.g., a DGK inhibitor described herein, such as, e.g., DGKinh1 (D5919) or DGKinh2 (D5794). In one embodiment, the kinase inhibitor is a CDK4 inhibitor selected from aloisine A; flavopiridol or HMR-1275, 2-(2-chlorophenyl)-5,7-dihydroxy-8-[(3S, 4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00);

1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of ibrutinib are administered.

In one embodiment, the kinase inhibitor is an mTOR inhibitor selected from temsirolimus; ridaforolimus (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl) methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7 (8H)-one (PF04691502); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo[3,4-d]pyrimidine (CGP57380); cercosporamide; ETC-1780445-2; and 4-amino-5-(4-fluoroanilino)-pyrazolo[3,4-d]pyrimidine.

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

The above-mentioned compounds, which can be used in combination with a compound of the present invention, can be prepared and administered as described in the art, such as in the documents cited above.

In one embodiment, the present invention provides pharmaceutical compositions comprising at least one compound of the present invention (e.g., a compound of the present invention) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of a compound of the present invention (e.g., a compound of the present invention) or a pharmaceutically acceptable salt thereof, either alone or in combination with other anti-cancer agents.

In particular, compositions will either be formulated together as a combination therapeutic or administered separately.

In combination therapy, the compound of the present invention and other anti-cancer agent(s) may be administered either simultaneously, concurrently or sequentially with no specific time limits, wherein such administration provides therapeutically effective levels of the two compounds in the body of the patient.

In a preferred embodiment, the compound of the present invention and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

A compound of the present invention may also be used to advantage in combination with known therapeutic processes, for example, the administration of hormones or especially radiation. A compound of the present invention may in particular be used as a radiosensitizer, especially for the treatment of tumors which exhibit poor sensitivity to radiotherapy.

In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthralgias, nausea, vomiting, and headache. CRS may include clinical skin signs and symptoms such as rash. CRS may include clinical gastrointestinal signs and symptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardiac output (early) and potentially diminished cardiac output (late). CRS may include clinical coagulation signs and symptoms such as elevated d-dimer, hyperfibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures. Accordingly, the methods described herein can comprise administering a CAR-expressing cell described herein to a subject and further administering one or more agents to manage elevated levels of a soluble factor resulting from treatment with a CAR-expressing cell. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fractalkine. Therefore, an agent administered to treat this side effect can be an agent that neutralizes one or more of these soluble factors. In one embodiment, the agent that neutralizes one or more of these soluble forms is an antibody or antigen binding fragment thereof. Examples of such agents include, but are not limited to a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as etanercept. Small molecule inhibitor of TNFα include, but are not limited to, xanthine derivatives (e.g. pentoxifylline) and bupropion. An example of an IL-6 inhibitor is an anti-IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 antibody molecule is tocilizumab. An example of an IL-1R based inhibitor is anakinra.

In some embodiment, the subject is administered a corticosteroid, such as, e.g., methylprednisolone, hydrocortisone, among others.

In some embodiments, the subject is administered a vasopressor, such as, e.g., norepinephrine, dopamine, phenylephrine, epinephrine, vasopressin, or a combination thereof.

In an embodiment, the subject can be administered an antipyretic agent. In an embodiment, the subject can be administered an analgesic agent.

In one embodiment, the subject can be administered an agent which enhances the activity of a CAR-expressing cell. For example, in one embodiment, the agent can be an agent which inhibits an inhibitory molecule. Inhibitory molecules, e.g., Programmed Death 1 (PD1), can, in some embodiments, decrease the ability of a CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGF beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, or a clustered regularly interspaced short palindromic repeats (CRISPR), a transcription-activator like effector nuclease (TALEN), or a zinc finger endonuclease (ZFN), can be used to inhibit expression of an inhibitory molecule in the CAR-expressing cell. In an embodiment the inhibitor is an shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206)). In an embodiment, the agent is an antibody or antibody fragment that binds to TIM3. In an embodiment, the agent is an antibody or antibody fragment that binds to LAG3. In an embodiment, the agent is an antibody or antibody fragment that binds to CEACAM (e.g., CEACAM-1, CEACAM-3 and/or CEACAM-5).

PD1 is an inhibitory member of the CD28 family of receptors that also includes CD28, CTLA-4, ICOS, and BTLA. PD1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094).

Immune suppression can be reversed by inhibiting the local interaction of PD1 with PD-L1. Antibodies, antibody fragments, and other inhibitors of PD1, PD-L1 and PD-L2 are available in the art and may be used combination with a CAR described herein. For example, nivolumab (also referred to as BMS-936558 or MDX1106; Bristol-Myers Squibb) is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. Pidilizumab (CT-011; Cure Tech) is a humanized IgG1k monoclonal antibody that binds to PD1 Pidilizumab and other humanized anti-PD1 monoclonal antibodies are disclosed in WO2009/101611. Pembrolizumab (formerly known as lambrolizumab, and also referred to as Keytruda, MK03475; Merck) is a humanized IgG4 monoclonal antibody that binds to PD1. Pembrolizumab and other humanized anti-PD1 antibodies are disclosed in U.S. Pat. No. 8,354,509 and WO2009/114335. MEDI4736 (Medimmune) is a human monoclonal antibody that binds to PDL1, and inhibits interaction of the ligand with PD1. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.S70 (heavy and light chain variable regions are shown in SEQ ID NOs: 20 and 21 in WO2010/077634) and MDX-1105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD1 and B7-H1. Other anti-PD1 antibodies include AMP 514 (Amplimmune), among others, e.g., anti-PD1 antibodies disclosed in U.S. Pat. No. 8,609,089, US 2010028330, and/or US 20120114649. TIM3 (T cell immunoglobulin-3) also negatively regulates T cell function, particularly in IFN-g-secreting CD4+ T helper 1 and CD8+ T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CAR, e.g., a described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In some embodiments, the agent which enhances the activity of a CAR-expressing cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In some embodiments, the anti-CEACAM antibody binds to CEACAM-5 as described in, e.g., Zheng et al. PLoS One. 2010 Sep. 2; 5 (9). pii: e12529 (DOI: 10:1371/journal-.pone.0021146), or cross reacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. J Immunol. 2002 Mar. 15; 168 (6): 2803-10; Markel et al. J Immunol. 2006 Nov. 1; 177 (9): 6062-71; Markel et al. Immunology. 2009 February; 126 (2): 186-200; Markel et al. Cancer Immunol Immunother. 2010 February; 59 (2): 215-30; Ortenberg et al. Mol Cancer Ther. 2012 June; 11 (6): 1300-10; Stern et al. J Immunol. 2005 Jun. 1; 174 (11): 6692-701; Zheng et al. PLoS One. 2010 Sep. 2; 5 (9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) Nature doi: 10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In some embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CAR, e.g., a CAR described herein. For example, BMS-986016 (Bristol-Myers Squib) is a monoclonal antibody that targets LAG3. IMP701 (Immutep) is an antagonist LAG3 antibody and IMP731 (Immutep and GlaxoSmithKline) is a depleting LAG3 antibody. Other LAG3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO2010/019570.

In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an intracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR.

In one embodiment, the agent which enhances activity of a CAR-expressing cell described herein is miR-17-92.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, *mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). In some embodiments, a pharmaceutical composition comprising the cells, e.g., T cells or NK cells described herein may be administered at a dosage of $10^4$ to $10^9$ cells/kg body weight, in some instances $10^5$ to $10^6$ cells/kg body weight, including all integer values within those ranges. In some embodiments, the cells, e.g., T cells or NK cells described herein may be administered at $3 \times 10^4$, $1 \times 10^6$, $3 \times 10^6$, or $1 \times 10^7$ cells/kg body weight. The cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated cells, e.g., T cells or NK cells, to a subject and then subsequently redraw blood (or have an apheresis performed), activate the cells therefrom according to the present invention, and reinfuse the patient with these activated and expanded cells. This process can be carried out multiple times every few weeks. In certain aspects, cells, e.g., T cells or NK cells, can be activated from blood draws of from 10 cc to 400 cc. In certain aspects, cells, e.g., T cells or NK cells, are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the cell compositions, e.g., T cell or NK cell compositions, of the present invention are administered to a patient by intradermal or subcutaneous injection. In one aspect, the cell compositions, e.g., T cell or NK cell compositions, of the present invention are administered by i.v. injection. The compositions of cells, e.g., T cell or NK cell compositions, may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T or NK cells. These cell isolates, e.g., T cell or NK cell isolates, may be expanded by methods known in the art and treated such that one or more CAR constructs of the invention may be introduced, thereby creating a CAR-expressing cell, e.g., CAR T cell or CAR-expressing NK cell, of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR-expressing cells of the present invention. In an additional aspect, expanded cells are administered before or following surgery.

In embodiments, lymphodepletion is performed on a subject, e.g., prior to administering one or more cells that express a CAR described herein. In embodiments, the lymphodepletion comprises administering one or more of melphalan, cytoxan, cyclophosphamide, and fludarabine.

The dosage of the above treatments to be administered to a patient will vary with the precise nature of the condition being treated and the recipient of the treatment. The scaling of dosages for human administration can be performed according to art-accepted practices. The dose for a therapeutic, e.g., an antibody, e.g., CAMPATH, for example, may generally be, e.g., in the range 1 to about 100 mg for an adult patient, e.g., administered daily for a period between 1 and 30 days. A suitable daily dose is 1 to 10 mg per day although in some instances larger doses of up to 40 mg per day may be used (described in U.S. Pat. No. 6,120,766).

In one embodiment, the CAR is introduced into cells, e.g., T cells or NK cells, e.g., using in vitro transcription, and the subject (e.g., human) receives an initial administration of CAR-expressing cells, e.g., CAR T cells or CAR-expressing NK cells of the invention, and one or more subsequent administrations of the CAR-expressing cells, e.g., CAR T cells or CAR-expressing NK cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR-expressing cells, e.g., CAR T cells or CAR-expressing NK cells of the invention are administered to the subject (e.g., human) per week, e.g., 2, 3, or 4 administrations of the CAR-expressing cells, e.g., CAR T cells or CAR-expressing NK cells of the invention are administered per week. In one embodiment, the subject (e.g., human subject) receives more than one administration of the CAR-expressing cells, e.g., CAR T cells per week or CAR-expressing NK cells (e.g., 2, 3 or 4 administrations per week) (also referred to herein as a cycle), followed by a week of no CAR-expressing cells, e.g., CAR T cell administrations or CAR-expressing NK cell administrations, and then one or more additional administration of the CAR-expressing cells, e.g., CAR T cells or CAR-expressing NK cells (e.g., more than one administration of the CAR-expressing cells, e.g., CAR T cells or CAR-expressing NK cells, per week) is administered to the subject. In another embodiment, the subject (e.g., human subject) receives more than one cycle of CAR-expressing cells, e.g., CAR T cells or CAR-expressing NK cells, and the time between each cycle is less than 10, 9, 8, 7, 6, 5, 4, or 3 days. In one embodiment, the CAR-expressing cells, e.g., CAR T cells or CAR-expressing NK cells, are administered every other day for 3 administrations per week. In one embodiment, the CAR-expressing cells, e.g., CAR T cells or CAR-expressing NK cells of the invention, are administered for at least two, three, four, five, six, seven, eight or more weeks.

In some embodiments, subjects may be adult subjects (i.e., 18 years of age and older). In certain embodiments, subjects may be between 1 and 30 years of age. In some embodiments, the subjects are 16 years of age or older. In certain embodiments, the subjects are between 16 and 30 years of age. In some embodiments, the subjects are child subjects (i.e., between 1 and 18 years of age).

In one aspect, CAR-expressing cells are generated using lentiviral viral vectors, such as lentivirus. CAR-expressing cells, e.g., CARTs, generated that way will have stable CAR expression.

In one aspect, CAR-expressing cells, e.g., CARTs, transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the cell, e.g., NK cell or T cell, by electroporation.

A potential issue that can arise in patients being treated using transiently expressing CAR T cells or CAR-expressing NK cells (particularly with murine scFv bearing CAR-expressing cells) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CART infusion breaks should not last more than ten to fourteen days.

Biopolymer Delivery Methods

In some embodiments, one or more CAR-expressing cells as disclosed herein can be administered or delivered to the subject via a biopolymer scaffold, e.g., a biopolymer implant. Biopolymer scaffolds can support or enhance the delivery, expansion, and/or dispersion of the CAR-expressing cells described herein. A biopolymer scaffold comprises a biocompatible (e.g., does not substantially induce an inflammatory or immune response) and/or a biodegradable polymer that can be naturally occurring or synthetic.

Examples of suitable biopolymers include, but are not limited to, agar, agarose, alginate, alginate/calcium phosphate cement (CPC), beta-galactosidase (β-GAL), (1,2,3,4,6-pentaacetyl a-D-galactose), cellulose, chitin, chitosan, collagen, elastin, gelatin, hyaluronic acid collagen, hydroxyapatite, poly(3-hydroxybutyrate-co-3-hydroxyhexanoate) (PHBHHx), poly(lactide), poly(caprolactone) (PCL), poly(lactide-co-glycolide) (PLG), polyethylene oxide (PEO), poly(lactic-co-glycolic acid) (PLGA), polypropylene oxide (PPO), polyvinyl alcohol) (PVA), silk, soy protein, and soy protein isolate, alone or in combination with any other polymer composition, in any concentration and in any ratio. The biopolymer can be augmented or modified with adhesion- or migration-promoting molecules, e.g., collagen-mimetic peptides that bind to the collagen receptor of lymphocytes, and/or stimulatory molecules to enhance the delivery, expansion, or function, e.g., anti-cancer activity, of the cells to be delivered. The biopolymer scaffold can be an injectable, e.g., a gel or a semi-solid, or a solid composition.

In some embodiments, CAR-expressing cells described herein are seeded onto the biopolymer scaffold prior to delivery to the subject. In embodiments, the biopolymer scaffold further comprises one or more additional therapeutic agents described herein (e.g., another CAR-expressing cell, an antibody, or a small molecule) or agents that enhance the activity of a CAR-expressing cell, e.g., incorporated or conjugated to the biopolymers of the scaffold. In embodiments, the biopolymer scaffold is injected, e.g., intratumorally, or surgically implanted at the tumor or within a proximity of the tumor sufficient to mediate an anti-tumor effect. Additional examples of biopolymer compositions and methods for their delivery are described in Stephan et al., *Nature Biotechnology*, 2015, 33:97-101; and WO2014/110591.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: In Vitro Activity of Tandem and Dual CAR T Cells Targeting CD19 and CD22

This Example demonstrates the in vitro activity of tandem and dual CAR T cells.

Tandem chimeric antigen receptors (CARs) express two distinct scFv domains as part of the same protein, in tandem. Dual CARs are composed of two full length CARs. Here, these two CARs are encoded by a single lentiviral vector, separated by a P2A ribosomal skip element. Both tandem and dual CARs described here make use of the same 4-1BB and CD3zeta stimulatory domains. Tandem and dual CARs were cloned into lentiviral expression vectors (Pelps) for the transduction of primary T cells.

The tandem CARs used in this Example are: c171, c182, c224 and c227. The Dual CARs tested in this Example are c201 and c230 (both of which have the CD22 CAR upstream of the CD19 CAR), and c203 (which has the CD19 CAR upstream of the CD22 CAR). C230, while having the same amino acid sequence as c201, has been generated using different codons, hence it has a different DNA sequence. Also used in this Example are the related mono CARs: CD22-65s, recognizing CD22, and c206, recognizing CD19.

Constructs were compared by testing the effector T cell responses of tandem and dual CAR-transduced T cells in response to CD19 and CD22 expressing (Nalm6), CD22 expressing (CD19KO), or CD19 expressing (CD22KO) targets. Effector T cell responses include, but are not limited to, cellular expansion, proliferation, doubling, cytokine production and target cell killing or cytolytic activity (degranulation).

Results

Generation of CAR T Cells

CAR encoding Pelps lentiviral transfer vectors were used to produce the genomic viral material packaged into the VSVg pseudotyped lentiviral particles. Lentiviral vector DNA encoding the CAR was mixed with the three packaging components VSVg, gag/pol and rev in combination with lipofectamine reagent to transfect Lenti-X 293T cells (Clontech), followed by medium replacement 12-18 h later. 30 hours after medium change, the medium was collected, filtered, concentrated by precipitation and stored at −80° C.

CAR T cells were generated by starting with blood from healthy apheresed donors whose T cells were enriched by negative selection (Pan T cell isolation, Miltenyi). T cells were then activated by addition of CD3/CD28 beads (Dynabeads® Human T-Expander CD3/CD28, ThermoFisher Scientific) at a ratio of 1:3 (T-cell to bead) and cultured in T cell medium (RPMI1640, 10% heat-inactivated fetal calf serum (FCS), 2 Mm L-glutamine, 1× Penicillin/Streptomycin, 100 mM non-essential amino acids, 1 mM Sodium Pyruvate, 10 mM Hepes, and 55 mM 2-mercaptoethanol) at 37° C., 5% $CO_2$. T cells were cultured at $0.5\times10^6$ T cells in 1 ml medium per well of a 24-well plate. After 24 hours, when T cells were blasting, viral supernatant was added; T cells were transduced at a multiplicity of infection (MOI) of 5. T cells began to proliferate, which was monitored by measuring the cell concentration (as counts per MI), and T cells were diluted in fresh T cell medium every two days. As the T cells began to rest down after approximately 10 days, the logarithmic growth wanes. The combination of slowing growth rate and reduced T cell size (approaching 350 Fl) determines the time for T cells to be cryopreserved for later analysis. All CAR T cells were produced under research grade (i.e., not clinical grade) manufacturing conditions. Before cryopreserving, the percentage of cells transduced (expressing the CD22-specific and/or CD19-specific CARs on the cell surface) were determined by flow cytometric analysis on a FACS Fortessa (BD). The viral transduction showed comparable expression levels, indicating similar transduction efficiency of the respective CARs. The cell counts of the CAR T cell cultures indicate that there is no detectable negative effect of the CARs on the T cells' ability to proliferate when compared to untransduced T cells ("UTD").

Evaluating Potency of CAR-Redirected T Cells

To evaluate the functional abilities of these dual CAR T cells, the CAR-Ts, generated as described above, were thawed, counted and co-cultured with cancer cells to read out their killing capabilities and secretion of cytokine. In one experiment, dual CAR-Ts c201 and c203 were compared to the mono CAR counterparts c206 (CART19) and CD22-65s. A second experiment compared the dual CAR-Ts c201 and c230 to the tandem CAR-Ts c171, c182, c188, c224, and c227, and to the mono CAR counterparts c206 (CART19) and CD22-65s. Non-transduced T cells (UTD) served as non-targeting T cells controls in both experiments.

Figure 3A:
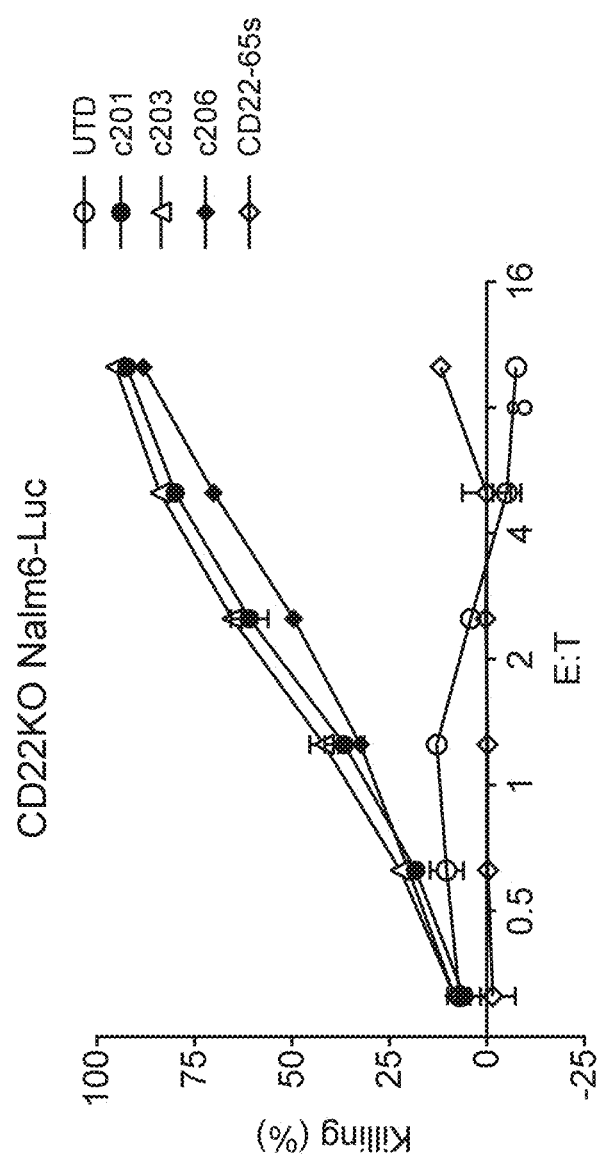
FIGS. 3A-3D show in vitro activity of tandem and dual CAR T cells targeting CD19 and CD22.
Figure 3B:
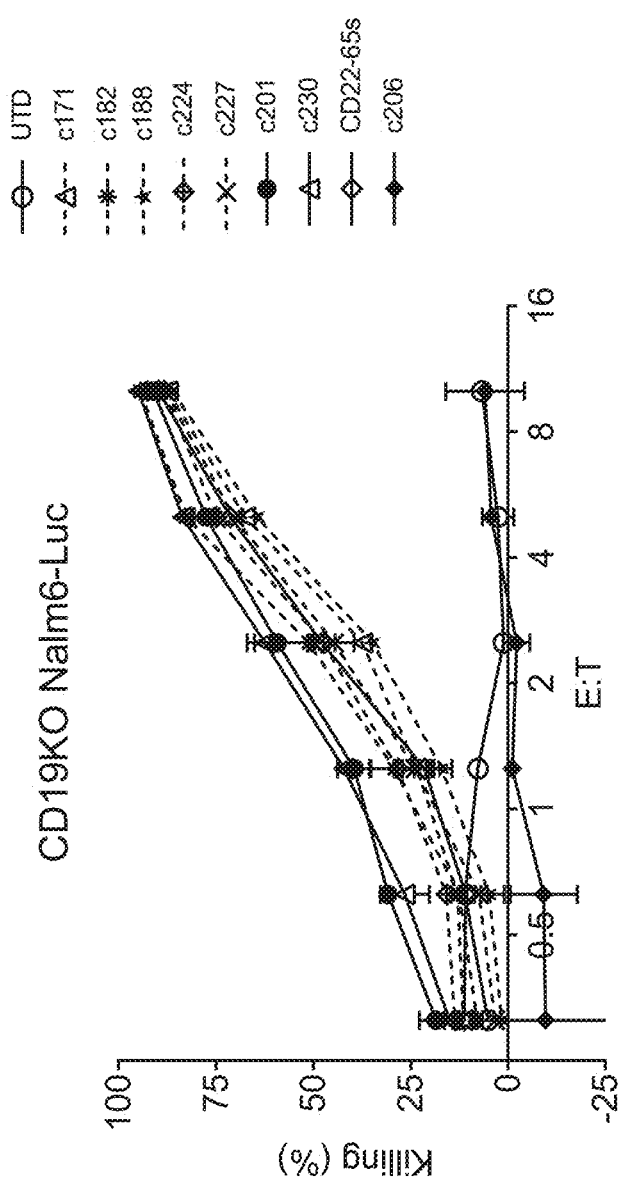

T cell killing was directed towards the acute lymphoblastic leukemia (ALL) lines Nalm6 (RRID: CVCL_0092) and the respective CD22-negative line (CD22KO), as well as the CD19-negative line (CD19KO), generated by CRISPR modification of Nalm6. All cell lines were transduced to express luciferase as a reporter for cell viability/killing. The cytolytic activities of CAR-Ts were measured at a titration of effector:target cell ratios (E:T) of 10:1, 5:1, 2.5:1, 1.25:1 0.63:1 and 0.31:1. Assays were initiated by mixing the respective number of T cells with a constant number of targets cells (25,000 cells per well of a 96-well plate). After 20 hours, remaining cells in the wells were lysed by addition of Bright-Glo™ Luciferase Assay System (Promega) reagent, to quantify the remaining Luc-expressing cancer cells in each well. "% Killing" was calculated in relation to wells containing target cells alone (0% killing, maximal Luc signal). The data with CD22KO Nalm6-Luc show that transduction with the dual or c206 CART encoding lentiviruses transfers anti-CD19 killing activity to T cells (FIG. 3A). The data with CD19KO Nalm6-Luc show that transduction with the dual, tandem or CD22-65s CART encoding lentiviruses transfers anti-CD22 killing activity to T cells (FIG. 3B). UTD T cells show background killing only. All three dual CAR-Ts showed slightly higher CD19- and CD22-mediated killing of both KO Nalm6 target cells.

Figure 3C:
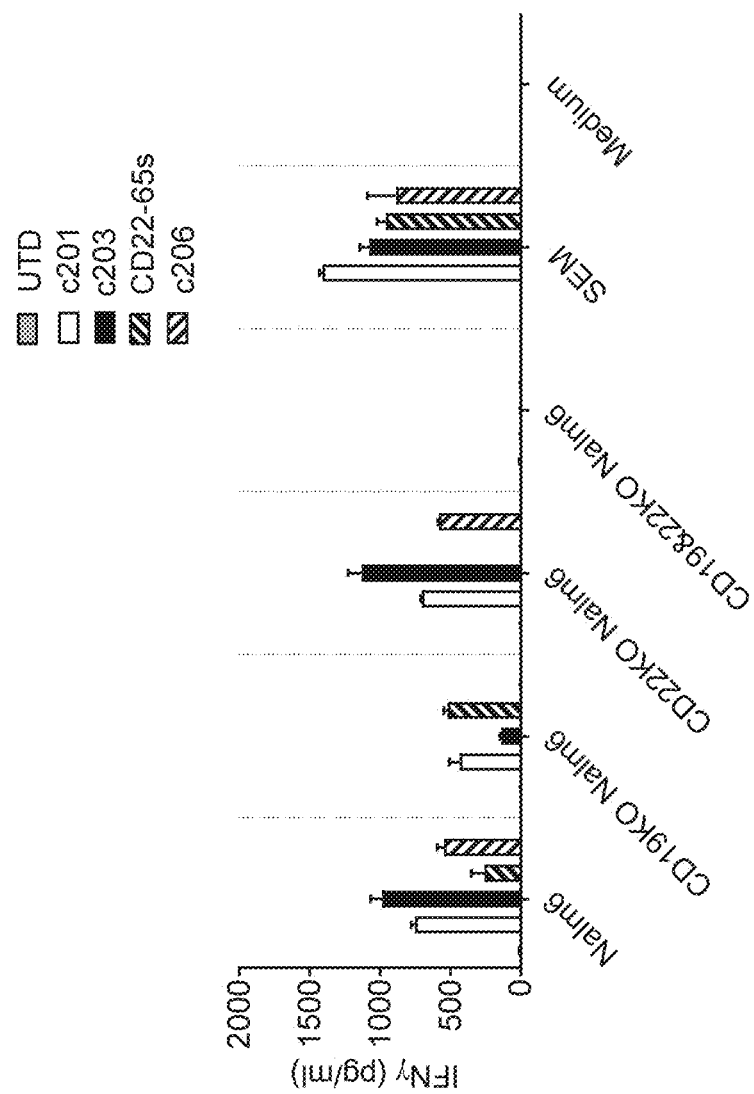
Figure 3D:
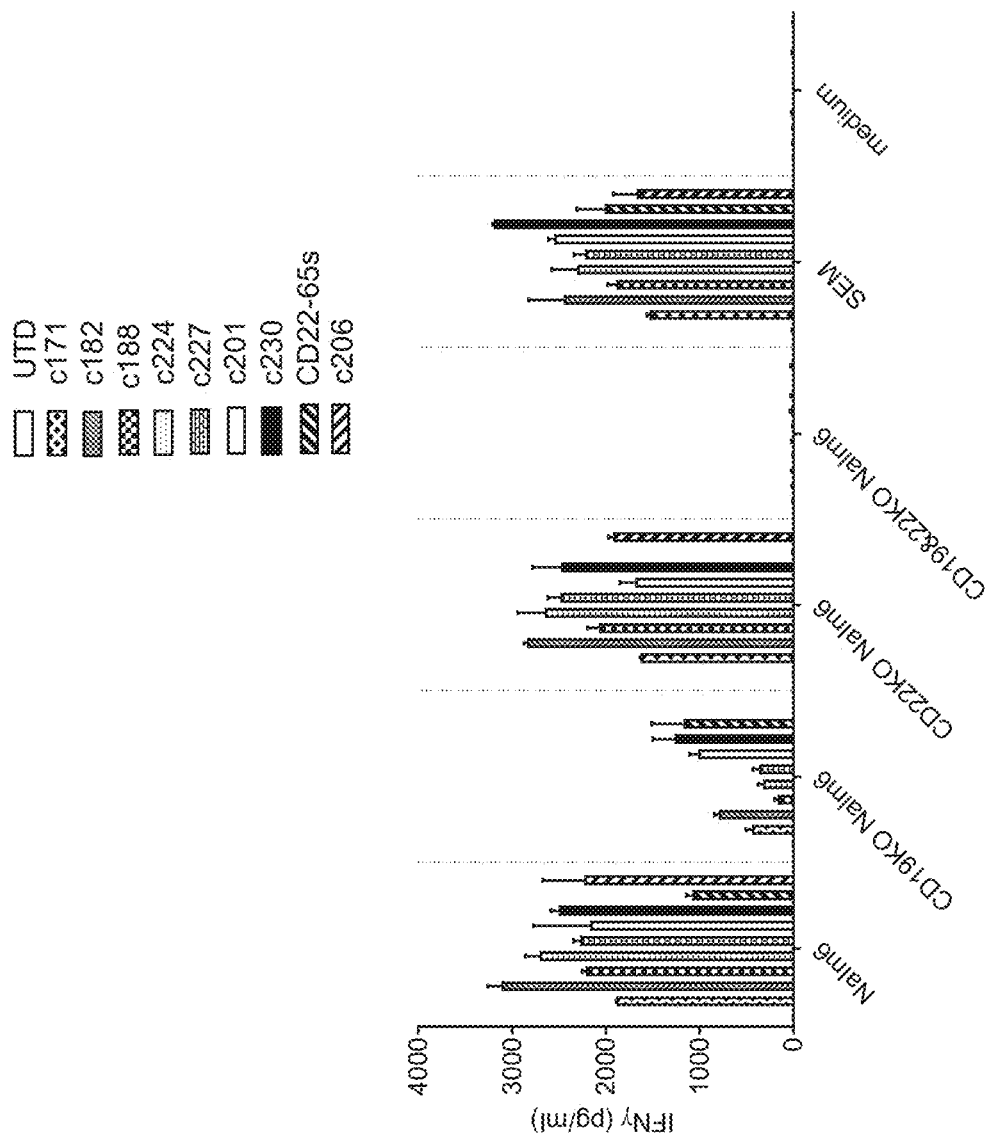

To measure cytokine production of these CAR T cells in response to CD22 and/or CD19-expressing target cells, CAR T cells were co-cultured with the same ALL lines as above. Additionally, CAR-Ts were cocultured with the ALL line SEM. Cells were cultured at an effector:target ratio of 1:1 and 25,000 cells per well of a 96-well plate for 24 h, after which the media was removed for cytokine analysis using the V-PLEX Human IFN-g Kit (Meso Scale Diagnostics). All dual, tandem and mono CAR-Ts were stimulated strongly by target cells expressing CD19 (Nalm6, CD22KO Nalm6 and SEM; FIGS. 3C and 3D). However, data on IFN-g levels secreted by CAR-Ts stimulated through CD22 alone (CD19KO Nalm6), showed improved stimulation of c201 and c230 dual CAR-Ts as compared to c203 and tandem CAR-Ts. C201 and c230 secreted levels of IFN-g comparable to the CD22-65s mono CAR-T (FIGS. 3C and 3D).

The dual CAR-Ts c201, c203 and c230 showed better killing activity than tandems and mono CAR-Ts in this study. While dual CAR-Ts were similarly active with respect to IFN-g secretion upon co-culture with CD19-expressing target cells, c201 showed superior activation as compared to c203. Both c201 and c230 showed better activation as compared to the tandem CAR-Ts tested in this study.

Example 2: In Vivo Activity of Dual and Tandem CAR-Ts Targeting CD19 and CD22

This Example demonstrates the in vivo activity of dual and tandem CAR-T cells. Tandem chimeric antigen receptors (CARs) express two distinct scFv domains as part of the same protein, in tandem. Dual CARs are composed of two full length CARs. In this Example, these two CARs are encoded by a single lentiviral vector, separated by a P2A ribosomal skip element. Both tandem and dual CARs described here make use of the same 4-1BB and CD3zeta stimulatory domains. Tandem and dual CARs were cloned into lentiviral expression vectors (Pelps) for the transduction of primary T cells.

The tandem CARs used in this Example are: c171, c182, c224 and c227. The Dual CARs used in this Example are c201 and c230, which have the CD22 CAR upstream of the CD19 CAR. C230, while having the same amino acid sequence as c201, has been generated using different codons, hence it has a different DNA sequence. The related mono CARs used in this study are CD22-65s, recognizing CD22, and c206, recognizing CD19. Anti-tumor activity of dual and tandem CAR T cells was assessed in vivo in an ALL xenograft relapse model.

Materials and Methods

Cell lines: Nalm6 (RRID: CVCL_0092) is a human acute lymphoblastic leukemia (ALL) cell line. Using CRISPR technology, the CD19 gene was knocked-out (CD19KO). Cells were grown in RMPI medium containing 10% fetal bovine serum and both grow in suspension. Cells persisted and expanded in mice when implanted intravenously. Cells have been modified to express luciferase, so that that tumor cell growth can also be monitored by imaging the mice after they have been injected with the substrate Luciferin.

Mice: 6 week old NSG (NOD.Cg-Prkdc$^{scid}$ Il2rg$^{tm1Wjl}$/SzJ) mice were received from the Jackson Laboratory (stock number 005557). Animals were allowed to acclimate for at least 3 days prior to experimentation. Animals were handled in accordance with relevant regulations and guidelines. Electronic transponders for animal identification were implanted on the left flank one day prior to tumor implantation.

Tumor implantation: Nalm6 and CD19KO Nalm6 cells in logarithmic growth phase were harvested and washed in 50 ml falcon tubes at 1200 rpm for 5 minutes, once in growth media and then twice in cold sterile PBS. Cells were resuspended in PBS at a concentration of $5\times10^6$ per ml and a ratio of 20:1 Nalm6 to CD19KO Nalm6, placed on ice, and injected in mice. Cancer cells were injected intravenously in 200 µl through the caudal vein. This model grows well when implanted intravenously in mice, which can be imaged for tumor burden measurements. Upon injection of $1\times10^6$ cancer cells, the tumors establish and can be accurately measured within 3 days. Baseline measurements are $4-6\times10^5$ photons/second (p/s). Within 7 days the mean bioluminescence measurement is $2-4\times10^6$ p/s and untreated tumors reach endpoint measurement ($2-3\times10^9$) by 20-30 days. Anti-tumor activities of therapeutic agents are often tested once tumors are fully engrafted. Thus, there is a large window with these models during which the anti-tumor activity of CAR T cells can be observed.

CAR T cell generation: All CAR T cells were produced under research grade (i.e., not clinical grade) manufacturing conditions. Traditional manufacturing: CAR T cells were generated by starting with blood from healthy apheresed donors whose T cells were enriched by negative selection (Pan T cell isolation, Miltenyi). T cells were then activated by addition of CD3/CD28 beads (Dynabeads® Human T-Expander CD3/CD28, ThermoFisher Scientific) at a ratio of 1:3 (T-cell to bead) and cultured in T cell medium (RPMI1640, 10% heat-inactivated fetal calf serum (FCS), 2 mM L-glutamine, 1× Penicillin/Streptomycin, 100 mM non-essential amino acids, 1 mM Sodium Pyruvate, 10 mM Hepes, and 55 mM 2-mercaptoethanol) at 37° C., 5% CO2. T cells were cultured at $0.5\times10^6$ T cells in 1 mL medium per well of a 24-well plate. After 24 hours, when T cells were blasting, viral supernatant was added; T cells were transduced at a multiplicity of infection (MOI) of 5. T cells began to proliferate, which was monitored by measuring the cell concentration (as counts per mL), and T cells were diluted in fresh T cell medium every two days. As the T cells began to rest down after approximately 10 days, the logarithmic growth wanes. The combination of slowing growth rate and reduced T cell size (approaching 350 Fl) determines the time for T cells to be cryopreserved for later analysis. Before cryopreserving, the percentage of cells transduced (expressing the CD22-specific and/or CD19-specific CARs on the cell surface) were determined by flow cytometric analysis on a FACS Fortessa (BD). The viral transduction showed comparable expression levels, indicating similar transduction efficiency of the respective CARs. The cell counts of the CAR T cell cultures indicate that there is no detectable negative effect of the CARs on the T cells' ability to proliferate when compared to untransduced T cells ("UTD").

CAR T cell dosing: In Nalm6 studies mice were dosed 7 days after tumor implantation. CAR T cells generated by traditional manufacturing were dosed at $1\times10^6$ CAR$^+$ T cells. Cells generated with the rapid process were dosed at 0.3 and $0.1\times10^6$ CAR$^+$ T cells. For mixed dosing, c206 and CD22-65s mono CAR-Ts were mixed at a 1:1 ratio at the dose indicated below. In the TMD8 study, mice were dosed 9 days after tumor implantation, with $1\times10^6$ or $3\times10^6$ CAR+ T cells. As controls, mice received either vehicle (PBS) or UTD. For dosing, cells were partially thawed in a 37° C. water bath and then completely thawed by the addition of 1 ml of warmed T cell medium. The thawed cells were transferred to a 50 ml falcon tube and adjusted to a final volume of 12 ml with T cell medium. The cells were washed twice and spun at 300 g for 10 minutes and then counted by Cellometer (Nexcelom). T cells were then resuspended at respective concentrations in cold PBS and kept on ice until the mice were dosed. The CAR-Ts were injected intravenously via the tail vein in 200 µl. All cells were prepared from the same donor in parallel. Animal monitoring: The health status of the mice was monitored daily, including twice weekly body weight measurements. Tumors were also monitored twice weekly by imaging for Nalm6 studies.

Results

The anti-tumor activity of dual and tandem CAR T cells was assessed in a B-cell acute lymphoblastic leukemia xenograft relapse model. Five percent (5%) of CD19-negative, CD22-positive Nalm6 cells (CD19KO) were mixed into Nalm6 wild-type cells, which express both CD22 and CD19. Cancer cells were counted, combined and injected as a mixed population. Following tumor cell implantation on day 0, tumor bearing mice were randomized into treatment groups and CAR T cells were administered intravenously via the lateral tail vein on day 7 after tumor implantation. Tumor growth and animal health were monitored until animals achieved endpoint.

Figure 4A:
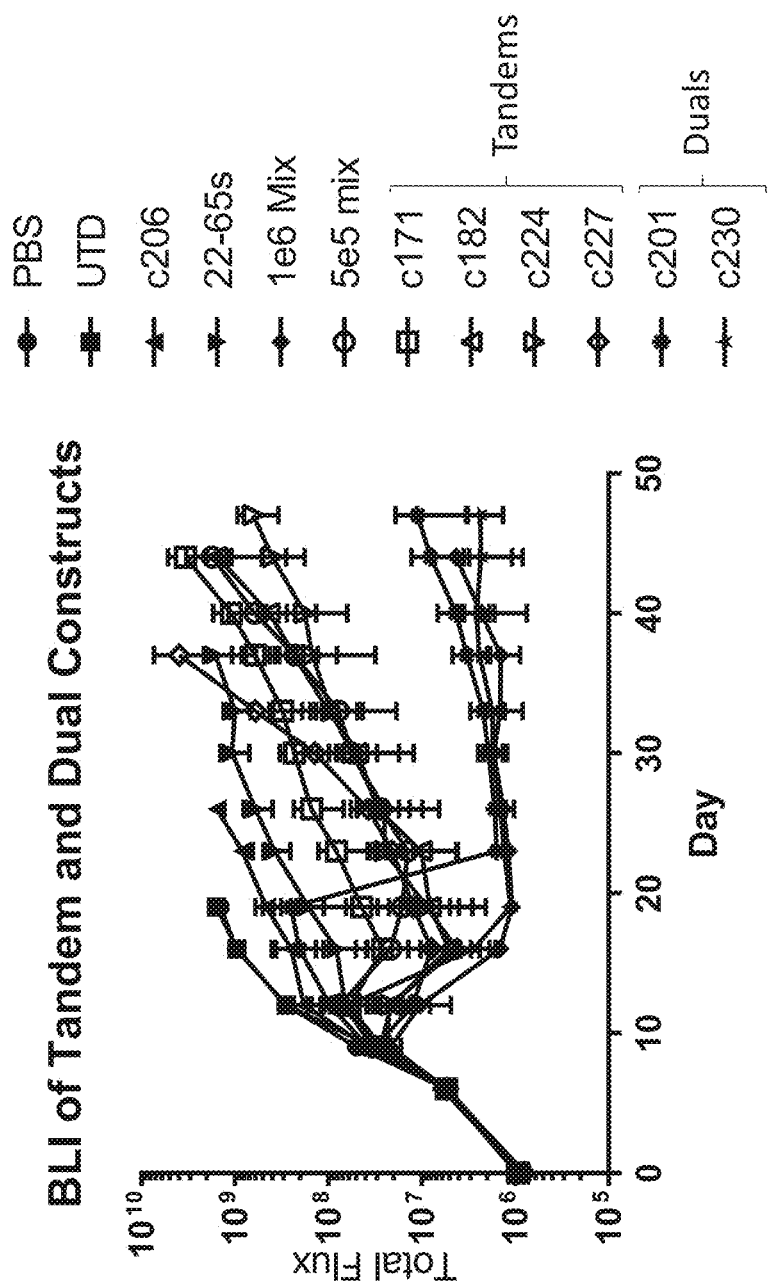
FIGS. 4A-4B show in vivo activity of tandem and dual CAR T cells targeting CD19 and CD22 in a B-cell acute lymphoblastic leukemia xenograft relapse model.

In the study using traditionally manufactured CAR-Ts, c171, c182, c224, and c227 tandem CAR-Ts were compared to c201 and c230 dual CAR-Ts. As reference, c206 and CD22-65s mono CAR-Ts were injected alone or in a 1:1 mix. While all single CAR-T populations were injected at $1\times10^6$ CAR+ dose, the mixed CAR-Ts were injected either at a dose of $1\times10^6$ CAR+ cells each ($2\times10^6$ total CAR-Ts, 1 e6 Mix) or at a dose of $0.5\times10^6$ CAR+ cells each ($1\times10^6$ total CAR-Ts, 5 e5 Mix). Mice, which received PBS or UTD T cells, were euthanized at week 3, before tumors caused decreased hind leg mobility. The other groups were euthanized between weeks 4 and 7. The mean bioluminescence for all treatment groups is plotted in FIG. 4A.

The PBS treatment group, which did not receive any T cells, demonstrates baseline Nalm6 tumor growth kinetics in intravenously injected NSG mice. The UTD treatment group served as a T cell control to show the non-specific response of human donor T cells in this model, which was not detected. c206, CD22-65s mono CAR-Ts showed the least response in this relapse model, at the dose used. All tandem CAR-Ts showed significantly slower tumor growth, but eventually mice were euthanized due to tumor burden. The dual CAR-Ts, c201 and c230, showed full tumor eradication in several mice of the treatment groups (see FIG. 4A). The 1 e6 Mix group showed similar efficacy, but required twice as many CAR+ T cells as compared to the duals. The 5 e5 Mix group, which received the same total number of CAR-Ts as the duals, did not perform as well, as was comparable to the tandem CAR-Ts tested here.

Figure 4B:
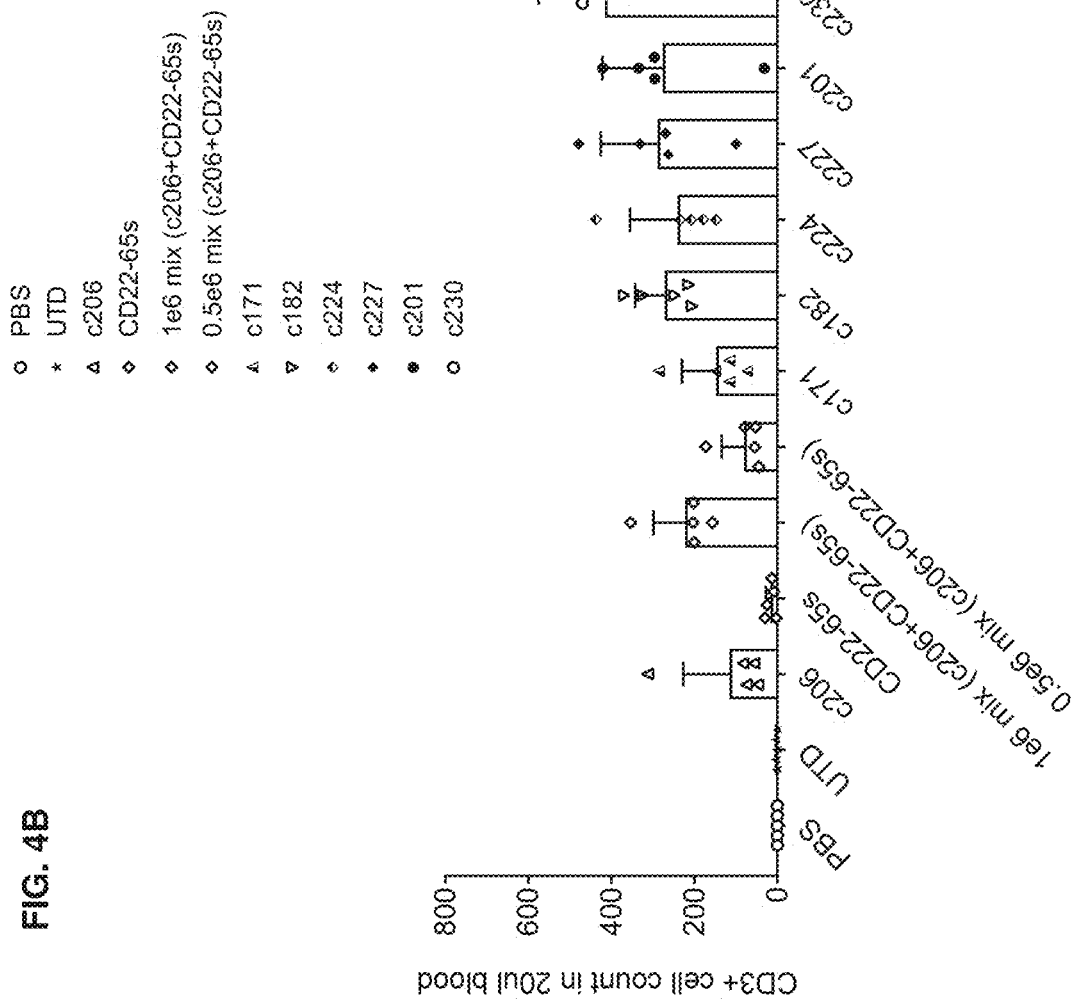

The kinetic of expansion and persistence of CAR-Ts was measured in these animals by weekly flow cytometric analysis of their blood. Representative data is shown for the analysis 2 weeks post CAR-T injection (FIG. 4B). Both dual CAR-Ts as well as the tandem CAR-Ts c182, c224, and c227 showed similar numbers of circulating T cells as the 1 e6 Mix group. These numbers were higher as compared to the mono CAR-Ts and the 5 e5 Mix group.

The first two studies demonstrated that the dual CAR T cells c201 and c230 are capable of eradicating NALM6 cancer and the CD19-negative variant thereof. The efficacy was superior to the respective mono CAR-Ts as well as tandem CAR-Ts tested here.

Example 3: Manufacturing c201 Cells Using the Activation Process at Small Scale

This example describes the assessment of the manufacturability of CD19- and CD22-targeting dual CAR-T cells using the activation process at small scale.

Aliquots of frozen T cells were thawed in a 37° C. water bath, put into Optimizer CM (Gibco Optimizer Media with Supplement+100 U/mL human IL2), and spun for 5 minutes at 1500 rpm. Cells were counted and plated into a 24-well plate at $3\times10^6$ cells/mL, 1 mL/well. TransAct was added to each well at 1/100 (10 µL/well). GMP-grade c201 virus was added at differing multiplicity of infections (MOIs) based on the qPCR titer. A non-transduced control (UTD) was plated as well. After 24 hours in culture, cells were harvested and washed three times in PBS+1% HSA. Cells were then counted and re-plated at $1\times10^6$ cells/mL final in a 24-well plate. 72 hours after re-plating, cells were harvested, counted and an aliquot of $5\times10^5$ cells from each sample was taken for flow cytometry analysis. Cells were stained with Live/Dead Aqua (BV510) for 15 minutes in 100 µl/well and were then washed twice. The antibody mix (Table 6) was then added at 50 µl/well for 25 minutes at 4° C. Cells were washed twice again and then fixed for 15 minutes in 1.6% PFA in PBS, 100 µl/well. After fixing, cells were washed as previously described and resuspended in a final volume of 150 µl/sample in flow cytometry buffer. 5 e4 cells were acquired on the Live CD3 positive gate of each sample on a BD LSRFortessa (BD Biosciences, San Jose CA) and data was analyzed using FlowJo v.10 software (Ashland, OR). This procedure was repeated 144 h after re-plating.

TABLE 6

Antibody and other reagents

| Marker | Clone | Fluoro-chrome | Vendor | Catalogue No. | Dilution |
|---|---|---|---|---|---|
| Live/Dead | | BV510 | Biolegend | 423102 | 1/500 |
| CD3 | SK7 | BUV395 | BD | 564001 | 1/200 |
| CAR19 | Anti-Id | PE | In House Reagent | | 1/160 |
| CD4 | SK3 | PerCP 5.5 | Biolegend | 344608 | 1/100 |
| CAR22 | Anti-Id | AF647 | In House Reagent | | 1/800 |
| CD8 | SK1 | APC H7 | BD | 560179 | 1/200 |
| FACS Buffer | | | Miltenyi Biotec | 130-091-222 | |
| BSA Stock Solution | | | Miltenyi Biotec | 130-091-376 | |
| Phosphate Buffer Saline (PBS) | | | Gibco | 14190-144 | |
| Para formaldehyde (PFA) | | | Polysciences Inc. | 18814-10 | |

Figure 5A:
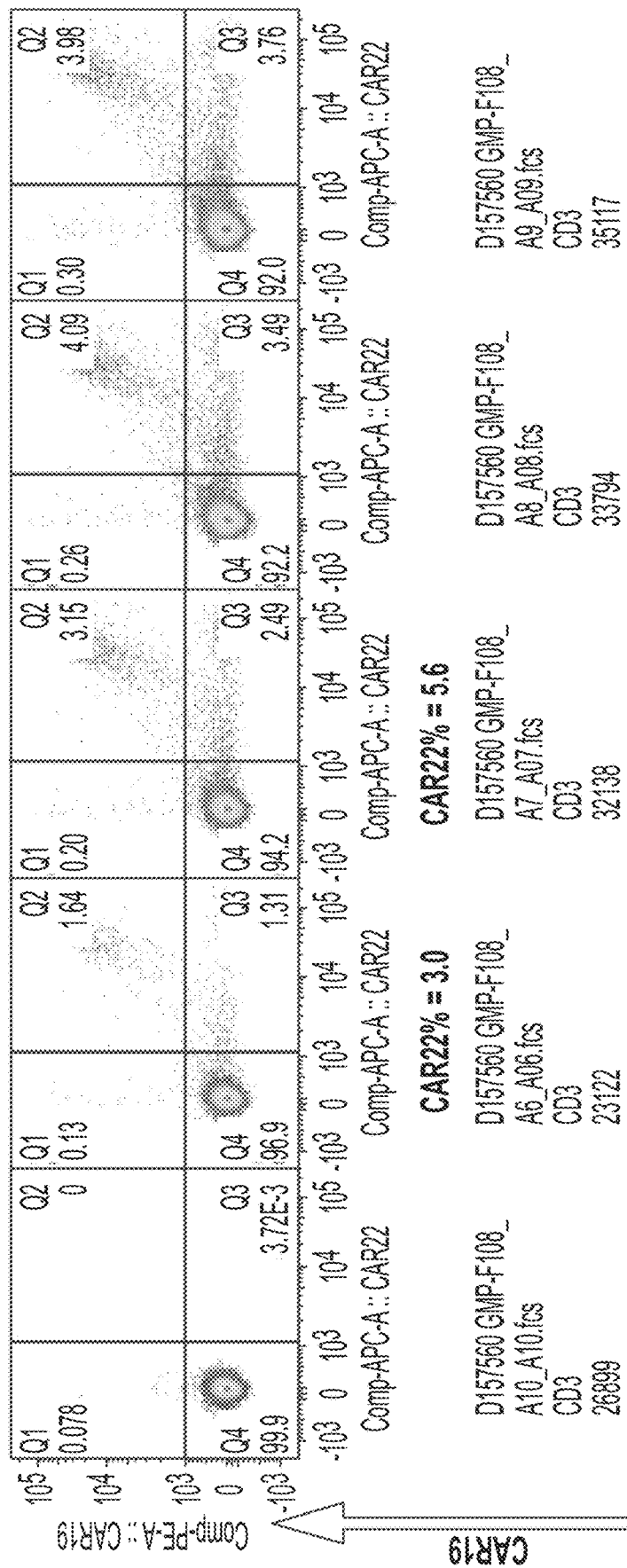
FIGS. 5A-5C show flow cytometry analysis of percentage of CAR19+, CAR22+, and double positive CAR T cells targeting CD19 and CD22 manufactured by the activation process.
Figure 5B:
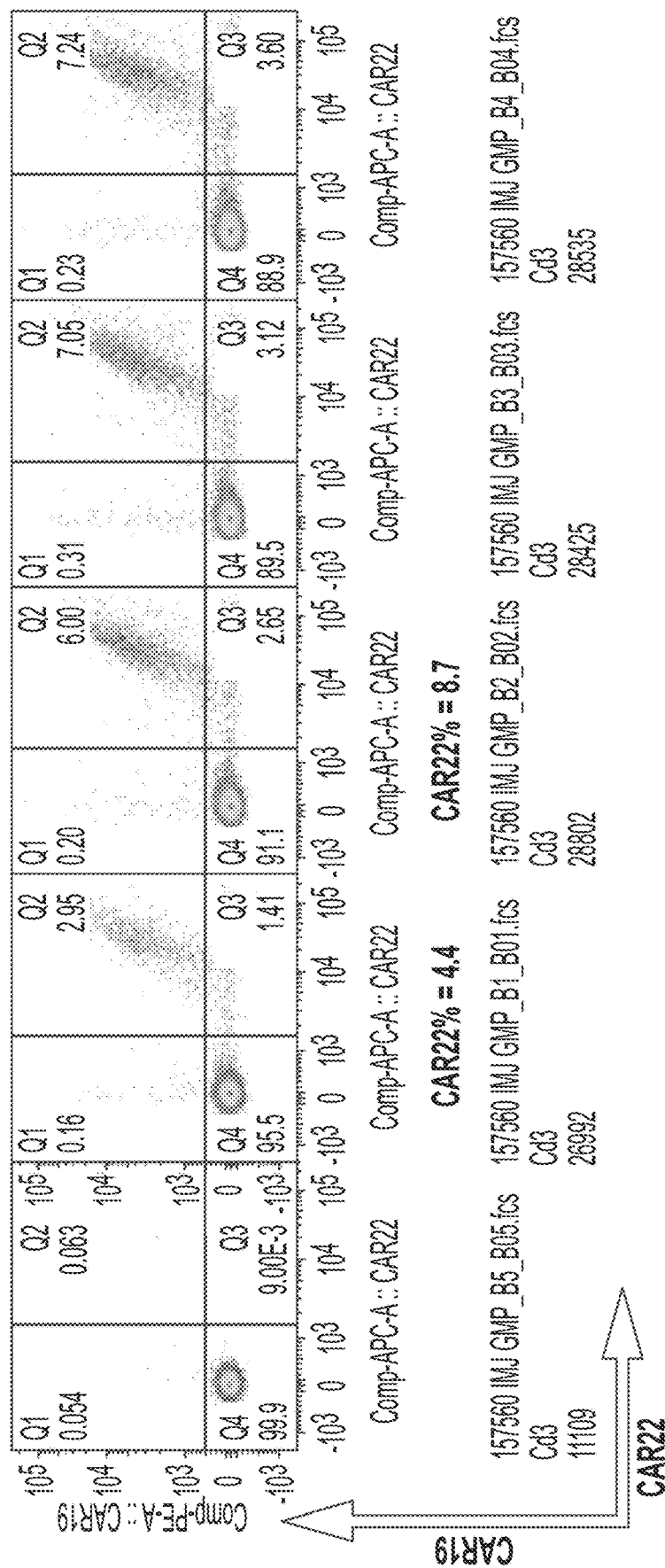

Flow analysis revealed a majority of CAR+ cells were expressing both CD19 and CD22 targeting CARs, as detected by the respective anti-Idiotype antibodies (FIGS. 5A and 5B). The ratio of mono over dual CAR expression shifted toward dual CAR expression over time and stabilized after 144 h. At the same time, total CAR expression increased as well. At both time points, CAR expression was dependent on the MOI, showing an increase with higher MOI. Data from one representative of several donors are shown here.

Example 4: Manufacturing c201 Cells Using the Activation Process at Large Scale This example describes the assessment of the manufacturability of CD19- and CD22-targeting dual CAR-T cells using the activation process at large, full clinical scale.

The activation process of CAR-T cells initiates with the preparation of the media as outlined in Table 7. Cryopreserved leukapheresis product was used as the starting material and processed for T cell enrichment.

TABLE 7

Media and Buffer type and point of use during CART manufacturing

| Media Type | Source | Point of Use |
| --- | --- | --- |
| CliniMACS ® Buffer/human serum albumin (HSA) (0.5% in working concentration) | Prepared by operator on day 0 | Day 0 Processing on Cell Wash/ Separator |
| Rapid Media | Prepared by operator on day 0 | Day 0 for Cell Seeding |
| PBS/HSA (1% or 2% in working concentration) | Prepared by operator on day 0 | Harvest and culture Wash Media (Day 1) |
| Cryostor10 (CS10) | Commercially available | Harvest Formulation |

Cryopreserved leukapheresis was thawed, washed, and then underwent T cell selection and enrichment using CliniMACS® microbead technology. The viable cells selected with the Miltenyi microbeads were seeded into the centricult on the Prodigy®, which is a non-humidified incubation chamber. While in culture, the cells were suspended in Rapid media, which is an OpTmizer™ CTS™ based medium that contains the CTS™ Supplement (ThermoFisher), Glutamax, IL-2 and 2% Immune cell serum replacement amongst its components to promote T cell activation and transduction. Viable nucleated cells (VNCs) were activated with Trans-ACT (Miltenyi) and transduced with the c201 lentiviral vector encoding for both CARs. Lentiviral transduction was performed on the day of seeding after the TransACT had been added to the diluted cells in the culture media. Cells were transduced with GMP-grade c201 virus was added at multiplicity of infections (MOIs) of 1, based on the qPCR titer. Lentiviral vector was thawed immediately prior to use for up to 30 minutes at room temperature.

From the start of the process on Day 0 to the initiation of the culture wash and harvest, CAR-T cells were cultured for 20 hours from seeding. Following culture, the cell suspension underwent two culture washes and one harvest wash within the centricult chamber.

After the harvest wash on the CliniMACS® Prodigy® on day 1, the cell suspension was sampled to determine viable cell count and viability. Cell suspension was then transferred to a centrifuge to be pelleted manually. The supernatant was removed, and the cell pellet was re-suspended in CS10 (BioLife Solution), resulting in a product formulation with a final DMSO concentration of ~10%. The cells were then distributed into individual cryobags and analytical sampling into cryovials.

Sentinel vials were thawed and cells were then counted and re-plated at $1 \times 10^6$ cells/mL final in a 24-well plate. 72 hours after re-plating, cells were harvested, counted and an aliquot of $5 \times 10^5$ cells from each sample was taken for flow cytometry analysis. Cells were stained with Live/Dead Aqua (BV510) for 15 minutes in 100 μl/well and were then washed twice. The antibody mix (Table 5) was then added at 50 μl/well for 25 minutes at 4° C. Cells were washed twice again and then fixed for 15 minutes in 1.6% PFA in PBS, 100 μl/well. After fixing, cells were washed as previously described and resuspended in a final volume of 150 μl/sample in flow cytometry buffer. 5 e4 cells were acquired on the Live CD3 positive gate of each sample on a BD LSRFortessa (BD Biosciences, San Jose CA) and data was analyzed using FlowJo v.10 software (Ashland, OR). This procedure was repeated 144 h after re-plating.

Figure 5C:
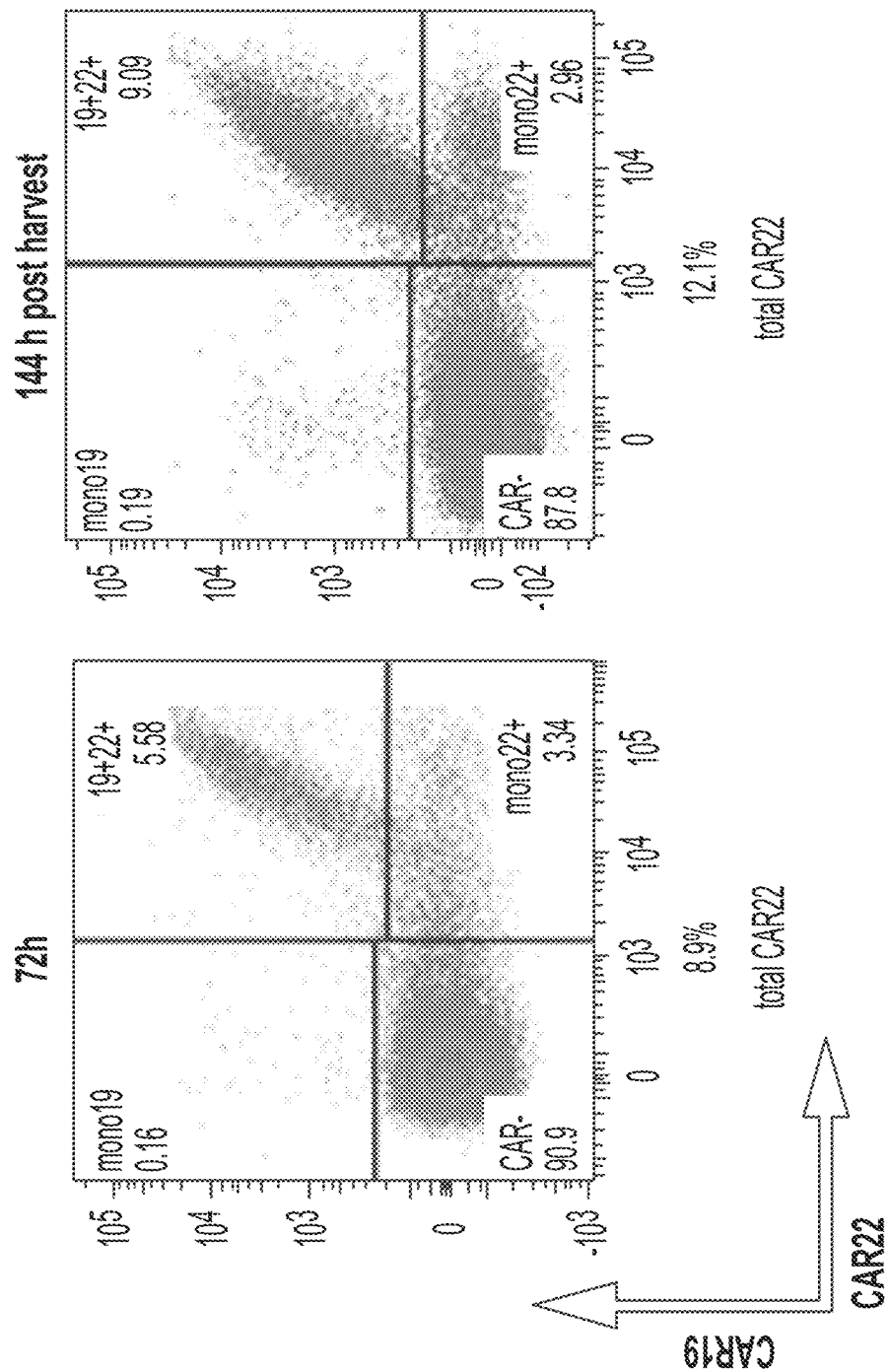

The full scale ARM process produced a CAR-T product with 12% total CAR expression, as determined 144 h post transduction; 9% dual CAR+ cells and 3% mono CAR22+ cells (FIG. 5C). As seen for small scale activation process experiments, the total CAR % as well as the proportion of dual CARs over mono CARs increased over time.

Example 5: In Vivo Activity of Dual and Mono CAR-Ts Targeting CD19 and/or CD22

This Example demonstrates the in vivo activity of dual and mono CAR-T cells manufactured according to the traditional method (TM) and the activation process (AP). The dual CAR-T used in this Example is c201, which has the CD22 CAR upstream of the CD19 CAR, produced by the activated process. The related mono CAR-Ts used in this study are CD22-65s, recognizing CD22 and produced by TM, and CAR19 (murine scFv), recognizing CD19 and produced by TM and AP. Anti-tumor activity of dual and mono CAR-T cells was assessed in vivo in an ALL xenograft model.

Materials and Methods

Example 2 has an outline of the animal study. In this example, wild-type Nalm6 (RRID: CVCL_0092), a human acute lymphoblastic leukemia (ALL) cell line, was used.

CAR T cell dosing: Mice were dosed 7 days after tumor implantation. CD22-65s CAR-T cells generated by traditional manufacturing were dosed at 3, 1, and $0.3 \times 10^6$ CAR$^+$ T cells. CAR19 cells generated with AP were dosed at 1 and $0.3 \times 10^6$ CAR$^+$ T cells; CAR19 generated by TM were dosed at 1, 0.3, and $0.1 \times 10^6$ CAR$^+$ T cells. C201 dual CAR-T cells generated with AP were dosed at 0.3, 0.1, and $0.03 \times 10^6$ CAR$^+$ T cells. As controls, mice received either vehicle (PBS) or UTD.

Results

Figure 6A:
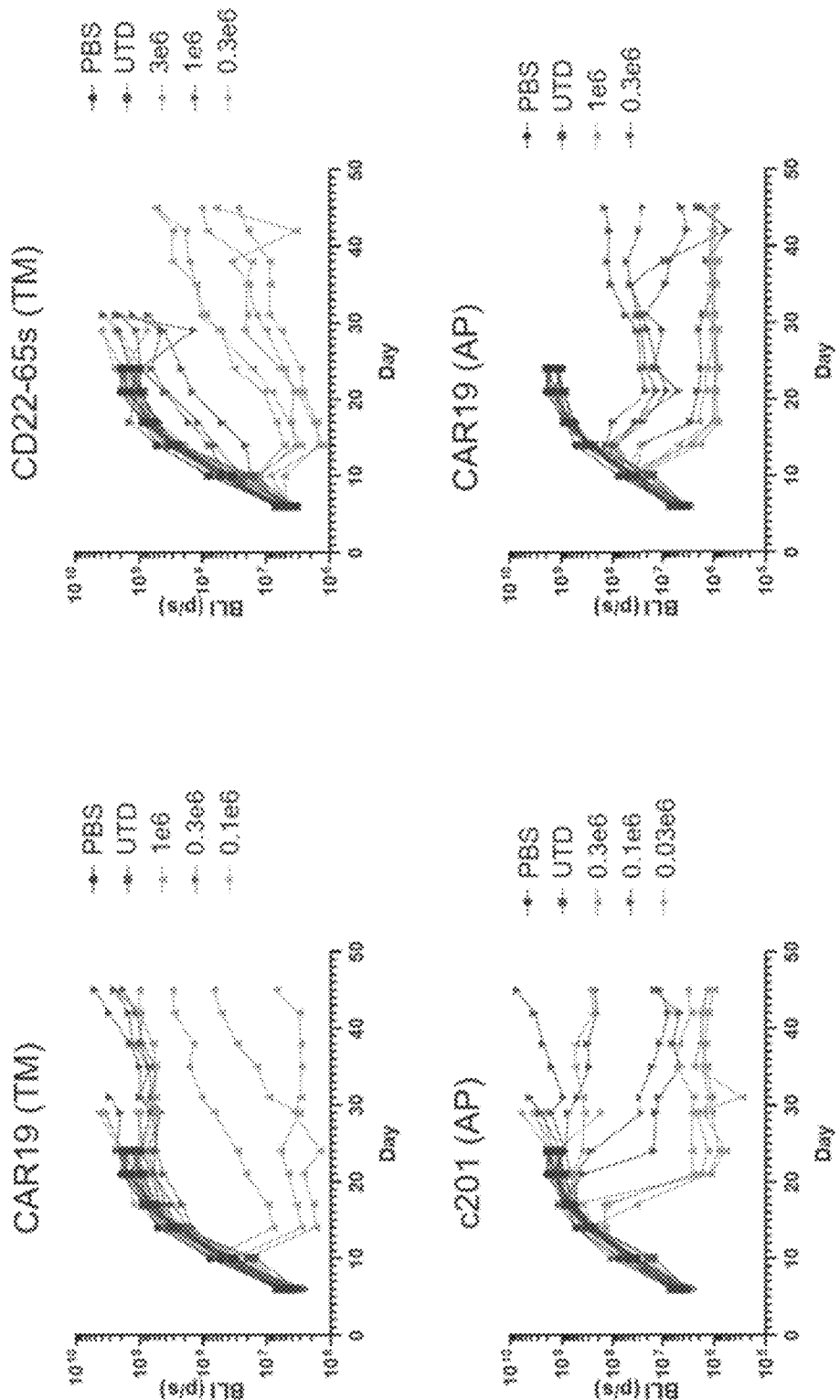
Figure 6C:
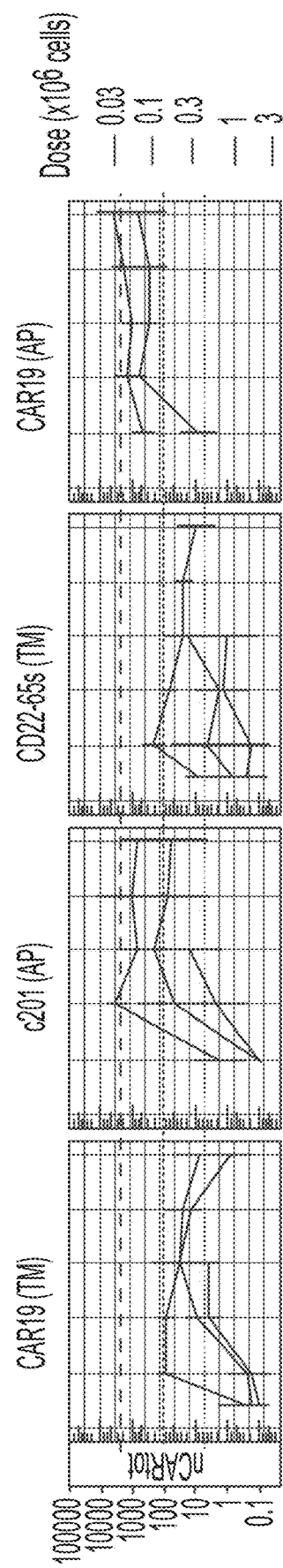
FIG. 6C is a graph depicting expansion kinetics of the various CAR-T cells, shown as number of CAR+ cells per 20 µl of blood (number of CAR-T cells, nCARtot).

The anti-tumor activity of dual and mono CAR T cells was assessed in a B-cell acute lymphoblastic leukemia xenograft model; Nalm6 cells express both CD19 and CD22. Following tumor cell implantation on day 0, tumor bearing mice were randomized into treatment groups and CAR T cells were administered intravenously via the lateral tail vein on day 7 after tumor implantation. Tumor growth and animal health were monitored until animals achieved endpoint. Mice, which received PBS or UTD T cells, were euthanized at week 3, before tumors caused decreased hind leg mobility. The other groups were euthanized between weeks 4 and 7. The mean bioluminescence for all treatment groups is plotted in FIG. 6A. The PBS treatment group, which did not receive any T cells, demonstrates baseline Nalm6 tumor growth kinetics in intravenously injected NSG mice. The UTD treatment group served as a T cell control to show the non-specific response of human donor T cells in this model, which was not detected. For better comparison, the different CAR-Ts at the $0.3 \times 10^6$ dose groups were graphed together in FIG. 6B. Both™ generated CAR-Ts showed lower activity, with a modest delay in tumor growth for CAR19 (TM). In contrast, both AP CAR-Ts markedly decreased tumor burden and c201 (AP) CAR-Ts lead to tumor eradication (BLI base line levels) in 4 out of 5 mice. The kinetic of expansion and persistence of CAR-Ts was measured in these animals by weekly flow cytometric analysis of their blood. Compiled data is shown in FIG. 6C. Comparing across the CAR-T groups at the $0.3 \times 10^6$ dose, AP processed CAR-Ts showed better expansion. The comparison of c201 and CAR19 (both AP) shows similar expansion of CAR-Ts for the 0.3 and $1 \times 10^6$ dose, respectively.

This study underlines the potency of c201 also when manufactured with AP. C201 AP was superior to CAR19 (AP) as well as CAR19 and CD22-65s (TM) with regard to anti-tumor activity and cell expansion in vivo.

Having described the present disclosure in detail, it will be apparent that modifications, variations, and equivalent aspects are possible without departing from the spirit and scope of the present disclosure as described herein and in the appended claims. Furthermore, it should be appreciated that all examples in the present disclosure are provided as non-limiting examples.

What is claimed is:

1. A method of making a cell comprising transducing an immune effector cell with a vector comprising a nucleic acid molecule encoding a chimeric antigen receptor (CAR) molecule, wherein said CAR molecule comprises:

(a) a first CAR comprising a first antigen binding domain which binds to CD22; a first transmembrane domain; a first co-stimulatory signaling domain; and/or a first primary signaling domain; and (b) a second CAR comprising a second antigen binding domain which binds to CD19; a second transmembrane domain; a second co-stimulatory domain; and/or a second primary signaling domain, wherein the first CAR and the second CAR each comprise an HCDR1, HCDR2, HCDR3, LCDR1, LCDR2, and LCDR3; and wherein the CAR molecule comprising the first CAR and the second CAR comprises the amino acid sequence of SEQ ID NO: 12 or 16, or an amino acid having at least 95%, 96%, 97%, 98%, or 99% identity thereto.

2. The method of claim 1, wherein:

(a) the first CAR comprises:

a first antigen binding domain which binds to CD22, a first transmembrane domain, and a first co-stimulatory signaling domain;

a first antigen binding domain which binds to CD22, a first transmembrane domain; and a first primary signaling domain; or a first antigen binding domain which binds to CD22, a first transmembrane domain, a first co-stimulatory signaling domain, and a first primary signaling domain; and (b) wherein the second CAR comprises:
a second antigen binding domain which binds to CD19; a second transmembrane domain; and a second co-stimulatory signaling domain;
a second antigen binding domain which binds to CD19; a second transmembrane domain; and a second primary signaling domain; or
a second antigen binding domain which binds to CD19; a second transmembrane domain; a second co-stimulatory signaling domain; and a second primary signaling domain.

3. The method of claim 1, wherein:
(i) a nucleotide sequence that encodes the first transmembrane domain and is comprised in the nucleic acid molecule is different from a nucleotide sequence that encodes the second transmembrane domain and is comprised in the nucleic acid molecule;
(ii) a nucleotide sequence that encodes the first co-stimulatory signaling domain and is comprised in the nucleic acid molecule is different from a nucleotide sequence that encodes the second co-stimulatory signaling domain and is comprised in the nucleic acid molecule; and/or
(iii) a nucleotide sequence that encodes the primary signaling domain and is comprised in the nucleic acid molecule is different from a nucleotide sequence that encodes the second primary signaling domain and is comprised in the nucleic acid molecule.

4. The nucleic acid molecule of claim 1, wherein the nucleotide sequence encoding the first CAR is disposed on a first vector and the nucleotide sequence encoding the second CAR is disposed on a second vector.

5. The method of claim 1, wherein the immune effector cell is a T cell or an NK cell.

6. The method of claim 1, wherein the vector is chosen from a DNA, a RNA, a plasmid, a lentivirus vector, adenoviral vector, or a retrovirus vector.

7. The method of claim 1, wherein the immune effector cell was previously isolated from a frozen or fresh leukapheresis product.

8. A method of making a cell comprising introducing a nucleic acid molecule encoding a CAR molecule, into an immune effector cell, wherein said CAR molecule comprises:
(a) a first CAR comprising a first antigen binding domain which binds to CD22; a first transmembrane domain; a first co-stimulatory signaling domain; and/or a first primary signaling domain; and
(b) a second CAR comprising a second antigen binding domain which binds to CD19; a second transmembrane domain; a second co-stimulatory domain; and/or a second primary signaling domain, wherein the first CAR and the second CAR each comprise an HCDR1, HCDR2, HCDR3, LCDR1, LCDR2, and LCDR3; and
wherein the CAR molecule comprising the first CAR and the second CAR comprises the amino acid sequence of SEQ ID NO: 12 or 16, or an amino acid having at least 95%, 96%, 97%, 98%, or 99% identity thereto.

9. The method of claim 8, wherein:
(a) the first CAR comprises:
a first antigen binding domain which binds to CD22, a first transmembrane domain, and a first co-stimulatory signaling domain;
a first antigen binding domain which binds to CD22, a first transmembrane domain; and a first primary signaling domain; or
a first antigen binding domain which binds to CD22, a first transmembrane domain, a first co-stimulatory signaling domain, and a first primary signaling domain; and
(b) wherein the second CAR comprises:
a second antigen binding domain which binds to CD19; a second transmembrane domain; and a second co-stimulatory signaling domain;
a second antigen binding domain which binds to CD19; a second transmembrane domain; and a second primary signaling domain; or
a second antigen binding domain which binds to CD19; a second transmembrane domain; a second co-stimulatory signaling domain; and a second primary signaling domain.

10. The method of claim 8, wherein:
(i) a nucleotide sequence that encodes the first transmembrane domain and is comprised in the nucleic acid molecule is different from a nucleotide sequence that encodes the second transmembrane domain and is comprised in the nucleic acid molecule;
(ii) a nucleotide sequence that encodes the first co-stimulatory signaling domain and is comprised in the nucleic acid molecule is different from a nucleotide sequence that encodes the second co-stimulatory signaling domain and is comprised in the nucleic acid molecule; and/or
(iii) a nucleotide sequence that encodes the primary signaling domain and is comprised in the nucleic acid molecule is different from a nucleotide sequence that encodes the second primary signaling domain and is comprised in the nucleic acid molecule.

11. The method of claim 8, wherein the immune effector cell is a T cell or an NK cell.

12. The method of claim 8, wherein the immune effector cell was previously isolated from a frozen or fresh leukapheresis product.

* * * * *